US011230717B2

(12) United States Patent
Pasternak et al.

(10) Patent No.: US 11,230,717 B2
(45) Date of Patent: *Jan. 25, 2022

(54) PLANTS HAVING INCREASED TOLERANCE TO HERBICIDES

(71) Applicant: BASF SE, Ludwigshafen (DE)

(72) Inventors: Maciej Pasternak, Ludwigshafen (DE); Stefan Tresch, Kirchheim (DE); Helmut Kraus, Wissembourg (DE); Johannes Hutzler, Waldsee (DE); Jens Lerchl, Golm (DE); Thomas Mietzner, Annweiler (DE); Jill Marie Paulik, Cary, NC (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,740

(22) PCT Filed: Apr. 28, 2014

(86) PCT No.: PCT/IB2014/061053
§ 371 (c)(1),
(2) Date: Oct. 28, 2016

(87) PCT Pub. No.: WO2014/177991
PCT Pub. Date: Nov. 6, 2014

(65) Prior Publication Data
US 2017/0114358 A1  Apr. 27, 2017

Related U.S. Application Data

(60) Provisional application No. 61/817,330, filed on Apr. 30, 2013, provisional application No. 61/817,333, filed on Apr. 30, 2013.

(51) Int. Cl.
| | | |
|---|---|---|
| C12N 15/82 | (2006.01) | |
| C12N 9/02 | (2006.01) | |
| A01N 43/653 | (2006.01) | |
| A01N 43/713 | (2006.01) | |

(52) U.S. Cl.
CPC ....... *C12N 15/8274* (2013.01); *A01N 43/653* (2013.01); *A01N 43/713* (2013.01); *C12N 9/0069* (2013.01); *C12Y 113/11027* (2013.01); *C12Y 205/01* (2013.01)

(58) Field of Classification Search
CPC .............. C12Y 113/11027; A01H 5/10; C12N 15/8274
See application file for complete search history.

(56) References Cited

U.S. PATENT DOCUMENTS

| | | |
|---|---|---|
| 5,380,831 A | 1/1995 | Adang et al. |
| 5,773,702 A | 6/1998 | Penner et al. |
| 5,859,348 A | 1/1999 | Penner et al. |
| 6,268,549 B1 | 7/2001 | Sailland et al. |
| 2009/0172831 A1 | 7/2009 | Andrews et al. |
| 2011/0023180 A1* | 1/2011 | Hawkes ................. A01N 41/10 800/278 |
| 2011/0152084 A1 | 6/2011 | Koehn et al. |
| 2012/0058892 A1 | 3/2012 | Braun et al. |

FOREIGN PATENT DOCUMENTS

| | | |
|---|---|---|
| AU | 8216998 A | 2/1999 |
| CN | 102159718 A1 | 8/2011 |
| CN | 102971428 A1 | 3/2013 |
| WO | WO-199638567 | 12/1996 |
| WO | WO-98/04685 | 2/1998 |
| WO | WO-99/04021 A1 | 1/1999 |
| WO | WO-2008009908 | 1/2008 |
| WO | WO-2008071918 | 6/2008 |
| WO | WO-2009090401 | 7/2009 |
| WO | WO-2009090402 | 7/2009 |
| WO | WO-2010029311 | 3/2010 |
| WO | WO-2010049270 | 5/2010 |
| WO | WO-20100496269 | 5/2010 |
| WO | WO-2011/035874 A1 | 3/2011 |

(Continued)

OTHER PUBLICATIONS

Siehl, Daniel L., et al. "Broad 4-hydroxyphenylpyruvate dioxygenase inhibitor herbicide tolerance in soybean with an optimized enzyme and expression cassette." Plant physiology 166.3 (2014): 1162-1176. (Year: 2014).*
Archer et al., J. Bioenerg. Biomemb., 1990, vol. 22, Issue 6, pp. 789-810.
Clark et al, J. Biol. Chem., 1989, vol. 264, pp. 17544-17550.
De Castro Silva Filho et al., Plant Mol. Biol., 1996, vol. 30, pp. 769-780.
Della-Cioppa et al., Plant Physiol., 1987, vol. 84, pp. 965-968. GenBank U89267.
Lamppa et al., J. Biol. Chem, 1998 vol. 263, pp. 14996-14999.
Lawrence et al., J. Biol. Chem., 1997, vol. 272, Issue 33, pp. 20357-20363.
Li Tian et al, Planta 2007, pp. 1067-1073 vol. 226.

(Continued)

*Primary Examiner* — Weihua Fan
(74) *Attorney, Agent, or Firm* — Mark S. Scott; BASF Global Intellectual Property

(57) ABSTRACT

The present invention refers to a method for controlling undesired vegetation at a plant cultivation site, the method comprising the steps of providing, at said site, a plant that comprises at least one nucleic acid comprising a nucleotide sequence encoding a wild-type hydroxyphenyl pyruvate dioxygenase or a mutated hydroxyphenyl pyruvate dioxygenase (mut-HPPD) which is resistant or tolerant to a HPPD-inhibiting herbicide and/or a nucleotide sequence encoding a wild-type homogentisate solanesyl transferase or a mutated homogentisate solanesyl transferase (mut-HST) which is resistant or tolerant to a HPPD-inhibiting herbicide, applying to said site an effective amount of said herbicide. The invention further refers to plants comprising mut-HPPD, and methods of obtaining such plants.

3 Claims, 6 Drawing Sheets

Specification includes a Sequence Listing.

(56) References Cited

FOREIGN PATENT DOCUMENTS

| WO | WO 2011/145015 A1 * | 11/2011 | ............. C12N 15/82 |
| WO | WO-2011145015 A1 * | 11/2011 | ........... C12N 9/0069 |
| WO | WO-2012/028579 A1 | 3/2012 | |
| WO | WO-2012082542 A2 | 6/2012 | |
| WO | WO-2012130684 A1 * | 10/2012 | ............. A01N 43/82 |

OTHER PUBLICATIONS

Loprasert Suvit et al., J. Bacterio., 2007, vol. 189, Issue 9, 3660-3664.
NCBI Database AM285678.
NCBI Database DQ231060.
NCBI Database No. AK360504.
NCBI Database XM_001694670.
NCBI Database XM_001694671.
Romer et al., Biochem. Biophys. Res. Commun., 1993, vol. 196 pp. 1414-1421.
Schmidt et al., J. Biol. Chem., 1993, vol. 268, Issue 36, pp. 27447-27457.
Schnell et al., J. Biol. Chem., 1991, vol. 266, Issue 5, pp. 3335-3342.
Shah et al., Science, 1986, vol. 233, pp. 478-481.
Von Heijne et al, Plant Mol. Biol. Rep., 1991, vol. 9, pp. 104-126.
Zhao et al., J. Biol. Chem., 1995, vol. 270, Issue 11, pp. 6081-6087.
"Arabidopsis thaliana prenyltransferase (AT3G11945) mRNA, complete cds", GenBank, Database Accession No. NM_001084669.1, Apr. 18, 2007, 2 pages.

* cited by examiner

PLANTS HAVING INCREASED TOLERANCE TO HERBICIDES

RELATED APPLICATIONS

This application is a national stage application under 35 U.S.C. § 371 of PCT/IB2014/061053, filed Apr. 28, 2014, which claims benefit of U.S. provisional application Nos. 61/817,330, filed Apr. 30, 2013 and 61/817,333, filed Apr. 30, 2013.

SUBMISSION OF SEQUENCE LISTING

The Sequence Listing associated with this application is filed in electronic format via EFS-Web and hereby incorporated by reference into the specification in its entirety. The name of the text file containing the Sequence Listing is PF75339_SEQLIST. The size of the text file is 195 KB, and the text file was created on Oct. 28, 2016.

FIELD OF THE INVENTION

The present invention relates in general to methods for conferring on plants agricultural levels of tolerance towards an herbicide. Particularly, the invention refers to plants having an increased tolerance to HPPD-inhibiting herbicides. More specifically, the present invention relates to methods and plants obtained by mutagenesis and crossbreeding and transformation that have an increased tolerance to "HPPD-inhibiting" herbicides.

BACKGROUND OF THE INVENTION

Herbicides that inhibit 4-hydroxyphenylpyruvate dioxygenase (4-HPPD; EC 1.13.11.27), a key enzyme in the biosynthesis of the prenylquinones plastoquinone and tocopherols, have been used for selective weed control since the early 1990s. They block the conversion of 4-hydroxyphenylpyruvate to homogentisate in the biosynthetic pathway (Matringe et al., 2005, Pest Manag Sci., vol. 61:269-276; Mitchell et al., 2001, Pest Manag Sci. vol 57:120-128). Plastoquinone is thought to be a necessary cofactor of the enzyme phytoene desaturase in carotenoid biosynthesis (Boeger and Sandmann, 1998, Pestic Outlook, vol 9:29-35). Its inhibition results in the depletion of the plant plastoquinone and vitamin E pools, leading to bleaching symptoms. The loss of carotenoids, particularly in their function as protectors of the photosystems against photooxidation, leads to oxidative degradation of chlorophyll and photosynthetic membranes in growing shoot tissues. Consequently, chloroplast synthesis and function are disturbed (Boeger and Sandmann, 1998). The enzyme homogentisate solanesyl transferase (HST) catalyses the step following HPPD in the plastoquinone biosynthetic pathway. HST is a prenyl transferase that both decarboxylates homogentisate and also transfers to it the solanesyl group from solanesyl diphosphate and thus forms 2-methyl-6-solanesyl-1,4-benzoquinol (MSBQ), an intermediate along the biosynthetic pathway to plastoquinone. HST enzymes are membrane bound and the genes that encode them include a plastid targeting sequence.

The most important chemical classes of commercial 4-HPPD-inhibiting herbicides include pyrazolones, triketones and isoxazoles. The inhibitors mimic the binding of the substrate 4-hydroxyphenylpyruvate to an enzyme-bound ferrous ion in the active site by forming a stable ion-dipole charge transfer complex. Among 4-HPPD-inhibiting herbicides, the triketone sulcotrione was the first example of this herbicide group to be used in agriculture and identified in its mechanism of action (Schulz et al., 1993, FEBS Lett. Vol 318:162-166) The triketones have been reported to be derivatives of leptospermone, a herbicidal component from the bottlebrush plant, *Callistemon* spp (Lee et al. 1997, Weed Sci. Vol 45, 162-166).

Some of these molecules have been used as herbicides since inhibition of the reaction in plants leads to whitening of the leaves of the treated plants and to the death of the said plants (Pallett, K. E. et al. 1997 Pestic. Sci. 50 83-84). The herbicides for which HPPD is the target, and which are described in the state of the art, are, in particular, isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO$_2$CH$_3$-4-CF3 phenyl)propane-1,3-dione and 2-cyano-3-cyclopropyl-1-(2-SO$_2$CH$_3$-4-2,3Cl$_2$phenyl)propane-1,3-dione, triketones such as described in EP625505, EP625508, U.S. Pat. No. 5,506,195, in particular sulcotrione, or else pyrazolinates. Furthermore, the well-known herbicide topramezone elicits the same type of phytotoxic symptoms, with chlorophyll loss and necrosis in the growing shoot tissues, as 4-HPPD inhibiting, bleaching herbicides described supra in susceptible plant species. Topramezone belongs to the chemical class of pyrazolones or benzoyl pyrazoles and was commercially introduced in 2006. When applied postemergence, the compound selectively controls a wide spectrum of annual grass and broadleaf weeds in corn.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to Basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to HPPD inhibitors (WO96/38567). US2009/0172831 discloses nucleotide sequences encoding amino acid sequences having enzymatic activity such that the amino acid sequences are resistant to HPPD inhibitor herbicidal chemicals, in particular triketone inhibitor specific HPPD mutants.

To date, the prior art has not described HPPD-inhibiting herbicide, preferably benzamide tolerant plants containing at least one mutated HPPD nucleic acid according to the present invention. What are needed in the art are crop plants and crop plants having increased tolerance to herbicides such as HPPD-inhibiting herbicide, preferably benzamide, and containing at least one mutated HPPD nucleic acid according to the present invention. Also needed are methods for controlling weed growth in the vicinity of such crop plants or crop plants. These compositions and methods would allow for the use of spray over techniques when applying herbicides to areas containing crop plant or crop plants.

SUMMARY OF THE INVENTION

The problem is solved by the present invention which refers to a method for controlling undesired vegetation at a plant cultivation site, the method comprising the steps of:

a) providing, at said site, a plant that comprises at least one nucleic acid comprising
   (i) a nucleotide sequence encoding a wild type hydroxyphenyl pyruvate dioxygenase or a mutated hydroxyphenyl pyruvate dioxygenase (mut-HPPD) which is resistant or tolerant to a HPPD-inhibiting herbicide and/or
   (ii) a nucleotide sequence encoding a wildtype homogentisate solanesyl transferase or a mutated homogentisate solanesyl transferase (mut-HST) which is resistant or tolerant to a HPPD-inhibiting herbicide
b) applying to said site an effective amount of said herbicide.

In addition, the present invention refers to a method for identifying a HPPD-inhibiting herbicide by using a mut-HPPD encoded by a nucleic acid which comprises the nucleotide sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant thereof, and/or by using a mut-HST encoded by a nucleic acid which comprises the nucleotide sequence of SEQ ID NO: 47 or 49 or a variant thereof.

Said method comprises the steps of:
a) generating a transgenic cell or plant comprising a nucleic acid encoding a wildtype or mut-HPPD, wherein the wildtype or mut-HPPD is expressed;
b) applying a HPPD-inhibiting herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a mut-HPPD which is resistant or tolerant to a HPPD-inhibiting herbicide, the method comprising:
a) generating a library of mut-HPPD-encoding nucleic acids,
b) screening a population of the resulting mut-HPPD-encoding nucleic acids by expressing each of said nucleic acids in a cell or plant and treating said cell or plant with a HPPD-inhibiting herbicide,
c) comparing the HPPD-inhibiting herbicide-tolerance levels provided by said population of mut-HPPD encoding nucleic acids with the HPPD-inhibiting herbicide-tolerance level provided by a control HPPD-encoding nucleic acid,
d) selecting at least one mut-HPPD-encoding nucleic acid that provides a significantly increased level of tolerance to a HPPD-inhibiting herbicide as compared to that provided by the control HPPD-encoding nucleic acid.

In a preferred embodiment, the mut-HPPD-encoding nucleic acid selected in step d) provides at least 2-fold as much or tolerance to a HPPD-inhibiting herbicide as compared to that provided by the control HPPD-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mut-HPPD or mut-HST which is resistant or tolerant to a HPPD-inhibiting herbicide, the method comprising:
a) identifying an effective amount of a HPPD-inhibiting herbicide in a culture of plant cells or green algae.
b) treating said plant cells or green algae with a mutagenizing agent,
c) contacting said mutagenized cells population with an effective amount of HPPD-inhibiting herbicide, identified in a),
d) selecting at least one cell surviving these test conditions,
e) PCR-amplification and sequencing of HPPD and/or HST genes from cells selected in d) and comparing such sequences to wild-type HPPD or HST gene sequences, respectively.

In a preferred embodiment, the mutagenizing agent is ethylmethanesulfonate.

Another object refers to an isolated nucleic acid encoding a mut-HPPD, the nucleic acid being identifiable by a method as defined above.

In another embodiment, the invention refers to a plant cell transformed by a wild-type or a mut-HPPD nucleic acid or a plant which has been mutated to obtain a plant expressing, preferably over-expressing, a wild-type or a mut-HPPD nucleic acid, wherein expression of the nucleic acid in the plant cell results in increased resistance or tolerance to a HPPD-inhibiting herbicide as compared to a wild type variety of the plant cell.

In a preferred embodiment, the plant cell of the present is transformed by a wild-type or a mut-HPPD nucleic acid comprising a sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69 or a variant or derivative thereof.

In another embodiment, the invention refers to a transgenic plant comprising a plant cell according to the present invention, wherein expression of the nucleic acid in the plant results in the plants increased resistance to HPPD-inhibiting herbicide as compared to a wild type variety of the plant.

The plants of the present invention can be transgenic or non-transgenic.

Preferably, the expression of the nucleic acid in the plant results in the plants increased resistance to HPPD-inhibiting herbicide as compared to a wild type variety of the plant.

In another embodiment, the invention refers to a seed produced by a transgenic plant comprising a plant cell of the present invention, wherein the seed is true breeding for an increased resistance to a HPPD-inhibiting herbicide as compared to a wild type variety of the seed.

In another embodiment, the invention refers to a method of producing a transgenic plant cell with an increased resistance to a HPPD-inhibiting herbicide as compared to a wild type variety of the plant cell comprising, transforming the plant cell with an expression cassette comprising a wild-type or a mut-HPPD nucleic acid.

In another embodiment, the invention refers to a method of producing a transgenic plant comprising, (a) transforming a plant cell with an expression cassette comprising a wild-type or a mut-HPPD nucleic acid, and (b) generating a plant with an increased resistance to HPPD-inhibiting herbicide from the plant cell.

Preferably, the expression cassette further comprises a transcription initiation regulatory region and a translation initiation regulatory region that are functional in the plant.

In another embodiment, the invention relates to using the mut-HPPD of the invention as selectable marker. The invention provides a method of identifying or selecting a transformed plant cell, plant tissue, plant or part thereof comprising a) providing a transformed plant cell, plant tissue, plant or part thereof, wherein said transformed plant cell, plant tissue, plant or part thereof comprises an isolated nucleic acid encoding a mut-HPPD polypeptide of the invention as described hereinafter, wherein the polypeptide is used as a selection marker, and wherein said transformed plant cell, plant tissue, plant or part thereof may optionally comprise a further isolated nucleic acid of interest; b) contacting the transformed plant cell, plant tissue, plant or part thereof with at least one HPPD-inhibiting inhibiting compound; c) determining whether the plant cell, plant tissue, plant or part thereof is affected by the inhibitor or inhibiting compound; and d) identifying or selecting the transformed plant cell, plant tissue, plant or part thereof.

The invention is also embodied in purified mut-HPPD proteins that contain the mutations described herein, which are useful in molecular modeling studies to design further improvements to herbicide tolerance. Methods of protein purification are well known, and can be readily accomplished using commercially available products or specially designed methods, as set forth for example, in Protein Biotechnology, Walsh and Headon (Wiley, 1994).

BRIEF DESCRIPTION OF THE DRAWINGS

Figure 1A:
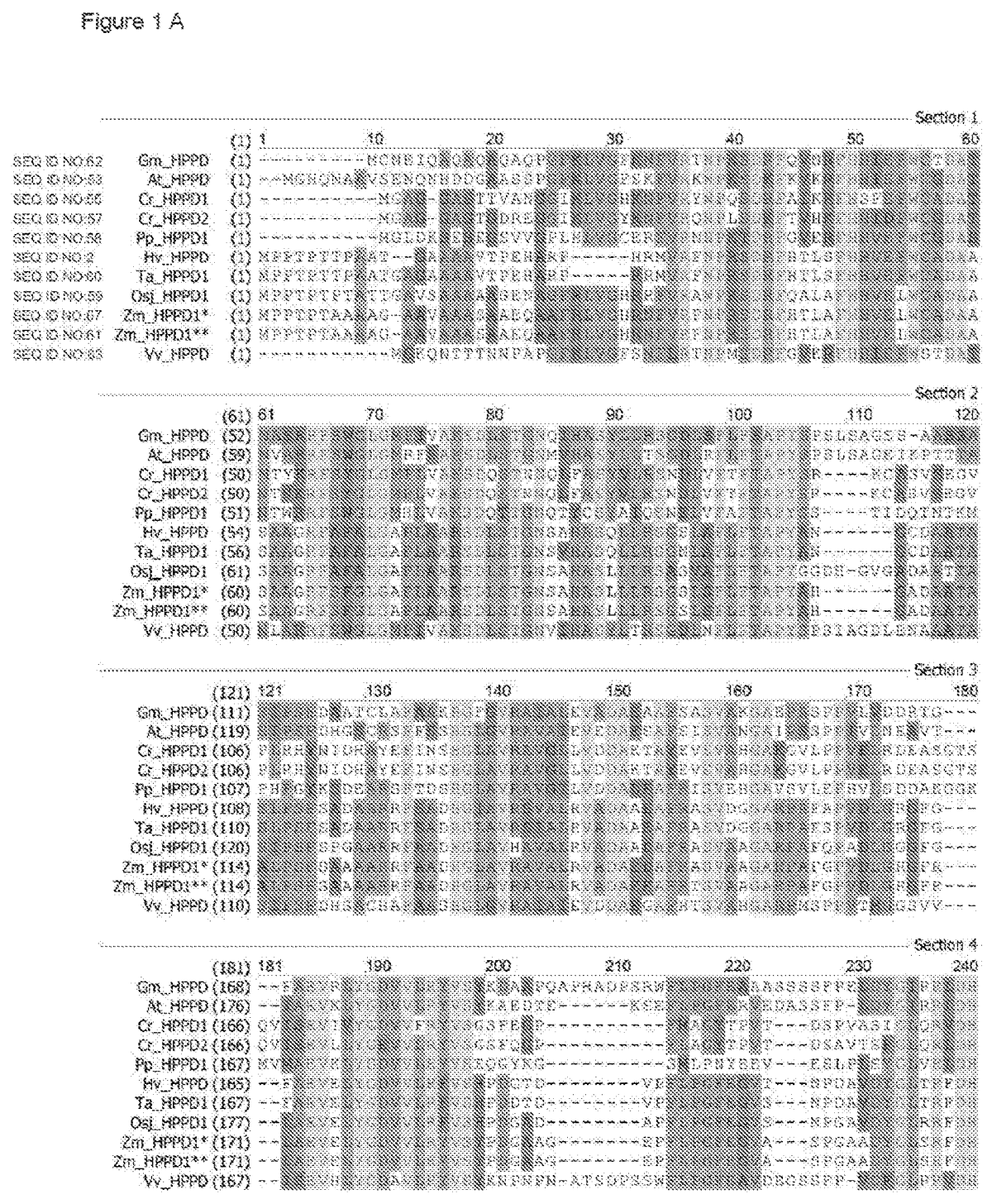
Figure 1B:
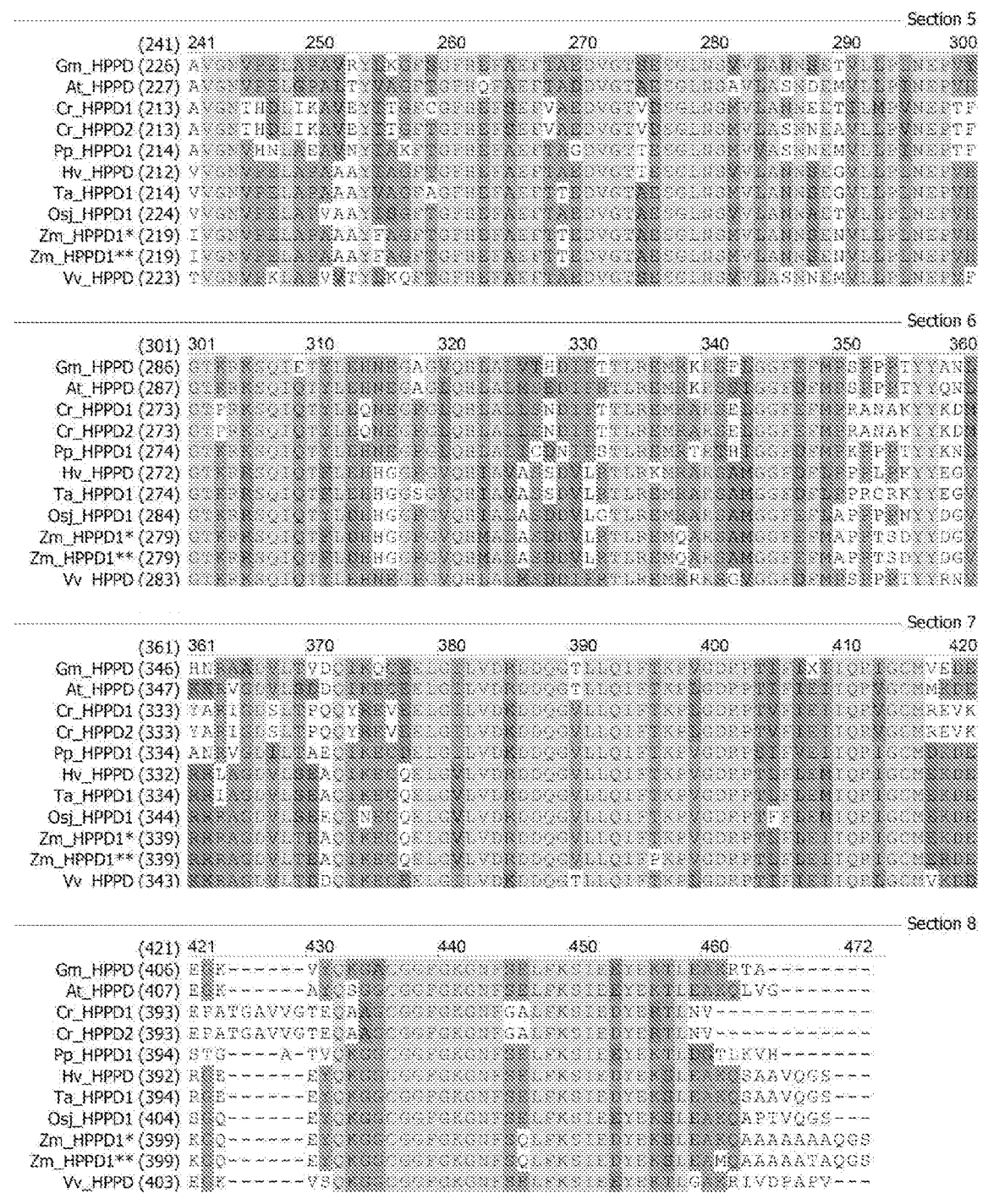

FIG. 1 Amino acid sequence alignment and conserved regions of HPPD enzymes from *Chlamydomonas reinhardtii* (Cr_HPPD1a, SEQ ID NO:55, Cr_HPPD1b; SEQ ID NO 57), *Physcomitrella patens* (Pp_HPPD1; SEQ ID NO:58), *Oryza sativa* (Osj_HPPD1; SEQ ID NO:59), *Triticum aestivum* (Ta_HPPD1; SEQ ID NO:60), *Zea mays* (Zm_HPPD1; SEQ ID NO:61**, SEQ ID NO:67*), *Arabidopsis thaliana* (At_HPPD; SEQ ID NO:53), *Glycine max* (Gm_HPPD; SEQ ID NO:62) and *Vitis vinifera* (Vv_HPPD; SEQ ID NO:63), and *Hordeum vulgare* (Hv_HPPD; SEQ ID NO:2).

*Sequence derived from genome sequencing project. Locus ID: GRMZM2G088396
**Amino acid sequence based on NCBI GenPept accession CAG25475

Figure 2:
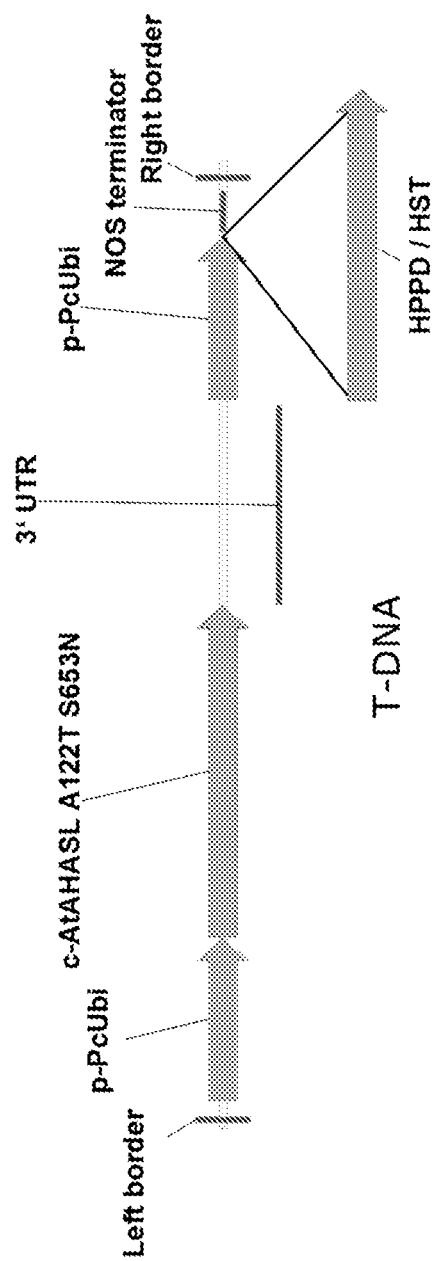

FIG. 2 shows a vector map of a plant transformation vector which is used for soybean transformation with HPPD/HST sequences.

Figure 3:
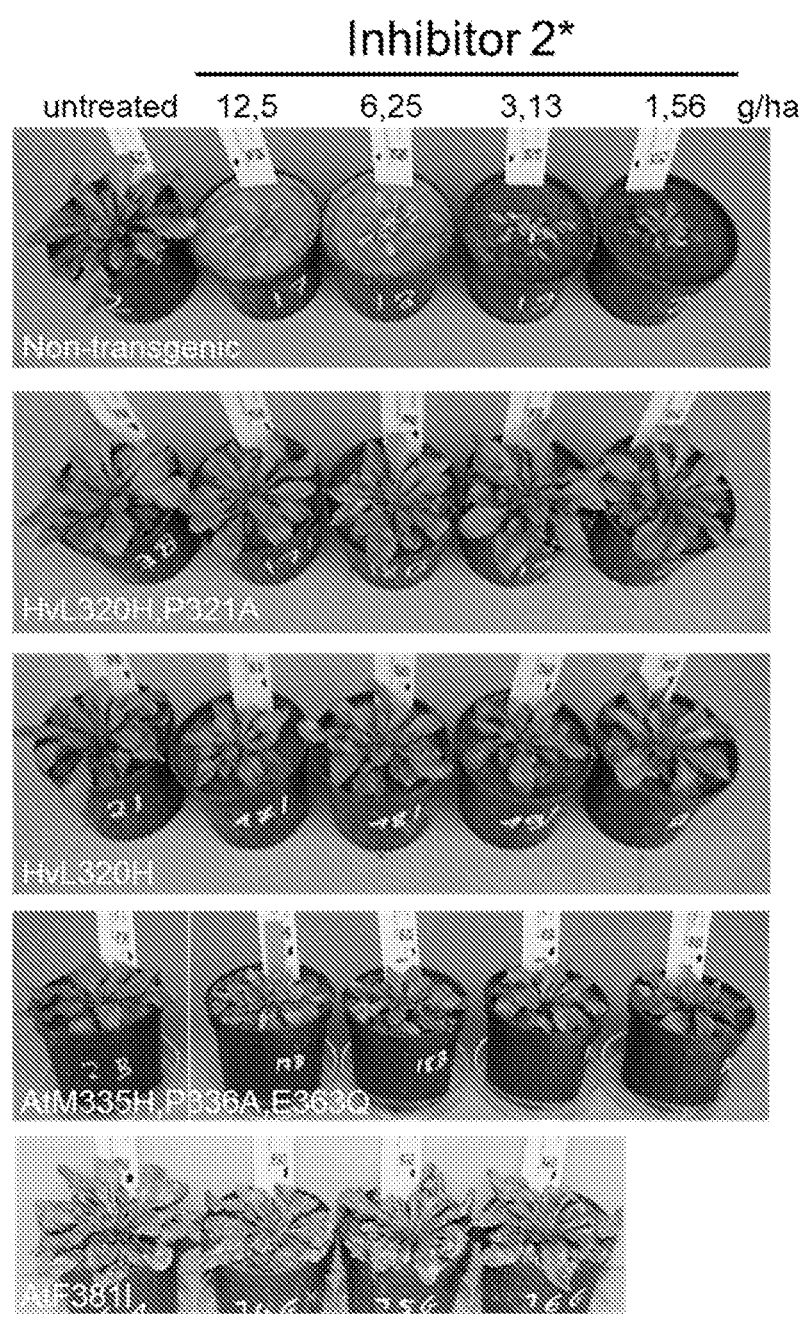

FIG. 3 shows a herbicide spray test with transgenic *Arabidopsis* plants expressing mutated variants of *Arabidopsis* HPPD or *Hordeum* HPPD. Non-transgenic control plants are treated in parallel and pictures are taken 14 days after treatment. Plants were sprayed with different concentrations of 2,4-dichloro-6-fluoro-3-methylsulfanyl-N-(1-methyltetrazol-5-yl)benzamide (Inhibitor 2).

Figure 4:
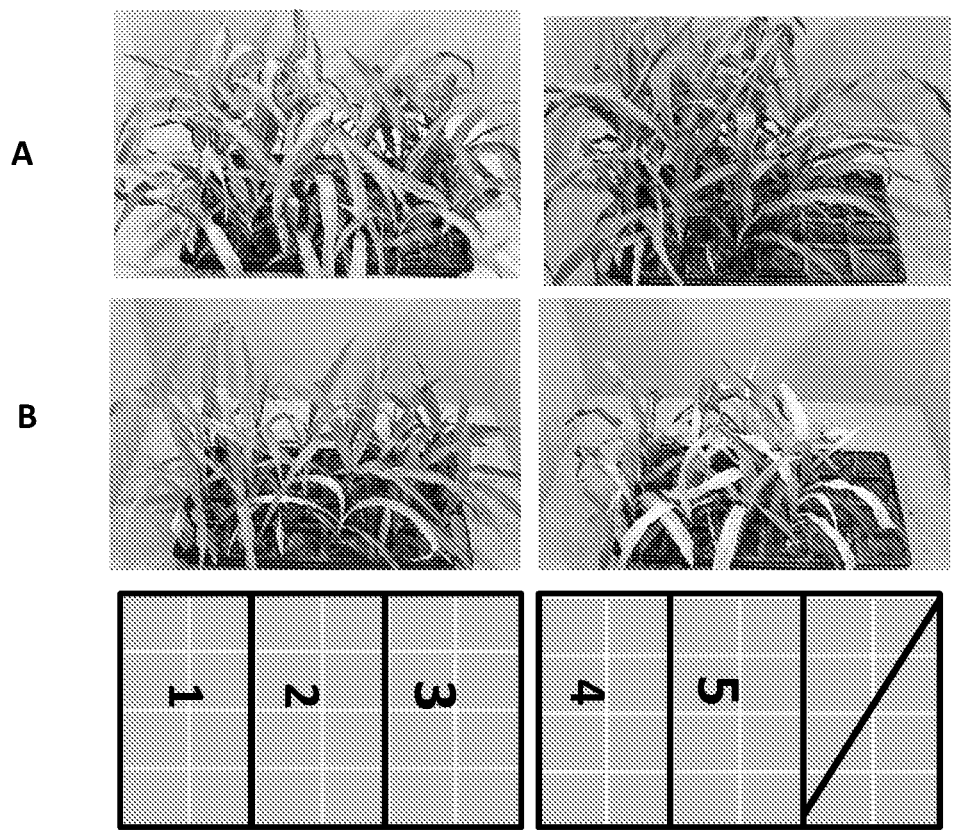
Figure 5:
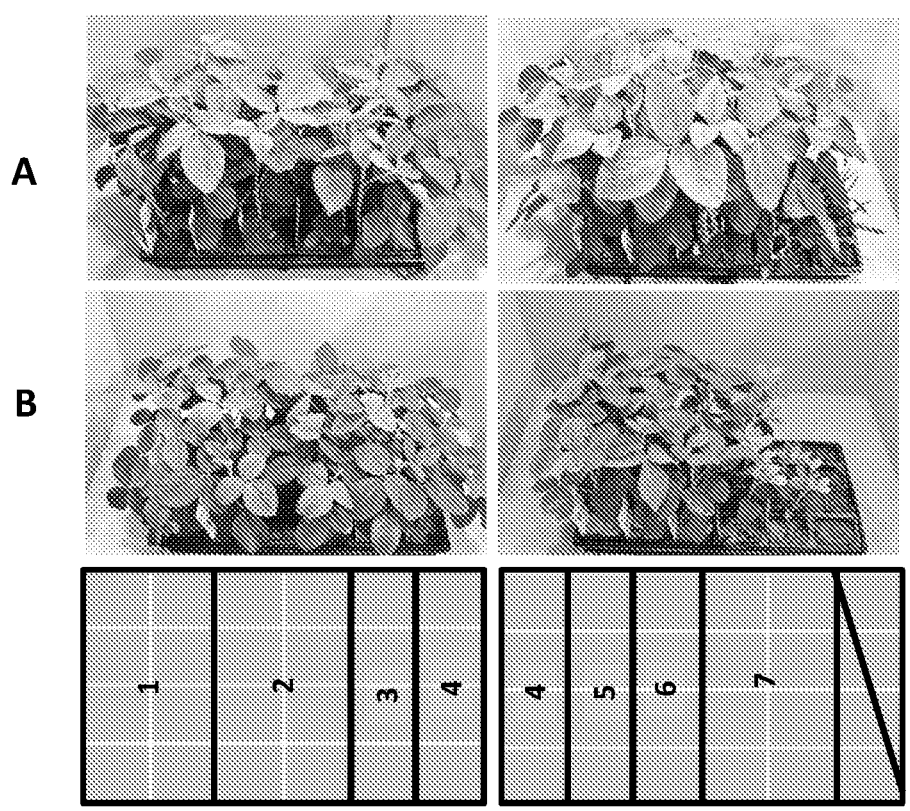

FIG. 4 shows a herbicide spray test with transgenic corn plants overexpressing mutated variants of *Arabidopsis* HPPD. Non-transgenic control plants are treated in parallel and pictures are taken 14 days after treatment. A) Unsprayed control and B) corn plants sprayed with 125 g/ha of 2,4-dichloro-6-fluoro-3-methylsulfanyl-N-(2-methyl-1,2,4-triazol-3-yl)benzamide (Inhibitor 3).
  1: AtHPPD I393L,L385V (Event 1)
  2: AtHPPD I393L,L385V (Event 2)
  3: AtHPPD M335H
  4: At HPPD Q293S
  5: untransformed control FIG. 5 shows a herbicide spray test with transgenic Soy plants overexpressing mutated variants of *Arabidopsis* HPPD, wild-type *Arabidopsis* HPPD and *Glycine max* HPPD. Non-transgenic control plants (Jake) are treated in parallel and pictures are taken 14 days after treatment. A) Unsprayed control and B) soy plants sprayed with 62.5 g/ha of 2,4-dichloro-6-fluoro-3-methylsulfanyl-N-(2-methyl-1,2,4-triazol-3-yl)benzamide (Inhibitor 3).
  1: overexpression of wild-type *Arabidopsis* HPPD
  2: AtHPPD L385V,I393L
  3: AtHPPD P336A,E363Q,L385V,I393L
  4: AtHPPD M335H
  5: AtHPPD M335Y
  6: GmHPPD1
  7: untransformed control

SEQUENCE LISTING

TABLE 1

| SEQ ID NO: | Description | Organism | Locus | Accession number |
|---|---|---|---|---|
| 1 | HPPD nucleic acid | Hordeum | | |
| 51 | HPPD nucl acid opt | Hordeum | | |
| 2 | HPPD amino acid | Hordeum | | |
| 3 | HPPD nucleic acid | Fragilariopsis | | |
| 4 | HPPD nucl acid opt | Fragilariopsis | | |
| 5 | HPPD amino acid | Fragilariopsis | | |
| 6 | HPPD nucleic acid | Chlorella | | |
| 7 | HPPD nucl acid opt | Chlorella | | |
| 8 | HPPD amino acid | Chlorella | | |
| 9 | HPPD nucleic acid | Thalassiosira | | |
| 10 | HPPD nucl acid opt | Thalassiosira | | |
| 11 | HPPD amino acid | Thalassiosira | | |
| 12 | HPPD nucleic acid | Cyanothece | | |
| 13 | HPPD nucl acid opt | Cyanothece | | |
| 14 | HPPD amino acid | Cyanothece | | |
| 15 | HPPD nucleic acid | Acaryochloris | | |
| 16 | HPPD nucl acid opt | Acaryochloris | | |
| 17 | HPPD amino acid | Acaryochloris | | |
| 18 | HPPD nucleic acid | Synechocystis | | |
| 19 | HPPD nucl acid opt | Synechocystis | | |
| 20 | HPPD amino acid | Synechocystis | | |
| 21 | HPPD nucleic acid1 | Alopecurus | | |
| 22 | HPPD amino acid1 | Alopecurus | | |
| 23 | HPPD nucleic acid2 | Alopecurus | | |
| 24 | HPPD amino acid2 | Alopecurus | | |
| 25 | HPPD nucleic acid1 | Sorghum | | |
| 26 | HPPD amino acid1 | Sorghum | | |
| 27 | HPPD nucleic acid2 | Sorghum | | |
| 28 | HPPD amino acid2 | Sorghum | | |

TABLE 1-continued

| SEQ ID NO: | Description | Organism | Locus | Accession number |
|---|---|---|---|---|
| 29 | HPPD nucleic acid1 | Poa | | |
| 30 | HPPD amino acid1 | Poa | | |
| 31 | HPPD nucleic acid2 | Poa | | |
| 32 | HPPD amino acid2 | Poa | | |
| 33 | HPPD nucleic acid | Lolium | | |
| 34 | HPPD amino acid | Lolium | | |
| 35 | HPPD nucleic acid | Synechococcus | | |
| 36 | HPPD amino acid | Synechococcus | | |
| 37 | HPPD nucleic acid | Blepharisma | | |
| 38 | HPPD amino acid | Blepharisma | | |
| 39 | HPPD nucleic acid | Picrophilus | | |
| 40 | HPPD amino acid | Picrophilus | | |
| 41 | HPPD nucleic acid | Kordia | | |
| 42 | HPPD amino acid | Kordia | | |
| 43 | HPPD nucleic acid1 | Rhodococcus | | |
| 44 | HPPD amino acid1 | Rhodococcus | | |
| 45 | HPPD nucleic acid2 | Rhodococcus | | |
| 46 | HPPD amino acid2 | Rhodococcus | | |
| 47 | HST nucleic acid | Arabidopsis | At3g11945 | DQ231060 |
| 48 | HST amino acid | Arabidopsis | At3g11945 | Q1ACB3 |
| 49 | HST nucleic acid | Chlamydomonas | | AM285678 |
| 50 | HST amino acid | Chlamydomonas | | A1JHN0 |
| 52 | HPPD nucleic acid | Arabidopsis | At1g06570 | AF047834 |
| 53 | HPPD amino acid | Arabidopsis | At1g06570 | AAC15697 |
| 54 | HPPD nucleic acid1 | Chlamydomonas | | |
| 55 | HPPD amino acid1 | Chlamydomonas | | |
| 56 | HPPD nucleic acid2 | Chlamydomonas | | XM_001694671.1 |
| 57 | HPPD amino acid2 | Chlamydomonas | | Q70ZL8 |
| 58 | HPPD amino acid | Physcomitrella | | A9RPY0 |
| 59 | HPPD amino acid | Oryza | Os02g07160 | |
| 60 | HPPD amino acid | Triticum | | Q45FE8 |
| 61 | HPPD amino acid | Zea | | CAG25475 |
| 62 | HPPD amino acid | Glycine | | A5Z1N7 |
| 63 | HPPD amino acid | Vitis | | A5ADC8 |
| 64 | HPPD amino acid | Pseudomonas fluorescens strain 87-79 | | AXW96633 |
| 65 | HPPD amino acid | Pseudomonas fluorescens | | ADR00548 |
| 66 | HPPD amino acid | Avena sativa | | AXW96634 |
| 67 | HPPD amino acid | Zea mays variant | | |
| 68 | HPPD nucleic acid | Zea mays mut 10 | | codon-optimised |
| 69 | HPPD nucleic acid | Zea mays mut 406 | | codon-optimised |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The inventors of the present invention have found, that the tolerance or resistance of a plant to a HPPD-inhibiting herbicide could be remarkably increased by overexpressing wild type or mutated HPPD enzymes comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67.

Consequently, the present invention refers to a method for controlling undesired vegetation at a plant cultivation site, the method comprising the steps of:
a) providing, at said site, a plant that comprises at least one nucleic acid comprising
  (i) a nucleotide sequence encoding a wild-type hydroxyphenyl pyruvate dioxygenase (HPPD) or a mutated hydroxyphenyl pyruvate dioxygenase (mut-HPPD) which is resistant or tolerant to a "HPPD-inhibiting herbicide" and/or
  (ii) a nucleotide sequence encoding a wild-type homogentisate solanesyl transferase (HST) or a mutated homogentisate solanesyl transferase (mut-HST) which is resistant or tolerant to a "HPPD-inhibiting herbicide"
b) applying to said site an effective amount of said herbicide.

The term "control of undesired vegetation" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis*, *Lepidium*, *Galium*, *Stellaria*, *Matricaria*, *Anthemis*, *Galinsoga*, *Chenopodium*, *Urtica*, *Senecio*, *Amaranthus*, *Portulaca*, *Xanthium*, *Convolvulus*, *Ipomoea*, *Polygonum*, *Sesbania*, *Ambrosia*, *Cirsium*, *Carduus*, *Sonchus*, *Solanum*, *Rorippa*, *Rotala*, *Lindemia*, *Lamium*, *Veronica*, *Abutilon*, *Emex*, *Datura*, *Viola*, *Galeopsis*, *Papaver*, *Centaurea*, *Trifolium*, *Ranunculus*, and *Taraxacum*. Monocotyledonous weeds include, but are not limited to, weeds of the genera: *Echinochloa*, *Setaria*, *Panicum*, *Digitaria*, *Phleum*, *Poa*, *Festuca*, *Eleusine*, *Brachiaria*,

*Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

In a preferred embodiment, the plant has been previously produced by a process comprising recombinantly preparing a plant by introducing and over-expressing a wild-type or mut-HPPD and/or wild-type or mut-HST transgene, as described in greater detail hereinafter.

In another preferred embodiment, the plant has been previously produced by a process comprising in situ mutagenizing plant cells, to obtain plant cells which express a mut-HPPD and/or mut-HST.

As disclosed herein, the nucleic acids of the invention find use in enhancing the herbicide tolerance of plants that comprise in their genomes a gene encoding a herbicide-tolerant wild-type or mut-HPPD and/or wild-type or mut-HST protein. Such a gene may be an endogenous gene or a transgene, as described hereinafter.

Therefore, in a other embodiment the present invention refers to a method of increasing or enhancing the HPPD-inhibiting herbicide tolerance or resistance of a plant, the method comprising overexpressing a nucleic acid encoding a wild type or mut HPPD enzymes comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67.

In one embodiment, the wild type HPPD enzyme comprises SEQ ID NO: 40, 44, or 46.

Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109). The combinations generated can also include multiple copies of any one of the polynucleotides of interest.

By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) Science 266:789; Martin et al., (1993) Science 262: 1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g., phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a particularly preferred embodiment, the plant comprises at least one additional heterologous nucleic acid comprising (iii) a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), Protoporphyrinogen oxidase (PPGO), Phytoene desaturase (PD) and dicamba degrading enzymes as disclosed in WO 02/068607.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by HPPD-inhibiting herbicide useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote nonselective or selective herbicidal action. Generally, it is preferred to apply the HPPD-inhibiting herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant mut-HPPD protein" or "herbicide-resistant mut-HPPD protein", it is intended that such a mut-HPPD protein displays higher HPPD activity, relative to the HPPD activity of a wild-type mut-HPPD protein, when in the presence of at least one herbicide that is known to interfere with HPPD activity and at a concentration or level of the herbicide that is known to inhibit the HPPD activity of the wild-type mut-HPPD protein. Furthermore, the HPPD activity of such a herbicide-tolerant or herbicide-resistant mut-HPPD protein may be referred to herein as "herbicide-tolerant" or "herbicide-resistant" HPPD activity.

The HPPD-inhibiting herbicides which are particularly useful for the present invention encompasses the compounds as depicted in the following Table 2.

TABLE 2

| | | Possible Substituents as defined in: | |
|---|---|---|---|
| No: | General Structure | Application number and reference | Publication Number |
| 1 | ![structure I] | PCT/EP2012/072469 PF72974 | WO 2013/072300 |

I

TABLE 2-continued

| No: | General Structure | Possible Substituents as defined in: | |
|---|---|---|---|
| | | Application number and reference | Publication Number |
| 2 | (structure II) | US 61/639079 PF73635 | WO 2013/083859 |

The above referenced application, in particular the disclosures referring to the compounds of Table 2 and their possible substitutents are entirely incorporated by reference.

In one embodiment of the present invention, the HPPD-inhibiting herbicide refers to a benzamide shown in Number 1 of Table 2 above having the above formula I:
wherein
X is selected from the group consisting of hydrogen, cyano, nitro, halogen, $C_1$-$C_6$-alkyl, $C_3$-$C_7$cycloalkyl, $C_3$-$C_7$cycloalkyl-$C_1$-$C_4$-alkyl, where the $C_3$-$C_7$-cycloalkyl groups in the two aformentioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, O—$R^a$, $R^b$—S(O)$_n$—Z, $R^c$—C(=O)—Z, O$R^d$—C(=O)—Z, N$R^e R^f$—C(=O)—Z, N$R^g R^h$—Z, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

In one embodiment of the present invention, the HPPD-inhibiting herbicide refers to a benzamide shown in Number 2 of Table 2 above having the above formula II:
where
B is N or CH;
Y is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^b$—S(O)$_n$—Z, $R^c$—C(=O)—Z, $R^d$O—C(=O)—Z, $R^e R^f$N—C(=O)—Z, $R^g R^h$N—Z, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

For both formula I and II, the following definitions apply:
$R^f$ is selected from the group consisting of cyano-$Z^1$, halogen, nitro, $C_1$-$C_8$-alkyl, $C_2$-$C_8$-alkenyl, $C_2$-$C_8$-alkynyl, $C_1$-$C_8$-haloalkyl, $C_1$-$C_8$-alkoxy, $C_1$-$C_4$-alkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^f$, $R^{1b}$—S(O)$_k$—$Z^1$, phenoxy-$Z^1$, and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

$R^2$, $R^3$ are identical or different and independently selected from the group consisting of hydrogen, halogen, OH—$Z^2$, $NO_2$—$Z^2$, cyano-$Z^2$, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_1$-$C_8$-alkoxy-$Z^2$, $C_1$-$C_8$-haloalkoxy-$Z^2$, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_2$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—S(O)$_k$—$Z^2$, $R^{2c}$—C(=O)—$Z^2$, $R^{2d}$O—C(=O)—$Z^2$, $R^{2e}R^{2f}$N—C(=O)—$Z^2$, $R^{2g}R^{2h}$N—$Z^2$, phenyl-$Z^{2a}$ and heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different;

$R^4$ is selected from the group consisting of hydrogen, halogen, cyano, nitro, $C_1$-$C_4$-alkyl and $C_1$-$C_4$-haloalkyl;
$R^5$ is selected from the group consisting of hydrogen, halogen, $C_1$-$C_4$-alkyl and $C_1$-$C_4$-haloalkyl;
provided that at least one of the radicals $R^4$ and $R^5$ is different from hydrogen;
n is 0, 1 or 2;
k is 0, 1 or 2;
R', $R^{11}$, $R^{21}$ independently of each other are selected from the group consisting of halogen, $NO_2$, CN, $C_1$-$C_6$-alkyl, $C_3$-$C_7$-cycloalkyl, $C_3$-$C_7$-halocycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy, $C_3$-$C_7$-cycloalkoxy and $C_1$-$C_6$-haloalkyloxy, or two vicinal radicals R', $R^{11}$ or $R^{21}$ together may form a group =O;
Z, $Z^1$, $Z^2$ independently of each other are selected from the group consisting of a covalent bond and $C_1$-$C_4$-alkanediyl;
$Z^{2a}$ is selected from the group consisting of a covalent bond, $C_1$-$C_4$-alkanediyl, O—$C_1$-$C_4$-alkanediyl, $C_1$-$C_4$-alkanediyl-O and $C_1$-$C_4$-alkanediyl-O—$C_1$-$C_4$-alkanediyl;
$R^a$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aformentioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^c$, $R^{2c}$ independently of each other are selected from the group consisting of hydrogen, $C_1$-$C_6$-alkyl, $C_3$-$C_7$cycloalkyl, $C_3$-$C_7$cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^d$, $R^{2d}$ independently of each other are selected from the group consisting of $C_1$-$C_6$-alkyl, $C_3$-$C_7$cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e$, $R^f$ independently of each other are selected from the group consisting of hydrogen, $C_1$-$C_6$-alkyl, $C_3$-$C_7$cycloalkyl, $C_3$-$C_7$cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^e$, $R^f$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^{2e}$, $R^{2f}$ independently of each other have the meanings given for $R^e$, $R^f$;

$R^g$ is selected from the group consisting of hydrogen, $C_1$-$C_6$-alkyl, $C_3$-$C_7$-cycloalkyl, $C_3$-$C_7$ cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$ cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, a radical C(=O)—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$; and $R^k$ has the meanings given for $R^c$;

or an N-oxide or an agriculturally suitable salt thereof.

Depending on the substitution pattern, the compounds of the formula I or formula II may have one or more centers of chirality, in which case they are present as mixtures of enantiomers or diastereomers. Useful are both the pure enantiomers or pure diastereomers of the compounds of formula I or formula II, and their mixtures and the use according to the invention of the pure enantiomers or pure diastereomers of the compound of formula I or formula II or its mixtures. Suitable compounds of the formula I or formula II also include all possible geometrical stereoisomers (cis/trans isomers) and mixtures thereof. Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

Depending on the substitution pattern, the compounds of the formula I or formula II may be present in the form of their tautomers. Hence the invention also relates to the tautomers of the formula I or formula II and the stereoisomers, salts and N-oxides of said tautomers.

The term "N-oxide" includes any compound of the present invention which has at least one tertiary nitrogen atom that is oxidized to an N-oxide moiety. N-oxides in compounds I or II can in particular be prepared by oxidizing the ring nitrogen atom(s) of the oxadiazole-, N(tetrazol-5-yl)- and N-(triazol-5-yl)arylcarboxamide ring with a suitable oxidizing agent, such as peroxo carboxylic acids or other peroxides, or the ring nitrogen atom(s) of a heterocyclic substituent X and Y, respectively, $R^1$, $R^2$ or $R^3$.

The HPPD-inhibiting herbicide, in particular the benzamides, as described herein relates to compounds as defined herein, wherein one or more of the atoms depicted in formula I or formula II have been replaced by its stable, preferably non-radioactive isotope (e.g., hydrogen by deuterium, $^{12}$C by $^{13}$C, $^{14}$N by $^{15}$N, $^{16}$O by $^{18}$O) and in particular wherein at least one hydrogen atom has been replaced by a deuterium atom. Of course, the compounds according to the invention contain more of the respective isotope than this naturally occurs and thus is anyway present in the compounds I.

The HPPD-inhibiting herbicide, in particular the benzamides, as described herein may be amorphous or may exist in one ore more different crystalline states (polymorphs) which may have different macroscopic properties such as stability or show different biological properties such as activities. The present invention includes both amorphous and crystalline compounds of formula I or formula II, their enantiomers or diastereomers, mixtures of different crystalline states of the respective compound of formula I or formula II, its enantiomers or diastereomers, as well as amorphous or crystalline salts thereof.

Salts of the HPPD-inhibiting herbicide, in particular the benzamides, as described herein, are preferably agriculturally suitable salts. They can be formed in a customary method, e.g. by reacting the compound with an acid if the compound of the present invention has a basic functionality or by reacting the compound with a suitable base if the compound of the present invention has an acidic functionality.

Useful agriculturally suitable salts are especially the salts of those cations or the acid addition salts of those acids whose cations and anions, respectively, do not have any adverse effect on the herbicidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of the present invention with an acid of the corresponding anion, preferably with hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "partially or completely halogenated" will be taken to mean that 1 or more, e.g. 1, 2, 3, 4 or 5 or all of the hydrogen atoms of a given radical have been replaced by a halogen atom, in particular by fluorine or chlorine. A partially or completely halogenated radical is termed below also "halo-radical". For example, partially or completely halogenated alkyl is also termed haloalkyl.

The term "alkyl" as used herein (and in the alkyl moieties of other groups comprising an alkyl group, e.g. alkoxy, alkylcarbonyl, alkoxycarbonyl, alkylthio, alkylsulfonyl and alkoxyalkyl) denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of $C_1$-$C_4$-alkyl are methyl, ethyl, n-propyl, isopropyl, n-butyl, 2-butyl (sec-butyl), isobutyl and tert-butyl. Examples for $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl, 2-propylpentyl, nonyl, decyl, 2-propylheptyl and 3-propylheptyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy, haloalkylthio, haloalkylcarbonyl, haloalkylsulfonyl and haloalkylsulfinyl) denotes in each case a straight-chain or branched alkyl group having usually from 1 to 8 carbon atoms ("$C_1$-$C_8$-haloalkyl"), frequently from 1 to 6 carbon atoms ("$C_1$-$C_6$-haloalkyl"), more frequently 1 to 4 carbon atoms ("$C_1$-$C_4$-haloalkyl"), wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl. Halomethyl is methyl in which 1, 2 or 3 of the hydrogen atoms are replaced by halogen atoms. Examples are bromomethyl, chloromethyl, dichloromethyl, trichloromethyl, fluoromethyl, difluoromethyl, trifluoromethyl, chlorofluoromethyl, dichlorofluoromethyl, chlorodifluoromethyl and the like. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Examples for $C_1$-$C_2$-haloalkyl are, apart those mentioned for $C_1$-$C_2$-fluoroalkyl, chloromethyl, dichloromethyl, trichloromethyl, bromomethyl, chlorofluoromethyl, dichlorofluoromethyl, chlorodifluoromethyl, 1-chloroethyl, 2-chloroethyl, 2,2,-dichloroethyl, 2,2,2-trichloroethyl, 2-chloro-2-fluoroethyl, 2-chloro-2,2-difluoroethyl, 2,2-dichloro-2-fluoroethyl, 1-bromoethyl, and the like. Examples for $C_1$-$C_4$-haloalkyl are, apart those mentioned for $C_1$-$C_2$-haloalkyl, 1-fluoropropyl, 2-fluoropropyl, 3-fluoropropyl, 3,3-difluoropropyl, 3,3,3-trifluoropropyl, heptafluoropropyl, 1,1,1-trifluoroprop-2-yl, 3-chloropropyl, 4-chlorobutyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms ("$C_3$-$C_{10}$-cycloalkyl"), preferably 3 to 7 carbon atoms ("$C_3$-$C_7$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 7 carbon atoms comprise cyclopropyl, cyclobutyl, cyclopentyl, cyclohexyl and cycloheptyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, preferably 3 to 7 carbon atoms or in particular 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkyl-alkyl" used herein denotes a cycloalkyl group, as defined above, which is bound to the remainder of the molecule via an alkylene group. The term "$C_3$-$C_7$-cycloalkyl-$C_1$-$C_4$-alkyl" refers to a $C_3$-$C_7$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "alkenyl" as used herein denotes in each case a monounsaturated straight-chain or branched hydrocarbon radical having usually 2 to 8 ("$C_2$-$C_8$-alkenyl"), preferably 2 to 6 carbon atoms ("$C_2$-$C_6$-alkenyl"), in particular 2 to 4 carbon atoms ("$C_2$-$C_4$-alkenyl"), and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_8$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl and the positional isomers thereof.

The term "haloalkenyl" as used herein, which may also be expressed as "alkenyl which is substituted by halogen", and the haloalkenyl moieties in haloalkenyloxy and the like refers to unsaturated straight-chain or branched hydrocarbon radicals having 2 to 8 ("$C_2$-$C_8$-haloalkenyl") or 2 to 6 ("$C_2$-$C_6$-haloalkenyl") or 2 to 4 ("$C_2$-$C_4$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes unsaturated straight-chain or branched hydrocarbon radicals having usually 2 to 8 ("$C_2$-$C_8$-alkynyl"), frequently 2 to 6 ("$C_2$-$C_6$-alkynyl"), preferably 2 to 4 carbon atoms ("$C_2$-$C_4$-alkynyl") and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "haloalkynyl" as used herein, which is also expressed as "alkynyl which is substituted by halogen", refers to unsaturated straight-chain or branched hydrocarbon radicals having usually 3 to 8 carbon atoms ("$C_2$-$C_8$-haloalkynyl"), frequently 2 to 6 ("$C_2$-$C_6$-haloalkynyl"), preferably 2 to 4 carbon atoms ("$C_2$-$C_4$-haloalkynyl"), and one or two triple bonds in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 8 carbon atoms ("$C_1$-$C_8$-alkoxy"), frequently from 1 to 6 carbon atoms ("$C_1$-$C_6$-alkoxy"), preferably 1 to 4 carbon atoms ("$C_1$-$C_4$-alkoxy"), which is bound to the remainder of the molecule via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof.

The term "haloalkoxy" as used herein denotes in each case a straight-chain or branched alkoxy group, as defined above, having from 1 to 8 carbon atoms ("$C_1$-$C_8$-haloalkoxy"), frequently from 1 to 6 carbon atoms ("$C_1$-$C_6$-haloalkoxy"), preferably 1 to 4 carbon atoms ("$C_1$-$C_4$-haloalkoxy"), more preferably 1 to 3 carbon atoms ("$C_1$-$C_3$-haloalkoxy"), wherein the hydrogen atoms of this group are partially or totally replaced with halogen atoms, in particular fluorine atoms. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy.

The term "alkoxyalkyl" as used herein denotes in each case alkyl usually comprising 1 to 6 carbon atoms, preferably 1 to 4 carbon atoms, wherein 1 carbon atom carries an alkoxy radical usually comprising 1 to 8, frequently 1 to 6, in particular 1 to 4, carbon atoms as defined above. "$C_1$-$C_6$-alkoxy-$C_1$-$C_6$-alkyl" is a $C_1$-$C_6$-alkyl group, as defined above, in which one hydrogen atom is replaced by a $C_1$-$C_6$-alkoxy group, as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methyl-propoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methyl-propoxy)-butyl, 4-(2-methylpropoxy)-butyl, 4-(1,1-dimethylethoxy)-butyl and the like.

The term "haloalkoxy-alkyl" as used herein denotes in each case alkyl as defined above, usually comprising 1 to 6 carbon atoms, preferably 1 to 4 carbon atoms, wherein 1 carbon atom carries an haloalkoxy radical as defined above, usually comprising 1 to 8, frequently 1 to 6, in particular 1 to 4, carbon atoms as defined above. Examples are fluoromethoxymethyl, difluoromethoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethoxymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl, "alkyl-S" or "alkyl-$S(O)_k$" (wherein k is 0)) as used herein denotes in each case a straight-chain or branched saturated alkyl group as defined above, usually comprising 1 to 8 carbon atoms ("$C_1$-$C_6$-alkylthio"), frequently comprising 1 to 6 carbon atoms ("$C_1$-$C_6$-alkylthio"), preferably 1 to 4 carbon atoms ("$C_1$-$C_4$-alkylthio"), which is attached via a sulfur atom at any position in the alkyl group. $C_1$-$C_2$-Alkylthio is methythio or ethythio. $C_1$-$C_4$-Alkylthio is additionally, for example, n-propythio, 1-methylethythio (iso-propythio), butylthio, 1-methylpropythio (sec-butythio), 2-methylpropythio (isobutylthio) or 1,1-dimethylethythio (tert-butylthio). $C_1$-$C_6$-Alkylthio is additionally, for example, pentylthio, 1-methylbutylthio, 2-methylbutylthio, 3-methylbutylthio, 1,1-dimethylpropythio, 1,2-dimethylpropythio, 2,2-dimethylpropythio, 1-ethylpropythio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropythio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof.

The term "haloalkythio" as used herein refers to an alkylthio group as defined above wherein the hydrogen atoms are partially or completely substituted by fluorine, chlorine, bromine and/or iodine. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethythio, 2-fluoroethylthio, 2-chloroethylthio, 2-bromoethythio, 2-iodoethylthio, 2,2-difluoroethylthio, 2,2,2-trifluoroethylthio, 2-chloro-2-fluoroethythio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethythio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentythio, 5-iodopentylthio, undecafluoropentythio, 6-fluorohexylthio, 6-chlorohexythio, 6-bromohexythio, 6-iodohexylthio or dodecafluorohexythio.

The terms "alkylsulfinyl" and "alkyl-$S(O)_k$" (wherein k is 1) are equivalent and, as used herein, denote an alkyl group, as defined above, attached via a sulfinyl [S(O)] group. For example, the term "$C_1$-$C_2$-alkylsulfinyl" refers to a $C_1$-$C_2$-alkyl group, as defined above, attached via a sulfinyl [S(O)] group. The term "$C_1$-$C_4$-alkylsulfinyl" refers to a $C_1$-$C_4$-alkyl group, as defined above, attached via a sulfinyl [S(O)] group. The term "$C_1$-$C_6$-alkylsulfinyl" refers to a $C_1$-$C_6$-alkyl group, as defined above, attached via a sulfinyl [S(O)] group. $C_1$-$C_2$-alkylsulfinyl is methylsulfinyl or ethylsulfinyl. $C_1$-$C_4$-alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The terms "alkylsulfonyl" and "alkyl-$S(O)_k$" (wherein k is 2) are equivalent and, as used herein, denote an alkyl group, as defined above, attached via a sulfonyl [$S(O)_2$] group. The term "$C_1$-$C_2$-alkylsulfonyl" refers to a $C_1$-$C_2$-alkyl group, as defined above, attached via a sulfonyl [$S(O)_2$] group. The term "$C_1$-$C_4$-alkylsulfonyl" refers to a $C_1$-$C_4$-alkyl group, as defined above, attached via a sulfonyl [$S(O)_2$] group. The term "$C_1$-$C_6$-alkylsulfonyl" refers to a $C_1$-$C_6$-alkyl group, as defined above, attached via a sulfonyl [$S(O)_2$] group. $C_1$-$C_2$-alkylsulfonyl is methylsulfonyl or ethylsulfonyl. $C_1$-$C_4$-alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "alkylamino" as used herein denotes in each case a group —R*HN—, wherein R* is a straight-chain or branched alkyl group usually having from 1 to 6 carbon atoms ("$C_1$-$C_5$-alkylamino"), preferably 1 to 4 carbon atoms ("$C_1$-$C_4$-alkylamino"). Examples of $C_1$-$C_6$-alkylamino are methylamino, ethylamino, n-propylamino, isopropylamino, n-butylamino, 2-butylamino, iso-butylamino, tert-butylamino, and the like.

The term "dialkylamino" as used herein denotes in each case a group R*R°N—, wherein R* and R°, independently of each other, are a straight-chain or branched alkyl group each usually having from 1 to 6 carbon atoms ("di-($C_1$-$C_6$-alkyl)-amino"), preferably 1 to 4 carbon atoms ("di-($C_1$-$C_4$-alkyl)-amino"). Examples of a di-($C_1$-$C_6$-alkyl)-amino group are dimethylamino, diethylamino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The suffix "-carbonyl" in a group denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl.

The term "het(ero)aryl" as used herein refers to a mono-, bi- or tricyclic heteroaromatic hydrocarbon radical, preferably to a monocyclic heteroaromatic radical, such as pyridyl, pyrimidyl and the like.

The term "5- or 6-membered monocyclic or 8-, 9- or 10-membered bicyclic saturated, unsaturated or aromatic heterocycle containing 1, 2, 3 or 4 heteroatoms as ring members selected from the groups consisting of N, O and S" as used herein denotes monocyclic or bicyclic heterocyclic radicals, the monocyclic or bicyclic heterocyclic radicals being saturated, unsaturated or aromatic. An unsaturated heterocyclic radical contains at least one C—C and/or C—N and/or N—N double bond(s). A partially unsaturated heterocyclic radical contains less conjugated C—C and/or C—N and/or N—N double bonds than maximally allowed by the size(s) of the ring(s). A fully unsaturated heterocyclic radical contains as many conjugated C—C and/or C—N and/or N—N double bonds as allowed by the size(s) of the ring(s). An aromatic monocyclic heterocyclic radical is a fully unsaturated 5- or 6-membered monocyclic heterocyclic radical. An aromatic bicyclic heterocyclic radical is an 8-, 9- or 10-membered bicyclic heterocyclic radical consisting of a 5- or 6-membered heteroaromatic ring which is fused to a phenyl ring or to another 5- or 6-membered heteroaromatic ring. The heterocyclic radical may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5- or 6-membered monocyclic saturated heterocycle include: oxirane-2-yl, aziridine-1-yl, aziridine-2-yl, oxetan-2-yl, azetidine-1-yl, azetidine-2-yl, azetidine-3-yl, thietane-1-yl, thietan-2-yl, thietane-3-yl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl and the like.

Examples of a 5- or 6-membered monocyclic partially unsaturated heterocycle include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl and 1,2,4-di- or tetrahydrotriazin-3-yl.

A 5- or 6-membered monocyclic fully unsaturated (including aromatic) heterocyclic ring is e.g. a 5- or 6-membered monocyclic fully unsaturated (including aromatic) heterocyclic ring. Examples are: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl.

Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like.

If two radicals bound on the same nitrogen atom (for example $R^e$ and $R^f$ or $R^{2e}$ and $R^{2f}$ or $R^g$ and $R^h$ or $R^{2g}$ and $R^{2h}$) together with the nitrogen atom, to which they are bound, form a 5-, 6 or 7-membered, saturated or unsaturated N-bound heterocyclic radical, which may carry as a ring member a further heteroatom selected from O, S and N, this is for example pyrrolidine-1-yl, pyrazolidin-1-yl, imidazolidin-1-yl, oxazolidin-3-yl, thiazolidin-3-yl, isoxazolidin-2-yl, isothiazolin-2-yl, [1,2,3]-triazolidin-1-yl, [1,2,3]-triazolidin-2-yl, [1,2,4]-triazolidin-1-yl, [1,2,4]-triazolidin-4-yl, [1,2,3]-oxadiazolidin-2-yl, [1,2,3]-oxadiazolidin-3-yl, [1,2,5]-oxadiazolidin-2-yl, [1,2,4]-oxadiazolidin-2-yl, [1,2,4]-oxadiazolidin-4-yl, [1,3,4]-oxadiazolidin-3-yl, [1,2,3]-thiadiazolidin-2-yl, [1,2,3]-thiadiazolidin-3-yl, [1,2,5]-thiadiazolidin-2-yl, [1,2,4]-thiadiazolidin-2-yl, [1,2,4]-thiadiazolidin-4-yl, [1,3,4]-thiadiazolidin-3-yl, piperdin-1-yl, piperazine-1-yl, morpholin-1-yl, thiomorpholin-1-yl, 1-oxothiomorpholin-1-yl, 1,1-dioxothiomorpholin-1-yl, azepan-1-yl, 1,4-diazepan-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

The term "fused 5-, 6-, 7-, 8-, 9- and 10-membered carbocycle or 5-, 6-, 7-, 8-, 9- and 10-membered heterocycle" refers to a carbo- or heterocycle that is adjoined at two consecutive positions with the phenyl group of the radical Cyc-1 or Cyc-1 in such a way that both rings share the ring atoms at said two positions. The fused carbo- and heterocycles may be saturated, partially unsaturated or fully unsaturated and in addition may be mono-, bi- or tricyclic, where each one of the two or three rings of the bi- and tricyclic fused carbo- and heterocycles is either fused to one or two of the other rings, i.e. two rings share two ring atoms, or spiro-linked, i.e. two rings share 1 ring atom. Examples of 5-, 6-, 7-, 8-, 9- and 10-membered fused carbocycles are cyclopentane, cyclohexane, cycloheptane, cyclo[3.3.0]octane, cyclo[4.3.0]nonane, cyclo[4.4.0]decane cyclopentene, cyclohexene and benzene. Examples of 5-, 6-, 7-, 8-, 9- and 10-membered fused carbocycles are pyrrolidine, tetrahydrofuran, tetrahydrothiophen, dihydrofuran, dihydrothiophen, pyrrole, furan, thiopene, thiazole, thiazine, piperidine, tetrahydropyran, tetrahydrothiopyrane, dioxane, piperazine, morpholine, pyridine, azepane, oxepane, thiepane, azepine, oxepine, thiepine, pyrazole, pyrazoline, imidazole, benzimidazole, imidazoline, indole, indoline, chinoline, isochinoline, pyrimidine, oxazole, isoxazole, oxazoline, isoxazoline and the like.

The remarks made below as to preferred embodiments of the variables (substituents) of the compounds of formula I or II are valid on their own as well as preferably in combination with each other, as well as in combination with the stereoisomers, salts, tautomers or N-oxides thereof.

The remarks made below concerning preferred embodiments of the variables further are valid on their own as well as preferably in combination with each other concerning the compounds of formula I or II, where applicable, as well as concerning the uses and methods according to the invention and the composition according to the invention.

Preferred compounds according to the invention are compounds of formula I or II or a stereoisomer, salt or N-oxide thereof, wherein the salt is an agriculturally suitable salt. Further preferred compounds according to the invention are compounds of formula I or II or an N-oxide or salt thereof, especially an agriculturally suitable salt. Particularly preferred compounds according to the invention are compounds of formula I or II or a salt thereof, especially an agriculturally suitable salt thereof.

According to a preferred embodiment of the invention the variable X in the compounds of formula I is selected from the group consisting of halogen, cyano, nitro, $C_1$-$C_6$-alkyl, $C_2$-$C_6$-alkenyl, $C_2$-$C_6$-haloalkenyl, $C_1$-$C_4$-alkoxy-$C_1$-$C_4$-alkyl, $C_3$-$C_7$-cycloalkyl, $C_1$-$C_5$-haloalkyl, $C(=O)$—$R^c$, $C(=O)$—$OR^d$, $C(=O)$—$NR^eR^f$, $NH$—$C(=O)R^k$ and $NR^gR^h$; where $R^c$, $R^d$, $R^e$, $R^f$, $R^k$, $R^g$ and $R^h$ are as defined above and which preferably have on their own or in particular in combination the following meanings:

$R^c$ is hydrogen, $C_1$-$C_6$-alkyl $C_3$-$C_7$-cycloalkyl, $C_2$-$C_6$-alkenyl, $C_2$-$C_6$-haloalkenyl, $C_1$-$C_6$-haloalkyl or phenyl, in particular $C_1$-$C_4$-alkyl or $C_1$-$C_4$-haloalkyl;

$R^d$ is $C_1$-$C_6$-alkyl or $C_1$-$C_6$-haloalkyl, in particular $C_1$-$C_4$-alkyl, $R^e$, $R^f$ are independently of each other selected from hydrogen, $C_1$-$C_6$-alkyl, $C_1$-$C_6$-haloalkyl and benzyl, and in particular from the group consisting of hydrogen and $C_1$-$C_4$-alkyl, or $R^e$, $R^f$ together with the nitrogen atom, to which they are bound form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl and $C_1$-$C_4$-haloalkyl, and in particular $R^e$, $R^f$ together with the nitrogen atom, to which they are bound may form a 5-, 6- or 7-membered, saturated N-bound heterocyclic radical, which may carry as a ring member a further heteroatom selected from O, S and N and which is unsubstituted or may carry 1, 2, 3 or 4 methyl groups;

$R^g$, $R^h$ are independently of each other selected from hydrogen, $C_1$-$C_6$-alkyl, $C_1$-$C_6$-haloalkyl and benzyl and in particular from the group consisting of hydrogen or $C_1$-$C_4$-alkyl, or $R^g$, $R^h$ together with the nitrogen atom, to which they are bound form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl and $C_1$-$C_4$-haloalkyl, and in particular $R^g$, $R^h$ together with the nitrogen atom, to which they are bound may form a 5-, 6- or 7-membered, saturated N-bound heterocyclic radical, which may carry as a ring member a further heteroatom selected from O, S and N and which is unsubstituted or may carry 1, 2, 3 or 4 methyl groups; and $R^k$ is H, $C_1$-$C_4$-alkyl, $C_1$-$C_4$-haloalkyl or phenyl, in particular $C_1$-$C_4$-alkyl.

According to a more preferred embodiment the variable X of the compounds of the formula I is selected from the group consisting of halogen, cyano, nitro, $NH_2$, $C_1$-$C_4$-alkyl, $C_1$-$C_4$-alkoxy-$C_1$-$C_4$-alkyl, $C_3$-$C_7$-cycloalkyl, $C_1$-$C_4$-haloalkyl, $C(=O)$—$R^c$, $C(=O)$—$OR^d$, $C(=O)$—$NR^eR^f$ and $NH$—$C(=O)R^k$, where $R^c$, $R^d$, $R^e$, $R^f$ and $R^k$ are as defined above and which preferably have on their own or in particular in combination the following meanings:

$R^c$ is $C_1$-$C_4$-alkyl or $C_1$-$C_4$-haloalkyl, $R^d$ is $C_1$-$C_4$-alkyl, $R^e$ is hydrogen or $C_1$-$C_4$-alkyl, $R^f$ is hydrogen or $C_1$-$C_4$-alkyl, or $R^e$, $R^f$ together with the nitrogen atom, to which they are bound may form a 5-, 6 or 7-membered, saturated N-bound heterocyclic radical, which may carry as a ring member a further heteroatom selected from O, S and N and which is unsubstituted or may carry 1, 2, 3 or 4 methyl groups, and $R^k$ is $C_1$-$C_4$-alkyl.

According to a particular preferred embodiment of the invention the variable X in the compounds of formula I is selected from halogen, cyano, nitro, $C_1$-$C_4$-alkyl, $C_3$-$C_7$-cycloalkyl, $C_1$-$C_4$-haloalkyl, acetylamino, methoxycarbonyl, ethoxycarbonyl, methylcarbonyl, piperidinylcarbonyl, trifluoromethylcarbonyl, amino, aminocarbonyl, methylaminocarbonyl, dimethylaminocarbonyl and methoxymethyl, in particular from Cl, Br, F, methyl, ethyl, isopropyl, tert-butyl, cyclopropyl, cyclopentyl, cyclohexyl, $CF_3$, $CHF_2$, $CClF_2$, $CH_2CF_3$, $CF_2CF_3$, $CH_2Cl$, $CHCl_2$, cyano, nitro, acetylamino, methoxycarbonyl, ethoxycarbonyl, methylcarbonyl, piperidinylcarbonyl, trifluoromethylcarbonyl, amino, aminocarbonyl, methylaminocarbonyl, dimethylaminocarbonyl and methoxymethyl.

According to a further preferred embodiment of the invention the variable X in the compounds of formula I is a radical $OR^a$, where $R^a$ is as defined above and in particular selected from the group consisting of H, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, preferably from H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_4$-alkoxy-$C_1$-$C_4$-alkyl and $C_3$-$C_7$-cycloalkyl, which is unsubstituted or partly or completely halogenated, and in particular from H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl and $C_3$-$C_6$-cycloalkyl. In this context $R^a$ specifically is H, $CH_3$, $CH_2H_3$, $CH(CH_3)_2$, $CH_2CH_2CH_3$, cylcopropyl, cyclobutyl, cyclopentyl, cyclohexyl, $CH_2Cl$, $C(CH_3)_3$, $CHF_2$, $CF_3$, $CH_2CH=CH_2$, $CH_2C$—$CH$, $CH_2OCH_3$, $CH_2CH_2OCH_3$ and $CH_2CH_2OCH_2CH_3$.

According to another preferred embodiment of the invention the variable X in the compounds of formula I is phenyl or heterocyclyl, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R' which are as defined above and which are independently from one another are preferably selected from the group consisting of halogen, $C_1$-$C_4$-alkyl, $C_3$-$C_6$-cycloalkyl, $C_3$-$C_6$-halocycloalkyl, $C_1$-$C_4$-haloalkyl, $C_1$-$C_4$-alkoxy, $C_1$-$C_4$-alkoxy-$C_1$-$C_4$-alkyl and $C_1$-$C_6$-haloalkyloxy, more preferably from halogen, $C_1$-$C_4$-alkyl, $C_3$-$C_6$-cycloalkyl, $C_1$-$C_4$-haloalkyl and $C_1$-$C_4$-alkoxy, in particular from halogen, methyl, ethyl, methoxy and trifluoromethyl, and specifically from Cl, F, Br, methyl, methoxy and trifluoromethyl.

According to a more preferred embodiment of the invention the variable X in the compounds of formula I is phenyl or heterocyclyl, where heterocyclyl is a partially unsaturated or aromatic 5- or 6-membered monocyclic or 9- or 10-membered bicyclic heterocycle containing 1, 2, 3 or 4 heteroatoms as ring members, which are selected from the group consisting of O, N and S, where the bicyclic heterocycle consists of a 5- or 6-membered heteroaromatic ring which is fused to a phenyl ring, and where phenyl and heterocyclyl are unsubstituted or substituted by 1, 2, 3 or 4 groups R' which independently from one another have the aforementioned preferred meanings.

According to particular preferred embodiments the variable X in the compounds of the formula I is phenyl or heterocyclyl selected from pyridin-2-yl, pyridin-3-yl, pyridin-4-yl, piperidin-2-yl, piperidin-3-yl, piperidin-4-yl, benzisoxazole-2-yl, 1,2,4-oxadiazol-3-yl, 1,2,4-triazol-3-yl, 1-ethylbenzimidazol-2-yl, 4-methylthiazol-2-yl, thiophen-2-yl, furan-2-yl, furan-3-yl, tetrahydrofuran-2-yl, tetrahydrofuran-3-yl, isoxazol-2-yl, isoxazol-3-yl, isoxazol-4-yl, isoxazol-5-yl, oxazol-2-yl, oxazol-3-yl, oxazol-4-yl, oxazol-5-yl, pyrrol-2-yl, pyrrol-3-yl, imidazol-2-yl, imidazol-4-yl, imidazol-5-yl, pyrazol-3-yl, pyrazol-4-yl, pyrazol-5-yl, isothiazol-3-yl, isothiazol-4-yl, isothiazol-5-yl, thiazol-2-yl, thiazol-4-yl, thiazol-5-yl, 1,2,3-triazol-4-yl, 1,2,3-triazol-5-yl, 1,2,5-triazol-3-yl, 1,3,4-triazol-2-yl, 1,2,4-triazol-3-yl, 1,2,4-triazol-5-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 2H-1,2,3,4-tetrazol-5-yl, 1H-1,2,3,4-tetrazol-1-yl, 1,2,3,4-oxatriazol-5-yl, 1,2,3,5-oxatriazol-4-yl, 1,2,3,4-thiatriazol-5-yl, 1,2,3,5-thiatriazol-4-yl, pyrazin-2-yl, pyrazin-3-yl, pyrimidin-2-yl, pyrimidin-4-yl, pyrimidin-5-yl, pyridazin-3-yl and pyridazin-4-yl, where phenyl and heterocyclyl are unsubstituted or carry 1, 2, or 3 groups R' which independently from one another have the aforementioned preferred meanings.

According to a preferred embodiment of the invention the variable X in the compounds of formula I is $S(O)_n$—$R^b$, where $R^b$ is as defined above and in particular selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl and heterocyclyl are unsubstituted or substituted by 1, 2 or 3 groups, which are identical or different and preferably selected from the group consisting of halogen, $C_1$-$C_4$-alkyl, $C_1$-$C_2$-haloalkyl and $C_1$-$C_2$-alkoxy.

According to a more preferred embodiment of the invention the variable X in the compounds of formula I is $S(O)_n$—$R^b$, where $R^b$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_7$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

According to an even more preferred embodiment of the invention the variable X in the compounds of formula I is $S(O)_n$—$R^b$, where $R^b$ is selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_7$-cycloalkyl, phenyl and heterocyclyl, where heterocyclyl is a 6-membered aromatic heterocyclic radical having 1 or 2 nitrogen atoms as ring members.

According to a particularly preferred embodiment of the invention the variable X in the compounds of formula I is $S(O)_2$—$R^b$, where $R^b$ is $CH_3$, $CH_2H_3$, $CH(CH_3)_2$, $CH_2CH_2CH_3$, $CH_2CH=CH_2$, $CH_2C≡CH$ or phenyl.

According to specifically preferred embodiments of the invention the variable X in the compounds of formula I is selected from the group consisting of Cl, Br, F, methyl, ethyl, isopropyl, tert-butyl, cyclopropyl, cyclopentyl, cyclohexyl, $CF_3$, $CHF_2$, $CClF_2$, $CH_2CF_3$, $CF_2CF_3$, $CH_2Cl$, $CHF_2$, $CHCl_2$, cyano, nitro, acetylamino, benzoylamino, methoxycarbonyl, ethoxycarbonyl, benzoyl, methylcarbonyl, piperidinylcarbonyl, trifluoromethylcarbonyl, amino, aminocarbonyl, methylaminocarbonyl, dimethylaminocarbonyl, methoxymethyl, OH, $OCH_3$, $OCH_2H_3$, $OCH(CH_3)_2$, $OCH_2CH_2CH_3$, O-cylcopropyl, O-cyclobutyl, O-cyclopentyl, O-cyclohexyl, O—$CH_2Cl$, O—$C(CH_3)_3$, O—$CHF_2$, O—$CF_3$, O—$CH_2CH=CH_2$, O—$CH_2C≡CH$, O—$CH_2OCH_3$, O—$CH_2CH_2OCH_3$, O—$CH_2CH_2OCH_2CH_3$, $S(O)_2$—$CH_3$, $S(O)_2$—$CH_2CH_3$, $S(O)_2$—$CH(CH_3)_2$, $S(O)_2$—$CH_2CH_2CH_3$, $S(O)_2$—$CH_2CH=CH_2$, $S(O)_2$—$CH_2C≡CH$ and $S(O)_2$-phenyl and in particular from methyl, ethyl and methoxy.

According to one embodiment of the invention the variable B in the compounds of formula II is N.

According to another embodiment of the invention the variable B in the compounds of formula II is CH.

According to a preferred embodiment of the invention the variable Y in the compounds of formula II is selected from the group consisting of $C_1$-$C_6$-alkyl, $C_2$-$C_6$-alkenyl, $C_2$-$C_6$-haloalkenyl, $C_1$-$C_4$-alkoxy-$C_1$-$C_4$-alkyl, $C_3$-$C_7$-cycloalkyl, $C_1$-$C_6$-haloalkyl, $R^c$—C(=O)—$C_1$-$C_2$-alkyl, $R^d$O—C(=O)—$C_1$-$C_2$-alkyl, $R^e R^f$N—C(=O)—$C_1$-$C_2$-alkyl and $R^k$—C(=O)NH—$C_1$-$C_2$-alkyl; where $R^c$, $R^d$, $R^e$, $R^f$, $R^k$, $R^g$ and $R^h$ are as defined above and which preferably have on their own or in particular in combination the following meanings:

$R^c$ is hydrogen, $C_1$-$C_6$-alkyl $C_3$-$C_7$-cycloalkyl, $C_2$-$C_6$-alkenyl, $C_2$-$C_6$-haloalkenyl, $C_1$-$C_6$-haloalkyl or phenyl, in particular $C_1$-$C_4$-alkyl or $C_1$-$C_4$-haloalkyl;

$R^d$ is $C_1$-$C_6$-alkyl or $C_1$-$C_6$-haloalkyl, in particular $C_1$-$C_4$-alkyl, $R^e$, $R^f$ are independently of each other selected from hydrogen, $C_1$-$C_6$-alkyl, $C_1$-$C_6$-haloalkyl and benzyl, and in particular from the group consisting of hydrogen and $C_1$-$C_4$-alkyl, or $R^e$, $R^f$ together with the nitrogen atom, to which they are bound form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl and $C_1$-$C_4$-haloalkyl, and in particular $R^e$, $R^f$ together with the nitrogen atom, to which they are bound may form a 5-, 6- or 7-membered, saturated N-bound heterocyclic radical, which may carry as a ring member a further heteroatom selected from O, S and N and which is unsubstituted or may carry 1, 2, 3 or 4 methyl groups;

$R^g$, $R^h$ are independently of each other selected from hydrogen, $C_1$-$C_6$-alkyl, $C_1$-$C_6$-haloalkyl and benzyl and in particular from the group consisting of hydrogen or $C_1$-$C_4$-alkyl, or $R^g$, $R^h$ together with the nitrogen atom, to which they are bound form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl and $C_1$-$C_4$-haloalkyl, and in particular $R^g$, $R^h$ together with the nitrogen atom, to which they are bound may form a 5-, 6- or 7-membered, saturated N-bound heterocyclic radical, which may carry as a ring member a further heteroatom selected from O, S and N and which is unsubstituted or may carry 1, 2, 3 or 4 methyl groups; and $R^k$ is H, $C_1$-$C_4$-alkyl, $C_1$-$C_4$-haloalkyl or phenyl, in particular $C_1$-$C_4$-alkyl.

According to a more preferred embodiment the variable Y of the compounds of the formula II is selected from the group consisting of $C_1$-$C_4$-alkyl, $C_1$-$C_4$-alkoxy-$C_1$-$C_4$-alkyl, $C_3$-$C_7$-cycloalkyl, $C_1$-$C_4$-haloalkyl, $R^c$—C(=O)—$C_1$-$C_2$-alkyl, $R^d$O—C(=O)—$C_1$-$C_2$-alkyl, $R^e R^f$N—C(=O)—$C_1$-$C_2$-alkyl and $R^k$—C(=O)NH—C—$C_2$-alkyl, where $R^c$, $R^d$, $R^e$, $R^f$ and $R^k$ are as defined above and which preferably have on their own or in particular in combination the following meanings:

$R^c$ is $C_1$-$C_4$-alkyl or $C_1$-$C_4$-haloalkyl, $R^d$ is $C_1$-$C_4$-alkyl, $R^e$ is hydrogen or $C_1$-$C_4$-alkyl, $R^f$ is hydrogen or $C_1$-$C_4$-alkyl, or $R^e$, $R^f$ together with the nitrogen atom, to which they are bound may form a 5-, 6 or 7-membered, saturated N-bound heterocyclic radical, which may carry as a ring member a further heteroatom selected from O, S and N and which is unsubstituted or may carry 1, 2, 3 or 4 methyl groups, and $R^k$ is $C_1$-$C_4$-alkyl.

According to a particular preferred embodiment of the invention the variable Y in the compounds of formula II is selected from $C_1$-$C_4$-alkyl, $C_3$-$C_7$-cycloalkyl, $C_1$-$C_4$-haloalkyl and $C_1$-$C_4$-alkoxy-$C_1$-$C_4$-alkyl, in particular from methyl, ethyl, isopropyl, tert-butyl, cyclopropyl, cyclopentyl, cyclohexyl, $CF_3$, $CHF_2$, $CClF_2$, $CH_2CF_3$, $CF_2CF_3$, $CH_2Cl$, $CHCl_2$, ethoxyethyl, ethoxymethyl, methoxyethyl and methoxymethyl.

According to another particular preferred embodiment of the invention the variable Y in the compounds of formula II is selected from $C_1$-$C_4$-alkyl, $C_3$-$C_7$-cycloalkyl, $C_1$-$C_4$-haloalkyl, methoxyethyl and methoxymethyl, in particular from methyl, ethyl, isopropyl, tert-butyl, cyclopropyl, cyclopentyl, cyclohexyl, $CF_3$, $CHF_2$, $CClF_2$, $CH_2CF_3$, $CF_2CF_3$, $CH_2Cl$, $CHCl_2$, methoxyethyl and methoxymethyl.

According to another preferred embodiment of the invention the variable Y in the compounds of formula II is phenyl or heterocyclyl, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R' which are as defined above and which are independently from one another are preferably selected from the group consisting of halogen, $C_1$-$C_4$-alkyl, $C_3$-$C_6$-cycloalkyl, $C_3$-$C_6$-halocycloalkyl, $C_1$-$C_4$-haloalkyl, $C_1$-$C_4$-alkoxy, $C_1$-$C_4$-alkoxy-$C_1$-$C_4$-alkyl and $C_1$-$C_6$-haloalkyloxy, more preferably from halogen, $C_1$-$C_4$-alkyl, $C_3$-$C_6$-cycloalkyl, $C_1$-$C_4$-haloalkyl and $C_1$-$C_4$-alkoxy, in particular from halogen, methyl, ethyl, methoxy and trifluoromethyl, and specifically from Cl, F, Br, methyl, methoxy and trifluoromethyl.

According to a more preferred embodiment of the invention the variable Y in the compounds of formula II is phenyl or heterocyclyl, where heterocyclyl is a partially unsaturated or aromatic 5- or 6-membered monocyclic or 9- or 10-membered bicyclic heterocycle containing 1, 2, 3 or 4 heteroatoms as ring members, which are selected from the group consisting of O, N and S, where the bicyclic heterocycle consists of a 5- or 6-membered heteroaromatic ring which is fused to a phenyl ring, and where phenyl and heterocyclyl are unsubstituted or substituted by 1, 2, 3 or 4 groups R' which independently from one another have the aforementioned preferred meanings.

According to particular preferred embodiments the variable Y in the compounds of the formula II is phenyl or heterocyclyl selected from pyridin-2-yl, pyridin-3-yl, pyridin-4-yl, piperidin-2-yl, piperidin-3-yl, piperidin-4-yl, benzisoxazole-2-yl, 1,2,4-oxadiazol-3-yl, 1,2,4-triazol-3-yl, 1-ethylbenzimidazol-2-yl, 4-methylthiazol-2-yl, thiophen-2-yl, furan-2-yl, furan-3-yl, tetrahydrofuran-2-yl, tetrahydrofuran-3-yl, isoxazol-2-yl, isoxazol-3-yl, isoxazol-4-yl, isoxazol-5-yl, oxazol-2-yl, oxazol-3-yl, oxazol-4-yl, oxazol-5-yl, pyrrol-2-yl, pyrrol-3-yl, imidazol-2-yl, imidazol-4-yl, imidazol-5-yl, pyrazol-3-yl, pyrazol-4-yl, pyrazol-5-yl, isothiazol-3-yl, isothiazol-4-yl, isothiazol-5-yl, thiazol-2-yl, thiazol-4-yl, thiazol-5-yl, 1,2,3-triazol-4-yl, 1,2,3-triazol-5-yl, 1,2,5-triazol-3-yl, 1,3,4-triazol-2-yl, 1,2,4-triazol-3-yl, 1,2,4-triazol-5-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 2H-1,2,3,4-tetrazol-5-yl, 1H-1,2,3,4-tetrazol-1-yl, 1,2,3,4-oxatriazol-5-yl, 1,2,3,5-oxatriazol-4-yl, 1,2,3,4-thiatriazol-5-yl, 1,2,3,5-thiatriazol-4-yl, pyrazin-2-yl, pyrazin-3-yl, pyrimidin-2-yl, pyrimidin-4-yl, pyrimidin-5-yl, pyridazin-3-yl and pyridazin-4-yl, where phenyl and heterocyclyl are unsubstituted or carry 1, 2, or 3 groups R' which independently from one another have the aforementioned preferred meanings.

According to a preferred embodiment of the invention the variable Y in the compounds of formula II is $R^b$—S(O)$_n$—$C_1$-$C_3$-alkyl, where $R^b$ is as defined above and in particular selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl and heterocyclyl are unsubstituted or substituted by 1, 2 or 3 groups, which are identical or different and preferably selected from the group consisting of halogen, $C_1$-$C_4$-alkyl, $C_1$-$C_2$-haloalkyl and $C_1$-$C_2$-alkoxy.

According to a more preferred embodiment of the invention the variable Y in the compounds of formula II is $R^b$—S(O)$_n$—C—$C_3$-alkyl, where $R^b$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_7$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

According to an even more preferred embodiment of the invention the variable Y in the compounds of formula II is $R^b$—S(O)$_n$—$C_1$-$C_2$-alkyl, where $R^b$ is selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_7$-cycloalkyl, phenyl and heterocyclyl, where heterocyclyl is a 6-membered aromatic heterocyclic radical having 1 or 2 nitrogen atoms as ring members.

According to a particularly preferred embodiment of the invention the variable Y in the compounds of formula II is $R^b$—S(O)$_2$—$C_1$-$C_2$-alkyl, where $R^b$ is $CH_3$, $CH_2H_3$, $CH(CH_3)_2$, $CH_2CH_2CH_3$, $CH_2CH=CH_2$, $CH_2C≡CH$ or phenyl.

According to specifically preferred embodiments of the invention the variable Y in the compounds of formula II is selected from the group consisting of methyl, ethyl, isopropyl, tert-butyl, cyclopropyl, cyclopentyl, cyclohexyl, $CF_3$, $CHF_2$, $CClF_2$, $CH_2CF_3$, $CF_2CF_3$, $CH_2Cl$, $CHCl_2$, methoxyethyl, methoxymethyl, and in particular from methyl and ethyl.

Preferred compounds according to the invention are compounds of formula I or formula II, wherein $R^1$ is selected from the group consisting of CN, halogen, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_4$-alkoxy-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy and $R^{1b}$—$S(O)_k$, where k and $Z^1$ are as defined herein and where Rib is as defined above and in particular selected from the group consisting of $C_1$-$C_4$-alkyl and $C_1$-$C_4$-haloalkyl. In this context $Z^1$ is in particular a covalent bond.

More preferably, $R^1$ is selected from halogen, CN, nitro, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $C_1$-$C_4$-alkyl-$S(O)_k$ and $C_1$-$C_4$-haloalkyl-$S(O)_k$, where k is 0 or 2.

In particular, $R^1$ is selected from the group consisting of halogen, $C_1$-$C_4$-alkyl, $C_1$-$C_4$-haloalkyl, $C_1$-$C_4$-alkoxy-$C$—$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl, specifically $R^1$ is F, Cl, Br, $CH_3$, $CF_3$, $OCH_3$, $OCF_3$, $SCF_3$, $SO_2CH_3$ or $CH_2OCH_2CH_2OCH_3$, and more specifically $R^1$ is Cl, $CH_3$, $CF_3$ or $SO_2CH_3$.

In one group of embodiments of the invention, the variable $R^2$ is hydrogen.

In one group of embodiments of the invention the variable $R^2$ of the compounds of formula I or formula II has any one of the meanings given above for $R^2$ with the exception of hydrogen.

According to preferred embodiment of the invention the variable $R^2$ in the compounds of formula I or formula II is a 5- or 6-membered heterocyclyl, where heterocyclyl is a saturated, partially unsaturated or aromatic heterocyclic radical, which contains as ring member 1 heteroatom selected from the group consisting of O, N and S and 0, 1, 2 or 3 further nitrogen atom(s), where heterocyclyl is unsubstituted or carries 1, 2 or 3 radicals $R^{21}$, as defined herein, which are identical or different.

According to an even more preferred embodiment of the invention the variable $R^2$ in the compounds of formula I or formula II is a 5- or 6-membered heterocyclyl selected from the group consisting of isoxazolinyl (4,5-dihydroisoxazolyl), 1,2-dihydrotetrazolonyl, 1,4-dihydrotetrazolonyl, tetrahydrofuryl, dioxolanyl, piperidinyl, morpholinyl, piperazinyl, isoxazolyl, pyrazolyl, thiazolyl, oxazolyl, furyl, pyridinyl, pyrimidinyl and pyrazinyl, where heterocyclyl is unsubstituted or carries 1, 2 or 3 radicals $R^{21}$ which are identical or different and are selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl and $C_1$-$C_4$-alkylthio-$C_1$-$C_4$-alkyl.

According to a particular embodiment of the invention the variable $R^2$ in the compounds of formula I or formula II is a 5- or 6-membered heterocyclyl selected from 4,5-dihydroisoxazol-3-yl, which is unsubstituted or substituted in position 5 with $CH_3$, $CH_2F$ or $CHF_2$, 4,5-dihydroisoxazol-5-yl, which is unsubstituted or substituted in position 3 with $CH_3$, $OCH_3$, $CH_2OCH_3$, $CH_2SCH_3$, 1-methyl-5-oxo-1,5-dihydrotetrazol-2-yl, 4-methyl-5-oxo-4,5-dihydrotetrazol-1-yl, morpholin-4-yl, isoxazol-3-yl, 5-methyl-isoxazol-3-yl, isoxazol-5-yl, 3-methyl-isoxazol-5-yl, 1-methyl-1H-pyrazol-3-yl, 2-methyl-2H-pyrazol-3-yl and thiazol-2-yl.

According to a preferred embodiment of the invention the variable $R^2$ in the compounds of formula I or formula II is phenyl-$Z^{2a}$, where $Z^{2a}$ is as defined herein, and where phenyl is unsubstituted or carries 1, 2 or 3 radicals $R^{21}$ which are identical or different and as defined above and which are in particular selected from halogen, $C_1$-$C_4$-alkyl, $C_1$-$C_4$-alkoxy, $C_1$-$C_4$-haloalkyl, $C_1$-$C_4$-alkoxy-$C_1$-$C_4$-alkyl and $C_1$-$C_4$-alkoxy-$C_1$-$C_4$-alkoxy, and preferably from halogen, $C_1$-$C_2$-alkyl, $C_1$-$C_2$-alkoxy, $C_1$-$C_2$-haloalkyl and $C_1$-$C_2$-alkoxy-$C_1$-$C_2$-alkoxy.

According to a more preferred embodiment of the invention the variable $R^2$ in the compounds of formula I or formula II is a radical of the following formula:

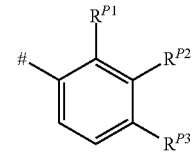

in which # denotes the bond through which the group $R^2$ is attached and:

$R^{P1}$ is hydrogen or halogen, preferably hydrogen, Cl, Br or F, and in particular H or F;

$R^{P2}$ is hydrogen, halogen or $C_1$-$C_2$-alkoxy, preferably hydrogen, Cl, Br, F, $OCH_3$ or $OCH_2CH_3$, and in particular H, F, Cl or $OCH_3$; and $R^{P3}$ is hydrogen, halogen, $C_1$-$C_2$-alkyl, $C_1$-$C_2$-haloalkyl, $C_1$-$C_2$-alkoxy, $C_1$-$C_2$-alkoxy-$C_1$-$C_2$-alkoxy, preferably hydrogen, Cl, Br, F, $CH_3$, $C_2H_5$, $CF_3$, $CHF_2$, $CH_2F$, $CCl_2F$, $CF_2Cl$, $CH_2CF_3$, $CH_2CHF_2$, $CF_2CF_3$, $OCH_3$, $OCH_2CH_3$, $OCH_2OCH_3$, $OCH_2CH_2OCH_2CH_3$, $OCH_2OCH_2CH_3$ or $OCH_2CH_2OCH_3$, and in particular is H, F, Cl, $CH_3$, $CF_3$, $OCH_3$, $OCH_2CH_3$, $OCH_2OCH_3$ or $OCH_2CH_2OCH_3$.

According to a particular embodiment of the invention the variable $R^2$ in the compounds of formula I or formula II is phenyl which is unsubstituted or carries one radical $R^{21}$, where $R^{21}$ is preferably attached to position 4 of the phenyl group and is as defined above and in particular selected from $C_1$-$C_2$-alkyl, $C_1$-$C_2$-alkoxy, $C_1$-$C_2$-haloalkyl and $C_1$-$C_2$-alkoxy-$C_1$-$C_2$-alkoxy, preferably form $CH_3$, $C_2H_5$, $OCH_3$, $OC_2H_5$, $CHF_2$, $CF_3$, $OCH_2OCH_3$ and $OCH_2CH_2OCH_3$, and specifically from $OCH_3$ and $OC_2H_5$.

According to a preferred embodiment of the invention the variable $R^2$ in the compounds of formula I or formula II is selected from the group consisting of hydrogen, halogen, $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $C_1$-$C_4$-alkyl-$S(O)_k$, k is 0, 1, 2, and $C_1$-$C_4$-haloalkyl-$S(O)_2$.

According to another preferred embodiment of the invention the variable $R^2$ in the compounds of formula I or formula II is selected from the group consisting of halogen, $C_1$-$C_6$-alkyl, $C_1$-$C_4$-alkoxy-$C_1$-$C_4$-alkyl, $C_1$-$C_4$-haloalkoxy- $C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $C_1$-$C_4$-alkyl-S(O)$_2$ and $C_1$-$C_4$-haloalkyl-S(O)$_2$.

According to a more preferred embodiment of the invention the variable $R^2$ in the compounds of formula I or formula II is selected from $C_2$-$C_4$-alkenyl, $C_2$-$C_4$-alkynyl, $C_2$-$C_4$-alkoxy, $C_1$-$C_2$-haloalkoxy-$C_1$-$C_2$-alkyl, $C_3$-$C_4$-alkenyloxy, $C_3$-$C_4$-alkynyloxy, $C_1$-$C_4$-alkoxycarbonyl and $C_1$-$C_4$-alkyl-S(O$_2$), and in particular from CH=CH$_2$, CH=CHCH$_3$, CH$_2$OCH$_2$CF$_3$, OC$_2$H$_5$, OCH$_2$CH=CH$_2$, OCH$_2$C≡CH, C(O)OCH$_3$, C(O)OC$_2$H$_5$, SO$_2$CH$_3$, SO$_2$C$_2$H$_5$ and SO$_2$CH(CH$_3$)$_2$.

According to a specifically preferred embodiment of the invention the variable $R^2$ in the compounds of formula I or formula II is selected from the group consisting of hydrogen, 4,5-dihydroisoxazol-3-yl, which is unsubstituted or substituted in position 5 with CH$_3$, CH$_2$F or CHF$_2$, 4,5-dihydroisoxazol-5-yl, which is unsubstituted or substituted in position 3 with CH$_3$, OCH$_3$, CH$_2$OCH$_3$, CH$_2$SCH$_3$, 1-methyl-5-oxo-1,5-dihydrotetrazol-2-yl, 4-methyl-5-oxo-4,5-dihydrotetrazol-1-yl, morpholin-4-yl, isoxazol-3-yl, 5-methyl-isoxazol-3-yl, isoxazol-5-yl, 3-methyl-isoxazol-5-yl, 1-methyl-1H-pyrazol-3-yl, 2-methyl-2H-pyrazol-3-yl, thiazol-2-yl, 4-CH$_3$-phenyl, 4-C$_2$H$_5$-phenyl, 4-OCH$_3$-phenyl, 4-OC$_2$H$_5$-phenyl, 4-CHF$_2$-phenyl, 4-CF$_3$-phenyl, 4-OCH$_2$OCH$_3$-phenyl, 4-OCH$_2$CH$_2$OCH$_3$-phenyl, CH=CH$_2$, CH=CHCH$_3$, CH$_2$OCH$_2$CF$_3$, OC$_2$H$_5$, OCH$_2$CH=CH$_2$, OCH$_2$C≡CH, C(O)OCH$_3$, C(O)OC$_2$H$_5$, SO$_2$CH$_3$, SO$_2$C$_2$H$_5$ and SO$_2$CH(CH$_3$)$_2$, in particular selected from hydrogen, halogen, methyl, CH$_2$OCH$_2$CF$_3$, methylsulfonyl, methylsulfanyl, methylsulfinyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl, and specifically selected from hydrogen, chlorine, methylsulfonyl, methylsulfanyl, methylsulfinyl, CH$_2$OCH$_2$CF$_3$, 3-isoxazolinyl, 5-methyl-3-isoxazolinyl, 3-methyl-5-isoxazolinyl, 3-isoxazolyl, 5-methyl-3-isoxazolyl and 3-methyl-5-isoxazolyl.

Preferred compounds according to the invention are compounds of formula I or formula II, wherein $R^3$ is selected from the group consisting of hydrogen, cyano, halogen, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy or $R^{2b}$—S(O)$_k$, where the variables k and $R^{2b}$ have one of the herein defined meanings.

More preferably, $R^3$ is selected from the group consisting of hydrogen, halogen, CN, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkyl-S(O)$_2$ and $C_1$-$C_4$-haloalkyl-S(O)$_2$.

In particular, $R^3$ is selected from the group consisting of hydrogen, halogen, CN, NO$_2$, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkyl-S(O)$_2$ and $C_1$-$C_2$-haloalkyl-S(O)$_2$, specifically from H, Cl, F, CN, NO$_2$, CH$_3$, CF$_3$, CHF$_2$, OCH$_3$, OCF$_3$, OCHF$_2$, SCH$_3$, SCF$_3$, SCHF$_2$, S(O)$_2$CH$_3$ and S(O)$_2$CH$_2$CH$_3$, and more specifically from Cl, F, CN, CF$_3$ and S(O)$_2$CH$_3$.

Preferred compounds according to the invention are compounds of formula I or formula II, wherein $R^4$ is selected from the group consisting of hydrogen, cyano, halogen, nitro, $C_1$-$C_2$-alkyl and $C_1$-$C_2$-haloalkyl, in particular from the group consisting of hydrogen, CHF$_2$, CF$_3$, CN, NO$_2$, CH$_3$ and halogen, and specifically from hydrogen, CHF$_2$, CF$_3$, CN, NO$_2$, CH$_3$, Cl, Br and F.

Preferred compounds according to the invention are compounds of formula I or formula II, wherein $R^5$ is selected from the group consisting of hydrogen, halogen, $C_1$-$C_2$-alkyl and $C_1$-$C_2$-haloalkyl, and in particular from the group consisting of hydrogen, CHF$_2$, CF$_3$ and halogen.

According to a particular embodiment of the invention either $R^4$ is hydrogen and $R^5$ is chlorine or fluorine, or $R^5$ is hydrogen and $R^4$ is chlorine or fluorine.

In this context, the variables R', $R^{11}$, $R^{21}$, Z, $Z^1$, $Z^2$, $Z^{2a}$, $R^a$, $R^b$, $R^{1b}$, $R^{2b}$, $R^c$, $R^{2c}$, $R^d$, $R^{2d}$, $R^e$, $R^{2e}$, $R^f$, $R^{2f}$, $R^g$, $R^{2g}$, $R^h$, $R^{2h}$, $R^k$, n and k, independently of each other, preferably have one of the following meanings:

R', $R^{11}$, $R^{21}$ independently of each other are selected from halogen, $C_1$-$C_4$-alkyl, $C_3$-$C_6$-cycloalkyl, $C_3$-$C_6$-halocycloalkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy and $C_1$-$C_6$-haloalkyloxy, more preferably from halogen, $C_1$-$C_4$-alkyl, $C_3$-$C_6$-cycloalkyl, $C_1$-$C_4$-haloalkyl and $C_1$-$C_4$-alkoxy.

More preferably R', $R^{11}$, $R^{21}$ independently of each other are selected from the group consisting of halogen, $C_1$-$C_4$-alkyl, $C_3$-$C_6$-cycloalkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl and $C_1$-$C_4$-alkoxy-$C_1$-$C_4$-alkoxy; in particular selected from halogen, $C_1$-$C_4$-alkyl, $C_1$-$C_4$-alkoxy, $C_1$-$C_4$-haloalkyl, $C_1$-$C_4$-alkoxy-$C_1$-$C_4$-alkyl and $C_1$-$C_4$-alkoxy-$C_1$-$C_4$-alkoxy; and specifically from Cl, F, Br, methyl, ethyl, methoxy and trifluoromethyl.

Z, $Z^1$, $Z^2$ independently of each other are selected from a covalent bond, methanediyl and ethanediyl, and in particular are a covalent bond.

$Z^{2a}$ is selected from a covalent bond, $C_1$-$C_2$-alkanediyl, O—$C_1$-$C_2$-alkanediyl, $C_1$-$C_2$-alkanediyl-O and $C_1$-$C_2$-alkanediyl-O—$C_1$-$C_2$-alkanediyl; more preferably from a covalent bond, methanediyl, ethanediyl, O-methanediyl, O-ethanediyl, methanediyl-O, and ethanediyl-O; and in particular from a covalent bond, methanediyl and ethanediyl.

$R^a$ is selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl.

More preferably $R^a$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_4$-alkoxy-$C_1$-$C_4$-alkyl and $C_3$-$C_7$-cycloalkyl, which is unsubstituted or partly or completely halogenated, and in particular selected from H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl and $C_3$-$C_6$-cycloalkyl.

$R^b$, $R^{1b}$, $R^{2b}$ independently of each other are selected from $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl and heterocyclyl are unsubstituted or substituted by 1, 2 or 3 groups, which are identical or different and selected from the group consisting of halogen, $C_1$-$C_4$-alkyl, $C_1$-$C_2$-haloalkyl and $C_1$-$C_2$-alkoxy.

More preferably $R^b$, $R^{1b}$, $R^{2b}$ independently of each other are selected from the group consisting of $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

In particular, $R^b$, $R^{1b}$, $R^{2b}$ independently of each other are selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_3$-$C_6$-cycloalkyl, phenyl and heterocyclyl, where heterocyclyl is a 5- or 6-membered aromatic heterocyclic radical having 1 or 2 nitrogen atoms as ring members.

$R^c$, $R^{2c}$, $R^k$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S, where phenyl, benzyl and heterocyclyl are unsubstituted or substituted by 1, 2 or 3 groups, which are identical or different and selected from the group consisting of halogen, $C_1$-$C_4$-alkyl, $C_1$-$C_4$-haloalkyl and $C_1$-$C_4$-alkoxy.

More preferably $R^c$, $R^{2c}$, $R^k$ independently of each other are selected from hydrogen, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_3$-$C_6$-cycloalkyl, phenyl and heterocyclyl, where heterocyclyl is a 5- or 6-membered monocyclic saturated, partially unsaturated or aromatic heterocycle, which contains 1, 2 or 3 heteroatoms as ring members, which are selected from the group consisting of O, N and S.

In particular, $R^c$, $R^{2c}$, $R^k$ independently of each other are selected from hydrogen, $C_1$-$C_4$-alkyl, $C_1$-$C_4$-haloalkyl, $C_2$-$C_4$-alkenyl, $C_2$-$C_4$-haloalkenyl, $C_3$-$C_6$-cycloalkyl, phenyl and heterocyclyl, where heterocyclyl is a 5- or 6-membered aromatic heterocyclic radical having 1 or 2 nitrogen atoms as ring members.

$R^d$, $R^{2d}$ independently of each other are selected from $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl.

More preferably $R^d$, $R^{2d}$ independently of each other are selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_4$-alkoxy-$C_1$-$C_4$-alkyl and $C_3$-$C_7$-cycloalkyl, which is unsubstituted or partly or completely halogenated, and in particular selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl and $C_3$-$C_6$-cycloalkyl.

$R^e$, $R^f$, $R^{2e}$, $R^{2f}$ independently of each other are selected from the group consisting of hydrogen, $C_1$-$C_6$-alkyl, $C_3$-$C_7$-cycloalkyl, which is unsubstituted or partially or completely halogenated, $C_1$-$C_6$-haloalkyl, $C_2$-$C_6$-alkenyl, $C_2$-$C_6$-haloalkenyl, $C_1$-$C_4$-alkoxy-$C_1$-$C_4$-alkyl, phenyl and benzyl, where phenyl and benzyl are unsubstituted or substituted by 1, 2 or 3 groups, which are identical or different and selected from the group consisting of halogen, $C_1$-$C_4$-alkyl, $C_1$-$C_4$-haloalkyl and $C_1$-$C_4$-alkoxy, or $R^e$ and $R^f$ or $R^{2e}$ and $R^{2f}$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl and $C_1$-$C_4$-alkoxy.

More preferably $R^e$, $R^f$, $R^{2e}$, $R^{2f}$ independently of each other are selected from hydrogen, $C_1$-$C_6$-alkyl, $C_1$-$C_6$-haloalkyl and benzyl, or $R^e$ and $R^f$ or $R^{2e}$ and $R^{2f}$ together with the nitrogen atom, to which they are bound may form a 5- or 6-membered, saturated or unsaturated N-bound heterocyclic radical, which may carry as a ring member a further heteroatom selected from O, S and N and which is unsubstituted or may carry 1, 2 or 3 groups, which are identical or different and selected from the group consisting of halogen, $C_1$-$C_4$-alkyl and $C_1$-$C_4$-haloalkyl.

In particular, $R^e$, $R^f$, $R^{2e}$, $R^{2f}$ independently of each other are selected from hydrogen and $C_1$-$C_4$-alkyl, or $R^e$ and $R^f$ or $R^{2e}$ and $R^{2f}$ together with the nitrogen atom, to which they are bound may form a 5- or 6-membered, saturated N-bound heterocyclic radical, which may carry as a ring member a further heteroatom selected from O, S and N and which is unsubstituted or may carry 1, 2 or 3 methyl groups.

$R^g$, $R^{2g}$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl.

More preferably $R^g$, $R^{2g}$ independently of each other are selected from hydrogen, $C_1$-$C_6$-alkyl, $C_1$-$C_6$-haloalkyl, $C_2$-$C_6$-alkenyl, $C_2$-$C_6$-haloalkenyl, benzyl, $C_1$-$C_4$-alkoxy-$C_1$-$C_4$-alkyl and $C_3$-$C_7$-cycloalkyl, which is unsubstituted or partly or completely halogenated, and in particular selected from hydrogen, $C_1$-$C_4$-alkyl, $C_1$-$C_4$-haloalkyl, $C_2$-$C_4$-alkenyl, $C_2$-$C_4$-haloalkenyl, benzyl and $C_3$-$C_6$-cycloalkyl.

$R^h$, $R^{2h}$ independently of each other are selected from hydrogen, $C_1$-$C_6$-alkyl, $C_3$-$C_7$-cycloalkyl, which is unsubstituted or partly or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and a radical $C(=O)$—$R^k$, where FR is H, $C_1$-$C_4$-alkyl, $C_1$-$C_4$-haloalkyl or phenyl.

More preferably $R^h$, $R^{2h}$ independently of each other are selected from hydrogen, $C_1$-$C_6$-alkyl, $C_1$-$C_6$-haloalkyl, $C_2$-$C_6$-alkenyl, $C_2$-$C_6$-haloalkenyl, benzyl, $C_1$-$C_4$-alkoxy-$C_1$-$C_4$-alkyl and $C_3$-$C_7$-cycloalkyl, which is unsubstituted or partly or completely halogenated, and in particular selected from hydrogen, $C_1$-$C_4$-alkyl, $C_1$-$C_4$-haloalkyl, $C_2$-$C_4$-alkenyl, $C_2$-$C_4$-haloalkenyl, benzyl and $C_3$-$C_6$-cycloalkyl; or $R^g$ and $R^h$ or $R^{2g}$ and $R^{2h}$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl and $C_1$-$C_4$-haloalkyl and $C_1$-$C_4$-alkoxy;

more preferably $R^g$ and $R^h$ or $R^{2g}$ and $R^{2h}$ together with the nitrogen atom, to which they are bound may form a 5- or 6-membered, saturated or unsaturated N-bound heterocyclic radical, which may carry as a ring member a further heteroatom selected from O, S and N and which is unsubstituted or may carry 1, 2 or 3 groups, which are identical or different and selected from the group consisting of halogen, $C_1$-$C_4$-alkyl and $C_1$-$C_4$-haloalkyl;

and in particular, $R^g$ and $R^h$ or $R^{2g}$ and $R^{2h}$ together with the nitrogen atom, to which they are bound may form a 5- or 6-membered, saturated N-bound heterocyclic radical, which may carry as a ring member a further heteroatom selected from O, S and N and which is unsubstituted or may carry 1, 2 or 3 methyl groups.

n and k independently of each other are 0 or 2, and in particular 2.

Particularly preferred are compounds of formula I or formula II, wherein the variables $R^1$ and $R^3$ have the following meanings:

$R^1$ is selected from the group consisting of halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and $C_1$-$C_4$-alkylsulfonyl, in particular from F, Cl, Br, $CH_3$, $CF_3$, $OCH_3$, $SCH_3$, $OCF_3$, $SCF_3$, $SO_2CH_3$, $CH_2OCH_3$ and $CH_2OCH_2CH_2OCH_3$; and $R^3$ is selected from the group consisting of hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-haloalkylthio and $C_1$-$C_4$-alkylsulfonyl, in particular from H, Cl, F, CN, $NO_2$, $CH_3$, $CF_3$, $CHF_2$, $OCH_3$, $OCF_3$, $OCHF_2$, $SCH_3$, $SCF_3$, $SCHF_2$, $S(O)_2CH_3$ and $S(O)_2CH_2CH_3$.

Especially preferred are compounds of formula I, wherein the variables X, $R^1$, $R^2$, $R^3$, $R^4$ and $R^5$ have the following meanings:

X is selected from the group consisting of $C_1$-$C_4$-alkyl and $C_1$-$C_4$-alkoxy, in particular from $CH_3$, $CH_2CH_3$, $CH(CH_3)_2$, $C(CH_3)_3$, $OCH_3$, $OCH_2CH_3$ and $OCH(CH_3)_2$;

$R^1$ is selected from the group consisting of halogen, $C_1$-$C_4$-alkyl, $C_1$-$C_4$-haloalkyl and $S(O)_2$—$C_1$-$C_4$-alkyl, in particular from Cl, Br, F, $CH_3$, $CH_2CH_3$, $CH(CH_3)_2$, $CF_3$, $CHF_2$, $S(O)_2CH_3$ and $S(O)_2CH_2CH_3$;

$R^2$ is selected from the group consisting of hydrogen, $C_1$-$C_2$-alkoxy-$C_1$-$C_2$-alkyl, $C_1$-$C_2$-haloalkoxy-$C_1$-$C_2$-alkyl, $S(O)_2$—$C_1$-$C_4$-alkyl, isoxazolyl and isoxazolinyl, where the last two mentioned radicals may be substituted or carry 1 or 2 radicals selected from halogen and $C_1$-$C_4$-alkyl. In particular, $R^2$ is selected from $CH_2OCH_3$, $CH_2OCH_2CH_3$, $CH_2CH_2OCH_3$, $CH_2CH_2OCH_2CH_3$, $CH_2OCF_3$, $CH_2OCHF_2$, $CH_2OCH_2F$, $CH_2OCH_2CHF_2$, $CH_2OCH_2CF_3$, $CH_2OCF_2CF_3$, $S(O)_2CH_3$, $S(O)_2CH_2CH_3$, isoxazolyl and isoxazolinyl;

$R^3$ is selected from the group consisting of halogen, CN, $C_1$-$C_4$-haloalkyl and $S(O)_2$—$C_1$-$C_4$-alkyl, in particular from Cl, F, CN, $CF_3$, $CHF_2$, $S(O)_2CH_3$ and $S(O)_2CH_2CH_3$;

$R^4$ is selected from the group consisting of hydrogen, CN, $CHF_2$, $CF_3$, $CH_3$, $NO_2$ and halogen, in particular from hydrogen, $CHF_2$, $CF_3$, $CH_3$, Cl and F; and $R^5$ is selected from the group consisting of hydrogen, halogen, $CHF_2$ and $CF_3$, in particular from hydrogen, Cl, F, $CHF_2$ and $CF_3$, provided that at least one of the radicals $R^4$ and $R^5$ is different from hydrogen.

Specifically preferred are compounds of formula I, wherein the variables X, $R^1$, $R^2$, $R^3$, $R^4$ and $R^5$ have the following meanings:

X is selected from the group consisting of methyl, ethyl and methoxy;

$R^1$ is selected from the group consisting of chlorine, methyl, trifluoromethyl and methylsulfonyl;

$R^2$ is selected from the group consisting of hydrogen, methyl, methylsulfonyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of fluorine, chlorine, trifluoromethyl, CN and methylsulfonyl;

and either $R^4$ is hydrogen and $R^5$ is chlorine or fluorine, or $R^5$ is hydrogen and $R^4$ is chlorine or fluorine.

Especially preferred are compounds of formula II, wherein B is CH and the variables Y, $R^1$, $R^2$, $R^3$, $R^4$ and $R^5$ have the following meanings:

Y is selected from $C_1$-$C_4$-alkyl, in particular from $CH_3$, $CH_2CH_3$, $CH(CH_3)_2$ and $C(CH_3)_3$;

$R^1$ is selected from the group consisting of halogen, $C_1$-$C_4$-alkyl, $C_1$-$C_4$-haloalkyl and $C_1$-$C_4$-alkyl-$S(O)_2$, in particular from Cl, Br, F, $CH_3$, $CH_2CH_3$, $CH(CH_3)_2$, $CF_3$, $CHF_2$, $S(O)_2CH_3$ and $S(O)_2CH_2CH_3$;

$R^2$ is selected from the group consisting of hydrogen, halogen, $C_1$-$C_2$-alkoxy-$C_1$-$C_2$-alkyl, $C_1$-$C_2$-haloalkoxy-$C_1$-$C_2$-alkyl, $C_1$-$C_4$-alkyl-$S(O)_2$, $C_1$-$C_4$-alkylthio, isoxazolyl and isoxazolinyl, where the last two mentioned radicals may be unsubstituted or carry 1 or 2 radicals selected from halogen and $C_1$-$C_4$-alkyl. In particular, $R^2$ is selected from $CH_2OCH_3$, $CH_2OCH_2CH_3$, $CH_2CH_2OCH_3$, $CH_2CH_2OCH_2CH_3$, $CH_2OCF_3$, $CH_2OCHF_2$, $CH_2OCH_2F$, $CH_2OCH_2CHF_2$, $CH_2OCH_2CF_3$, $CH_2OCF_2CF_3$, $S(O)_2CH_3$, $S(O)_2CH_2CH_3$, isoxazolyl and isoxazolinyl;

$R^3$ is selected from the group consisting of hydrogen, halogen, CN, $C_1$-$C_4$-haloalkyl and $C_1$-$C_4$-alkyl-$S(O)_2$, in particular from Cl, F, CN, $CF_3$, $CHF_2$, $S(O)_2CH_3$ and $S(O)_2CH_2CH_3$;

$R^4$ is selected from the group consisting of hydrogen, CN, $CHF_2$, $CF_3$, $CH_3$, $NO_2$ and halogen, in particular from hydrogen, $CHF_2$, $CF_3$, $CH_3$, Cl and F; and $R^5$ is selected from the group consisting of hydrogen, halogen, $CHF_2$ and $CF_3$, in particular from hydrogen, Cl, F, $CHF_2$ and $CF_3$, provided that at least one of the radicals $R^4$ and $R^5$ is different from hydrogen.

Specifically preferred are compounds of formula II, wherein B is CH and the variables Y, $R^1$, $R^2$, $R^3$, $R^4$ and $R^5$ have the following meanings:

Y is selected from the group consisting of methyl and ethyl;

$R^1$ is selected from the group consisting of chlorine, methyl, trifluoromethyl and methylsulfonyl;

$R^2$ is selected from the group consisting of hydrogen, Cl, F, methyl, methylsulfonyl, methylsulfinyl, methylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, trifluoromethyl, CN and methylsulfonyl;

and either $R^4$ is hydrogen and $R^5$ is chlorine or fluorine, or $R^5$ is hydrogen and $R^4$ is chlorine or fluorine.

Also specifically preferred are compounds of formula II, wherein B is CH and the variables Y, $R^1$, $R^2$, $R^3$, $R^4$ and $R^5$ have the following meanings:

Y is selected from the group consisting of methoxyethyl and methoxymethyl;

$R^1$ is selected from the group consisting of chlorine, methyl, trifluoromethyl and methylsulfonyl;

$R^2$ is selected from the group consisting of hydrogen, Cl, F, methyl, methylsulfonyl, methylsulfinyl, methylsulfanyl, 3-isoxazolinyl, 5-methyl-3-isoxazolinyl, 5-isoxazolinyl, 3-methyl-5-isoxazolinyl, 3-isoxazolyl, 5-methyl-3-isoxazolyl, 5-isoxazolyl and 3-methyl-5-isoxazolyl;

$R^3$ is selected from the group consisting of hydrogen, fluorine, chlorine, trifluoromethyl, CN and methylsulfonyl;

and either $R^4$ is hydrogen and $R^5$ is chlorine or fluorine, or $R^5$ is hydrogen and $R^4$ is chlorine or fluorine.

According to a preferred embodiment of the invention the radicals $R^1$, $R^2$, $R^3$, $R^4$ and $R^5$ together form one of the following substitution patterns on the phenyl ring of compounds of formula I or formula II, provided that position 1 is the attachment point of the phenyl ring to the remainder of the molecule:

2-Br-4,6-$Cl_2$, 2,6-$Cl_2$-4-CN, 2,4,6-$Cl_3$, 2,6-$Cl_2$-4-F, 2,6-$Cl_2$-4-$CF_3$, 2,6-$Cl_2$-4-$S(O)_2CH_3$, 2-$CF_3$-4-CN-6-Cl, 2-$CF_3$-4,6-$Cl_2$, 2-$CF_3$-4-$CF_3$-6-Cl, 2-$CF_3$-4-$S(O)_2CH_3$-6-Cl, 2-$CF_3$-4-F-6-Cl, 2-$CH_3$—CN-6-Cl, 2-$CH_3$-4,6-$Cl_2$, 2-$CH_3$-

4-CF₃-6-Cl, 2-CH₃-4-S(O)₂CH₃-6-Cl, 2-CH₃-4-F-6-Cl, 2-S(O)₂CH₃-4-CN-6-Cl, 2-S(O)₂CH₃-4,6-Cl₂, 2-S(O)₂CH₃-4-CF₃-6-Cl, 2-S(O)₂CH₃-4-S(O)₂CH₃-6-Cl, 2-S(O)₂CH₃-4-F-6-Cl, 2-Cl-4-CN-6-F, 2-Cl-4-CF₃-6-F, 2-Cl-4-S(O)₂CH₃-6-F, 2,4-Cl₂-6-F, 2-Cl-4,6-F₂, 2-CF₃-4-CN-6-F, 2-CF₃-4-CF₃-6-F, 2-CF₃-4-S(O)₂CH₃-6-F, 2-CF₃-4-Cl-6-F, 2-CF₃-4,6-F₂, 2-CH₃-4-CN-6-F, 2-CH₃-4-CF₃-6-F, 2-CH₃-4-S(O)₂CH₃-6-F, 2-CH₃-4-Cl-6-F, 2-CH₃-4,6-F₂, 2-S(O)₂CH₃-4-CN-6-F, 2-S(O)₂CH₃-4-CF₃-6-F, 2-S(O)₂CH₃-4-S(O)₂CH₃-6-F, 2-S(O)₂CH₃-4-Cl-6-F, 2-S(O)₂CH₃-4,6-F₂, 2,5-Cl₂-4-CN, 2,4,5-Cl₃, 2,5-Cl₂-4-F, 2,5-Cl₂-4-CF₃, 2,5-Cl₂-4-S(O)₂CH₃, 2-CF₃-4-CN-5-Cl, 2-CF₃-4,5-C₂, 2-CF₃-4-CF₃-5-Cl, 2-CF₃-4-S(O)₂CH₃-5-Cl, 2-CF₃-4-F-5-Cl, 2-CH₃-4-CN-5-Cl, 2-CH₃-4,5-C₂, 2-CH₃-4-CF₃-5-Cl, 2-CH₃-4-S(O)₂CH₃-5-Cl, 2-CH₃-4-F-5-Cl, 2-S(O)₂CH₃-4-CN-5-Cl, 2-S(O)₂CH₃-4,5-C₂, 2-S(O)₂CH₃-4-CF₃-5-Cl, 2-S(O)₂CH₃-4-S(O)₂CH₃-5-Cl, 2-S(O)₂CH₃-4-F-5-Cl, 2-Cl-4-CN-5-F, 2-Cl-4-CF₃-5-F, 2-Cl-4-S(O)₂CH₃-5-F, 2,4-Cl₂-5-F, 2-C₁₋₄,5-F₂, 2-CF₃-4-CN-5-F, 2-CF₃-4-CF₃-5-F, 2-CF₃-4-S(O)₂CH₃-5-F, 2-CF₃-4-Cl-5-F, 2-CF₃-4,5-F₂, 2-CH₃-4-CN-5-F, 2-CH₃-4-CF₃-5-F, 2-CH₃-4-S(O)₂CH₃-5-F, 2-CH₃-4-Cl-5-F, 2-CH₃-4,5-F₂, 2-S(O)₂CH₃-4-CN-5-F, 2-S(O)₂CH₃-4-CF₃-5-F, 2-S(O)₂CH₃-4-S(O)₂CH₃-5-F, 2-S(O)₂CH₃-4-Cl-5-F or 2-S(O)₂CH₃-4,5-F₂.

According to another preferred embodiment of the invention the radicals R¹, R², R³, R⁴ and R⁵ together form one of the following substitution patterns on the phenyl ring of compounds of formula I or formula II, provided that position 1 is the attachment point of the phenyl ring to the remainder of the molecule:

2,6-Cl₂-3-(3-isoxazolinyl)-4-CN, 2,4,6-Cl₃-3-(3-isoxazolinyl), 2,6-Cl₂-3-(3-isoxazolinyl)-4-F, 2,6-Cl₂-(3-isoxazolinyl)-4-CF₃, 2,6-Cl₂-3-(3-isoxazolinyl)-4-S(O)₂CH₃, 2-CF₃-3-(3-isoxazolinyl)-4-CN-6-Cl, 2-CF₃-3-(3-isoxazolinyl)-4,6-Cl₂, 2-CF₃₋₃-(3-isoxazolinyl)-4-CF₃-6-Cl, 2-CF₃-3-(3-isoxazlinyl)-4-S(O)₂CH₃-6-Cl, 2-CF₃-3-(3-isoxazolinyl)-4-F-6-Cl, 2-CH₃-3-(3-isoxazolinyl)-4-CN-6-Cl, 2-CH₃-3-(3-isoxazolinyl)-4,6-Cl₂, 2-CH₃-3-(3-isoxazlinyl)-4-CF₃-6-Cl, 2-CH₃-3-(3-isoxazlinyl)-4-S(O)₂CH₃-6-Cl, 2-CH₃-3-(3-isoxazlinyl)-4-F-6-Cl, 2-S(O)₂CH₃-3-(3-isoxazolinyl)-4-CN-6-Cl, 2-S(O)₂CH₃-3-(3-isoxazolinyl)-4,6-Cl₂, 2-S(O)₂CH₃-3-(3-isoxazolinyl)-4-CF₃-6-Cl, 2-S(O)₂CH₃-3-(3-isoxazolinyl)-4-S(O)₂CH₃-6-Cl, 2-S(O)₂CH₃-3-(3-isoxazolinyl)-4-F-6-Cl, 2-Cl-3-(3-isoxazolinyl)-4-CN-6-F, 2-Cl-3-(3-isoxazolinyl)-4-CF₃-6-F, 2-Cl-3-(3-isoxazolinyl)-4-S(O) 2C H₃-6-F, 2,4-Cl₂-3-(3-isoxazolinyl)-6-F, 2-Cl-3-(3-isoxazolinyl)-4,6-F₂, 2-CF₃-3-(3-isoxazolinyl)-4-CN-6-F, 2-CF₃-3-(3-isoxazolinyl)-4-CF₃-6-F, 2-CF₃-3-(3-isoxazlinyl)-4-S(O)₂CH₃-6-F, 2-CF₃-3-(3-isoxazolinyl)-4-Cl-6-F, 2-CF₃-3-(3-isoxazlinyl)-4,6-F₂, 2-CH₃-3-(3-isoxazolinyl)-4-CN-6-F, 2-CH₃-3-(3-isoxazolinyl)-4-CF₃-6-F, 2-CH₃-3-(3-isoxazolinyl)-4-S(O)₂CH₃-6-F, 2-CH₃-3-(3-isoxazolinyl)-4-Cl-6-F, 2-CH₃-3-(3-isoxazolinyl)-4,6-F₂, 2-S(O)₂CH₃-3-(3-isoxazolinyl)-4-CN-6-F, 2-S(O)₂CH₃-3-(3-isoxazolinyl)-4-CF₃-6-F, 2-S(O)₂CH₃-3-(3-isoxazolinyl)-4-S(O)₂CH₃-6-F, 2-S(O)₂CH₃-3-(3-isoxazolinyl)-4-Cl-6-F, 2-S(O)₂CH₃-3-(3-isoxazolinyl)-4,6-F₂, 2,5-Cl₂-3-(3-isoxazolinyl)-4-CN, 2,4,5-Cl₃-3-(3-isoxazolinyl), 2,5-Cl₂-3-(3-isoxazolinyl)-4-F, 2,5-Cl₂-3-(3-isoxazolinyl)-4-CF₃, 2,5-Cl₂-3-(3-isoxazolinyl)-4-S(O)₂CH₃, 2-CF₃-3-(3-isoxazlinyl)-4-CN-5-Cl, 2-CF₃-3-(3-isoxazolinyl)-4,5-Cl₂, 2-CF₃-3-(3-isoxazlinyl)-4-CF₃-5-Cl, 2-CF₃-3-(3-isoxazlinyl)-4-S(O)₂CH₃-5-Cl, 2-CF₃-3-(3-isoxazlinyl)-4-F-5-Cl, 2-CH₃-3-(3-isoxazolinyl)-4-CN-5-Cl, 2-CH₃-3-(3-isoxazolinyl)-4,5-Cl₂, 2-CH₃-3-(3-isoxazlinyl)-4-CF₃-5-Cl, 2-CH₃-3-(3-isoxazlinyl)-4-S(O)₂CH₃-5-Cl, 2-CH₃-3-(3-isoxazolinyl)-4-F-5-Cl, 2-S(O)₂CH₃-3-(3-isoxazolinyl)-4-CN-5-Cl, 2-S(O)₂CH₃-3-(3-isoxazolinyl)-4,5-Cl₂, 2-S(O)₂CH₃-3-(3-isoxazolinyl)-4-CF₃-5-Cl, 2-S(O)₂CH₃-3-(3-isoxazolinyl)-4-S(O)₂CH₃-5-Cl, 2-S(O)₂CH₃-3-(3-isoxazolinyl)-4-F-5-Cl, 2-Cl-3-(3-isoxazolinyl)-4-CN-5-F, 2-Cl-3-(3-isoxazolinyl)-4-CF₃-5-F, 2-Cl-3-(3-isoxazolinyl)-4-S(O)₂CH₃-5-F, 2,4-Cl₂-3-(3-isoxazolinyl)-5-F, 2-Cl-3-(3-isoxazolinyl)-4,5-F₂, 2-CF₃-3-(3-isoxazolinyl)-4-CN-5-F, 2-CF₃-3-(3-isoxazolinyl)-4-CF₃-5-F, 2-CF₃-3-(3-isoxazlinyl)-4-S(O)₂CH₃-5-F, 2-CF₃-3-(3-isoxazolinyl)-4-Cl-5-F, 2-CF₃-3-(3-isoxazlinyl)-4,5-F₂, 2-CH₃-3-(3-isoxazolinyl)-4-CN-5-F, 2-CH₃-3-(3-isoxazlinyl)-4-CF₃-5-F, 2-CH₃-3-(3-isoxazolinyl)-4-S(O)₂CH₃-5-F, 2-CH₃-3-(3-isoxazolinyl)-4-Cl-5-F, 2-CH₃-3-(3-isoxazolinyl)-4,5-F₂, 2-S(O)₂CH₃-3-(3-isoxazolinyl)-4-CN-5-F, 2-S(O)₂CH₃-3-(3-isoxazolinyl)-4-CF₃-5-F, 2-S(O)₂CH₃-3-(3-isoxazolinyl)-4-S(O)₂CH₃-5-F, 2-S(O)₂CH₃-3-(3-isoxazlinyl)-4,5-F₂, 2,6-Cl₂-3-(CH₂—O—CH₂CF₃)-4-CN, 2,4,6-Cl₃-3-(3-isoxazolinyl), 2,6-Cl₂-3-(CH₂—O—CH₂CF₃)-4-F, 2,6-Cl₂-3-(CH₂—O—CH₂CF₃)-4-CF₃, 2,6-Cl₂-3-(CH₂—O—CH₂CF₃)-4-S(O)₂CH₃, 2-CF₃-3-(CH₂—O—CH₂CF₃)-4-CN-6-Cl, 2-CF₃-3-(CH₂—O—CH₂CF₃)-4,6-C₂, 2-CF₃-3-(CH₂—O—CH₂CF₃)-4-CF₃-6-Cl, 2-CF₃-3-(CH₂—O—CH₂CF₃)-4-S(O)₂CH₃-6-Cl, 2-CF₃-3-(CH₂—O—CH₂CF₃)-4-F-6-Cl, 2-CH₃-3-(CH₂—O—CH₂CF₃)-4-CN-6-Cl, 2-CH₃-3-(CH₂—O—CH₂CF₃)-4,6-C₂, 2-CH₃-3-(CH₂—O—CH₂CF₃)-4-CF₃-6-Cl, 2-CH₃-3-(CH₂—O—CH₂CF₃)-4-S(O)₂CH₃-6-Cl, 2-CH₃-3-(CH₂—O—CH₂CF₃)-4-F-6-Cl, 2-S(O)₂CH₃-3-(CH₂—O—CH₂CF₃)-4-CN-6-Cl, 2-S(O)₂CH₃-3-(CH₂—O—CH₂CF₃)-4,6-C₂, 2-S(O)₂CH₃-3-(CH₂—O—CH₂CF₃)-4-CF₃-6-Cl, 2-S(O)₂CH₃-3-(CH₂—O—CH₂CF₃)-4-S(O)₂CH₃-6-Cl, 2-S(O)₂CH₃-3-(CH₂—O—CH₂CF₃)-4-F-6-Cl, 2-Cl-3-(CH₂—O—CH₂CF₃)-4-CN-6-F, 2-Cl-3-(CH₂—O—CH₂CF₃)-4-CF₃-6-F, 2-Cl-3-(CH₂—O—CH₂CF₃)-4-S(O)₂CH₃-6-F, 2,4-Cl₂-3-(CH₂—O—CH₂CF₃)-6-F, 2-Cl-3-(CH₂—O—CH₂CF₃)-4,6-F₂, 2-CF₃-3-(CH₂—O—CH₂CF₃)-4-CN-6-F, 2-CF₃-3-(CH₂—O—CH₂CF₃)-4-CF₃-6-F, 2-CF₃-3-(CH₂—O—CH₂CF₃)-4-S(O)₂CH₃-6-F, 2-CF₃-3-(CH₂—O—CH₂CF₃)-4-Cl-6-F, 2-CF₃-3-(CH₂—O—CH₂CF₃)4,6-F₂, 2-CH₃-3-(CH₂—O—CH₂CF₃)-4-CN-6-F, 2-CH₃-3-(CH₂—O—CH₂CF₃)-4-CF₃-6-F, 2-CH₃-3-(CH₂—O—CH₂CF₃)-4-S(O)₂CH₃-6-F, 2-CH₃-3-(CH₂—O—CH₂CF₃)-4-Cl-6-F, 2-CH₃-3-(CH₂—O—CH₂CF₃)4,6-F₂, 2-S(O)₂CH₃-3-(CH₂—O—CH₂CF₃)-4-CN-6-F, 2-S(O)₂CH₃-3-(CH₂—O—CH₂CF₃)-4-CF₃-6-F, 2-S(O)₂CH₃-3-(CH₂—O—CH₂CF₃)-4-S(O)₂CH₃-6-F, 2-S(O)₂CH₃-3-(CH₂—O—CH₂CF₃)-4-Cl-6-F, 2-S(O)₂CH₃-3-(CH₂—O—CH₂CF₃)4, 6- F₂, 2,5-Cl₂-3-(CH₂—O—CH₂CF₃)-4-CN, 2,4,5-Cl₃-3-(CH₂—O—CH₂CF₃), 2,5-Cl₂-3-(CH₂—O—CH₂CF₃)-4-F, 2,5-Cl₂-3-(CH₂—O—CH₂CF₃)-4-CF₃, 2,5-Cl₂-3-(CH₂—O—CH₂CF₃)-4-S(O)₂CH₃, 2-CF₃-3-(CH₂—O—CH₂CF₃)-4-CN-5-Cl, 2-CF₃-3-(CH₂—O—CH₂CF₃)-4,5-C₂, 2-CF₃-3-(CH₂—O—CH₂CF₃)-4-CF₃-5-Cl, 2-CF₃-3-(CH₂—O—CH₂CF₃)-4-S(O)₂CH₃-5-Cl, 2-CF₃-3-(CH₂—O—CH₂CF₃)-4-F-5-Cl, 2-CH₃-3-(CH₂—O—CH₂CF₃)-4-CN-5-Cl, 2-CH₃-3-(CH₂—O—CH₂CF₃)-4,5-C₂, 2-CH₃-3-(CH₂—O—CH₂CF₃)-4-CF₃-5-Cl, 2-CH₃-3-(CH₂—O—CH₂CF₃)-4-S(O)₂CH₃-5-Cl, 2-CH₃-3-(CH₂—O—CH₂CF₃)-4-F-5-Cl, 2-S(O)₂CH₃-3-(CH₂—O—CH₂CF₃)-4-CN-5-Cl, 2-S(O)₂CH₃-3-(CH₂—O—CH₂CF₃)-4,5-Cl₂, 2-S(O)₂CH₃-3-(CH₂—O—CH₂CF₃)-4-CF₃-5-Cl, 2-S(O)₂CH₃-3-(CH₂—O—CH₂CF₃)-4-S(O)₂CH₃-5-Cl, 2-S(O)₂CH₃-3-(CH₂—O—CH₂CF₃)-4-F-5-Cl, 2-Cl-3-(CH₂—O—CH₂CF₃)-4-CN-5-F, 2-Cl-3-(CH₂—O—CH₂CF₃)-4-CF₃-5-F, 2-Cl-3-(CH₂—O—CH₂CF₃)-4-S(O)₂CH₃-5-F, 2,4-Cl₂-3-(CH₂—O—CH₂CF₃)-5-F, 2-Cl-3-(CH₂—O—CH₂CF₃)-4,5-F₂, 2-CF₃-3-(CH₂—O—CH₂CF₃)-4-CN-5-F, 2-CF₃-3-

(CH₂—O—CH₂CF₃)-4-CF₃-5-F, 2-CF₃-3-(CH₂—O—CH₂CF₃)-4-S(O)₂CH₃-5-F, 2-CF₃-3-(CH₂—O—CH₂CF₃)-4-Cl-5-F, 2-CF₃-3-(CH₂—O—CH₂CF₃)-4,5-F₂, 2-CH₃-3-(CH₂—O—CH₂CF₃)-4-CN-5-F, 2-CH₃-3-(CH₂—O—CH₂CF₃)-4-CF₃-5-F, 2-CH₃-3-(CH₂—O—CH₂CF₃)-4-S(O)₂CH₃-5-F, 2-CH₃-3-(CH₂—O—CH₂CF₃)-4-Cl-5-F, 2-CH₃-3-(CH₂—O—CH₂CF₃)-4,5-F₂, 2-S(O)₂CH₃-3-(CH₂—O—CH₂CF₃)-4-CN-5-F, 2-S(O)₂CH₃-3-(CH₂—O—CH₂CF₃)-4-CF₃-5-F, 2-S(O)₂CH₃-3-(CH₂—O—CH₂CF₃)-4-S(O)₂CH₃-5-F, 2-S(O)₂CH₃-3-(CH₂—O—CH₂CF₃)-4-Cl-5-F or 2-S(O)₂CH₃-3-(CH₂—O—CH₂CF₃)-4,5- F₂.

Examples of preferred compounds are the individual compounds compiled in Tables 1 to 10 below. Moreover, the meanings mentioned below for the individual variables in the Tables are per se, independently of the combination in which they are mentioned, a particularly preferred embodiment of the substituents in question.

Table 1 Compounds of formula I (1.A-1-1.A-1442) in which X is methyl and the combination of $R^1$, $R^2$, $R^3$, $R^4$ and $R^5$ for a compound corresponds in each case to one row of Table A;

Table 2 Compounds of formula I (2.A-1-2.A-1442) in which X is ethyl and the combination of $R^1$, $R^2$, $R^3$, $R^4$ and $R^5$ for a compound corresponds in each case to one row of Table A;

Table 3 Compounds of formula II (3.A-1-3.A-1442) in which B is CH and Y is methyl and the combination of $R^1$, $R^2$, $R^3$, $R^4$ and $R^5$ for a compound corresponds in each case to one row of Table A;

Table 4 Compounds of formula II (4.A-1-4.A-1442) in which B is CH and Y is ethyl and the combination of $R^1$, $R^2$, $R^3$, $R^4$ and $R^5$ for a compound corresponds in each case to one row of Table A;

Table 5 Compounds of formula II (5.A-1-5.A-1442) in which B is CH and Y is methoxymethyl and the combination of $R^1$, $R^2$, $R^3$, $R^4$ and $R^5$ for a compound corresponds in each case to one row of Table A;

Table 6 Compounds of formula II (6.A-1-6.A-1442) in which B is CH and Y is methoxyethyl and the combination of $R^1$, $R^2$, $R^3$, $R^4$ and $R^5$ for a compound corresponds in each case to one row of Table A;

Table 7 Compounds of formula II (7.A-1-7.A-1442) in which B is N and Y is methyl and the combination of $R^1$, $R^2$, $R^3$, $R^4$ and $R^5$ for a compound corresponds in each case to one row of Table A;

Table 8 Compounds of formula II (8.A-1-8.A-1442) in which B is N and Y is ethyl and the combination of $R^1$, $R^2$, $R^3$, $R^4$ and $R^5$ for a compound corresponds in each case to one row of Table A;

Table 9 Compounds of formula II (9.A-1-9.A-1442) in which B is N and Y is methoxymethyl and the combination of $R^1$, $R^2$, $R^3$, $R^4$ and $R^5$ for a compound corresponds in each case to one row of Table A;

Table 10 Compounds of formula II (10.A-1-10.A-1442) in which B is N and Y is methoxyethyl and the combination of $R^1$, $R^2$, $R^3$, $R^4$ and $R^5$ for a compound corresponds in each case to one row of Table A;

TABLE A

| | $R^1$ | $R^2$ | $R^3$ | $R^4$ | $R^5$ |
|---|---|---|---|---|---|
| A-1 | Cl | H | Cl | H | F |
| A-2 | Cl | H | Cl | H | Cl |
| A-3 | Cl | H | Cl | F | F |
| A-4 | Cl | H | Cl | F | Cl |
| A-5 | Cl | H | Cl | F | H |
| A-6 | Cl | H | Cl | Cl | F |
| A-7 | Cl | H | Cl | Cl | Cl |
| A-8 | Cl | H | Cl | Cl | H |
| A-9 | Cl | H | F | H | F |
| A-10 | Cl | H | F | H | Cl |
| A-11 | Cl | H | F | F | F |
| A-12 | Cl | H | F | F | Cl |
| A-13 | Cl | H | F | F | H |
| A-14 | Cl | H | F | Cl | F |
| A-15 | Cl | H | F | Cl | Cl |
| A-16 | Cl | H | F | Cl | H |
| A-17 | Cl | H | CF₃ | H | F |
| A-18 | Cl | H | CF₃ | H | Cl |
| A-19 | Cl | H | CF₃ | F | F |
| A-20 | Cl | H | CF₃ | F | Cl |
| A-21 | Cl | H | CF₃ | F | H |
| A-22 | Cl | H | CF₃ | Cl | F |
| A-23 | Cl | H | CF₃ | Cl | Cl |
| A-24 | Cl | H | CF₃ | Cl | H |
| A-25 | Cl | H | SO₂CH₃ | H | F |
| A-26 | Cl | H | SO₂CH₃ | H | Cl |
| A-27 | Cl | H | SO₂CH₃ | F | F |
| A-28 | Cl | H | SO₂CH₃ | F | Cl |
| A-29 | Cl | H | SO₂CH₃ | F | H |
| A-30 | Cl | H | SO₂CH₃ | Cl | F |
| A-31 | Cl | H | SO₂CH₃ | Cl | Cl |
| A-32 | Cl | H | SO₂CH₃ | Cl | H |
| A-33 | Cl | H | CN | H | F |
| A-34 | Cl | H | CN | H | Cl |
| A-35 | Cl | H | CN | F | F |
| A-36 | Cl | H | CN | F | Cl |
| A-37 | Cl | H | CN | F | H |
| A-38 | Cl | H | CN | Cl | F |
| A-39 | Cl | H | CN | Cl | Cl |
| A-40 | Cl | H | CN | Cl | H |
| A-41 | Cl | SO₂CH₃ | Cl | H | F |
| A-42 | Cl | SO₂CH₃ | Cl | H | Cl |
| A-43 | Cl | SO₂CH₃ | Cl | F | F |
| A-44 | Cl | SO₂CH₃ | Cl | F | Cl |
| A-45 | Cl | SO₂CH₃ | Cl | F | H |
| A-46 | Cl | SO₂CH₃ | Cl | Cl | F |
| A-47 | Cl | SO₂CH₃ | Cl | Cl | Cl |
| A-48 | Cl | SO₂CH₃ | Cl | Cl | H |
| A-49 | Cl | SO₂CH₃ | F | H | F |
| A-50 | Cl | SO₂CH₃ | F | H | Cl |
| A-51 | Cl | SO₂CH₃ | F | F | F |
| A-52 | Cl | SO₂CH₃ | F | F | Cl |
| A-53 | Cl | SO₂CH₃ | F | F | H |
| A-54 | Cl | SO₂CH₃ | F | Cl | F |
| A-55 | Cl | SO₂CH₃ | F | Cl | Cl |
| A-56 | Cl | SO₂CH₃ | F | Cl | H |
| A-57 | Cl | SO₂CH₃ | CF₃ | H | F |
| A-58 | Cl | SO₂CH₃ | CF₃ | H | Cl |
| A-59 | Cl | SO₂CH₃ | CF₃ | F | F |
| A-60 | Cl | SO₂CH₃ | CF₃ | F | Cl |
| A-61 | Cl | SO₂CH₃ | CF₃ | F | H |
| A-62 | Cl | SO₂CH₃ | CF₃ | Cl | F |
| A-63 | Cl | SO₂CH₃ | CF₃ | Cl | Cl |
| A-64 | Cl | SO₂CH₃ | CF₃ | Cl | H |
| A-65 | Cl | SO₂CH₃ | SO₂CH₃ | H | F |
| A-66 | Cl | SO₂CH₃ | SO₂CH₃ | H | Cl |
| A-67 | Cl | SO₂CH₃ | SO₂CH₃ | F | F |
| A-68 | Cl | SO₂CH₃ | SO₂CH₃ | F | Cl |
| A-69 | Cl | SO₂CH₃ | SO₂CH₃ | F | H |
| A-70 | Cl | SO₂CH₃ | SO₂CH₃ | Cl | F |
| A-71 | Cl | SO₂CH₃ | SO₂CH₃ | Cl | Cl |
| A-72 | Cl | SO₂CH₃ | SO₂CH₃ | Cl | H |
| A-73 | Cl | SO₂CH₃ | CN | H | F |
| A-74 | Cl | SO₂CH₃ | CN | H | Cl |
| A-75 | Cl | SO₂CH₃ | CN | F | F |
| A-76 | Cl | SO₂CH₃ | CN | F | Cl |
| A-77 | Cl | SO₂CH₃ | CN | F | H |
| A-78 | Cl | SO₂CH₃ | CN | Cl | F |
| A-79 | Cl | SO₂CH₃ | CN | Cl | Cl |
| A-80 | Cl | SO₂CH₃ | CN | Cl | H |
| A-81 | Cl | CH₂OCH₂CF₃ | Cl | H | F |
| A-82 | Cl | CH₂OCH₂CF₃ | Cl | H | Cl |

TABLE A-continued

| | R¹ | R² | R³ | R⁴ | R⁵ |
|---|---|---|---|---|---|
| A-83 | Cl | CH₂OCH₂CF₃ | Cl | F | F |
| A-84 | Cl | CH₂OCH₂CF₃ | Cl | F | Cl |
| A-85 | Cl | CH₂OCH₂CF₃ | Cl | F | H |
| A-86 | Cl | CH₂OCH₂CF₃ | Cl | Cl | F |
| A-87 | Cl | CH₂OCH₂CF₃ | Cl | Cl | Cl |
| A-88 | Cl | CH₂OCH₂CF₃ | Cl | Cl | H |
| A-89 | Cl | CH₂OCH₂CF₃ | F | H | F |
| A-90 | Cl | CH₂OCH₂CF₃ | F | H | Cl |
| A-91 | Cl | CH₂OCH₂CF₃ | F | F | F |
| A-92 | Cl | CH₂OCH₂CF₃ | F | F | Cl |
| A-93 | Cl | CH₂OCH₂CF₃ | F | F | H |
| A-94 | Cl | CH₂OCH₂CF₃ | F | Cl | F |
| A-95 | Cl | CH₂OCH₂CF₃ | F | Cl | Cl |
| A-96 | Cl | CH₂OCH₂CF₃ | F | Cl | H |
| A-97 | Cl | CH₂OCH₂CF₃ | CF₃ | H | F |
| A-98 | Cl | CH₂OCH₂CF₃ | CF₃ | H | Cl |
| A-99 | Cl | CH₂OCH₂CF₃ | CF₃ | F | F |
| A-100 | Cl | CH₂OCH₂CF₃ | CF₃ | F | Cl |
| A-101 | Cl | CH₂OCH₂CF₃ | CF₃ | F | H |
| A-102 | Cl | CH₂OCH₂CF₃ | CF₃ | Cl | F |
| A-103 | Cl | CH₂OCH₂CF₃ | CF₃ | Cl | Cl |
| A-104 | Cl | CH₂OCH₂CF₃ | CF₃ | Cl | H |
| A-105 | Cl | CH₂OCH₂CF₃ | SO₂CH₃ | H | F |
| A-106 | Cl | CH₂OCH₂CF₃ | SO₂CH₃ | H | Cl |
| A-107 | Cl | CH₂OCH₂CF₃ | SO₂CH₃ | F | F |
| A-108 | Cl | CH₂OCH₂CF₃ | SO₂CH₃ | F | Cl |
| A-109 | Cl | CH₂OCH₂CF₃ | SO₂CH₃ | F | H |
| A-110 | Cl | CH₂OCH₂CF₃ | SO₂CH₃ | Cl | F |
| A-111 | Cl | CH₂OCH₂CF₃ | SO₂CH₃ | Cl | Cl |
| A-112 | Cl | CH₂OCH₂CF₃ | SO₂CH₃ | Cl | H |
| A-113 | Cl | CH₂OCH₂CF₃ | CN | H | F |
| A-114 | Cl | CH₂OCH₂CF₃ | CN | H | Cl |
| A-115 | Cl | CH₂OCH₂CF₃ | CN | F | F |
| A-116 | Cl | CH₂OCH₂CF₃ | CN | F | Cl |
| A-117 | Cl | CH₂OCH₂CF₃ | CN | F | H |
| A-118 | Cl | CH₂OCH₂CF₃ | CN | Cl | F |
| A-119 | Cl | CH₂OCH₂CF₃ | CN | Cl | Cl |
| A-120 | Cl | CH₂OCH₂CF₃ | CN | Cl | H |
| A-121 | Cl | Isoxazolin-3-yl | Cl | H | F |
| A-122 | Cl | Isoxazolin-3-yl | Cl | H | Cl |
| A-123 | Cl | Isoxazolin-3-yl | Cl | F | F |
| A-124 | Cl | Isoxazolin-3-yl | Cl | F | Cl |
| A-125 | Cl | Isoxazolin-3-yl | Cl | F | H |
| A-126 | Cl | Isoxazolin-3-yl | Cl | Cl | F |
| A-127 | Cl | Isoxazolin-3-yl | Cl | Cl | Cl |
| A-128 | Cl | Isoxazolin-3-yl | Cl | Cl | H |
| A-129 | Cl | Isoxazolin-3-yl | F | H | F |
| A-130 | Cl | Isoxazolin-3-yl | F | H | Cl |
| A-131 | Cl | Isoxazolin-3-yl | F | F | F |
| A-132 | Cl | Isoxazolin-3-yl | F | F | Cl |
| A-133 | Cl | Isoxazolin-3-yl | F | F | H |
| A-134 | Cl | Isoxazolin-3-yl | F | Cl | F |
| A-135 | Cl | Isoxazolin-3-yl | F | Cl | Cl |
| A-136 | Cl | Isoxazolin-3-yl | F | Cl | H |
| A-137 | Cl | Isoxazolin-3-yl | CF₃ | H | F |
| A-138 | Cl | Isoxazolin-3-yl | CF₃ | H | Cl |
| A-139 | Cl | Isoxazolin-3-yl | CF₃ | F | F |
| A-140 | Cl | Isoxazolin-3-yl | CF₃ | F | Cl |
| A-141 | Cl | Isoxazolin-3-yl | CF₃ | F | H |
| A-142 | Cl | Isoxazolin-3-yl | CF₃ | Cl | F |
| A-143 | Cl | Isoxazolin-3-yl | CF₃ | Cl | Cl |
| A-144 | Cl | Isoxazolin-3-yl | CF₃ | Cl | H |
| A-145 | Cl | Isoxazolin-3-yl | SO₂CH₃ | H | F |
| A-146 | Cl | Isoxazolin-3-yl | SO₂CH₃ | H | Cl |
| A-147 | Cl | Isoxazolin-3-yl | SO₂CH₃ | F | F |
| A-148 | Cl | Isoxazolin-3-yl | SO₂CH₃ | F | Cl |
| A-149 | Cl | Isoxazolin-3-yl | SO₂CH₃ | F | H |
| A-150 | Cl | Isoxazolin-3-yl | SO₂CH₃ | Cl | F |
| A-151 | Cl | Isoxazolin-3-yl | SO₂CH₃ | Cl | Cl |
| A-152 | Cl | Isoxazolin-3-yl | SO₂CH₃ | Cl | H |
| A-153 | Cl | Isoxazolin-3-yl | CN | H | F |
| A-154 | Cl | Isoxazolin-3-yl | CN | H | Cl |
| A-155 | Cl | Isoxazolin-3-yl | CN | F | F |
| A-156 | Cl | Isoxazolin-3-yl | CN | F | Cl |
| A-157 | Cl | Isoxazolin-3-yl | CN | F | H |
| A-158 | Cl | Isoxazolin-3-yl | CN | Cl | F |
| A-159 | Cl | Isoxazolin-3-yl | CN | Cl | Cl |
| A-160 | Cl | Isoxazolin-3-yl | CN | Cl | H |
| A-161 | Cl | 5-Methyl-isoxazolin-3-yl | Cl | H | F |
| A-162 | Cl | 5-Methyl-isoxazolin-3-yl | Cl | H | Cl |
| A-163 | Cl | 5-Methyl-isoxazolin-3-yl | Cl | F | F |
| A-164 | Cl | 5-Methyl-isoxazolin-3-yl | Cl | F | Cl |
| A-165 | Cl | 5-Methyl-isoxazolin-3-yl | Cl | F | H |
| A-166 | Cl | 5-Methyl-isoxazolin-3-yl | Cl | Cl | F |
| A-167 | Cl | 5-Methyl-isoxazolin-3-yl | Cl | Cl | Cl |
| A-168 | Cl | 5-Methyl-isoxazolin-3-yl | Cl | Cl | H |
| A-169 | Cl | 5-Methyl-isoxazolin-3-yl | F | H | F |
| A-170 | Cl | 5-Methyl-isoxazolin-3-yl | F | H | Cl |
| A-171 | Cl | 5-Methyl-isoxazolin-3-yl | F | F | F |
| A-172 | Cl | 5-Methyl-isoxazolin-3-yl | F | F | Cl |
| A-173 | Cl | 5-Methyl-isoxazolin-3-yl | F | F | H |
| A-174 | Cl | 5-Methyl-isoxazolin-3-yl | F | Cl | F |
| A-175 | Cl | 5-Methyl-isoxazolin-3-yl | F | Cl | Cl |
| A-176 | Cl | 5-Methyl-isoxazolin-3-yl | F | Cl | H |
| A-177 | Cl | 5-Methyl-isoxazolin-3-yl | CF₃ | H | F |
| A-178 | Cl | 5-Methyl-isoxazolin-3-yl | CF₃ | H | Cl |
| A-179 | Cl | 5-Methyl-isoxazolin-3-yl | CF₃ | F | F |
| A-180 | Cl | 5-Methyl-isoxazolin-3-yl | CF₃ | F | Cl |
| A-181 | Cl | 5-Methyl-isoxazolin-3-yl | CF₃ | F | H |
| A-182 | Cl | 5-Methyl-isoxazolin-3-yl | CF₃ | Cl | F |
| A-183 | Cl | 5-Methyl-isoxazolin-3-yl | CF₃ | Cl | Cl |
| A-184 | Cl | 5-Methyl-isoxazolin-3-yl | CF₃ | Cl | H |
| A-185 | Cl | 5-Methyl-isoxazolin-3-yl | SO₂CH₃ | H | F |
| A-186 | Cl | 5-Methyl-isoxazolin-3-yl | SO₂CH₃ | H | Cl |
| A-187 | Cl | 5-Methyl-isoxazolin-3-yl | SO₂CH₃ | F | F |
| A-188 | Cl | 5-Methyl-isoxazolin-3-yl | SO₂CH₃ | F | Cl |
| A-189 | Cl | 5-Methyl-isoxazolin-3-yl | SO₂CH₃ | F | H |
| A-190 | Cl | 5-Methyl-isoxazolin-3-yl | SO₂CH₃ | Cl | F |
| A-191 | Cl | 5-Methyl-isoxazolin-3-yl | SO₂CH₃ | Cl | Cl |
| A-192 | Cl | 5-Methyl-isoxazolin-3-yl | SO₂CH₃ | Cl | H |
| A-193 | Cl | 5-Methyl-isoxazolin-3-yl | CN | H | F |
| A-194 | Cl | 5-Methyl-isoxazolin-3-yl | CN | H | Cl |
| A-195 | Cl | 5-Methyl-isoxazolin-3-yl | CN | F | F |
| A-196 | Cl | 5-Methyl-isoxazolin-3-yl | CN | F | Cl |
| A-197 | Cl | 5-Methyl-isoxazolin-3-yl | CN | F | H |
| A-198 | Cl | 5-Methyl-isoxazolin-3-yl | CN | Cl | F |
| A-199 | Cl | 5-Methyl-isoxazolin-3-yl | CN | Cl | Cl |
| A-200 | Cl | 5-Methyl-isoxazolin-3-yl | CN | Cl | H |
| A-201 | Cl | Isoxazol-3-yl | Cl | H | F |
| A-202 | Cl | Isoxazol-3-yl | Cl | H | Cl |
| A-203 | Cl | Isoxazol-3-yl | Cl | F | F |
| A-204 | Cl | Isoxazol-3-yl | Cl | F | Cl |
| A-205 | Cl | Isoxazol-3-yl | Cl | F | H |
| A-206 | Cl | Isoxazol-3-yl | Cl | Cl | F |
| A-207 | Cl | Isoxazol-3-yl | Cl | Cl | Cl |
| A-208 | Cl | Isoxazol-3-yl | Cl | Cl | H |
| A-209 | Cl | Isoxazol-3-yl | F | H | F |
| A-210 | Cl | Isoxazol-3-yl | F | H | Cl |
| A-211 | Cl | Isoxazol-3-yl | F | F | F |
| A-212 | Cl | Isoxazol-3-yl | F | F | Cl |
| A-213 | Cl | Isoxazol-3-yl | F | F | H |
| A-214 | Cl | Isoxazol-3-yl | F | Cl | F |
| A-215 | Cl | Isoxazol-3-yl | F | Cl | Cl |
| A-216 | Cl | Isoxazol-3-yl | F | Cl | H |
| A-217 | Cl | Isoxazol-3-yl | CF₃ | H | F |
| A-218 | Cl | Isoxazol-3-yl | CF₃ | H | Cl |
| A-219 | Cl | Isoxazol-3-yl | CF₃ | F | F |
| A-220 | Cl | Isoxazol-3-yl | CF₃ | F | Cl |
| A-221 | Cl | Isoxazol-3-yl | CF₃ | F | H |
| A-222 | Cl | Isoxazol-3-yl | CF₃ | Cl | F |
| A-223 | Cl | Isoxazol-3-yl | CF₃ | Cl | Cl |
| A-224 | Cl | Isoxazol-3-yl | CF₃ | Cl | H |
| A-225 | Cl | Isoxazol-3-yl | SO₂CH₃ | H | F |
| A-226 | Cl | Isoxazol-3-yl | SO₂CH₃ | H | Cl |
| A-227 | Cl | Isoxazol-3-yl | SO₂CH₃ | F | F |
| A-228 | Cl | Isoxazol-3-yl | SO₂CH₃ | F | Cl |
| A-229 | Cl | Isoxazol-3-yl | SO₂CH₃ | F | H |
| A-230 | Cl | Isoxazol-3-yl | SO₂CH₃ | Cl | F |
| A-231 | Cl | Isoxazol-3-yl | SO₂CH₃ | Cl | Cl |
| A-232 | Cl | Isoxazol-3-yl | SO₂CH₃ | Cl | H |
| A-233 | Cl | Isoxazol-3-yl | CN | H | F |
| A-234 | Cl | Isoxazol-3-yl | CN | H | Cl |
| A-235 | Cl | Isoxazol-3-yl | CN | F | F |
| A-236 | Cl | Isoxazol-3-yl | CN | F | Cl |
| A-237 | Cl | Isoxazol-3-yl | CN | F | H |
| A-238 | Cl | Isoxazol-3-yl | CN | Cl | F |

TABLE A-continued

| | R¹ | R² | R³ | R⁴ | R⁵ |
|---|---|---|---|---|---|
| A-239 | Cl | Isoxazol-3-yl | CN | Cl | Cl |
| A-240 | Cl | Isoxazol-3-yl | CN | Cl | H |
| A-241 | Cl | 5-Methyl-isoxazol-3-yl | Cl | H | F |
| A-242 | Cl | 5-Methyl-isoxazol-3-yl | Cl | H | Cl |
| A-243 | Cl | 5-Methyl-isoxazol-3-yl | Cl | F | F |
| A-244 | Cl | 5-Methyl-isoxazol-3-yl | Cl | F | Cl |
| A-245 | Cl | 5-Methyl-isoxazol-3-yl | Cl | F | H |
| A-246 | Cl | 5-Methyl-isoxazol-3-yl | Cl | Cl | F |
| A-247 | Cl | 5-Methyl-isoxazol-3-yl | Cl | Cl | Cl |
| A-248 | Cl | 5-Methyl-isoxazol-3-yl | Cl | Cl | H |
| A-249 | Cl | 5-Methyl-isoxazol-3-yl | F | H | F |
| A-250 | Cl | 5-Methyl-isoxazol-3-yl | F | H | Cl |
| A-251 | Cl | 5-Methyl-isoxazol-3-yl | F | F | F |
| A-252 | Cl | 5-Methyl-isoxazol-3-yl | F | F | Cl |
| A-253 | Cl | 5-Methyl-isoxazol-3-yl | F | F | H |
| A-254 | Cl | 5-Methyl-isoxazol-3-yl | F | Cl | F |
| A-255 | Cl | 5-Methyl-isoxazol-3-yl | F | Cl | Cl |
| A-256 | Cl | 5-Methyl-isoxazol-3-yl | F | Cl | H |
| A-257 | Cl | 5-Methyl-isoxazol-3-yl | $CF_3$ | H | F |
| A-258 | Cl | 5-Methyl-isoxazol-3-yl | $CF_3$ | H | Cl |
| A-259 | Cl | 5-Methyl-isoxazol-3-yl | $CF_3$ | F | F |
| A-260 | Cl | 5-Methyl-isoxazol-3-yl | $CF_3$ | F | Cl |
| A-261 | Cl | 5-Methyl-isoxazol-3-yl | $CF_3$ | F | H |
| A-262 | Cl | 5-Methyl-isoxazol-3-yl | $CF_3$ | Cl | F |
| A-263 | Cl | 5-Methyl-isoxazol-3-yl | $CF_3$ | Cl | Cl |
| A-264 | Cl | 5-Methyl-isoxazol-3-yl | $CF_3$ | Cl | H |
| A-265 | Cl | 5-Methyl-isoxazol-3-yl | $SO_2CH_3$ | H | F |
| A-266 | Cl | 5-Methyl-isoxazol-3-yl | $SO_2CH_3$ | H | Cl |
| A-267 | Cl | 5-Methyl-isoxazol-3-yl | $SO_2CH_3$ | F | F |
| A-268 | Cl | 5-Methyl-isoxazol-3-yl | $SO_2CH_3$ | F | Cl |
| A-269 | Cl | 5-Methyl-isoxazol-3-yl | $SO_2CH_3$ | F | H |
| A-270 | Cl | 5-Methyl-isoxazol-3-yl | $SO_2CH_3$ | Cl | F |
| A-271 | Cl | 5-Methyl-isoxazol-3-yl | $SO_2CH_3$ | Cl | Cl |
| A-272 | Cl | 5-Methyl-isoxazol-3-yl | $SO_2CH_3$ | Cl | H |
| A-273 | Cl | 5-Methyl-isoxazol-3-yl | CN | H | F |
| A-274 | Cl | 5-Methyl-isoxazol-3-yl | CN | H | Cl |
| A-275 | Cl | 5-Methyl-isoxazol-3-yl | CN | F | F |
| A-276 | Cl | 5-Methyl-isoxazol-3-yl | CN | F | Cl |
| A-277 | Cl | 5-Methyl-isoxazol-3-yl | CN | F | H |
| A-278 | Cl | 5-Methyl-isoxazol-3-yl | CN | Cl | F |
| A-279 | Cl | 5-Methyl-isoxazol-3-yl | CN | Cl | Cl |
| A-280 | Cl | 5-Methyl-isoxazol-3-yl | CN | Cl | H |
| A-281 | Cl | 3-Methyl-isoxazolin-5-yl | Cl | H | F |
| A-282 | Cl | 3-Methyl-isoxazolin-5-yl | Cl | H | Cl |
| A-283 | Cl | 3-Methyl-isoxazolin-5-yl | Cl | F | F |
| A-284 | Cl | 3-Methyl-isoxazolin-5-yl | Cl | F | Cl |
| A-285 | Cl | 3-Methyl-isoxazolin-5-yl | Cl | F | H |
| A-286 | Cl | 3-Methyl-isoxazolin-5-yl | Cl | Cl | F |
| A-287 | Cl | 3-Methyl-isoxazolin-5-yl | Cl | Cl | Cl |
| A-288 | Cl | 3-Methyl-isoxazolin-5-yl | Cl | Cl | H |
| A-289 | Cl | 3-Methyl-isoxazolin-5-yl | F | H | F |
| A-290 | Cl | 3-Methyl-isoxazolin-5-yl | F | H | Cl |
| A-291 | Cl | 3-Methyl-isoxazolin-5-yl | F | F | F |
| A-292 | Cl | 3-Methyl-isoxazolin-5-yl | F | F | Cl |
| A-293 | Cl | 3-Methyl-isoxazolin-5-yl | F | F | H |
| A-294 | Cl | 3-Methyl-isoxazolin-5-yl | F | Cl | F |
| A-295 | Cl | 3-Methyl-isoxazolin-5-yl | F | Cl | Cl |
| A-296 | Cl | 3-Methyl-isoxazolin-5-yl | F | Cl | H |
| A-297 | Cl | 3-Methyl-isoxazolin-5-yl | $CF_3$ | H | F |
| A-298 | Cl | 3-Methyl-isoxazolin-5-yl | $CF_3$ | H | Cl |
| A-299 | Cl | 3-Methyl-isoxazolin-5-yl | $CF_3$ | F | F |
| A-300 | Cl | 3-Methyl-isoxazolin-5-yl | $CF_3$ | F | Cl |
| A-301 | Cl | 3-Methyl-isoxazolin-5-yl | $CF_3$ | F | H |
| A-302 | Cl | 3-Methyl-isoxazolin-5-yl | $CF_3$ | Cl | F |
| A-303 | Cl | 3-Methyl-isoxazolin-5-yl | $CF_3$ | Cl | Cl |
| A-304 | Cl | 3-Methyl-isoxazolin-5-yl | $CF_3$ | Cl | H |
| A-305 | Cl | 3-Methyl-isoxazolin-5-yl | $SO_2CH_3$ | H | F |
| A-306 | Cl | 3-Methyl-isoxazolin-5-yl | $SO_2CH_3$ | H | Cl |
| A-307 | Cl | 3-Methyl-isoxazolin-5-yl | $SO_2CH_3$ | F | F |
| A-308 | Cl | 3-Methyl-isoxazolin-5-yl | $SO_2CH_3$ | F | Cl |
| A-309 | Cl | 3-Methyl-isoxazolin-5-yl | $SO_2CH_3$ | F | H |
| A-310 | Cl | 3-Methyl-isoxazolin-5-yl | $SO_2CH_3$ | Cl | F |
| A-311 | Cl | 3-Methyl-isoxazolin-5-yl | $SO_2CH_3$ | Cl | Cl |
| A-312 | Cl | 3-Methyl-isoxazolin-5-yl | $SO_2CH_3$ | Cl | H |
| A-313 | Cl | 3-Methyl-isoxazolin-5-yl | CN | H | F |
| A-314 | Cl | 3-Methyl-isoxazolin-5-yl | CN | H | Cl |
| A-315 | Cl | 3-Methyl-isoxazolin-5-yl | CN | F | F |
| A-316 | Cl | 3-Methyl-isoxazolin-5-yl | CN | F | Cl |
| A-317 | Cl | 3-Methyl-isoxazolin-5-yl | CN | F | H |
| A-318 | Cl | 3-Methyl-isoxazolin-5-yl | CN | Cl | F |
| A-319 | Cl | 3-Methyl-isoxazolin-5-yl | CN | Cl | Cl |
| A-320 | Cl | 3-Methyl-isoxazolin-5-yl | CN | Cl | H |
| A-321 | Cl | 3-Methyl-isoxazol-5-yl | Cl | H | F |
| A-322 | Cl | 3-Methyl-isoxazol-5-yl | Cl | H | Cl |
| A-323 | Cl | 3-Methyl-isoxazol-5-yl | Cl | F | F |
| A-324 | Cl | 3-Methyl-isoxazol-5-yl | Cl | F | Cl |
| A-325 | Cl | 3-Methyl-isoxazol-5-yl | Cl | F | H |
| A-326 | Cl | 3-Methyl-isoxazol-5-yl | Cl | Cl | F |
| A-327 | Cl | 3-Methyl-isoxazol-5-yl | Cl | Cl | Cl |
| A-328 | Cl | 3-Methyl-isoxazol-5-yl | Cl | Cl | H |
| A-329 | Cl | 3-Methyl-isoxazol-5-yl | F | H | F |
| A-330 | Cl | 3-Methyl-isoxazol-5-yl | F | H | Cl |
| A-331 | Cl | 3-Methyl-isoxazol-5-yl | F | F | F |
| A-332 | Cl | 3-Methyl-isoxazol-5-yl | F | F | Cl |
| A-333 | Cl | 3-Methyl-isoxazol-5-yl | F | F | H |
| A-334 | Cl | 3-Methyl-isoxazol-5-yl | F | Cl | F |
| A-335 | Cl | 3-Methyl-isoxazol-5-yl | F | Cl | Cl |
| A-336 | Cl | 3-Methyl-isoxazol-5-yl | F | Cl | H |
| A-337 | Cl | 3-Methyl-isoxazol-5-yl | $CF_3$ | H | F |
| A-338 | Cl | 3-Methyl-isoxazol-5-yl | $CF_3$ | H | Cl |
| A-339 | Cl | 3-Methyl-isoxazol-5-yl | $CF_3$ | F | F |
| A-340 | Cl | 3-Methyl-isoxazol-5-yl | $CF_3$ | F | Cl |
| A-341 | Cl | 3-Methyl-isoxazol-5-yl | $CF_3$ | F | H |
| A-342 | Cl | 3-Methyl-isoxazol-5-yl | $CF_3$ | Cl | F |
| A-343 | Cl | 3-Methyl-isoxazol-5-yl | $CF_3$ | Cl | Cl |
| A-344 | Cl | 3-Methyl-isoxazol-5-yl | $CF_3$ | Cl | H |
| A-345 | Cl | 3-Methyl-isoxazol-5-yl | $SO_2CH_3$ | H | F |
| A-346 | Cl | 3-Methyl-isoxazol-5-yl | $SO_2CH_3$ | H | Cl |
| A-347 | Cl | 3-Methyl-isoxazol-5-yl | $SO_2CH_3$ | F | F |
| A-348 | Cl | 3-Methyl-isoxazol-5-yl | $SO_2CH_3$ | F | Cl |
| A-349 | Cl | 3-Methyl-isoxazol-5-yl | $SO_2CH_3$ | F | H |
| A-350 | Cl | 3-Methyl-isoxazol-5-yl | $SO_2CH_3$ | Cl | F |
| A-351 | Cl | 3-Methyl-isoxazol-5-yl | $SO_2CH_3$ | Cl | Cl |
| A-352 | Cl | 3-Methyl-isoxazol-5-yl | $SO_2CH_3$ | Cl | H |
| A-353 | Cl | 3-Methyl-isoxazol-5-yl | CN | H | F |
| A-354 | Cl | 3-Methyl-isoxazol-5-yl | CN | H | Cl |
| A-355 | Cl | 3-Methyl-isoxazol-5-yl | CN | F | F |
| A-356 | Cl | 3-Methyl-isoxazol-5-yl | CN | F | Cl |
| A-357 | Cl | 3-Methyl-isoxazol-5-yl | CN | F | H |
| A-358 | Cl | 3-Methyl-isoxazol-5-yl | CN | Cl | F |
| A-359 | Cl | 3-Methyl-isoxazol-5-yl | CN | Cl | Cl |
| A-360 | Cl | 3-Methyl-isoxazol-5-yl | CN | Cl | H |
| A-361 | $CH_3$ | H | Cl | H | F |
| A-362 | $CH_3$ | H | Cl | H | Cl |
| A-363 | $CH_3$ | H | Cl | F | F |
| A-364 | $CH_3$ | H | Cl | F | Cl |
| A-365 | $CH_3$ | H | Cl | F | H |
| A-366 | $CH_3$ | H | Cl | Cl | F |
| A-367 | $CH_3$ | H | Cl | Cl | Cl |
| A-368 | $CH_3$ | H | Cl | Cl | H |
| A-369 | $CH_3$ | H | F | H | F |
| A-370 | $CH_3$ | H | F | H | Cl |
| A-371 | $CH_3$ | H | F | F | F |
| A-372 | $CH_3$ | H | F | F | Cl |
| A-373 | $CH_3$ | H | F | F | H |
| A-374 | $CH_3$ | H | F | Cl | F |
| A-375 | $CH_3$ | H | F | Cl | Cl |
| A-376 | $CH_3$ | H | F | Cl | H |
| A-377 | $CH_3$ | H | $CF_3$ | H | F |
| A-378 | $CH_3$ | H | $CF_3$ | H | Cl |
| A-379 | $CH_3$ | H | $CF_3$ | F | F |
| A-380 | $CH_3$ | H | $CF_3$ | F | Cl |
| A-381 | $CH_3$ | H | $CF_3$ | F | H |
| A-382 | $CH_3$ | H | $CF_3$ | Cl | F |
| A-383 | $CH_3$ | H | $CF_3$ | Cl | Cl |
| A-384 | $CH_3$ | H | $CF_3$ | Cl | H |
| A-385 | $CH_3$ | H | $SO_2CH_3$ | H | F |
| A-386 | $CH_3$ | H | $SO_2CH_3$ | H | Cl |
| A-387 | $CH_3$ | H | $SO_2CH_3$ | F | F |
| A-388 | $CH_3$ | H | $SO_2CH_3$ | F | Cl |
| A-389 | $CH_3$ | H | $SO_2CH_3$ | F | H |
| A-390 | $CH_3$ | H | $SO_2CH_3$ | Cl | F |
| A-391 | $CH_3$ | H | $SO_2CH_3$ | Cl | Cl |
| A-392 | $CH_3$ | H | $SO_2CH_3$ | Cl | H |
| A-393 | $CH_3$ | H | CN | H | F |
| A-394 | $CH_3$ | H | CN | H | Cl |

TABLE A-continued

| | R¹ | R² | R³ | R⁴ | R⁵ |
|---|---|---|---|---|---|
| A-395 | CH₃ | H | CN | F | F |
| A-396 | CH₃ | H | CN | F | Cl |
| A-397 | CH₃ | H | CN | F | H |
| A-398 | CH₃ | H | CN | Cl | F |
| A-399 | CH₃ | H | CN | Cl | Cl |
| A-400 | CH₃ | H | CN | Cl | H |
| A-401 | CH₃ | SO₂CH₃ | Cl | H | F |
| A-402 | CH₃ | SO₂CH₃ | Cl | H | Cl |
| A-403 | CH₃ | SO₂CH₃ | Cl | F | F |
| A-404 | CH₃ | SO₂CH₃ | Cl | F | Cl |
| A-405 | CH₃ | SO₂CH₃ | Cl | F | H |
| A-406 | CH₃ | SO₂CH₃ | Cl | Cl | F |
| A-407 | CH₃ | SO₂CH₃ | Cl | Cl | Cl |
| A-408 | CH₃ | SO₂CH₃ | Cl | Cl | H |
| A-409 | CH₃ | SO₂CH₃ | F | H | F |
| A-410 | CH₃ | SO₂CH₃ | F | H | Cl |
| A-411 | CH₃ | SO₂CH₃ | F | F | F |
| A-412 | CH₃ | SO₂CH₃ | F | F | Cl |
| A-413 | CH₃ | SO₂CH₃ | F | F | H |
| A-414 | CH₃ | SO₂CH₃ | F | Cl | F |
| A-415 | CH₃ | SO₂CH₃ | F | Cl | Cl |
| A-416 | CH₃ | SO₂CH₃ | F | Cl | H |
| A-417 | CH₃ | SO₂CH₃ | CF₃ | H | F |
| A-418 | CH₃ | SO₂CH₃ | CF₃ | H | Cl |
| A-419 | CH₃ | SO₂CH₃ | CF₃ | F | F |
| A-420 | CH₃ | SO₂CH₃ | CF₃ | F | Cl |
| A-421 | CH₃ | SO₂CH₃ | CF₃ | F | H |
| A-422 | CH₃ | SO₂CH₃ | CF₃ | Cl | F |
| A-423 | CH₃ | SO₂CH₃ | CF₃ | Cl | Cl |
| A-424 | CH₃ | SO₂CH₃ | CF₃ | Cl | H |
| A-425 | CH₃ | SO₂CH₃ | SO₂CH₃ | H | F |
| A-426 | CH₃ | SO₂CH₃ | SO₂CH₃ | H | Cl |
| A-427 | CH₃ | SO₂CH₃ | SO₂CH₃ | F | F |
| A-428 | CH₃ | SO₂CH₃ | SO₂CH₃ | F | Cl |
| A-429 | CH₃ | SO₂CH₃ | SO₂CH₃ | F | H |
| A-430 | CH₃ | SO₂CH₃ | SO₂CH₃ | Cl | F |
| A-431 | CH₃ | SO₂CH₃ | SO₂CH₃ | Cl | Cl |
| A-432 | CH₃ | SO₂CH₃ | SO₂CH₃ | Cl | H |
| A-433 | CH₃ | SO₂CH₃ | CN | H | F |
| A-434 | CH₃ | SO₂CH₃ | CN | H | Cl |
| A-435 | CH₃ | SO₂CH₃ | CN | F | F |
| A-436 | CH₃ | SO₂CH₃ | CN | F | Cl |
| A-437 | CH₃ | SO₂CH₃ | CN | F | H |
| A-438 | CH₃ | SO₂CH₃ | CN | Cl | F |
| A-439 | CH₃ | SO₂CH₃ | CN | Cl | Cl |
| A-440 | CH₃ | SO₂CH₃ | CN | Cl | H |
| A-441 | CH₃ | CH₂OCH₂CF₃ | Cl | H | F |
| A-442 | CH₃ | CH₂OCH₂CF₃ | Cl | H | Cl |
| A-443 | CH₃ | CH₂OCH₂CF₃ | Cl | F | F |
| A-444 | CH₃ | CH₂OCH₂CF₃ | Cl | F | Cl |
| A-445 | CH₃ | CH₂OCH₂CF₃ | Cl | F | H |
| A-446 | CH₃ | CH₂OCH₂CF₃ | Cl | Cl | F |
| A-447 | CH₃ | CH₂OCH₂CF₃ | Cl | Cl | Cl |
| A-448 | CH₃ | CH₂OCH₂CF₃ | Cl | Cl | H |
| A-449 | CH₃ | CH₂OCH₂CF₃ | F | H | F |
| A-450 | CH₃ | CH₂OCH₂CF₃ | F | H | Cl |
| A-451 | CH₃ | CH₂OCH₂CF₃ | F | F | F |
| A-452 | CH₃ | CH₂OCH₂CF₃ | F | F | Cl |
| A-453 | CH₃ | CH₂OCH₂CF₃ | F | F | H |
| A-454 | CH₃ | CH₂OCH₂CF₃ | F | Cl | F |
| A-455 | CH₃ | CH₂OCH₂CF₃ | F | Cl | Cl |
| A-456 | CH₃ | CH₂OCH₂CF₃ | F | Cl | H |
| A-457 | CH₃ | CH₂OCH₂CF₃ | CF₃ | H | F |
| A-458 | CH₃ | CH₂OCH₂CF₃ | CF₃ | H | Cl |
| A-459 | CH₃ | CH₂OCH₂CF₃ | CF₃ | F | F |
| A-460 | CH₃ | CH₂OCH₂CF₃ | CF₃ | F | Cl |
| A-461 | CH₃ | CH₂OCH₂CF₃ | CF₃ | F | H |
| A-462 | CH₃ | CH₂OCH₂CF₃ | CF₃ | Cl | F |
| A-463 | CH₃ | CH₂OCH₂CF₃ | CF₃ | Cl | Cl |
| A-464 | CH₃ | CH₂OCH₂CF₃ | CF₃ | Cl | H |
| A-465 | CH₃ | CH₂OCH₂CF₃ | SO₂CH₃ | H | F |
| A-466 | CH₃ | CH₂OCH₂CF₃ | SO₂CH₃ | H | Cl |
| A-467 | CH₃ | CH₂OCH₂CF₃ | SO₂CH₃ | F | F |
| A-468 | CH₃ | CH₂OCH₂CF₃ | SO₂CH₃ | F | Cl |
| A-469 | CH₃ | CH₂OCH₂CF₃ | SO₂CH₃ | F | H |
| A-470 | CH₃ | CH₂OCH₂CF₃ | SO₂CH₃ | Cl | F |
| A-471 | CH₃ | CH₂OCH₂CF₃ | SO₂CH₃ | Cl | Cl |
| A-472 | CH₃ | CH₂OCH₂CF₃ | SO₂CH₃ | Cl | H |
| A-473 | CH₃ | CH₂OCH₂CF₃ | CN | H | F |
| A-474 | CH₃ | CH₂OCH₂CF₃ | CN | H | Cl |
| A-475 | CH₃ | CH₂OCH₂CF₃ | CN | F | F |
| A-476 | CH₃ | CH₂OCH₂CF₃ | CN | F | Cl |
| A-477 | CH₃ | CH₂OCH₂CF₃ | CN | F | H |
| A-478 | CH₃ | CH₂OCH₂CF₃ | CN | Cl | F |
| A-479 | CH₃ | CH₂OCH₂CF₃ | CN | Cl | Cl |
| A-480 | CH₃ | CH₂OCH₂CF₃ | CN | Cl | H |
| A-481 | CH₃ | Isoxazolin-3-yl | Cl | H | F |
| A-482 | CH₃ | Isoxazolin-3-yl | Cl | H | Cl |
| A-483 | CH₃ | Isoxazolin-3-yl | Cl | F | F |
| A-484 | CH₃ | Isoxazolin-3-yl | Cl | F | Cl |
| A-485 | CH₃ | Isoxazolin-3-yl | Cl | F | H |
| A-486 | CH₃ | Isoxazolin-3-yl | Cl | Cl | F |
| A-487 | CH₃ | Isoxazolin-3-yl | Cl | Cl | Cl |
| A-488 | CH₃ | Isoxazolin-3-yl | Cl | Cl | H |
| A-489 | CH₃ | Isoxazolin-3-yl | F | H | F |
| A-490 | CH₃ | Isoxazolin-3-yl | F | H | Cl |
| A-491 | CH₃ | Isoxazolin-3-yl | F | F | F |
| A-492 | CH₃ | Isoxazolin-3-yl | F | F | Cl |
| A-493 | CH₃ | Isoxazolin-3-yl | F | F | H |
| A-494 | CH₃ | Isoxazolin-3-yl | F | Cl | F |
| A-495 | CH₃ | Isoxazolin-3-yl | F | Cl | Cl |
| A-496 | CH₃ | Isoxazolin-3-yl | F | Cl | H |
| A-497 | CH₃ | Isoxazolin-3-yl | CF₃ | H | F |
| A-498 | CH₃ | Isoxazolin-3-yl | CF₃ | H | Cl |
| A-499 | CH₃ | Isoxazolin-3-yl | CF₃ | F | F |
| A-500 | CH₃ | Isoxazolin-3-yl | CF₃ | F | Cl |
| A-501 | CH₃ | Isoxazolin-3-yl | CF₃ | F | H |
| A-502 | CH₃ | Isoxazolin-3-yl | CF₃ | Cl | F |
| A-503 | CH₃ | Isoxazolin-3-yl | CF₃ | Cl | Cl |
| A-504 | CH₃ | Isoxazolin-3-yl | CF₃ | Cl | H |
| A-505 | CH₃ | Isoxazolin-3-yl | SO₂CH₃ | H | F |
| A-506 | CH₃ | Isoxazolin-3-yl | SO₂CH₃ | H | Cl |
| A-507 | CH₃ | Isoxazolin-3-yl | SO₂CH₃ | F | F |
| A-508 | CH₃ | Isoxazolin-3-yl | SO₂CH₃ | F | Cl |
| A-509 | CH₃ | Isoxazolin-3-yl | SO₂CH₃ | F | H |
| A-510 | CH₃ | Isoxazolin-3-yl | SO₂CH₃ | Cl | F |
| A-511 | CH₃ | Isoxazolin-3-yl | SO₂CH₃ | Cl | Cl |
| A-512 | CH₃ | Isoxazolin-3-yl | SO₂CH₃ | Cl | H |
| A-513 | CH₃ | Isoxazolin-3-yl | CN | H | F |
| A-514 | CH₃ | Isoxazolin-3-yl | CN | H | Cl |
| A-515 | CH₃ | Isoxazolin-3-yl | CN | F | F |
| A-516 | CH₃ | Isoxazolin-3-yl | CN | F | Cl |
| A-517 | CH₃ | Isoxazolin-3-yl | CN | F | H |
| A-518 | CH₃ | Isoxazolin-3-yl | CN | Cl | F |
| A-519 | CH₃ | Isoxazolin-3-yl | CN | Cl | Cl |
| A-520 | CH₃ | Isoxazolin-3-yl | CN | Cl | H |
| A-521 | CH₃ | 5-Methyl-isoxazolin-3-yl | Cl | H | F |
| A-522 | CH₃ | 5-Methyl-isoxazolin-3-yl | Cl | H | Cl |
| A-523 | CH₃ | 5-Methyl-isoxazolin-3-yl | Cl | F | F |
| A-524 | CH₃ | 5-Methyl-isoxazolin-3-yl | Cl | F | Cl |
| A-525 | CH₃ | 5-Methyl-isoxazolin-3-yl | Cl | F | H |
| A-526 | CH₃ | 5-Methyl-isoxazolin-3-yl | Cl | Cl | F |
| A-527 | CH₃ | 5-Methyl-isoxazolin-3-yl | Cl | Cl | Cl |
| A-528 | CH₃ | 5-Methyl-isoxazolin-3-yl | Cl | Cl | H |
| A-529 | CH₃ | 5-Methyl-isoxazolin-3-yl | F | H | F |
| A-530 | CH₃ | 5-Methyl-isoxazolin-3-yl | F | H | Cl |
| A-531 | CH₃ | 5-Methyl-isoxazolin-3-yl | F | F | F |
| A-532 | CH₃ | 5-Methyl-isoxazolin-3-yl | F | F | Cl |
| A-533 | CH₃ | 5-Methyl-isoxazolin-3-yl | F | F | H |
| A-534 | CH₃ | 5-Methyl-isoxazolin-3-yl | F | Cl | F |
| A-535 | CH₃ | 5-Methyl-isoxazolin-3-yl | F | Cl | Cl |
| A-536 | CH₃ | 5-Methyl-isoxazolin-3-yl | F | Cl | H |
| A-537 | CH₃ | 5-Methyl-isoxazolin-3-yl | CF₃ | H | F |
| A-538 | CH₃ | 5-Methyl-isoxazolin-3-yl | CF₃ | H | Cl |
| A-539 | CH₃ | 5-Methyl-isoxazolin-3-yl | CF₃ | F | F |
| A-540 | CH₃ | 5-Methyl-isoxazolin-3-yl | CF₃ | F | Cl |
| A-541 | CH₃ | 5-Methyl-isoxazolin-3-yl | CF₃ | F | H |
| A-542 | CH₃ | 5-Methyl-isoxazolin-3-yl | CF₃ | Cl | F |
| A-543 | CH₃ | 5-Methyl-isoxazolin-3-yl | CF₃ | Cl | Cl |
| A-544 | CH₃ | 5-Methyl-isoxazolin-3-yl | CF₃ | Cl | H |
| A-545 | CH₃ | 5-Methyl-isoxazolin-3-yl | SO₂CH₃ | H | F |
| A-546 | CH₃ | 5-Methyl-isoxazolin-3-yl | SO₂CH₃ | H | Cl |
| A-547 | CH₃ | 5-Methyl-isoxazolin-3-yl | SO₂CH₃ | F | F |
| A-548 | CH₃ | 5-Methyl-isoxazolin-3-yl | SO₂CH₃ | F | Cl |
| A-549 | CH₃ | 5-Methyl-isoxazolin-3-yl | SO₂CH₃ | F | H |
| A-550 | CH₃ | 5-Methyl-isoxazolin-3-yl | SO₂CH₃ | Cl | F |

TABLE A-continued

| | R¹ | R² | R³ | R⁴ | R⁵ |
|---|---|---|---|---|---|
| A-551 | CH₃ | 5-Methyl-isoxazolin-3-yl | SO₂CH₃ | Cl | Cl |
| A-552 | CH₃ | 5-Methyl-isoxazolin-3-yl | SO₂CH₃ | Cl | H |
| A-553 | CH₃ | 5-Methyl-isoxazolin-3-yl | CN | H | F |
| A-554 | CH₃ | 5-Methyl-isoxazolin-3-yl | CN | H | Cl |
| A-555 | CH₃ | 5-Methyl-isoxazolin-3-yl | CN | F | F |
| A-556 | CH₃ | 5-Methyl-isoxazolin-3-yl | CN | F | Cl |
| A-557 | CH₃ | 5-Methyl-isoxazolin-3-yl | CN | F | H |
| A-558 | CH₃ | 5-Methyl-isoxazolin-3-yl | CN | Cl | F |
| A-559 | CH₃ | 5-Methyl-isoxazolin-3-yl | CN | Cl | Cl |
| A-560 | CH₃ | 5-Methyl-isoxazolin-3-yl | CN | Cl | H |
| A-561 | CH₃ | Isoxazol-3-yl | Cl | H | F |
| A-562 | CH₃ | Isoxazol-3-yl | Cl | H | Cl |
| A-563 | CH₃ | Isoxazol-3-yl | Cl | F | F |
| A-564 | CH₃ | Isoxazol-3-yl | Cl | F | Cl |
| A-565 | CH₃ | Isoxazol-3-yl | Cl | F | H |
| A-566 | CH₃ | Isoxazol-3-yl | Cl | Cl | F |
| A-567 | CH₃ | Isoxazol-3-yl | Cl | Cl | Cl |
| A-568 | CH₃ | Isoxazol-3-yl | Cl | Cl | H |
| A-569 | CH₃ | Isoxazol-3-yl | F | H | F |
| A-570 | CH₃ | Isoxazol-3-yl | F | H | Cl |
| A-571 | CH₃ | Isoxazol-3-yl | F | F | F |
| A-572 | CH₃ | Isoxazol-3-yl | F | F | Cl |
| A-573 | CH₃ | Isoxazol-3-yl | F | F | H |
| A-574 | CH₃ | Isoxazol-3-yl | F | Cl | F |
| A-575 | CH₃ | Isoxazol-3-yl | F | Cl | Cl |
| A-576 | CH₃ | Isoxazol-3-yl | F | Cl | H |
| A-577 | CH₃ | Isoxazol-3-yl | CF₃ | H | F |
| A-578 | CH₃ | Isoxazol-3-yl | CF₃ | H | Cl |
| A-579 | CH₃ | Isoxazol-3-yl | CF₃ | F | F |
| A-580 | CH₃ | Isoxazol-3-yl | CF₃ | F | Cl |
| A-581 | CH₃ | Isoxazol-3-yl | CF₃ | F | H |
| A-582 | CH₃ | Isoxazol-3-yl | CF₃ | Cl | F |
| A-583 | CH₃ | Isoxazol-3-yl | CF₃ | Cl | Cl |
| A-584 | CH₃ | Isoxazol-3-yl | CF₃ | Cl | H |
| A-585 | CH₃ | Isoxazol-3-yl | SO₂CH₃ | H | F |
| A-586 | CH₃ | Isoxazol-3-yl | SO₂CH₃ | H | Cl |
| A-587 | CH₃ | Isoxazol-3-yl | SO₂CH₃ | F | F |
| A-588 | CH₃ | Isoxazol-3-yl | SO₂CH₃ | F | Cl |
| A-589 | CH₃ | Isoxazol-3-yl | SO₂CH₃ | F | H |
| A-590 | CH₃ | Isoxazol-3-yl | SO₂CH₃ | Cl | F |
| A-591 | CH₃ | Isoxazol-3-yl | SO₂CH₃ | Cl | Cl |
| A-592 | CH₃ | Isoxazol-3-yl | SO₂CH₃ | Cl | H |
| A-593 | CH₃ | Isoxazol-3-yl | CN | H | F |
| A-594 | CH₃ | Isoxazol-3-yl | CN | H | Cl |
| A-595 | CH₃ | Isoxazol-3-yl | CN | F | F |
| A-596 | CH₃ | Isoxazol-3-yl | CN | F | Cl |
| A-597 | CH₃ | Isoxazol-3-yl | CN | F | H |
| A-598 | CH₃ | Isoxazol-3-yl | CN | Cl | F |
| A-599 | CH₃ | Isoxazol-3-yl | CN | Cl | Cl |
| A-600 | CH₃ | Isoxazol-3-yl | CN | Cl | H |
| A-601 | CH₃ | 5-Methyl-isoxazol-3-yl | Cl | H | F |
| A-602 | CH₃ | 5-Methyl-isoxazol-3-yl | Cl | H | Cl |
| A-603 | CH₃ | 5-Methyl-isoxazol-3-yl | Cl | F | F |
| A-604 | CH₃ | 5-Methyl-isoxazol-3-yl | Cl | F | Cl |
| A-605 | CH₃ | 5-Methyl-isoxazol-3-yl | Cl | F | H |
| A-606 | CH₃ | 5-Methyl-isoxazol-3-yl | Cl | Cl | F |
| A-607 | CH₃ | 5-Methyl-isoxazol-3-yl | Cl | Cl | Cl |
| A-608 | CH₃ | 5-Methyl-isoxazol-3-yl | Cl | Cl | H |
| A-609 | CH₃ | 5-Methyl-isoxazol-3-yl | F | H | F |
| A-610 | CH₃ | 5-Methyl-isoxazol-3-yl | F | H | Cl |
| A-611 | CH₃ | 5-Methyl-isoxazol-3-yl | F | F | F |
| A-612 | CH₃ | 5-Methyl-isoxazol-3-yl | F | F | Cl |
| A-613 | CH₃ | 5-Methyl-isoxazol-3-yl | F | F | H |
| A-614 | CH₃ | 5-Methyl-isoxazol-3-yl | F | Cl | F |
| A-615 | CH₃ | 5-Methyl-isoxazol-3-yl | F | Cl | Cl |
| A-616 | CH₃ | 5-Methyl-isoxazol-3-yl | F | Cl | H |
| A-617 | CH₃ | 5-Methyl-isoxazol-3-yl | CF₃ | H | F |
| A-618 | CH₃ | 5-Methyl-isoxazol-3-yl | CF₃ | H | Cl |
| A-619 | CH₃ | 5-Methyl-isoxazol-3-yl | CF₃ | F | F |
| A-620 | CH₃ | 5-Methyl-isoxazol-3-yl | CF₃ | F | Cl |
| A-621 | CH₃ | 5-Methyl-isoxazol-3-yl | CF₃ | F | H |
| A-622 | CH₃ | 5-Methyl-isoxazol-3-yl | CF₃ | Cl | F |
| A-623 | CH₃ | 5-Methyl-isoxazol-3-yl | CF₃ | Cl | Cl |
| A-624 | CH₃ | 5-Methyl-isoxazol-3-yl | CF₃ | Cl | H |
| A-625 | CH₃ | 5-Methyl-isoxazol-3-yl | SO₂CH₃ | H | F |
| A-626 | CH₃ | 5-Methyl-isoxazol-3-yl | SO₂CH₃ | H | Cl |
| A-627 | CH₃ | 5-Methyl-isoxazol-3-yl | SO₂CH₃ | F | F |
| A-628 | CH₃ | 5-Methyl-isoxazol-3-yl | SO₂CH₃ | F | Cl |
| A-629 | CH₃ | 5-Methyl-isoxazol-3-yl | SO₂CH₃ | F | H |
| A-630 | CH₃ | 5-Methyl-isoxazol-3-yl | SO₂CH₃ | Cl | F |
| A-631 | CH₃ | 5-Methyl-isoxazol-3-yl | SO₂CH₃ | Cl | Cl |
| A-632 | CH₃ | 5-Methyl-isoxazol-3-yl | SO₂CH₃ | Cl | H |
| A-633 | CH₃ | 5-Methyl-isoxazol-3-yl | CN | H | F |
| A-634 | CH₃ | 5-Methyl-isoxazol-3-yl | CN | H | Cl |
| A-635 | CH₃ | 5-Methyl-isoxazol-3-yl | CN | F | F |
| A-636 | CH₃ | 5-Methyl-isoxazol-3-yl | CN | F | Cl |
| A-637 | CH₃ | 5-Methyl-isoxazol-3-yl | CN | F | H |
| A-638 | CH₃ | 5-Methyl-isoxazol-3-yl | CN | Cl | F |
| A-639 | CH₃ | 5-Methyl-isoxazol-3-yl | CN | Cl | Cl |
| A-640 | CH₃ | 5-Methyl-isoxazol-3-yl | CN | Cl | H |
| A-641 | CH₃ | 3-Methyl-isoxazolin-5-yl | Cl | H | F |
| A-642 | CH₃ | 3-Methyl-isoxazolin-5-yl | Cl | H | Cl |
| A-643 | CH₃ | 3-Methyl-isoxazolin-5-yl | Cl | F | F |
| A-644 | CH₃ | 3-Methyl-isoxazolin-5-yl | Cl | F | Cl |
| A-645 | CH₃ | 3-Methyl-isoxazolin-5-yl | Cl | F | H |
| A-646 | CH₃ | 3-Methyl-isoxazolin-5-yl | Cl | Cl | F |
| A-647 | CH₃ | 3-Methyl-isoxazolin-5-yl | Cl | Cl | Cl |
| A-648 | CH₃ | 3-Methyl-isoxazolin-5-yl | Cl | Cl | H |
| A-649 | CH₃ | 3-Methyl-isoxazolin-5-yl | F | H | F |
| A-650 | CH₃ | 3-Methyl-isoxazolin-5-yl | F | H | Cl |
| A-651 | CH₃ | 3-Methyl-isoxazolin-5-yl | F | F | F |
| A-652 | CH₃ | 3-Methyl-isoxazolin-5-yl | F | F | Cl |
| A-653 | CH₃ | 3-Methyl-isoxazolin-5-yl | F | F | H |
| A-654 | CH₃ | 3-Methyl-isoxazolin-5-yl | F | Cl | F |
| A-655 | CH₃ | 3-Methyl-isoxazolin-5-yl | F | Cl | Cl |
| A-656 | CH₃ | 3-Methyl-isoxazolin-5-yl | F | Cl | H |
| A-657 | CH₃ | 3-Methyl-isoxazolin-5-yl | CF₃ | H | F |
| A-658 | CH₃ | 3-Methyl-isoxazolin-5-yl | CF₃ | H | Cl |
| A-659 | CH₃ | 3-Methyl-isoxazolin-5-yl | CF₃ | F | F |
| A-660 | CH₃ | 3-Methyl-isoxazolin-5-yl | CF₃ | F | Cl |
| A-661 | CH₃ | 3-Methyl-isoxazolin-5-yl | CF₃ | F | H |
| A-662 | CH₃ | 3-Methyl-isoxazolin-5-yl | CF₃ | Cl | F |
| A-663 | CH₃ | 3-Methyl-isoxazolin-5-yl | CF₃ | Cl | Cl |
| A-664 | CH₃ | 3-Methyl-isoxazolin-5-yl | CF₃ | Cl | H |
| A-665 | CH₃ | 3-Methyl-isoxazolin-5-yl | SO₂CH₃ | H | F |
| A-666 | CH₃ | 3-Methyl-isoxazolin-5-yl | SO₂CH₃ | H | Cl |
| A-667 | CH₃ | 3-Methyl-isoxazolin-5-yl | SO₂CH₃ | F | F |
| A-668 | CH₃ | 3-Methyl-isoxazolin-5-yl | SO₂CH₃ | F | Cl |
| A-669 | CH₃ | 3-Methyl-isoxazolin-5-yl | SO₂CH₃ | F | H |
| A-670 | CH₃ | 3-Methyl-isoxazolin-5-yl | SO₂CH₃ | Cl | F |
| A-671 | CH₃ | 3-Methyl-isoxazolin-5-yl | SO₂CH₃ | Cl | Cl |
| A-672 | CH₃ | 3-Methyl-isoxazolin-5-yl | SO₂CH₃ | Cl | H |
| A-673 | CH₃ | 3-Methyl-isoxazolin-5-yl | CN | H | F |
| A-674 | CH₃ | 3-Methyl-isoxazolin-5-yl | CN | H | Cl |
| A-675 | CH₃ | 3-Methyl-isoxazolin-5-yl | CN | F | F |
| A-676 | CH₃ | 3-Methyl-isoxazolin-5-yl | CN | F | Cl |
| A-677 | CH₃ | 3-Methyl-isoxazolin-5-yl | CN | F | H |
| A-678 | CH₃ | 3-Methyl-isoxazolin-5-yl | CN | Cl | F |
| A-679 | CH₃ | 3-Methyl-isoxazolin-5-yl | CN | Cl | Cl |
| A-680 | CH₃ | 3-Methyl-isoxazolin-5-yl | CN | Cl | H |
| A-681 | CH₃ | 3-Methyl-isoxazol-5-yl | Cl | H | F |
| A-682 | CH₃ | 3-Methyl-isoxazol-5-yl | Cl | H | Cl |
| A-683 | CH₃ | 3-Methyl-isoxazol-5-yl | Cl | F | F |
| A-684 | CH₃ | 3-Methyl-isoxazol-5-yl | Cl | F | Cl |
| A-685 | CH₃ | 3-Methyl-isoxazol-5-yl | Cl | F | H |
| A-686 | CH₃ | 3-Methyl-isoxazol-5-yl | Cl | Cl | F |
| A-687 | CH₃ | 3-Methyl-isoxazol-5-yl | Cl | Cl | Cl |
| A-688 | CH₃ | 3-Methyl-isoxazol-5-yl | Cl | Cl | H |
| A-689 | CH₃ | 3-Methyl-isoxazol-5-yl | F | H | F |
| A-690 | CH₃ | 3-Methyl-isoxazol-5-yl | F | H | Cl |
| A-691 | CH₃ | 3-Methyl-isoxazol-5-yl | F | F | F |
| A-692 | CH₃ | 3-Methyl-isoxazol-5-yl | F | F | Cl |
| A-693 | CH₃ | 3-Methyl-isoxazol-5-yl | F | F | H |
| A-694 | CH₃ | 3-Methyl-isoxazol-5-yl | F | Cl | F |
| A-695 | CH₃ | 3-Methyl-isoxazol-5-yl | F | Cl | Cl |
| A-696 | CH₃ | 3-Methyl-isoxazol-5-yl | F | Cl | H |
| A-697 | CH₃ | 3-Methyl-isoxazol-5-yl | CF₃ | H | F |
| A-698 | CH₃ | 3-Methyl-isoxazol-5-yl | CF₃ | H | Cl |
| A-699 | CH₃ | 3-Methyl-isoxazol-5-yl | CF₃ | F | F |
| A-700 | CH₃ | 3-Methyl-isoxazol-5-yl | CF₃ | F | Cl |
| A-701 | CH₃ | 3-Methyl-isoxazol-5-yl | CF₃ | F | H |
| A-702 | CH₃ | 3-Methyl-isoxazol-5-yl | CF₃ | Cl | F |
| A-703 | CH₃ | 3-Methyl-isoxazol-5-yl | CF₃ | Cl | Cl |
| A-704 | CH₃ | 3-Methyl-isoxazol-5-yl | CF₃ | Cl | H |
| A-705 | CH₃ | 3-Methyl-isoxazol-5-yl | SO₂CH₃ | H | F |
| A-706 | CH₃ | 3-Methyl-isoxazol-5-yl | SO₂CH₃ | H | Cl |

TABLE A-continued

| | R¹ | R² | R³ | R⁴ | R⁵ |
|---|---|---|---|---|---|
| A-707 | CH₃ | 3-Methyl-isoxazol-5-yl | SO₂CH₃ | F | F |
| A-708 | CH₃ | 3-Methyl-isoxazol-5-yl | SO₂CH₃ | F | Cl |
| A-709 | CH₃ | 3-Methyl-isoxazol-5-yl | SO₂CH₃ | F | H |
| A-710 | CH₃ | 3-Methyl-isoxazol-5-yl | SO₂CH₃ | Cl | F |
| A-711 | CH₃ | 3-Methyl-isoxazol-5-yl | SO₂CH₃ | Cl | Cl |
| A-712 | CH₃ | 3-Methyl-isoxazol-5-yl | SO₂CH₃ | Cl | H |
| A-713 | CH₃ | 3-Methyl-isoxazol-5-yl | CN | H | F |
| A-714 | CH₃ | 3-Methyl-isoxazol-5-yl | CN | H | Cl |
| A-715 | CH₃ | 3-Methyl-isoxazol-5-yl | CN | F | F |
| A-716 | CH₃ | 3-Methyl-isoxazol-5-yl | CN | F | Cl |
| A-717 | CH₃ | 3-Methyl-isoxazol-5-yl | CN | F | H |
| A-718 | CH₃ | 3-Methyl-isoxazol-5-yl | CN | Cl | F |
| A-719 | CH₃ | 3-Methyl-isoxazol-5-yl | CN | Cl | Cl |
| A-720 | CH₃ | 3-Methyl-isoxazol-5-yl | CN | Cl | H |
| A-721 | CF₃ | H | Cl | H | F |
| A-722 | CF₃ | H | Cl | H | Cl |
| A-723 | CF₃ | H | Cl | F | F |
| A-724 | CF₃ | H | Cl | F | Cl |
| A-725 | CF₃ | H | Cl | F | H |
| A-726 | CF₃ | H | Cl | Cl | F |
| A-727 | CF₃ | H | Cl | Cl | Cl |
| A-728 | CF₃ | H | Cl | Cl | H |
| A-729 | CF₃ | H | F | H | F |
| A-730 | CF₃ | H | F | H | Cl |
| A-731 | CF₃ | H | F | F | F |
| A-732 | CF₃ | H | F | F | Cl |
| A-733 | CF₃ | H | F | F | H |
| A-734 | CF₃ | H | F | Cl | F |
| A-735 | CF₃ | H | F | Cl | Cl |
| A-736 | CF₃ | H | F | Cl | H |
| A-737 | CF₃ | H | CF₃ | H | F |
| A-738 | CF₃ | H | CF₃ | H | Cl |
| A-739 | CF₃ | H | CF₃ | F | F |
| A-740 | CF₃ | H | CF₃ | F | Cl |
| A-741 | CF₃ | H | CF₃ | F | H |
| A-742 | CF₃ | H | CF₃ | Cl | F |
| A-743 | CF₃ | H | CF₃ | Cl | Cl |
| A-744 | CF₃ | H | CF₃ | Cl | H |
| A-745 | CF₃ | H | SO₂CH₃ | H | F |
| A-746 | CF₃ | H | SO₂CH₃ | H | Cl |
| A-747 | CF₃ | H | SO₂CH₃ | F | F |
| A-748 | CF₃ | H | SO₂CH₃ | F | Cl |
| A-749 | CF₃ | H | SO₂CH₃ | F | H |
| A-750 | CF₃ | H | SO₂CH₃ | Cl | F |
| A-751 | CF₃ | H | SO₂CH₃ | Cl | Cl |
| A-752 | CF₃ | H | SO₂CH₃ | Cl | H |
| A-753 | CF₃ | H | CN | H | F |
| A-754 | CF₃ | H | CN | H | Cl |
| A-755 | CF₃ | H | CN | F | F |
| A-756 | CF₃ | H | CN | F | Cl |
| A-757 | CF₃ | H | CN | F | H |
| A-758 | CF₃ | H | CN | Cl | F |
| A-759 | CF₃ | H | CN | Cl | Cl |
| A-760 | CF₃ | H | CN | Cl | H |
| A-761 | CF₃ | SO₂CH₃ | Cl | H | F |
| A-762 | CF₃ | SO₂CH₃ | Cl | H | Cl |
| A-763 | CF₃ | SO₂CH₃ | Cl | F | F |
| A-764 | CF₃ | SO₂CH₃ | Cl | F | Cl |
| A-765 | CF₃ | SO₂CH₃ | Cl | F | H |
| A-766 | CF₃ | SO₂CH₃ | Cl | Cl | F |
| A-767 | CF₃ | SO₂CH₃ | Cl | Cl | Cl |
| A-768 | CF₃ | SO₂CH₃ | Cl | Cl | H |
| A-769 | CF₃ | SO₂CH₃ | F | H | F |
| A-770 | CF₃ | SO₂CH₃ | F | H | Cl |
| A-771 | CF₃ | SO₂CH₃ | F | F | F |
| A-772 | CF₃ | SO₂CH₃ | F | F | Cl |
| A-773 | CF₃ | SO₂CH₃ | F | F | H |
| A-774 | CF₃ | SO₂CH₃ | F | Cl | F |
| A-775 | CF₃ | SO₂CH₃ | F | Cl | Cl |
| A-776 | CF₃ | SO₂CH₃ | F | Cl | H |
| A-777 | CF₃ | SO₂CH₃ | CF₃ | H | F |
| A-778 | CF₃ | SO₂CH₃ | CF₃ | H | Cl |
| A-779 | CF₃ | SO₂CH₃ | CF₃ | F | F |
| A-780 | CF₃ | SO₂CH₃ | CF₃ | F | Cl |
| A-781 | CF₃ | SO₂CH₃ | CF₃ | F | H |
| A-782 | CF₃ | SO₂CH₃ | CF₃ | Cl | F |
| A-783 | CF₃ | SO₂CH₃ | CF₃ | Cl | Cl |
| A-784 | CF₃ | SO₂CH₃ | CF₃ | Cl | H |
| A-785 | CF₃ | SO₂CH₃ | SO₂CH₃ | H | F |
| A-786 | CF₃ | SO₂CH₃ | SO₂CH₃ | H | Cl |
| A-787 | CF₃ | SO₂CH₃ | SO₂CH₃ | F | F |
| A-788 | CF₃ | SO₂CH₃ | SO₂CH₃ | F | Cl |
| A-789 | CF₃ | SO₂CH₃ | SO₂CH₃ | F | H |
| A-790 | CF₃ | SO₂CH₃ | SO₂CH₃ | Cl | F |
| A-791 | CF₃ | SO₂CH₃ | SO₂CH₃ | Cl | Cl |
| A-792 | CF₃ | SO₂CH₃ | SO₂CH₃ | Cl | H |
| A-793 | CF₃ | SO₂CH₃ | CN | H | F |
| A-794 | CF₃ | SO₂CH₃ | CN | H | Cl |
| A-795 | CF₃ | SO₂CH₃ | CN | F | F |
| A-796 | CF₃ | SO₂CH₃ | CN | F | Cl |
| A-797 | CF₃ | SO₂CH₃ | CN | F | H |
| A-798 | CF₃ | SO₂CH₃ | CN | Cl | F |
| A-799 | CF₃ | SO₂CH₃ | CN | Cl | Cl |
| A-800 | CF₃ | SO₂CH₃ | CN | Cl | H |
| A-801 | CF₃ | CH₂OCH₂CF₃ | Cl | H | F |
| A-802 | CF₃ | CH₂OCH₂CF₃ | Cl | H | Cl |
| A-803 | CF₃ | CH₂OCH₂CF₃ | Cl | F | F |
| A-804 | CF₃ | CH₂OCH₂CF₃ | Cl | F | Cl |
| A-805 | CF₃ | CH₂OCH₂CF₃ | Cl | F | H |
| A-806 | CF₃ | CH₂OCH₂CF₃ | Cl | Cl | F |
| A-807 | CF₃ | CH₂OCH₂CF₃ | Cl | Cl | Cl |
| A-808 | CF₃ | CH₂OCH₂CF₃ | Cl | Cl | H |
| A-809 | CF₃ | CH₂OCH₂CF₃ | F | H | F |
| A-810 | CF₃ | CH₂OCH₂CF₃ | F | H | Cl |
| A-811 | CF₃ | CH₂OCH₂CF₃ | F | F | F |
| A-812 | CF₃ | CH₂OCH₂CF₃ | F | F | Cl |
| A-813 | CF₃ | CH₂OCH₂CF₃ | F | F | H |
| A-814 | CF₃ | CH₂OCH₂CF₃ | F | Cl | F |
| A-815 | CF₃ | CH₂OCH₂CF₃ | F | Cl | Cl |
| A-816 | CF₃ | CH₂OCH₂CF₃ | F | Cl | H |
| A-817 | CF₃ | CH₂OCH₂CF₃ | CF₃ | H | F |
| A-818 | CF₃ | CH₂OCH₂CF₃ | CF₃ | H | Cl |
| A-819 | CF₃ | CH₂OCH₂CF₃ | CF₃ | F | F |
| A-820 | CF₃ | CH₂OCH₂CF₃ | CF₃ | F | Cl |
| A-821 | CF₃ | CH₂OCH₂CF₃ | CF₃ | F | H |
| A-822 | CF₃ | CH₂OCH₂CF₃ | CF₃ | Cl | F |
| A-823 | CF₃ | CH₂OCH₂CF₃ | CF₃ | Cl | Cl |
| A-824 | CF₃ | CH₂OCH₂CF₃ | CF₃ | Cl | H |
| A-825 | CF₃ | CH₂OCH₂CF₃ | SO₂CH₃ | H | F |
| A-826 | CF₃ | CH₂OCH₂CF₃ | SO₂CH₃ | H | Cl |
| A-827 | CF₃ | CH₂OCH₂CF₃ | SO₂CH₃ | F | F |
| A-828 | CF₃ | CH₂OCH₂CF₃ | SO₂CH₃ | F | Cl |
| A-829 | CF₃ | CH₂OCH₂CF₃ | SO₂CH₃ | F | H |
| A-830 | CF₃ | CH₂OCH₂CF₃ | SO₂CH₃ | Cl | F |
| A-831 | CF₃ | CH₂OCH₂CF₃ | SO₂CH₃ | Cl | Cl |
| A-832 | CF₃ | CH₂OCH₂CF₃ | SO₂CH₃ | Cl | H |
| A-833 | CF₃ | CH₂OCH₂CF₃ | CN | H | F |
| A-834 | CF₃ | CH₂OCH₂CF₃ | CN | H | Cl |
| A-835 | CF₃ | CH₂OCH₂CF₃ | CN | F | F |
| A-836 | CF₃ | CH₂OCH₂CF₃ | CN | F | Cl |
| A-837 | CF₃ | CH₂OCH₂CF₃ | CN | F | H |
| A-838 | CF₃ | CH₂OCH₂CF₃ | CN | Cl | F |
| A-839 | CF₃ | CH₂OCH₂CF₃ | CN | Cl | Cl |
| A-840 | CF₃ | CH₂OCH₂CF₃ | CN | Cl | H |
| A-841 | CF₃ | Isoxazolin-3-yl | Cl | H | F |
| A-842 | CF₃ | Isoxazolin-3-yl | Cl | H | Cl |
| A-843 | CF₃ | Isoxazolin-3-yl | Cl | F | F |
| A-844 | CF₃ | Isoxazolin-3-yl | Cl | F | Cl |
| A-845 | CF₃ | Isoxazolin-3-yl | Cl | F | H |
| A-846 | CF₃ | Isoxazolin-3-yl | Cl | Cl | F |
| A-847 | CF₃ | Isoxazolin-3-yl | Cl | Cl | Cl |
| A-848 | CF₃ | Isoxazolin-3-yl | Cl | Cl | H |
| A-849 | CF₃ | Isoxazolin-3-yl | F | H | F |
| A-850 | CF₃ | Isoxazolin-3-yl | F | H | Cl |
| A-851 | CF₃ | Isoxazolin-3-yl | F | F | F |
| A-852 | CF₃ | Isoxazolin-3-yl | F | F | Cl |
| A-853 | CF₃ | Isoxazolin-3-yl | F | F | H |
| A-854 | CF₃ | Isoxazolin-3-yl | F | Cl | F |
| A-855 | CF₃ | Isoxazolin-3-yl | F | Cl | Cl |
| A-856 | CF₃ | Isoxazolin-3-yl | F | Cl | H |
| A-857 | CF₃ | Isoxazolin-3-yl | CF₃ | H | F |
| A-858 | CF₃ | Isoxazolin-3-yl | CF₃ | H | Cl |
| A-859 | CF₃ | Isoxazolin-3-yl | CF₃ | F | F |
| A-860 | CF₃ | Isoxazolin-3-yl | CF₃ | F | Cl |
| A-861 | CF₃ | Isoxazolin-3-yl | CF₃ | F | H |
| A-862 | CF₃ | Isoxazolin-3-yl | CF₃ | Cl | F |

TABLE A-continued

| | R¹ | R² | R³ | R⁴ | R⁵ |
|---|---|---|---|---|---|
| A-863 | CF₃ | Isoxazolin-3-yl | CF₃ | Cl | Cl |
| A-864 | CF₃ | Isoxazolin-3-yl | CF₃ | Cl | H |
| A-865 | CF₃ | Isoxazolin-3-yl | SO₂CH₃ | H | F |
| A-866 | CF₃ | Isoxazolin-3-yl | SO₂CH₃ | H | Cl |
| A-867 | CF₃ | Isoxazolin-3-yl | SO₂CH₃ | F | F |
| A-868 | CF₃ | Isoxazolin-3-yl | SO₂CH₃ | F | Cl |
| A-869 | CF₃ | Isoxazolin-3-yl | SO₂CH₃ | F | H |
| A-870 | CF₃ | Isoxazolin-3-yl | SO₂CH₃ | Cl | F |
| A-871 | CF₃ | Isoxazolin-3-yl | SO₂CH₃ | Cl | Cl |
| A-872 | CF₃ | Isoxazolin-3-yl | SO₂CH₃ | Cl | H |
| A-873 | CF₃ | Isoxazolin-3-yl | CN | H | F |
| A-874 | CF₃ | Isoxazolin-3-yl | CN | H | Cl |
| A-875 | CF₃ | Isoxazolin-3-yl | CN | F | F |
| A-876 | CF₃ | Isoxazolin-3-yl | CN | F | Cl |
| A-877 | CF₃ | Isoxazolin-3-yl | CN | F | H |
| A-878 | CF₃ | Isoxazolin-3-yl | CN | Cl | F |
| A-879 | CF₃ | Isoxazolin-3-yl | CN | Cl | Cl |
| A-880 | CF₃ | Isoxazolin-3-yl | CN | Cl | H |
| A-881 | CF₃ | 5-Methyl-isoxazolin-3-yl | Cl | H | F |
| A-882 | CF₃ | 5-Methyl-isoxazolin-3-yl | Cl | H | Cl |
| A-883 | CF₃ | 5-Methyl-isoxazolin-3-yl | Cl | F | F |
| A-884 | CF₃ | 5-Methyl-isoxazolin-3-yl | Cl | F | Cl |
| A-885 | CF₃ | 5-Methyl-isoxazolin-3-yl | Cl | F | H |
| A-886 | CF₃ | 5-Methyl-isoxazolin-3-yl | Cl | Cl | F |
| A-887 | CF₃ | 5-Methyl-isoxazolin-3-yl | Cl | Cl | Cl |
| A-888 | CF₃ | 5-Methyl-isoxazolin-3-yl | Cl | Cl | H |
| A-889 | CF₃ | 5-Methyl-isoxazolin-3-yl | F | H | F |
| A-890 | CF₃ | 5-Methyl-isoxazolin-3-yl | F | H | Cl |
| A-891 | CF₃ | 5-Methyl-isoxazolin-3-yl | F | F | F |
| A-892 | CF₃ | 5-Methyl-isoxazolin-3-yl | F | F | Cl |
| A-893 | CF₃ | 5-Methyl-isoxazolin-3-yl | F | F | H |
| A-894 | CF₃ | 5-Methyl-isoxazolin-3-yl | F | Cl | F |
| A-895 | CF₃ | 5-Methyl-isoxazolin-3-yl | F | Cl | Cl |
| A-896 | CF₃ | 5-Methyl-isoxazolin-3-yl | F | Cl | H |
| A-897 | CF₃ | 5-Methyl-isoxazolin-3-yl | CF₃ | H | F |
| A-898 | CF₃ | 5-Methyl-isoxazolin-3-yl | CF₃ | H | Cl |
| A-899 | CF₃ | 5-Methyl-isoxazolin-3-yl | CF₃ | F | F |
| A-900 | CF₃ | 5-Methyl-isoxazolin-3-yl | CF₃ | F | Cl |
| A-901 | CF₃ | 5-Methyl-isoxazolin-3-yl | CF₃ | F | H |
| A-902 | CF₃ | 5-Methyl-isoxazolin-3-yl | CF₃ | Cl | F |
| A-903 | CF₃ | 5-Methyl-isoxazolin-3-yl | CF₃ | Cl | Cl |
| A-904 | CF₃ | 5-Methyl-isoxazolin-3-yl | CF₃ | Cl | H |
| A-905 | CF₃ | 5-Methyl-isoxazolin-3-yl | SO₂CH₃ | H | F |
| A-906 | CF₃ | 5-Methyl-isoxazolin-3-yl | SO₂CH₃ | H | Cl |
| A-907 | CF₃ | 5-Methyl-isoxazolin-3-yl | SO₂CH₃ | F | F |
| A-908 | CF₃ | 5-Methyl-isoxazolin-3-yl | SO₂CH₃ | F | Cl |
| A-909 | CF₃ | 5-Methyl-isoxazolin-3-yl | SO₂CH₃ | F | H |
| A-910 | CF₃ | 5-Methyl-isoxazolin-3-yl | SO₂CH₃ | Cl | F |
| A-911 | CF₃ | 5-Methyl-isoxazolin-3-yl | SO₂CH₃ | Cl | Cl |
| A-912 | CF₃ | 5-Methyl-isoxazolin-3-yl | SO₂CH₃ | Cl | H |
| A-913 | CF₃ | 5-Methyl-isoxazolin-3-yl | CN | H | F |
| A-914 | CF₃ | 5-Methyl-isoxazolin-3-yl | CN | H | Cl |
| A-915 | CF₃ | 5-Methyl-isoxazolin-3-yl | CN | F | F |
| A-916 | CF₃ | 5-Methyl-isoxazolin-3-yl | CN | F | Cl |
| A-917 | CF₃ | 5-Methyl-isoxazolin-3-yl | CN | F | H |
| A-918 | CF₃ | 5-Methyl-isoxazolin-3-yl | CN | Cl | F |
| A-919 | CF₃ | 5-Methyl-isoxazolin-3-yl | CN | Cl | Cl |
| A-920 | CF₃ | 5-Methyl-isoxazolin-3-yl | CN | Cl | H |
| A-921 | CF₃ | Isoxazol-3-yl | Cl | H | F |
| A-922 | CF₃ | Isoxazol-3-yl | Cl | H | Cl |
| A-923 | CF₃ | Isoxazol-3-yl | Cl | F | F |
| A-924 | CF₃ | Isoxazol-3-yl | Cl | F | Cl |
| A-925 | CF₃ | Isoxazol-3-yl | Cl | F | H |
| A-926 | CF₃ | Isoxazol-3-yl | Cl | Cl | F |
| A-927 | CF₃ | Isoxazol-3-yl | Cl | Cl | Cl |
| A-928 | CF₃ | Isoxazol-3-yl | Cl | Cl | H |
| A-929 | CF₃ | Isoxazol-3-yl | F | H | F |
| A-930 | CF₃ | Isoxazol-3-yl | F | H | Cl |
| A-931 | CF₃ | Isoxazol-3-yl | F | F | F |
| A-932 | CF₃ | Isoxazol-3-yl | F | F | Cl |
| A-933 | CF₃ | Isoxazol-3-yl | F | F | H |
| A-934 | CF₃ | Isoxazol-3-yl | F | Cl | F |
| A-935 | CF₃ | Isoxazol-3-yl | F | Cl | Cl |
| A-936 | CF₃ | Isoxazol-3-yl | F | Cl | H |
| A-937 | CF₃ | Isoxazol-3-yl | CF₃ | H | F |
| A-938 | CF₃ | Isoxazol-3-yl | CF₃ | H | Cl |
| A-939 | CF₃ | Isoxazol-3-yl | CF₃ | F | F |
| A-940 | CF₃ | Isoxazol-3-yl | CF₃ | F | Cl |
| A-941 | CF₃ | Isoxazol-3-yl | CF₃ | F | H |
| A-942 | CF₃ | Isoxazol-3-yl | CF₃ | Cl | F |
| A-943 | CF₃ | Isoxazol-3-yl | CF₃ | Cl | Cl |
| A-944 | CF₃ | Isoxazol-3-yl | CF₃ | Cl | H |
| A-945 | CF₃ | Isoxazol-3-yl | SO₂CH₃ | H | F |
| A-946 | CF₃ | Isoxazol-3-yl | SO₂CH₃ | H | Cl |
| A-947 | CF₃ | Isoxazol-3-yl | SO₂CH₃ | F | F |
| A-948 | CF₃ | Isoxazol-3-yl | SO₂CH₃ | F | Cl |
| A-949 | CF₃ | Isoxazol-3-yl | SO₂CH₃ | F | H |
| A-950 | CF₃ | Isoxazol-3-yl | SO₂CH₃ | Cl | F |
| A-951 | CF₃ | Isoxazol-3-yl | SO₂CH₃ | Cl | Cl |
| A-952 | CF₃ | Isoxazol-3-yl | SO₂CH₃ | Cl | H |
| A-953 | CF₃ | Isoxazol-3-yl | CN | H | F |
| A-954 | CF₃ | Isoxazol-3-yl | CN | H | Cl |
| A-955 | CF₃ | Isoxazol-3-yl | CN | F | F |
| A-956 | CF₃ | Isoxazol-3-yl | CN | F | Cl |
| A-957 | CF₃ | Isoxazol-3-yl | CN | F | H |
| A-958 | CF₃ | Isoxazol-3-yl | CN | Cl | F |
| A-959 | CF₃ | Isoxazol-3-yl | CN | Cl | Cl |
| A-960 | CF₃ | Isoxazol-3-yl | CN | Cl | H |
| A-961 | CF₃ | 5-Methyl-isoxazol-3-yl | Cl | H | F |
| A-962 | CF₃ | 5-Methyl-isoxazol-3-yl | Cl | H | Cl |
| A-963 | CF₃ | 5-Methyl-isoxazol-3-yl | Cl | F | F |
| A-964 | CF₃ | 5-Methyl-isoxazol-3-yl | Cl | F | Cl |
| A-965 | CF₃ | 5-Methyl-isoxazol-3-yl | Cl | F | H |
| A-966 | CF₃ | 5-Methyl-isoxazol-3-yl | Cl | Cl | F |
| A-967 | CF₃ | 5-Methyl-isoxazol-3-yl | Cl | Cl | Cl |
| A-968 | CF₃ | 5-Methyl-isoxazol-3-yl | Cl | Cl | H |
| A-969 | CF₃ | 5-Methyl-isoxazol-3-yl | F | H | F |
| A-970 | CF₃ | 5-Methyl-isoxazol-3-yl | F | H | Cl |
| A-971 | CF₃ | 5-Methyl-isoxazol-3-yl | F | F | F |
| A-972 | CF₃ | 5-Methyl-isoxazol-3-yl | F | F | Cl |
| A-973 | CF₃ | 5-Methyl-isoxazol-3-yl | F | F | H |
| A-974 | CF₃ | 5-Methyl-isoxazol-3-yl | F | Cl | F |
| A-975 | CF₃ | 5-Methyl-isoxazol-3-yl | F | Cl | Cl |
| A-976 | CF₃ | 5-Methyl-isoxazol-3-yl | F | Cl | H |
| A-977 | CF₃ | 5-Methyl-isoxazol-3-yl | CF₃ | H | F |
| A-978 | CF₃ | 5-Methyl-isoxazol-3-yl | CF₃ | H | Cl |
| A-979 | CF₃ | 5-Methyl-isoxazol-3-yl | CF₃ | F | F |
| A-980 | CF₃ | 5-Methyl-isoxazol-3-yl | CF₃ | F | Cl |
| A-981 | CF₃ | 5-Methyl-isoxazol-3-yl | CF₃ | F | H |
| A-982 | CF₃ | 5-Methyl-isoxazol-3-yl | CF₃ | Cl | F |
| A-983 | CF₃ | 5-Methyl-isoxazol-3-yl | CF₃ | Cl | Cl |
| A-984 | CF₃ | 5-Methyl-isoxazol-3-yl | CF₃ | Cl | H |
| A-985 | CF₃ | 5-Methyl-isoxazol-3-yl | SO₂CH₃ | H | F |
| A-986 | CF₃ | 5-Methyl-isoxazol-3-yl | SO₂CH₃ | H | Cl |
| A-987 | CF₃ | 5-Methyl-isoxazol-3-yl | SO₂CH₃ | F | F |
| A-988 | CF₃ | 5-Methyl-isoxazol-3-yl | SO₂CH₃ | F | Cl |
| A-989 | CF₃ | 5-Methyl-isoxazol-3-yl | SO₂CH₃ | F | H |
| A-990 | CF₃ | 5-Methyl-isoxazol-3-yl | SO₂CH₃ | Cl | F |
| A-991 | CF₃ | 5-Methyl-isoxazol-3-yl | SO₂CH₃ | Cl | Cl |
| A-992 | CF₃ | 5-Methyl-isoxazol-3-yl | SO₂CH₃ | Cl | H |
| A-993 | CF₃ | 5-Methyl-isoxazol-3-yl | CN | H | F |
| A-994 | CF₃ | 5-Methyl-isoxazol-3-yl | CN | H | Cl |
| A-995 | CF₃ | 5-Methyl-isoxazol-3-yl | CN | F | F |
| A-996 | CF₃ | 5-Methyl-isoxazol-3-yl | CN | F | Cl |
| A-997 | CF₃ | 5-Methyl-isoxazol-3-yl | CN | F | H |
| A-998 | CF₃ | 5-Methyl-isoxazol-3-yl | CN | Cl | F |
| A-999 | CF₃ | 5-Methyl-isoxazol-3-yl | CN | Cl | Cl |
| A-1000 | CF₃ | 5-Methyl-isoxazol-3-yl | CN | Cl | H |
| A-1001 | CF₃ | 3-Methyl-isoxazolin-5-yl | Cl | H | F |
| A-1002 | CF₃ | 3-Methyl-isoxazolin-5-yl | Cl | H | Cl |
| A-1003 | CF₃ | 3-Methyl-isoxazolin-5-yl | Cl | F | F |
| A-1004 | CF₃ | 3-Methyl-isoxazolin-5-yl | Cl | F | Cl |
| A-1005 | CF₃ | 3-Methyl-isoxazolin-5-yl | Cl | F | H |
| A-1006 | CF₃ | 3-Methyl-isoxazolin-5-yl | Cl | Cl | F |
| A-1007 | CF₃ | 3-Methyl-isoxazolin-5-yl | Cl | Cl | Cl |
| A-1008 | CF₃ | 3-Methyl-isoxazolin-5-yl | Cl | Cl | H |
| A-1009 | CF₃ | 3-Methyl-isoxazolin-5-yl | F | H | F |
| A-1010 | CF₃ | 3-Methyl-isoxazolin-5-yl | F | H | Cl |
| A-1011 | CF₃ | 3-Methyl-isoxazolin-5-yl | F | F | F |
| A-1012 | CF₃ | 3-Methyl-isoxazolin-5-yl | F | F | Cl |
| A-1013 | CF₃ | 3-Methyl-isoxazolin-5-yl | F | F | H |
| A-1014 | CF₃ | 3-Methyl-isoxazolin-5-yl | F | Cl | F |
| A-1015 | CF₃ | 3-Methyl-isoxazolin-5-yl | F | Cl | Cl |
| A-1016 | CF₃ | 3-Methyl-isoxazolin-5-yl | F | Cl | H |
| A-1017 | CF₃ | 3-Methyl-isoxazolin-5-yl | CF₃ | H | F |
| A-1018 | CF₃ | 3-Methyl-isoxazolin-5-yl | CF₃ | H | Cl |

TABLE A-continued

| | R¹ | R² | R³ | R⁴ | R⁵ |
|---|---|---|---|---|---|
| A-1019 | $CF_3$ | 3-Methyl-isoxazolin-5-yl | $CF_3$ | F | F |
| A-1020 | $CF_3$ | 3-Methyl-isoxazolin-5-yl | $CF_3$ | F | Cl |
| A-1021 | $CF_3$ | 3-Methyl-isoxazolin-5-yl | $CF_3$ | F | H |
| A-1022 | $CF_3$ | 3-Methyl-isoxazolin-5-yl | $CF_3$ | Cl | F |
| A-1023 | $CF_3$ | 3-Methyl-isoxazolin-5-yl | $CF_3$ | Cl | Cl |
| A-1024 | $CF_3$ | 3-Methyl-isoxazolin-5-yl | $CF_3$ | Cl | H |
| A-1025 | $CF_3$ | 3-Methyl-isoxazolin-5-yl | $SO_2CH_3$ | H | F |
| A-1026 | $CF_3$ | 3-Methyl-isoxazolin-5-yl | $SO_2CH_3$ | H | Cl |
| A-1027 | $CF_3$ | 3-Methyl-isoxazolin-5-yl | $SO_2CH_3$ | F | F |
| A-1028 | $CF_3$ | 3-Methyl-isoxazolin-5-yl | $SO_2CH_3$ | F | Cl |
| A-1029 | $CF_3$ | 3-Methyl-isoxazolin-5-yl | $SO_2CH_3$ | F | H |
| A-1030 | $CF_3$ | 3-Methyl-isoxazolin-5-yl | $SO_2CH_3$ | Cl | F |
| A-1031 | $CF_3$ | 3-Methyl-isoxazolin-5-yl | $SO_2CH_3$ | Cl | Cl |
| A-1032 | $CF_3$ | 3-Methyl-isoxazolin-5-yl | $SO_2CH_3$ | Cl | H |
| A-1033 | $CF_3$ | 3-Methyl-isoxazolin-5-yl | CN | H | F |
| A-1034 | $CF_3$ | 3-Methyl-isoxazolin-5-yl | CN | H | Cl |
| A-1035 | $CF_3$ | 3-Methyl-isoxazolin-5-yl | CN | F | F |
| A-1036 | $CF_3$ | 3-Methyl-isoxazolin-5-yl | CN | F | Cl |
| A-1037 | $CF_3$ | 3-Methyl-isoxazolin-5-yl | CN | F | H |
| A-1038 | $CF_3$ | 3-Methyl-isoxazolin-5-yl | CN | Cl | F |
| A-1039 | $CF_3$ | 3-Methyl-isoxazolin-5-yl | CN | Cl | Cl |
| A-1040 | $CF_3$ | 3-Methyl-isoxazolin-5-yl | CN | Cl | H |
| A-1041 | $CF_3$ | 3-Methyl-isoxazol-5-yl | Cl | H | F |
| A-1042 | $CF_3$ | 3-Methyl-isoxazol-5-yl | Cl | H | Cl |
| A-1043 | $CF_3$ | 3-Methyl-isoxazol-5-yl | Cl | F | F |
| A-1044 | $CF_3$ | 3-Methyl-isoxazol-5-yl | Cl | F | Cl |
| A-1045 | $CF_3$ | 3-Methyl-isoxazol-5-yl | Cl | F | H |
| A-1046 | $CF_3$ | 3-Methyl-isoxazol-5-yl | Cl | Cl | F |
| A-1047 | $CF_3$ | 3-Methyl-isoxazol-5-yl | Cl | Cl | Cl |
| A-1048 | $CF_3$ | 3-Methyl-isoxazol-5-yl | Cl | Cl | H |
| A-1049 | $CF_3$ | 3-Methyl-isoxazol-5-yl | F | H | F |
| A-1050 | $CF_3$ | 3-Methyl-isoxazol-5-yl | F | H | Cl |
| A-1051 | $CF_3$ | 3-Methyl-isoxazol-5-yl | F | F | F |
| A-1052 | $CF_3$ | 3-Methyl-isoxazol-5-yl | F | F | Cl |
| A-1053 | $CF_3$ | 3-Methyl-isoxazol-5-yl | F | F | H |
| A-1054 | $CF_3$ | 3-Methyl-isoxazol-5-yl | F | Cl | F |
| A-1055 | $CF_3$ | 3-Methyl-isoxazol-5-yl | F | Cl | Cl |
| A-1056 | $CF_3$ | 3-Methyl-isoxazol-5-yl | F | Cl | H |
| A-1057 | $CF_3$ | 3-Methyl-isoxazol-5-yl | $CF_3$ | H | F |
| A-1058 | $CF_3$ | 3-Methyl-isoxazol-5-yl | $CF_3$ | H | Cl |
| A-1059 | $CF_3$ | 3-Methyl-isoxazol-5-yl | $CF_3$ | F | F |
| A-1060 | $CF_3$ | 3-Methyl-isoxazol-5-yl | $CF_3$ | F | Cl |
| A-1061 | $CF_3$ | 3-Methyl-isoxazol-5-yl | $CF_3$ | F | H |
| A-1062 | $CF_3$ | 3-Methyl-isoxazol-5-yl | $CF_3$ | Cl | F |
| A-1063 | $CF_3$ | 3-Methyl-isoxazol-5-yl | $CF_3$ | Cl | Cl |
| A-1064 | $CF_3$ | 3-Methyl-isoxazol-5-yl | $CF_3$ | Cl | H |
| A-1065 | $CF_3$ | 3-Methyl-isoxazol-5-yl | $SO_2CH_3$ | H | F |
| A-1066 | $CF_3$ | 3-Methyl-isoxazol-5-yl | $SO_2CH_3$ | H | Cl |
| A-1067 | $CF_3$ | 3-Methyl-isoxazol-5-yl | $SO_2CH_3$ | F | F |
| A-1068 | $CF_3$ | 3-Methyl-isoxazol-5-yl | $SO_2CH_3$ | F | Cl |
| A-1069 | $CF_3$ | 3-Methyl-isoxazol-5-yl | $SO_2CH_3$ | F | H |
| A-1070 | $CF_3$ | 3-Methyl-isoxazol-5-yl | $SO_2CH_3$ | Cl | F |
| A-1071 | $CF_3$ | 3-Methyl-isoxazol-5-yl | $SO_2CH_3$ | Cl | Cl |
| A-1072 | $CF_3$ | 3-Methyl-isoxazol-5-yl | $SO_2CH_3$ | Cl | H |
| A-1073 | $CF_3$ | 3-Methyl-isoxazol-5-yl | CN | H | F |
| A-1074 | $CF_3$ | 3-Methyl-isoxazol-5-yl | CN | H | Cl |
| A-1075 | $CF_3$ | 3-Methyl-isoxazol-5-yl | CN | F | F |
| A-1076 | $CF_3$ | 3-Methyl-isoxazol-5-yl | CN | F | Cl |
| A-1077 | $CF_3$ | 3-Methyl-isoxazol-5-yl | CN | F | H |
| A-1078 | $CF_3$ | 3-Methyl-isoxazol-5-yl | CN | Cl | F |
| A-1079 | $CF_3$ | 3-Methyl-isoxazol-5-yl | CN | Cl | Cl |
| A-1080 | $CF_3$ | 3-Methyl-isoxazol-5-yl | CN | Cl | H |
| A-1081 | $SO_2CH_3$ | H | Cl | H | F |
| A-1082 | $SO_2CH_3$ | H | Cl | H | Cl |
| A-1083 | $SO_2CH_3$ | H | Cl | F | F |
| A-1084 | $SO_2CH_3$ | H | Cl | F | Cl |
| A-1085 | $SO_2CH_3$ | H | Cl | F | H |
| A-1086 | $SO_2CH_3$ | H | Cl | Cl | F |
| A-1087 | $SO_2CH_3$ | H | Cl | Cl | Cl |
| A-1088 | $SO_2CH_3$ | H | Cl | Cl | H |
| A-1089 | $SO_2CH_3$ | H | F | H | F |
| A-1090 | $SO_2CH_3$ | H | F | H | Cl |
| A-1091 | $SO_2CH_3$ | H | F | F | F |
| A-1092 | $SO_2CH_3$ | H | F | F | Cl |
| A-1093 | $SO_2CH_3$ | H | F | F | H |
| A-1094 | $SO_2CH_3$ | H | F | Cl | F |
| A-1095 | $SO_2CH_3$ | H | F | Cl | Cl |
| A-1096 | $SO_2CH_3$ | H | F | Cl | H |
| A-1097 | $SO_2CH_3$ | H | $CF_3$ | H | F |
| A-1098 | $SO_2CH_3$ | H | $CF_3$ | H | Cl |
| A-1099 | $SO_2CH_3$ | H | $CF_3$ | F | F |
| A-1100 | $SO_2CH_3$ | H | $CF_3$ | F | Cl |
| A-1101 | $SO_2CH_3$ | H | $CF_3$ | F | H |
| A-1102 | $SO_2CH_3$ | H | $CF_3$ | Cl | F |
| A-1103 | $SO_2CH_3$ | H | $CF_3$ | Cl | Cl |
| A-1104 | $SO_2CH_3$ | H | $CF_3$ | Cl | H |
| A-1105 | $SO_2CH_3$ | H | $SO_2CH_3$ | H | F |
| A-1106 | $SO_2CH_3$ | H | $SO_2CH_3$ | H | Cl |
| A-1107 | $SO_2CH_3$ | H | $SO_2CH_3$ | F | F |
| A-1108 | $SO_2CH_3$ | H | $SO_2CH_3$ | F | Cl |
| A-1109 | $SO_2CH_3$ | H | $SO_2CH_3$ | F | H |
| A-1110 | $SO_2CH_3$ | H | $SO_2CH_3$ | Cl | F |
| A-1111 | $SO_2CH_3$ | H | $SO_2CH_3$ | Cl | Cl |
| A-1112 | $SO_2CH_3$ | H | $SO_2CH_3$ | Cl | H |
| A-1113 | $SO_2CH_3$ | H | CN | H | F |
| A-1114 | $SO_2CH_3$ | H | CN | H | Cl |
| A-1115 | $SO_2CH_3$ | H | CN | F | F |
| A-1116 | $SO_2CH_3$ | H | CN | F | Cl |
| A-1117 | $SO_2CH_3$ | H | CN | F | H |
| A-1118 | $SO_2CH_3$ | H | CN | Cl | F |
| A-1119 | $SO_2CH_3$ | H | CN | Cl | Cl |
| A-1120 | $SO_2CH_3$ | H | CN | Cl | H |
| A-1121 | $SO_2CH_3$ | $SO_2CH_3$ | Cl | H | F |
| A-1122 | $SO_2CH_3$ | $SO_2CH_3$ | Cl | H | Cl |
| A-1123 | $SO_2CH_3$ | $SO_2CH_3$ | Cl | F | F |
| A-1124 | $SO_2CH_3$ | $SO_2CH_3$ | Cl | F | Cl |
| A-1125 | $SO_2CH_3$ | $SO_2CH_3$ | Cl | F | H |
| A-1126 | $SO_2CH_3$ | $SO_2CH_3$ | Cl | Cl | F |
| A-1127 | $SO_2CH_3$ | $SO_2CH_3$ | Cl | Cl | Cl |
| A-1128 | $SO_2CH_3$ | $SO_2CH_3$ | Cl | Cl | H |
| A-1129 | $SO_2CH_3$ | $SO_2CH_3$ | F | H | F |
| A-1130 | $SO_2CH_3$ | $SO_2CH_3$ | F | H | Cl |
| A-1131 | $SO_2CH_3$ | $SO_2CH_3$ | F | F | F |
| A-1132 | $SO_2CH_3$ | $SO_2CH_3$ | F | F | Cl |
| A-1133 | $SO_2CH_3$ | $SO_2CH_3$ | F | F | H |
| A-1134 | $SO_2CH_3$ | $SO_2CH_3$ | F | Cl | F |
| A-1135 | $SO_2CH_3$ | $SO_2CH_3$ | F | Cl | Cl |
| A-1136 | $SO_2CH_3$ | $SO_2CH_3$ | F | Cl | H |
| A-1137 | $SO_2CH_3$ | $SO_2CH_3$ | $CF_3$ | H | F |
| A-1138 | $SO_2CH_3$ | $SO_2CH_3$ | $CF_3$ | H | Cl |
| A-1139 | $SO_2CH_3$ | $SO_2CH_3$ | $CF_3$ | F | F |
| A-1140 | $SO_2CH_3$ | $SO_2CH_3$ | $CF_3$ | F | Cl |
| A-1141 | $SO_2CH_3$ | $SO_2CH_3$ | $CF_3$ | F | H |
| A-1142 | $SO_2CH_3$ | $SO_2CH_3$ | $CF_3$ | Cl | F |
| A-1143 | $SO_2CH_3$ | $SO_2CH_3$ | $CF_3$ | Cl | Cl |
| A-1144 | $SO_2CH_3$ | $SO_2CH_3$ | $CF_3$ | Cl | H |
| A-1145 | $SO_2CH_3$ | $SO_2CH_3$ | $SO_2CH_3$ | H | F |
| A-1146 | $SO_2CH_3$ | $SO_2CH_3$ | $SO_2CH_3$ | H | Cl |
| A-1147 | $SO_2CH_3$ | $SO_2CH_3$ | $SO_2CH_3$ | F | F |
| A-1148 | $SO_2CH_3$ | $SO_2CH_3$ | $SO_2CH_3$ | F | Cl |
| A-1149 | $SO_2CH_3$ | $SO_2CH_3$ | $SO_2CH_3$ | F | H |
| A-1150 | $SO_2CH_3$ | $SO_2CH_3$ | $SO_2CH_3$ | Cl | F |
| A-1151 | $SO_2CH_3$ | $SO_2CH_3$ | $SO_2CH_3$ | Cl | Cl |
| A-1152 | $SO_2CH_3$ | $SO_2CH_3$ | $SO_2CH_3$ | Cl | H |
| A-1153 | $SO_2CH_3$ | $SO_2CH_3$ | CN | H | F |
| A-1154 | $SO_2CH_3$ | $SO_2CH_3$ | CN | H | Cl |
| A-1155 | $SO_2CH_3$ | $SO_2CH_3$ | CN | F | F |
| A-1156 | $SO_2CH_3$ | $SO_2CH_3$ | CN | F | Cl |
| A-1157 | $SO_2CH_3$ | $SO_2CH_3$ | CN | F | H |
| A-1158 | $SO_2CH_3$ | $SO_2CH_3$ | CN | Cl | F |
| A-1159 | $SO_2CH_3$ | $SO_2CH_3$ | CN | Cl | Cl |
| A-1160 | $SO_2CH_3$ | $SO_2CH_3$ | CN | Cl | H |
| A-1161 | $SO_2CH_3$ | $CH_2OCH_2CF_3$ | Cl | H | F |
| A-1162 | $SO_2CH_3$ | $CH_2OCH_2CF_3$ | Cl | H | Cl |
| A-1163 | $SO_2CH_3$ | $CH_2OCH_2CF_3$ | Cl | F | F |
| A-1164 | $SO_2CH_3$ | $CH_2OCH_2CF_3$ | Cl | F | Cl |
| A-1165 | $SO_2CH_3$ | $CH_2OCH_2CF_3$ | Cl | F | H |
| A-1166 | $SO_2CH_3$ | $CH_2OCH_2CF_3$ | Cl | Cl | F |
| A-1167 | $SO_2CH_3$ | $CH_2OCH_2CF_3$ | Cl | Cl | Cl |
| A-1168 | $SO_2CH_3$ | $CH_2OCH_2CF_3$ | Cl | Cl | H |
| A-1169 | $SO_2CH_3$ | $CH_2OCH_2CF_3$ | F | H | F |
| A-1170 | $SO_2CH_3$ | $CH_2OCH_2CF_3$ | F | H | Cl |
| A-1171 | $SO_2CH_3$ | $CH_2OCH_2CF_3$ | F | F | F |
| A-1172 | $SO_2CH_3$ | $CH_2OCH_2CF_3$ | F | F | Cl |
| A-1173 | $SO_2CH_3$ | $CH_2OCH_2CF_3$ | F | F | H |
| A-1174 | $SO_2CH_3$ | $CH_2OCH_2CF_3$ | F | Cl | F |

TABLE A-continued

| | R¹ | R² | R³ | R⁴ | R⁵ |
|---|---|---|---|---|---|
| A-1175 | SO₂CH₃ | CH₂OCH₂CF₃ | F | Cl | Cl |
| A-1176 | SO₂CH₃ | CH₂OCH₂CF₃ | F | Cl | H |
| A-1177 | SO₂CH₃ | CH₂OCH₂CF₃ | CF₃ | H | F |
| A-1178 | SO₂CH₃ | CH₂OCH₂CF₃ | CF₃ | H | Cl |
| A-1179 | SO₂CH₃ | CH₂OCH₂CF₃ | CF₃ | F | F |
| A-1180 | SO₂CH₃ | CH₂OCH₂CF₃ | CF₃ | F | Cl |
| A-1181 | SO₂CH₃ | CH₂OCH₂CF₃ | CF₃ | F | H |
| A-1182 | SO₂CH₃ | CH₂OCH₂CF₃ | CF₃ | Cl | F |
| A-1183 | SO₂CH₃ | CH₂OCH₂CF₃ | CF₃ | Cl | Cl |
| A-1184 | SO₂CH₃ | CH₂OCH₂CF₃ | CF₃ | Cl | H |
| A-1185 | SO₂CH₃ | CH₂OCH₂CF₃ | SO₂CH₃ | H | F |
| A-1186 | SO₂CH₃ | CH₂OCH₂CF₃ | SO₂CH₃ | H | Cl |
| A-1187 | SO₂CH₃ | CH₂OCH₂CF₃ | SO₂CH₃ | F | F |
| A-1188 | SO₂CH₃ | CH₂OCH₂CF₃ | SO₂CH₃ | F | Cl |
| A-1189 | SO₂CH₃ | CH₂OCH₂CF₃ | SO₂CH₃ | F | H |
| A-1190 | SO₂CH₃ | CH₂OCH₂CF₃ | SO₂CH₃ | Cl | F |
| A-1191 | SO₂CH₃ | CH₂OCH₂CF₃ | SO₂CH₃ | Cl | Cl |
| A-1192 | SO₂CH₃ | CH₂OCH₂CF₃ | SO₂CH₃ | Cl | H |
| A-1193 | SO₂CH₃ | CH₂OCH₂CF₃ | CN | H | F |
| A-1194 | SO₂CH₃ | CH₂OCH₂CF₃ | CN | H | Cl |
| A-1195 | SO₂CH₃ | CH₂OCH₂CF₃ | CN | F | F |
| A-1196 | SO₂CH₃ | CH₂OCH₂CF₃ | CN | F | Cl |
| A-1197 | SO₂CH₃ | CH₂OCH₂CF₃ | CN | F | H |
| A-1198 | SO₂CH₃ | CH₂OCH₂CF₃ | CN | Cl | F |
| A-1199 | SO₂CH₃ | CH₂OCH₂CF₃ | CN | Cl | Cl |
| A-1200 | SO₂CH₃ | CH₂OCH₂CF₃ | CN | Cl | H |
| A-1201 | SO₂CH₃ | Isoxazolin-3-yl | Cl | H | F |
| A-1202 | SO₂CH₃ | Isoxazolin-3-yl | Cl | H | Cl |
| A-1203 | SO₂CH₃ | Isoxazolin-3-yl | Cl | F | F |
| A-1204 | SO₂CH₃ | Isoxazolin-3-yl | Cl | F | Cl |
| A-1205 | SO₂CH₃ | Isoxazolin-3-yl | Cl | F | H |
| A-1206 | SO₂CH₃ | Isoxazolin-3-yl | Cl | Cl | F |
| A-1207 | SO₂CH₃ | Isoxazolin-3-yl | Cl | Cl | Cl |
| A-1208 | SO₂CH₃ | Isoxazolin-3-yl | Cl | Cl | H |
| A-1209 | SO₂CH₃ | Isoxazolin-3-yl | F | H | F |
| A-1210 | SO₂CH₃ | Isoxazolin-3-yl | F | H | Cl |
| A-1211 | SO₂CH₃ | Isoxazolin-3-yl | F | F | F |
| A-1212 | SO₂CH₃ | Isoxazolin-3-yl | F | F | Cl |
| A-1213 | SO₂CH₃ | Isoxazolin-3-yl | F | F | H |
| A-1214 | SO₂CH₃ | Isoxazolin-3-yl | F | Cl | F |
| A-1215 | SO₂CH₃ | Isoxazolin-3-yl | F | Cl | Cl |
| A-1216 | SO₂CH₃ | Isoxazolin-3-yl | F | Cl | H |
| A-1217 | SO₂CH₃ | Isoxazolin-3-yl | CF₃ | H | F |
| A-1218 | SO₂CH₃ | Isoxazolin-3-yl | CF₃ | H | Cl |
| A-1219 | SO₂CH₃ | Isoxazolin-3-yl | CF₃ | F | F |
| A-1220 | SO₂CH₃ | Isoxazolin-3-yl | CF₃ | F | Cl |
| A-1221 | SO₂CH₃ | Isoxazolin-3-yl | CF₃ | F | H |
| A-1222 | SO₂CH₃ | Isoxazolin-3-yl | CF₃ | Cl | F |
| A-1223 | SO₂CH₃ | Isoxazolin-3-yl | CF₃ | Cl | Cl |
| A-1224 | SO₂CH₃ | Isoxazolin-3-yl | CF₃ | Cl | H |
| A-1225 | SO₂CH₃ | Isoxazolin-3-yl | SO₂CH₃ | H | F |
| A-1226 | SO₂CH₃ | Isoxazolin-3-yl | SO₂CH₃ | H | Cl |
| A-1227 | SO₂CH₃ | Isoxazolin-3-yl | SO₂CH₃ | F | F |
| A-1228 | SO₂CH₃ | Isoxazolin-3-yl | SO₂CH₃ | F | Cl |
| A-1229 | SO₂CH₃ | Isoxazolin-3-yl | SO₂CH₃ | F | H |
| A-1230 | SO₂CH₃ | Isoxazolin-3-yl | SO₂CH₃ | Cl | F |
| A-1231 | SO₂CH₃ | Isoxazolin-3-yl | SO₂CH₃ | Cl | Cl |
| A-1232 | SO₂CH₃ | Isoxazolin-3-yl | SO₂CH₃ | Cl | H |
| A-1233 | SO₂CH₃ | Isoxazolin-3-yl | CN | H | F |
| A-1234 | SO₂CH₃ | Isoxazolin-3-yl | CN | H | Cl |
| A-1235 | SO₂CH₃ | Isoxazolin-3-yl | CN | F | F |
| A-1236 | SO₂CH₃ | Isoxazolin-3-yl | CN | F | Cl |
| A-1237 | SO₂CH₃ | Isoxazolin-3-yl | CN | F | H |
| A-1238 | SO₂CH₃ | Isoxazolin-3-yl | CN | Cl | F |
| A-1239 | SO₂CH₃ | Isoxazolin-3-yl | CN | Cl | Cl |
| A-1240 | SO₂CH₃ | Isoxazolin-3-yl | CN | Cl | H |
| A-1241 | SO₂CH₃ | 5-Methyl-isoxazolin-3-yl | Cl | H | F |
| A-1242 | SO₂CH₃ | 5-Methyl-isoxazolin-3-yl | Cl | H | Cl |
| A-1243 | SO₂CH₃ | 5-Methyl-isoxazolin-3-yl | Cl | F | F |
| A-1244 | SO₂CH₃ | 5-Methyl-isoxazolin-3-yl | Cl | F | Cl |
| A-1245 | SO₂CH₃ | 5-Methyl-isoxazolin-3-yl | Cl | F | H |
| A-1246 | SO₂CH₃ | 5-Methyl-isoxazolin-3-yl | Cl | Cl | F |
| A-1247 | SO₂CH₃ | 5-Methyl-isoxazolin-3-yl | Cl | Cl | Cl |
| A-1248 | SO₂CH₃ | 5-Methyl-isoxazolin-3-yl | Cl | Cl | H |
| A-1249 | SO₂CH₃ | 5-Methyl-isoxazolin-3-yl | F | H | F |
| A-1250 | SO₂CH₃ | 5-Methyl-isoxazolin-3-yl | F | H | Cl |
| A-1251 | SO₂CH₃ | 5-Methyl-isoxazolin-3-yl | F | F | F |
| A-1252 | SO₂CH₃ | 5-Methyl-isoxazolin-3-yl | F | F | Cl |
| A-1253 | SO₂CH₃ | 5-Methyl-isoxazolin-3-yl | F | F | H |
| A-1254 | SO₂CH₃ | 5-Methyl-isoxazolin-3-yl | F | Cl | F |
| A-1255 | SO₂CH₃ | 5-Methyl-isoxazolin-3-yl | F | Cl | Cl |
| A-1256 | SO₂CH₃ | 5-Methyl-isoxazolin-3-yl | F | Cl | H |
| A-1257 | SO₂CH₃ | 5-Methyl-isoxazolin-3-yl | CF₃ | H | F |
| A-1258 | SO₂CH₃ | 5-Methyl-isoxazolin-3-yl | CF₃ | H | Cl |
| A-1259 | SO₂CH₃ | 5-Methyl-isoxazolin-3-yl | CF₃ | F | F |
| A-1260 | SO₂CH₃ | 5-Methyl-isoxazolin-3-yl | CF₃ | F | Cl |
| A-1261 | SO₂CH₃ | 5-Methyl-isoxazolin-3-yl | CF₃ | F | H |
| A-1262 | SO₂CH₃ | 5-Methyl-isoxazolin-3-yl | CF₃ | Cl | F |
| A-1263 | SO₂CH₃ | 5-Methyl-isoxazolin-3-yl | CF₃ | Cl | Cl |
| A-1264 | SO₂CH₃ | 5-Methyl-isoxazolin-3-yl | CF₃ | Cl | H |
| A-1265 | SO₂CH₃ | 5-Methyl-isoxazolin-3-yl | SO₂CH₃ | H | F |
| A-1266 | SO₂CH₃ | 5-Methyl-isoxazolin-3-yl | SO₂CH₃ | H | Cl |
| A-1267 | SO₂CH₃ | 5-Methyl-isoxazolin-3-yl | SO₂CH₃ | F | F |
| A-1268 | SO₂CH₃ | 5-Methyl-isoxazolin-3-yl | SO₂CH₃ | F | Cl |
| A-1269 | SO₂CH₃ | 5-Methyl-isoxazolin-3-yl | SO₂CH₃ | F | H |
| A-1270 | SO₂CH₃ | 5-Methyl-isoxazolin-3-yl | SO₂CH₃ | Cl | F |
| A-1271 | SO₂CH₃ | 5-Methyl-isoxazolin-3-yl | SO₂CH₃ | Cl | Cl |
| A-1272 | SO₂CH₃ | 5-Methyl-isoxazolin-3-yl | SO₂CH₃ | Cl | H |
| A-1273 | SO₂CH₃ | 5-Methyl-isoxazolin-3-yl | CN | H | F |
| A-1274 | SO₂CH₃ | 5-Methyl-isoxazolin-3-yl | CN | H | Cl |
| A-1275 | SO₂CH₃ | 5-Methyl-isoxazolin-3-yl | CN | F | F |
| A-1276 | SO₂CH₃ | 5-Methyl-isoxazolin-3-yl | CN | F | Cl |
| A-1277 | SO₂CH₃ | 5-Methyl-isoxazolin-3-yl | CN | F | H |
| A-1278 | SO₂CH₃ | 5-Methyl-isoxazolin-3-yl | CN | Cl | F |
| A-1279 | SO₂CH₃ | 5-Methyl-isoxazolin-3-yl | CN | Cl | Cl |
| A-1280 | SO₂CH₃ | 5-Methyl-isoxazolin-3-yl | CN | Cl | H |
| A-1281 | SO₂CH₃ | Isoxazol-3-yl | Cl | H | F |
| A-1282 | SO₂CH₃ | Isoxazol-3-yl | Cl | H | Cl |
| A-1283 | SO₂CH₃ | Isoxazol-3-yl | Cl | F | F |
| A-1284 | SO₂CH₃ | Isoxazol-3-yl | Cl | F | Cl |
| A-1285 | SO₂CH₃ | Isoxazol-3-yl | Cl | F | H |
| A-1286 | SO₂CH₃ | Isoxazol-3-yl | Cl | Cl | F |
| A-1287 | SO₂CH₃ | Isoxazol-3-yl | Cl | Cl | Cl |
| A-1288 | SO₂CH₃ | Isoxazol-3-yl | Cl | Cl | H |
| A-1289 | SO₂CH₃ | Isoxazol-3-yl | F | H | F |
| A-1290 | SO₂CH₃ | Isoxazol-3-yl | F | H | Cl |
| A-1291 | SO₂CH₃ | Isoxazol-3-yl | F | F | F |
| A-1292 | SO₂CH₃ | Isoxazol-3-yl | F | F | Cl |
| A-1293 | SO₂CH₃ | Isoxazol-3-yl | F | F | H |
| A-1294 | SO₂CH₃ | Isoxazol-3-yl | F | Cl | F |
| A-1295 | SO₂CH₃ | Isoxazol-3-yl | F | Cl | Cl |
| A-1296 | SO₂CH₃ | Isoxazol-3-yl | F | Cl | H |
| A-1297 | SO₂CH₃ | Isoxazol-3-yl | CF₃ | H | F |
| A-1298 | SO₂CH₃ | Isoxazol-3-yl | CF₃ | H | Cl |
| A-1299 | SO₂CH₃ | Isoxazol-3-yl | CF₃ | F | F |
| A-1300 | SO₂CH₃ | Isoxazol-3-yl | CF₃ | F | Cl |
| A-1301 | SO₂CH₃ | Isoxazol-3-yl | CF₃ | F | H |
| A-1302 | SO₂CH₃ | Isoxazol-3-yl | CF₃ | Cl | F |
| A-1303 | SO₂CH₃ | Isoxazol-3-yl | CF₃ | Cl | Cl |
| A-1304 | SO₂CH₃ | Isoxazol-3-yl | CF₃ | Cl | H |
| A-1305 | SO₂CH₃ | Isoxazol-3-yl | SO₂CH₃ | H | F |
| A-1306 | SO₂CH₃ | Isoxazol-3-yl | SO₂CH₃ | H | Cl |
| A-1307 | SO₂CH₃ | Isoxazol-3-yl | SO₂CH₃ | F | F |
| A-1308 | SO₂CH₃ | Isoxazol-3-yl | SO₂CH₃ | F | Cl |
| A-1309 | SO₂CH₃ | Isoxazol-3-yl | SO₂CH₃ | F | H |
| A-1310 | SO₂CH₃ | Isoxazol-3-yl | SO₂CH₃ | Cl | F |
| A-1311 | SO₂CH₃ | Isoxazol-3-yl | SO₂CH₃ | Cl | Cl |
| A-1312 | SO₂CH₃ | Isoxazol-3-yl | SO₂CH₃ | Cl | H |
| A-1313 | SO₂CH₃ | Isoxazol-3-yl | CN | H | F |
| A-1314 | SO₂CH₃ | Isoxazol-3-yl | CN | H | Cl |
| A-1315 | SO₂CH₃ | Isoxazol-3-yl | CN | F | F |
| A-1316 | SO₂CH₃ | Isoxazol-3-yl | CN | F | Cl |
| A-1317 | SO₂CH₃ | Isoxazol-3-yl | CN | F | H |
| A-1318 | SO₂CH₃ | Isoxazol-3-yl | CN | Cl | F |
| A-1319 | SO₂CH₃ | Isoxazol-3-yl | CN | Cl | Cl |
| A-1320 | SO₂CH₃ | Isoxazol-3-yl | CN | Cl | H |
| A-1321 | SO₂CH₃ | 5-Methyl-isoxazol-3-yl | Cl | H | F |
| A-1322 | SO₂CH₃ | 5-Methyl-isoxazol-3-yl | Cl | H | Cl |
| A-1323 | SO₂CH₃ | 5-Methyl-isoxazol-3-yl | Cl | F | F |
| A-1324 | SO₂CH₃ | 5-Methyl-isoxazol-3-yl | Cl | F | Cl |
| A-1325 | SO₂CH₃ | 5-Methyl-isoxazol-3-yl | Cl | F | H |
| A-1326 | SO₂CH₃ | 5-Methyl-isoxazol-3-yl | Cl | Cl | F |
| A-1327 | SO₂CH₃ | 5-Methyl-isoxazol-3-yl | Cl | Cl | Cl |
| A-1328 | SO₂CH₃ | 5-Methyl-isoxazol-3-yl | Cl | Cl | H |
| A-1329 | SO₂CH₃ | 5-Methyl-isoxazol-3-yl | F | H | F |
| A-1330 | SO₂CH₃ | 5-Methyl-isoxazol-3-yl | F | H | Cl |

TABLE A-continued

| | R¹ | R² | R³ | R⁴ | R⁵ |
|---|---|---|---|---|---|
| A-1331 | SO₂CH₃ | 5-Methyl-isoxazol-3-yl | F | F | F |
| A-1332 | SO₂CH₃ | 5-Methyl-isoxazol-3-yl | F | F | Cl |
| A-1333 | SO₂CH₃ | 5-Methyl-isoxazol-3-yl | F | F | H |
| A-1334 | SO₂CH₃ | 5-Methyl-isoxazol-3-yl | F | Cl | F |
| A-1335 | SO₂CH₃ | 5-Methyl-isoxazol-3-yl | F | Cl | Cl |
| A-1336 | SO₂CH₃ | 5-Methyl-isoxazol-3-yl | F | Cl | H |
| A-1337 | SO₂CH₃ | 5-Methyl-isoxazol-3-yl | CF₃ | H | F |
| A-1338 | SO₂CH₃ | 5-Methyl-isoxazol-3-yl | CF₃ | H | Cl |
| A-1339 | SO₂CH₃ | 5-Methyl-isoxazol-3-yl | CF₃ | F | F |
| A-1340 | SO₂CH₃ | 5-Methyl-isoxazol-3-yl | CF₃ | F | Cl |
| A-1341 | SO₂CH₃ | 5-Methyl-isoxazol-3-yl | CF₃ | F | H |
| A-1342 | SO₂CH₃ | 5-Methyl-isoxazol-3-yl | CF₃ | Cl | F |
| A-1343 | SO₂CH₃ | 5-Methyl-isoxazol-3-yl | CF₃ | Cl | Cl |
| A-1344 | SO₂CH₃ | 5-Methyl-isoxazol-3-yl | CF₃ | Cl | H |
| A-1345 | SO₂CH₃ | 5-Methyl-isoxazol-3-yl | SO₂CH₃ | H | F |
| A-1346 | SO₂CH₃ | 5-Methyl-isoxazol-3-yl | SO₂CH₃ | H | Cl |
| A-1347 | SO₂CH₃ | 5-Methyl-isoxazol-3-yl | SO₂CH₃ | F | F |
| A-1348 | SO₂CH₃ | 5-Methyl-isoxazol-3-yl | SO₂CH₃ | F | Cl |
| A-1349 | SO₂CH₃ | 5-Methyl-isoxazol-3-yl | SO₂CH₃ | F | H |
| A-1350 | SO₂CH₃ | 5-Methyl-isoxazol-3-yl | SO₂CH₃ | Cl | F |
| A-1351 | SO₂CH₃ | 5-Methyl-isoxazol-3-yl | SO₂CH₃ | Cl | Cl |
| A-1352 | SO₂CH₃ | 5-Methyl-isoxazol-3-yl | SO₂CH₃ | Cl | H |
| A-1353 | SO₂CH₃ | 5-Methyl-isoxazol-3-yl | CN | H | F |
| A-1354 | SO₂CH₃ | 5-Methyl-isoxazol-3-yl | CN | H | Cl |
| A-1355 | SO₂CH₃ | 5-Methyl-isoxazol-3-yl | CN | F | F |
| A-1356 | SO₂CH₃ | 5-Methyl-isoxazol-3-yl | CN | F | Cl |
| A-1357 | SO₂CH₃ | 5-Methyl-isoxazol-3-yl | CN | F | H |
| A-1358 | SO₂CH₃ | 5-Methyl-isoxazol-3-yl | CN | Cl | F |
| A-1359 | SO₂CH₃ | 5-Methyl-isoxazol-3-yl | CN | Cl | Cl |
| A-1360 | SO₂CH₃ | 5-Methyl-isoxazol-3-yl | CN | Cl | H |
| A-1361 | SO₂CH₃ | 3-Methyl-isoxazolin-5-yl | Cl | H | F |
| A-1362 | SO₂CH₃ | 3-Methyl-isoxazolin-5-yl | Cl | H | Cl |
| A-1363 | SO₂CH₃ | 3-Methyl-isoxazolin-5-yl | Cl | F | F |
| A-1364 | SO₂CH₃ | 3-Methyl-isoxazolin-5-yl | Cl | F | Cl |
| A-1365 | SO₂CH₃ | 3-Methyl-isoxazolin-5-yl | Cl | F | H |
| A-1366 | SO₂CH₃ | 3-Methyl-isoxazolin-5-yl | Cl | Cl | F |
| A-1367 | SO₂CH₃ | 3-Methyl-isoxazolin-5-yl | Cl | Cl | Cl |
| A-1368 | SO₂CH₃ | 3-Methyl-isoxazolin-5-yl | Cl | Cl | H |
| A-1369 | SO₂CH₃ | 3-Methyl-isoxazolin-5-yl | F | H | F |
| A-1370 | SO₂CH₃ | 3-Methyl-isoxazolin-5-yl | F | H | Cl |
| A-1371 | SO₂CH₃ | 3-Methyl-isoxazolin-5-yl | F | F | F |
| A-1372 | SO₂CH₃ | 3-Methyl-isoxazolin-5-yl | F | F | Cl |
| A-1373 | SO₂CH₃ | 3-Methyl-isoxazolin-5-yl | F | F | H |
| A-1374 | SO₂CH₃ | 3-Methyl-isoxazolin-5-yl | F | Cl | F |
| A-1375 | SO₂CH₃ | 3-Methyl-isoxazolin-5-yl | F | Cl | Cl |
| A-1376 | SO₂CH₃ | 3-Methyl-isoxazolin-5-yl | F | Cl | H |
| A-1377 | SO₂CH₃ | 3-Methyl-isoxazolin-5-yl | CF₃ | H | F |
| A-1378 | SO₂CH₃ | 3-Methyl-isoxazolin-5-yl | CF₃ | H | Cl |
| A-1379 | SO₂CH₃ | 3-Methyl-isoxazolin-5-yl | CF₃ | F | F |
| A-1380 | SO₂CH₃ | 3-Methyl-isoxazolin-5-yl | CF₃ | F | Cl |
| A-1381 | SO₂CH₃ | 3-Methyl-isoxazolin-5-yl | CF₃ | F | H |
| A-1382 | SO₂CH₃ | 3-Methyl-isoxazolin-5-yl | CF₃ | Cl | F |
| A-1383 | SO₂CH₃ | 3-Methyl-isoxazolin-5-yl | CF₃ | Cl | Cl |
| A-1384 | SO₂CH₃ | 3-Methyl-isoxazolin-5-yl | CF₃ | Cl | H |
| A-1385 | SO₂CH₃ | 3-Methyl-isoxazolin-5-yl | SO₂CH₃ | H | F |
| A-1386 | SO₂CH₃ | 3-Methyl-isoxazolin-5-yl | SO₂CH₃ | H | Cl |
| A-1387 | SO₂CH₃ | 3-Methyl-isoxazolin-5-yl | SO₂CH₃ | F | F |
| A-1388 | SO₂CH₃ | 3-Methyl-isoxazolin-5-yl | SO₂CH₃ | F | Cl |
| A-1389 | SO₂CH₃ | 3-Methyl-isoxazolin-5-yl | SO₂CH₃ | F | H |
| A-1390 | SO₂CH₃ | 3-Methyl-isoxazolin-5-yl | SO₂CH₃ | Cl | F |
| A-1391 | SO₂CH₃ | 3-Methyl-isoxazolin-5-yl | SO₂CH₃ | Cl | Cl |
| A-1392 | SO₂CH₃ | 3-Methyl-isoxazolin-5-yl | SO₂CH₃ | Cl | H |
| A-1393 | SO₂CH₃ | 3-Methyl-isoxazolin-5-yl | CN | H | F |
| A-1394 | SO₂CH₃ | 3-Methyl-isoxazolin-5-yl | CN | H | Cl |
| A-1395 | SO₂CH₃ | 3-Methyl-isoxazolin-5-yl | CN | F | F |
| A-1396 | SO₂CH₃ | 3-Methyl-isoxazolin-5-yl | CN | F | Cl |
| A-1397 | SO₂CH₃ | 3-Methyl-isoxazolin-5-yl | CN | F | H |
| A-1398 | SO₂CH₃ | 3-Methyl-isoxazolin-5-yl | CN | Cl | F |
| A-1399 | SO₂CH₃ | 3-Methyl-isoxazolin-5-yl | CN | Cl | Cl |
| A-1400 | SO₂CH₃ | 3-Methyl-isoxazolin-5-yl | CN | Cl | H |
| A-1401 | SO₂CH₃ | 3-Methyl-isoxazol-5-yl | Cl | H | F |
| A-1402 | SO₂CH₃ | 3-Methyl-isoxazol-5-yl | Cl | H | Cl |
| A-1403 | SO₂CH₃ | 3-Methyl-isoxazol-5-yl | Cl | F | F |
| A-1404 | SO₂CH₃ | 3-Methyl-isoxazol-5-yl | Cl | F | Cl |
| A-1405 | SO₂CH₃ | 3-Methyl-isoxazol-5-yl | Cl | F | H |
| A-1406 | SO₂CH₃ | 3-Methyl-isoxazol-5-yl | Cl | Cl | F |
| A-1407 | SO₂CH₃ | 3-Methyl-isoxazol-5-yl | Cl | Cl | Cl |
| A-1408 | SO₂CH₃ | 3-Methyl-isoxazol-5-yl | Cl | Cl | H |
| A-1409 | SO₂CH₃ | 3-Methyl-isoxazol-5-yl | F | H | F |
| A-1410 | SO₂CH₃ | 3-Methyl-isoxazol-5-yl | F | H | Cl |
| A-1411 | SO₂CH₃ | 3-Methyl-isoxazol-5-yl | F | F | F |
| A-1412 | SO₂CH₃ | 3-Methyl-isoxazol-5-yl | F | F | Cl |
| A-1413 | SO₂CH₃ | 3-Methyl-isoxazol-5-yl | F | F | H |
| A-1414 | SO₂CH₃ | 3-Methyl-isoxazol-5-yl | F | Cl | F |
| A-1415 | SO₂CH₃ | 3-Methyl-isoxazol-5-yl | F | Cl | Cl |
| A-1416 | SO₂CH₃ | 3-Methyl-isoxazol-5-yl | F | Cl | H |
| A-1417 | SO₂CH₃ | 3-Methyl-isoxazol-5-yl | CF₃ | H | F |
| A-1418 | SO₂CH₃ | 3-Methyl-isoxazol-5-yl | CF₃ | H | Cl |
| A-1419 | SO₂CH₃ | 3-Methyl-isoxazol-5-yl | CF₃ | F | F |
| A-1420 | SO₂CH₃ | 3-Methyl-isoxazol-5-yl | CF₃ | F | Cl |
| A-1421 | SO₂CH₃ | 3-Methyl-isoxazol-5-yl | CF₃ | F | H |
| A-1422 | SO₂CH₃ | 3-Methyl-isoxazol-5-yl | CF₃ | Cl | F |
| A-1423 | SO₂CH₃ | 3-Methyl-isoxazol-5-yl | CF₃ | Cl | Cl |
| A-1424 | SO₂CH₃ | 3-Methyl-isoxazol-5-yl | CF₃ | Cl | H |
| A-1425 | SO₂CH₃ | 3-Methyl-isoxazol-5-yl | SO₂CH₃ | H | F |
| A-1426 | SO₂CH₃ | 3-Methyl-isoxazol-5-yl | SO₂CH₃ | H | Cl |
| A-1427 | SO₂CH₃ | 3-Methyl-isoxazol-5-yl | SO₂CH₃ | F | F |
| A-1428 | SO₂CH₃ | 3-Methyl-isoxazol-5-yl | SO₂CH₃ | F | Cl |
| A-1429 | SO₂CH₃ | 3-Methyl-isoxazol-5-yl | SO₂CH₃ | F | H |
| A-1430 | SO₂CH₃ | 3-Methyl-isoxazol-5-yl | SO₂CH₃ | Cl | F |
| A-1431 | SO₂CH₃ | 3-Methyl-isoxazol-5-yl | SO₂CH₃ | Cl | Cl |
| A-1432 | SO₂CH₃ | 3-Methyl-isoxazol-5-yl | SO₂CH₃ | Cl | H |
| A-1433 | SO₂CH₃ | 3-Methyl-isoxazol-5-yl | CN | H | F |
| A-1434 | SO₂CH₃ | 3-Methyl-isoxazol-5-yl | CN | H | Cl |
| A-1435 | SO₂CH₃ | 3-Methyl-isoxazol-5-yl | CN | F | F |
| A-1436 | SO₂CH₃ | 3-Methyl-isoxazol-5-yl | CN | F | Cl |
| A-1437 | SO₂CH₃ | 3-Methyl-isoxazol-5-yl | CN | F | H |
| A-1438 | SO₂CH₃ | 3-Methyl-isoxazol-5-yl | CN | Cl | F |
| A-1439 | SO₂CH₃ | 3-Methyl-isoxazol-5-yl | CN | Cl | Cl |
| A-1440 | SO₂CH₃ | 3-Methyl-isoxazol-5-yl | CN | Cl | H |
| A-1441 | Cl | Cl | H | H | F |
| A-1442 | Cl | SMe | Cl | H | F |

The HPPD-inhibiting herbicides useful for the present invention are often best applied in conjunction with one or more other HPPD- and/or HST targeting herbicides to obtain control of a wider variety of undesirable vegetation. When used in conjunction with other HPPD- and/or HST targeting herbicides, the presently claimed compounds can be formulated with the other herbicide or herbicides, tank mixed with the other herbicide or herbicides, or applied sequentially with the other herbicide or herbicides.

Some of the herbicides that are useful in conjunction with the HPPD-inhibiting herbicides of the present invention include benzobicyclon, mesotrione, sulcotrione, tefuryltrione, tembotrione, 4-hydroxy-3-[[2-(2-methoxyethoxy)methyl]-6-(trifluoromethyl)-3-pyridinyl]carbonyl]-bicyclo[3.2.1]-oct-3-en-2-one (bicyclopyrone), ketospiradox or the free acid thereof, benzofenap, pyrasulfotole, pyrazolynate, pyrazoxyfen, topramezone, [2-chloro-3-(2-methoxyethoxy)-4-(methylsulfonyl)phenyl](1-ethyl-5-hydroxy-1H-pyrazol-4-yl)-methanone, (2,3-dihydro-3,3,4-trimethyl-1,1-dioxido-benzo[b]thien-5-yl)(5-hydroxy-1-methyl-1H-pyrazol-4-yl)-methanone, isoxachlortole, isoxaflutole, α-(cyclopropylcarbonyl)-2-(methylsulfonyl)-β-oxo-4-chloro-benzenepropanenitrile, and α-(cyclopropylcarbonyl)-2-(methyisulfonyl)-β-oxo-4-(trifluoromethyl)-benzenepropanenitrile.

In a preferred embodiment the additional herbicide is topramezone.

In a particularly preferred embodiment the additional herbicide is
(1-Ethyl-5-prop-2-ynyloxy-1H-pyrazol-4-yl)-[4-methanesulfonyl-2-methyl-3-(3-methyl-4,5-dihydro-isoxazol-5-yl)-phenyl]-methanon

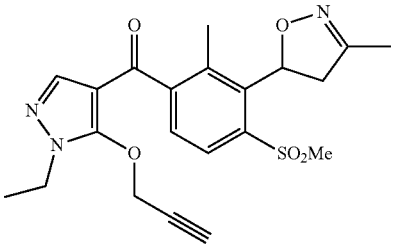 [SMILES: C#CCOc1c(C(=O)c2ccc(S(C)(=O)=O)c(C3CC(C)=NO3)c2C)cnn1CC]

or (1-Ethyl-5-hydroxy-1H-pyrazol-4-yl)-[4-methanesulfonyl-2-methyl-3-(3-methyl-4,5-dihydro-isoxazol-5-yl)-phenyl]-methanon

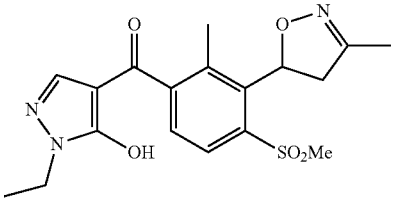 [SMILES: CCn1ncc(C(=O)c2ccc(S(C)(=O)=O)c(C3CC(C)=NO3)c2C)c1O]

The above described compounds are described in great detail in WO2011067184 which is entirely incorporated herein by reference.

The herbicidal compounds useful for the present invention may further be used in conjunction with additional herbicides to which the crop plant is naturally tolerant, or to which it is resistant via expression of one or more additional transgenes as mentioned supra. Some of the herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, ima-zethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione.

The HPPD-inhibiting herbicides employed for the present invention can, further, be used in conjunction with glyphosate and glufosinate on glyphosate-tolerant or glufosinate-tolerant crops.

Unless already included in the disclosure above, the HPPD-inhibiting herbicides of the present invention can, further, be used in conjunction with compounds:

a) from the group of Lipid Biosynthesis Inhibitors:

Alloxydim, Alloxydim-natrium, Butroxydim, Clethodim, Clodinafop, Clodinafop-propargyl, Cycloxydim, Cyhalofop, Cyhalofop-butyl, Diclofop, Diclofop-methyl, Fenoxaprop, Fenoxaprop-ethyl, Fenoxaprop-P, Fenoxaprop-P-ethyl, Fluazifop, Fluazifop-butyl, Fluazifop-P, Fluazifop-P-butyl, Haloxyfop, Haloxyfop-methyl, Haloxyfop-P, Haloxyfop-P-methyl, Metamifop, Pinoxaden, Profoxydim, Propaquizafop, Quizalofop, Quizalofop-ethyl, Quizalofoptefuryl, Quizalofop-P, Quizalofop-P-ethyl, Quizalofop-P-tefuryl, Sethoxydim, Tepraloxydim, Tralkoxydim, Benfuresat, Butylat, Cycloat, Dalapon, Dimepiperat, EPTC, Esprocarb, Ethofumesat, Flupropanat, Molinat, Orbencarb, Pebulat, Prosulfocarb, TCA, Thiobencarb, Tiocarbazil, Triallat and Vemolat;

b) from the group of ALS-Inhibitors:

Amidosulfuron, Azimsulfuron, Bensulfuron, Bensulfuron-methyl, Bispyribac, Bispyribacnatrium, Chlorimuron, Chlorimuron-ethyl, Chlorsulfuron, Cinosulfuron, Cloransulam, Cloransulam-methyl, Cyclosulfamuron, Diclosulam, Ethametsulfuron, Ethametsulfuron-methyl, Ethoxysulfuron, Flazasulfuron, Florasulam, Flucarbazon, Flucarbazon-natnum, Flucetosulfuron, Flumetsulam, Flupyrsulfuron, Flupyrsulfuron-methyl-natrium, Foramsulfuron, Halosulfuron, Halosulfuron-methyl, Imazamethabenz, Imazamethabenz-methyl, Imazamox, Imazapic, Imazapyr, Imazaquin, Imazethapyr, Imazosulfuron, Iodosulfuron, Iodosulfuronmethyl-natrium, Mesosulfuron, Metosulam, Metsulfuron, Metsulfuron-methyl, Nicosulfuron, Orthosulfamuron, Oxasulfuron, Penoxsulam, Primisulfuron, Primisulfuron-methyl, Propoxycarbazon, Propoxycarbazon-natrium, Prosulfuron, Pyrazosulfuron, Pyrazosulfuronethyl, Pyribenzoxim, Pyrimisulfan, Pyriftalid, Pyriminobac, Pyriminobac-methyl, Pyrithiobac, Pyrithiobac-natrium, Pyroxsulam, Rimsulfuron, Sulfometuron, Sulfometuron-methyl, Sulfosulfuron, Thiencarbazon, Thiencarbazon-methyl, Thifensulfuron, Thifensulfuron-methyl, Triasulfuron, Tribenuron, Tribenuron-methyl, Trifloxysulfuron, Triflusulfuron, Triflusulfuronmethyl and Tritosulfuron;

c) from the group of Photosynthese-Inhibitors:

Ametryn, Amicarbazon, Atrazin, Bentazon, Bentazon-natrium, Bromacil, Bromofenoxim, Bromoxynil and its salts and esters, Chlorobromuron, Chloridazon, Chlorotoluron, Chloroxuron, Cyanazin, Desmedipham, Desmetryn, Dimefuron, Dimethametryn, Diquat, Diquat-dibromid, Diuron, Fluometuron, Hexazinon, loxynil and its salts and esters, Isoproturon, Isouron, Karbutilat, Lenacil, Linuron, Metamitron, Methabenzthiazuron, Metobenzuron, Metoxuron, Metribuzin, Monolinuron, Neburon, Paraquat, Paraquat-dichlorid, Paraquat-dimetilsulfat, Pentanochlor, Phenmedipham, Phenmedipham-ethyl, Prometon, Prometryn, Propanil, Propazin, Pyridafol, Pyridat, Siduron, Simazin, Simetryn, Tebuthiuron, Terbacil, Terbumeton, Terbuthylazin, Terbutryn, Thidiazuron and Trietazin;

d) from the group of Protoporphyrinogen-IX-Oxidase-Inhibitors:

Acifluorfen, Acifluorfen-natrium, Azafenidin, Bencarbazon, Benzfendizon, Benzoxazinone (as described in WO2010/145992), Bifenox, Butafenacil, Carfentrazon, Carfentrazon-ethyl, Chlomethoxyfen, Cinidon-ethyl, Fluazolat, Flufenpyr, Flufenpyr-ethyl, Flumiclorac, Flumiclorac-pentyl, Flumioxazin, Fluoroglycofen, Fluoroglycofen-ethyl, Fluthiacet, Fluthiacet-methyl, Fomesafen, Halosafen, Lactofen, Oxadiargyl, Oxadiazon, Oxyfluorfen, Pentoxazon, Profluazol, Pyraclonil, Pyraflufen, Pyraflufen-ethyl, Saflufenacil, Sulfentrazon, Thidiazimin, 2-Chlor-5-[3,6-dihydro-3-methyl-2,6-dioxo-4-(trifluormethyl)-1(2H)-pyrimidinyl]-4-fluor-N-[(isopropyl)methylsulfamoyl]benzamid (H-1; CAS 372137-35-4), [3-[2-Chlor-4-fluor-5-(1-methyl-6-trifluormethyl-2,4-dioxo-1,2,3,4,-tetrahydropyrimidin-3-yl)phenoxy]-2-pyridyloxy]acetic acidethylester (H-2; CAS 353292-31-6), N-Ethyl-3-(2,6-dichlor-4-trifluormethylphenoxy)-5-methyl-1H-pyrazol-1-carboxamid (H-3; CAS 452098-92-9), N-Tetrahydrofurfuryl-3-(2,6-dichlor-4-trifluormethylphenoxy)-5-methyl-1H-pyrazol-1-carboxamid (H-4; CAS 915396-43-9), N-Ethyl-3-(2-chlor-6-fluor-4-trifluormethylphenoxy)-5-methyl-1H-pyrazol-1-carboxamid (H-5; CAS 452099-05-7) and N-Tetrahydrofurfuryl-3-(2-chlor-6-fluor-4-trifluormethylphenoxy)-5-methyl-1H-pyrazol-1-carboxamid (H-6; CAS 45100-03-7);

e) from the group of Bleacher-Herbicides:
Aclonifen, Amitrol, Beflubutamid, Benzobicyclon, Benzofenap, Clomazon, Diflufenican, Fluridon, Flurochloridon, Flurtamon, Isoxaflutol, Mesotrion, Norflurazon, Picolinafen, Pyrasulfutol, Pyrazolynat, Pyrazoxyfen, Sulcotrion, Tefuryltrion, Tembotrion, Topramezon, 4-Hydroxy-3-[[2-[(2-methoxyethoxy)methyl]-6-(trifluormethyl)-3-pyridyl]carbonyl]bicyclo[3.2.1]oct-3-en-2-one (H-7; CAS 352010-68-5) and 4-(3-Trifluormethyl-phenoxy)-2-(4-trifluormethylphenyl)pyrimidin (H-8; CAS 180608-33-7);

f) from the group of EPSP-Synthase-Inhibitors:
Glyphosat, Glyphosat-isopropylammonium and Glyphosat-trimesium (Sulfosat);

g) from the group of Glutamin-Synthase-Inhibitors:
Bilanaphos (Bialaphos), Bilanaphos-natrium, Glufosinat and Glufosinat-ammonium;

h) from the group of DHP-Synthase-Inhibitors: Asulam;

i) from the group of Mitose-Inhibitors:
Amiprophos, Amiprophos-methyl, Benfluralin, Butamiphos, Butralin, Carbetamid, Chlorpropham, Chlorthal, Chlorthal-dimethyl, Dinitramin, Dithiopyr, Ethalfluralin, Fluchloralin, Oryzalin, Pendimethalin, Prodiamin, Propham, Propyzamid, Tebutam, Thiazopyr and Trifluralin;

j) from the group of VLCFA-Inhibitors:
Acetochlor, Alachlor, Anilofos, Butachlor, Cafenstrol, Dimethachlor, Dimethanamid, Dimethenamid-P, Diphenamid, Fentrazamid, Flufenacet, Mefenacet, Metazachlor, Metolachlor, Metolachlor-S, Naproanilid, Napropamid, Pethoxamid, Piperophos, Pretilachlor, Propachlor, Propisochlor, Pyroxasulfon (KIH-485) and Thenylchlor; Compounds of the formula 2:

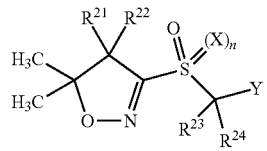

Particularly preferred Compounds of the formula 2 are:
3-[5-(2,2-Difluor-ethoxy)-1-methyl-3-trifluormethyl-1H-pyrazol-4-ylmethansulfonyl]-4-fluor-5,5-dimethyl-4,5-dihydro-isoxazol (2-1); 3-{[5-(2,2-Difluor-ethoxy)-1-methyl-3-trifluormethyl-1H-pyrazol-4-yl]-fluor-methansulfonyl}-5,5-dimethyl-4,5-dihydro-isoxazol (2-2); 4-(4-Fluor-5,5-dimethyl-4,5-dihydro-isoxazol-3-sulfonylmethyl)-2-methyl-5-trifluormethyl-2H-[1,2,3]triazol (2-3); 4-[(5,5-Dimethyl-4,5-dihydro-isoxazol-3-sulfonyl)-fluor-methyl]-2-methyl-5-trifluormethyl-2H-[1,2,3]triazol (2-4); 4-(5,5-Dimethyl-4,5-dihydro-isoxazol-3-sulfonylmethyl)-2-methyl-5-trifluormethyl-2H-[,2,3]triazol (2-5); 3-{[5-(2,2-Difluor-ethoxy)-1-methyl-3-trifluormethyl-1H-pyrazol-4-yl]-difluor-methansulfonyl}-5,5-dimethyl-4,5-dihydro-isoxazol (2-6); 4-[(5,5-Dimethyl-4,5-dihydro-isoxazol-3-sulfonyl)-difluor-methyl]-2-methyl-5-trifluormethyl-2H-[1,2,3]triazol (2-7); 3-{[5-(2,2-Difluor-ethoxy)-1-methyl-3-trifluormethyl-1H-pyrazol-4-yl]-difluor-methansulfonyl}-4-fluor-5,5-dimethyl-4,5-dihydro-isoxazol (2-8); 4-[Difluor-(4-fluor-5,5-dimethyl-4,5-dihydro-isoxazol-3-sulfonyl)-methyl]-2-methyl-5-trifluormethyl-2H-[1,2,3]triazol (2-9);

k) from the group of Cellulose-Biosynthese-Inhibitors:
Chlorthiamid, Dichlobenil, Flupoxam and Isoxaben;

l) from the group of Uncoupling-Herbicides:
Dinoseb, Dinoterb and DNOC and its salts;

m) from the group of Auxin-Herbicides:
2,4-D and its salts and esters, 2,4-DB and its salts and esters, Aminopyralid and its salts wie Aminopyralid-tris(2-hydroxypropyl)ammonium and its esters, Benazolin, Benazolin-ethyl, Chloramben and its salts and esters, Clomeprop, Clopyralid and its salts and esters, Dicamba and its salts and esters, Dichlorprop and its salts and esters, Dichlorprop-P and its salts and esters, Fluroxypyr, Fluroxypyr-butometyl, Fluroxypyr-meptyl, MCPA and its salts and esters, MCPA-thioethyl, MCPB and its salts and esters, Mecoprop and its salts and esters, Mecoprop-P and its salts and esters, Picloram and its salts and esters, Quinclorac, Quinmerac, TBA (2,3,6) and its salts and esters, Triclopyr and its salts and esters, and 5,6-Dichlor-2-cyclopropyl-4-pyrimidincarbonic acid (H-9; CAS 858956-08-8) and its salts and esters;

n) from the group of Auxin-Transport-Inhibitors:
Diflufenzopyr, Diflufenzopyr-natrium, Naptalam and Naptalam-natrium;

o) from the group of other Herbicides: Bromobutid, Chlorflurenol, Chlorflurenol-methyl, Cinmethylin, Cumyluron, Dalapon, Dazomet, Difenzoquat, Difenzoquat-metilsulfate, Dimethipin, DSMA, Dymron, Endothal and its salts, Etobenzanid, Flamprop, Flamprop-isopropyl, Flamprop-methyl Flamprop-M-isopropyl, Flamprop-M-methyl, Flurenol, Flurenol-butyl, Flurprimidol, Fosamin, Fosamine-ammonium, Indanofan, Maleinic acid-hydrazid, Mefluidid, Metam, Methylazid, Methylbromid, Methyl-dymron, Methyljodid. MSMA, oleic acid, Oxaziclomefon, Pelargonic acid, Pyributicarb, Quinoclamin, Triazifiam, Tridiphan and 6-Chlor-3-(2-cyclopropyl-6-methylphenoxy)-4-pyridazinol (H-10; CAS 499223-49-3) and its salts and esters.

Examples for preferred Safeners C are Benoxacor, Cloquintocet, Cyometrinil, Cyprosulfamid, Dichlormid, Dicyclonon, Dietholate, Fenchlorazol, Fenclorim, Flurazol, Fluxofenim, Furilazol, Isoxadifen, Mefenpyr, Mephenat, Naphthalic acid anhydrid, Oxabetrinil, 4-(Dichloracetyl)-1-oxa-4-azaspiro[4.5]decan (H-11; MON4660, CAS 71526-07-3) and 2,2,5-Trimethyl-3-(dichloracetyl)-1,3-oxazolidin (H-12; R-29148, CAS 52836-31-4).

The compounds of groups a) to o) and the Safeners C are known Herbicides and Safeners, see e.g. The Compendium of Pesticide Common Names (http://www.alanwood.net/pesticides/); B. Hock, C. Fedtke, R. R. Schmidt, Herbicides, Georg Thieme Verlag, Stuttgart 1995. Other herbicidal effectors are known from WO 96/26202, WO 97/41116, WO 97/41117, WO 97/41118, WO 01/83459 and WO 2008/074991 as well as from W. Kramer et al. (ed.) "Modern Crop Protection Compounds", Vol. 1, Wiley VCH, 2007 and the literature cited therein.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The term "mut-HPPD nucleic acid" refers to an HPPD nucleic acid having a sequence that is mutated from a wild-type HPPD nucleic acid and that confers increased "HPPD-inhibiting herbicide" tolerance to a plant in which it is expressed. Furthermore, the term "mutated hydroxyphenyl pyruvate dioxygenase (mut-HPPD)" refers to the replacement of an amino acid of the wild-type primary sequences SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

The term "mut-HST nucleic acid" refers to an HST nucleic acid having a sequence that is mutated from a wild-type HST nucleic acid and that confers increased "HPPD-inhibiting herbicide" tolerance to a plant in which it is expressed. Furthermore, the term "mutated homogentisate solanesyl transferase (mut-HST)" refers to the replacement of an amino acid of the wild-type primary sequences SEQ ID NO: 48 or 50 with another amino acid. The expression "mutated amino acid" will be used below to designate the amino acid which is replaced by another amino acid, thereby designating the site of the mutation in the primary sequence of the protein.

Several HPPDs and their primary sequences have been described in the state of the art, in particular the HPPDs of bacteria such as *Pseudomonas* (Ruetschi et al., Eur. J. Biochem., 205, 459-466, 1992, WO96/38567), of plants such as *Arabidopsis* (WO96/38567, Genebank AF047834) or of carrot (WO96/38567, Genebank 87257), of Coccicoides (Genebank COITRP), HPPDs of *Brassica*, cotton, *Synechocystis*, and tomato (U.S. Pat. No. 7,297,541), of mammals such as the mouse or the pig. Furthermore, artificial HPPD sequences have been described, for example in U.S. Pat. Nos. 6,768,044; 6,268,549;

In a preferred embodiment, the nucleotide sequence of (i) comprises the sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69 or a variant or derivative thereof.

In a particularly preferred embodiment, the mut-HPPD nucleic acid useful for the present invention comprises a mutated nucleic acid sequence of SEQ ID NO: 1 or SEQ ID NO: 52, or a variant or derivative thereof.

In another preferred embodiment, the nucleotide sequence of (ii) comprises the sequence of SEQ ID NO: 47 or 49, or a variant or derivative thereof.

Furthermore, it will be understood by the person skilled in the art that the nucleotide sequences of (i) or (ii) encompasses homologues, paralogues and and orthologues of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, and respectively SEQ ID NO: 47 or 49, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO:1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, 47, or 49. By "variant" polypeptide is intended a polypeptide derived from the protein of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

In a preferred embodiment, variants of the polynucleotides useful for the present invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO:1, or SEQ ID NO: 52.

It is recognized that the polynucleotide molecules and polypeptides of the invention encompass polynucleotide molecules and polypeptides comprising a nucleotide or an amino acid sequence that is sufficiently identical to nucleotide sequences set forth in SEQ ID Nos: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, 47, or 49, or to the amino acid sequences set forth in SEQ ID Nos: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, 48, or 50. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

"Sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds).

TABLE 3

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |

TABLE 3-continued

Examples of conserved amino acid substitutions

| Residue | Conservative Substitutions | Residue | Conservative Substitutions |
|---|---|---|---|
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuikChange Site Directed mutagenesis (Stratagene, San Diego, Calif.), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speculation, and are also derived from a common ancestral gene. A non-limiting list of examples of such orthologues is shown in Table 1.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd Inter-national Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The inventors of the present invention have surprisingly found that by substituting one or more of the key amino acid residues the herbicide tolerance or resistance could be remarkably increased as compared to the activity of the wild type HPPD enzymes with SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67. Preferred substitutions of mut-HPPD are those that increase the herbicide tolerance of the plant, but leave the biological activity of the dioxygenase activity substantially unaffected.

Accordingly, in another object of the present invention the key amino acid residues of a HPPD enzyme comprising SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, a variant, derivative, othologue, paralogue or homologue thereof, is substituted by any other amino acid.

In one embodiment, the key amino acid residues of a HPPD enzyme, a variant, derivative, othologue, paralogue or homologue thereof, is substituted by a conserved amino acid as depicted in Table 3 above.

It will be understood by the person skilled in the art that amino acids located in a close proximity to the positions of amino acids mentioned below may also be substituted. Thus, in another embodiment the mut HPPD useful for the present invention comprises a sequence of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant, derivative, orthologue, paralogue or homologue thereof, wherein an amino acid ±3, ±2 or ±1 amino acid positions from a key amino acid is substituted by any other amino acid.

Based on techniques well-known in the art, a highly characteristic sequence pattern can be developed, by means of which further of mut-HPPD candidates with the desired activity may be searched.

Searching for further mut-HPPD candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

In line with said above functional and spatial analysis of individual amino acid residues based on the crystallographic data as obtained according to the present invention, unique partial amino acid sequences characteristic of potentially useful mut-HPPD candidates of the invention may be identified.

In a particularly preferred embodiment, the mut-HPPD refers to a variant or derivative of SEQ ID NO: 2 wherein the substitutions are selected from the following Table 4a.

TABLE 4a (Sequence ID No: 2): single amino acid substitutions

| Key amino acid position | Substituents |
| --- | --- |
| Val212 | Ile, Leu |
| Val213 | Thr, Ala |
| Asn215 | Ala, His |
| Ala236 | Leu, Ser, Arg |
| Phe238 | Val, Ala |

TABLE 4a-continued (Sequence ID No: 2): single amino acid substitutions

| Key amino acid position | Substituents |
|---|---|
| Leu250 | Val, Met |
| Ser252 | Thr |
| Pro265 | Ala |
| Asn267 | Tyr, Gln |
| Gln278 | His, Asn, Ser |
| Ile279 | Thr |
| Arg309 | Lys, Ala |
| Leu320 | Asn, Gln, His, Tyr, |
| Pro321 | Ala, Arg, Gly, Asn |
| Leu334 | Glu, Cys |
| Leu353 | Met, Tyr, Ala, Ser |
| Phe366 | Ile, Leu, Tyr |
| Gly371 | Ile, Phe |
| Thr375 | Pro |
| Phe377 | Ala, Leu, Ser |
| Gly403 | Arg |
| Phe404 | Leu, Pro |
| Lys406 | Thr |
| Gly407 | Cys, His |
| Phe409 | Ile, His |
| Glu411 | Thr |
| Leu412 | Met, Phe, Trp, Ala, Ser |
| Ile416 | Val, Phe |
| Ser410 | Gly |
| Val254 | Ala |

It is to be understood that any amino acid besides the ones mentioned in the above tables could be used as a substitutent. Assays to test for the functionality of such mutants are readily available in the art, and respectively, described in the Example section of the present invention.

In a preferred embodiment, the amino acid sequence of a mut-HPPD differs from an amino acid sequence of a wild-type HPPD at one or more of the following positions corresponding to positions: 212, 213, 215, 236, 238, 250, 252, 254, 265, 267, 278, 279, 309, 320, 321, 334, 353, 366, 371, 375, 377, 403, 404, 406, 407, 409, 411, 410, 412 or 416 of SEQ ID NO:2.

Examples of differences at these amino acid positions include, but are not limited to, one or more of the following:
the amino acid corresponding to or at position 236 is other than alanine;
the amino acid corresponding to or at position 411 is other than glutamic acid;
the amino acid corresponding to or at position 320 is other than leucine;
the amino acid corresponding to or at position 403 is other than glycine;
the amino acid corresponding to or at position 334 is other than leucine;
the amino acid corresponding to or at position 353 is other than leucine;
the amino acid corresponding to or at position 321 is other than proline;
the amino acid corresponding to or at position 212 is other than valine;
the amino acid corresponding to or at position 407 is other than glycine;
the amino acid corresponding to or at position 377 is other than phenylalanine;
the amino acid corresponding to or at position 412 is other than leucine;
the amino acid corresponding to or at position 278 is other than glutamine;
the amino acid corresponding to or at position 406 is other than lysine;
the amino acid corresponding to or at position 404 is other than phenylalanine;
the amino acid corresponding to or at position 409 is other than phenylalanine;
the amino acid corresponding to or at position 416 is other than isoleucine;
the amino acid corresponding to or at position 250 is other than leucine;
the amino acid corresponding to or at position 267 is other than asparagine;
the amino acid corresponding to or at position 252 is other than serine;
the amino acid corresponding to or at position 265 is other than proline;
the amino acid corresponding to or at position 371 is other than glycine;
the amino acid corresponding to or at position 375 is other than threonine;
the amino acid corresponding to or at position 309 is other than arginine;
the amino acid corresponding to or at position 279 is other than isoleucine;
the amino acid corresponding to or at position 366 is other than phenylalanine;
the amino acid corresponding to or at position 238 is other than phenylalanine;
the amino acid corresponding to or at position 213 is other than valine;
the amino acid corresponding to or at position 215 is other than asparagine;
the amino acid corresponding to or at position 410 is other than serine;
the amino acid corresponding to or at position 254 is other than valine.

In some embodiments, the mut HPPD enzyme comprises a polypeptide of SEQ ID NO:2, a variant, derivative, homologue or orthologue thereof, having one or more substitutions at the following positions:
the amino acid corresponding to or at position 236 is leucine, serine or arginine;
the amino acid corresponding to or at position 411 is threonine;
the amino acid corresponding to or at position 320 is asparagine, glutamine, histidine or tyrosine;
the amino acid corresponding to or at position 403 is arginine;
the amino acid corresponding to or at position 334 is glutamic acid or cysteine;
the amino acid corresponding to or at position 353 is methionine, tyrosine, alanine, or serine;
the amino acid corresponding to or at position 321 is alanine, arginine, glycine or asparagine;
the amino acid corresponding to or at position 212 is isoleucine or leucine;
the amino acid corresponding to or at position 407 is cysteine or histidine;
the amino acid corresponding to or at position 377 is alanine, leucine or serine;
the amino acid corresponding to or at position 412 is methionine, phenylalanine, tryptophan, alanine or serine;
the amino acid corresponding to or at position 278 is histidine, asparagine or serine;
the amino acid corresponding to or at position 406 is threonine;
the amino acid corresponding to or at position 404 is leucine or proline;

the amino acid corresponding to or at position 409 is isoleucine or histidine;

the amino acid corresponding to or at position 416 is valine or phenylalanine;

the amino acid corresponding to or at position 250 is valine or methionine;

the amino acid corresponding to or at position 267 is tyrosine or glutamine;

the amino acid corresponding to or at position 252 is threonine;

the amino acid corresponding to or at position 265 is alanine;

the amino acid corresponding to or at position 371 is isoleucine or phenylalanine;

the amino acid corresponding to or at position 375 is proline;

the amino acid corresponding to or at position 309 is lysine or alanine;

the amino acid corresponding to or at position 279 is threonine;

the amino acid corresponding to or at position 366 is isoleucine, leucine or tyrosine;

the amino acid corresponding to or at position 238 is valine or alanine;

the amino acid corresponding to or at position 213 is threonine or alanine;

the amino acid corresponding to or at position 215 is alanine or histidine;

the amino acid corresponding to or at position 410 is glycine;

the amino acid corresponding to or at position 254 is alanine.

Furthermore, the inventors of the present invention have surprisingly found that by substituting at least two of the key amino acid residues of SEQ ID NO: 2 with specific residues, the herbicide tolerance or resistance could be remarkably increased as compared to the activity of the wild type HPPD enzymes or HPPD enzymes in which only one amino acid residue had been substituted. Therefore, in another preferred embodiment the present invention the variant or derivative of the mut-HPPD refers to a polypeptide of SEQ ID NO: 2, wherein two, three, four or five key amino acids are substituted by another amino acid residue. Particularly preferred double, triple, quadruple, or quintuple mutations are described in Table 4b.

TABLE 4b (with reference to Sequence ID No: 2): combined amino acid substitutions

| Combination No | Key amino acid position and and its substitutents |
|---|---|
| 1 | A236L, E411T |
| 2 | L320H, P321A |
| 3 | L320H, P321R |
| 4 | L320N, P321A |
| 5 | L320N, P321R |
| 6 | L320Q, P321A |
| 7 | L320Q, P321R |
| 8 | L320Y, P321A |
| 9 | L320Y, P321R |
| 10 | L353M, P321R |
| 11 | L353M, P321R, A236L |
| 12 | L353M, P321R, A236L, E411T |
| 13 | L353M, P321R, E411T |
| 14 | L353M, P321R, L320H |
| 15 | L353M, P321R, L320N |
| 16 | L353M, P321R, L320Q |
| 17 | L353M, P321R, L320Y |

TABLE 4b-continued (with reference to Sequence ID No: 2): combined amino acid substitutions

| Combination No | Key amino acid position and and its substitutents |
|---|---|
| 18 | L353M, P321R, V212I |
| 19 | L353M, P321R, V212I, L334E |
| 20 | L353M, P321R, V212L, L334E |
| 21 | L353M, P321R, V212L, L334E, A236L |
| 22 | L353M, P321R, V212L, L334E, A236L, E411T |
| 23 | L353M, P321R, V212L, L334E, E411T |
| 24 | L353M, P321R, V212L, L334E, L320H |
| 25 | L353M, P321R, V212L, L334E, L320N |
| 26 | L353M, P321R, V212L, L334E, L320Q |
| 27 | L353M, P321R, V212L, L334E, L320Y |
| 28 | L353M, V212I |

In a particularly preferred embodiment, the mut HPPD enzyme comprising a polypeptide of SEQ ID NO: 2, a variant, derivative, homologue, paralogue or orthologue thereof, useful for the present invention comprises one or more of the following: the amino acid corresponding to or at position 320 is histidine, asparagine or glutamine; the amino acid position 334 is glutamic acid; the amino acid position 353 is methionine; the amino acid corresponding to or at position 321 alanine or arginine; the amino acid corresponding to or at position 212 is isoleucine.

In an especially particularly preferred embodiment, the mut HPPD refers to a polypeptide comprising SEQ ID NO: 2, wherein the leucine corresponding to or at position 320 is substituted by a histidine, and the proline corresponding to or at position 321 is substituted by an alanine.

In another especially particularly preferred embodiment, the mut HPPD refers to a polypeptide comprising SEQ ID NO: 2, wherein Leucine corresponding to or at position 353 is substituted by a Methionine, the Proline corresponding to or at position 321 is substituted by an Arginine, and the Leucine corresponding to or at position 320 is substituted by an Asparagine.

In another especially particularly preferred embodiment, the mut HPPD refers to a polypeptide comprising SEQ ID NO: 2, wherein the Leucine corresponding to or at position 353 is substituted by a Methionine, the Proline corresponding to or at position 321 is substituted by an Arginine, and the Leucine corresponding to or at position 320 is substituted by a glutamine.

In another preferred embodiment, the mut-HPPD refers to a variant or derivative of SEQ ID NO: 53 wherein the substitutions are selected from the following Table 4c.

TABLE 4c (Sequence ID No: 53): single amino acid substitutions

| Key amino acid position | Substituents | Preferred substituents |
|---|---|---|
| Val228 | Thr, Ala | Thr, Ala |
| Asn230 | Ala, His | Ala, His |
| Ala251 | Ser, Arg | Ser, Arg |
| Phe253 | Val, Ala | Val, Ala |
| Leu265 | Val, Met | Val, Met |
| Ser267 | Thr | Thr |
| Pro280 | Ala | Ala |
| Asn282 | Tyr, Gln | Tyr, Gln |
| Lys291 | Arg, Ala | Arg |
| Gln293 | Ala, Leu, Ile, Val, His, Asn, Ser | His, Asn, Ser |
| Ile294 | Thr | Thr |
| Arg324 | Lys, Ala | Lys, Ala |
| Met335 | Ala, Trp, Phe, Leu, Ile, Val, Asn, Gln, | Gln, Asn, His, |

TABLE 4c-continued (Sequence ID No: 53): single amino acid substitutions

| Key amino acid position | Substituents | Preferred substituents |
|---|---|---|
| | His, Tyr, Ser, Thr, Cys | Tyr |
| Pro336 | Ala, Arg, Gly, Asn | Ala, Gly |
| Ser337 | Ala, Pro, Thr | Pro, Thr |
| Pro339 | Deletion | Deletion |
| Pro340 | Gly | Gly |
| Glu363 | Gln | Gln |
| Leu368 | Met, Tyr, | Met |
| Phe381 | Ile, Leu, Tyr | Ile, Leu |
| Leu385 | Ala, Val, Gln, Asp | Val, Asp |
| Gly386 | Ile, Phe | Ile, Phe |
| Thr390 | Pro | Pro |
| Phe392 | Ala, Leu, Ser | Ala |
| Ile393 | Ala, Leu, Phe, Val | Leu |
| Phe419 | Leu, Pro | Leu, Pro |
| Lys421 | Thr | Thr |
| Gly422 | His, Met, Phe, Cys | His, Cys |
| Phe424 | Ile, His | Ile, His |
| Leu427 | Phe, Trp, Ala, Ser, Met | Phe |
| Ile431 | Val, Phe | Val, Phe |
| Ser425 | Gly | Gly |
| Val269 | Ala | Ala |

It is to be understood that any amino acid besides the ones mentioned in the above tables could be used as a substitutent. Assays to test for the functionality of such mutants are readily available in the art, and respectively, described in the Example section of the present invention.

In another preferred embodiment, the mut-HPPD amino acid sequence differs from a wildtype amino acid sequence of an HPPD at one or more positions corresponding to or at the following positions of SEQ ID NO:53:

228, 230, 251, 253, 265, 267, 280, 282, 291, 293, 294, 324, 335, 336, 337, 339, 340, 363, 368, 381, 385, 386, 390, 392, 393, 419, 421, 422, 424, 427, 431, 425, 269.

Examples of differences at these amino acid positions include, but are not limited to, one or more of the following:

the amino acid corresponding to or at position 228 is other than valine;

the amino acid corresponding to or at position 230 is other than asparagine;

the amino acid corresponding to or at position 251 is other than alanine;

the amino acid corresponding to or at position 253 is other than phenylalanine;

the amino acid corresponding to or at position 265 is other than leucine;

the amino acid corresponding to or at position 267 is other than serine;

the amino acid corresponding to or at position 280 is other than proline;

the amino acid corresponding to or at position 282 is other than asparagine;

the amino acid corresponding to or at position 291 is other than lysine;

the amino acid corresponding to or at position 293 is other than glutamine;

the amino acid corresponding to or at position 294 is other than isoleucine;

the amino acid corresponding to or at position 324 is other than arginine;

the amino acid corresponding to or at position 335 is other than methionine;

the amino acid corresponding to or at position 336 is other than proline;

the amino acid corresponding to or at position 337 is other than serine;

the amino acid corresponding to or at position 339 is other than proline;

the amino acid corresponding to or at position 340 is other than proline;

the amino acid corresponding to or at position 363 is other than glutamic acid;

the amino acid corresponding to or at position 368 is other than leucine;

the amino acid corresponding to or at position 381 is other than phenylalanine;

the amino acid corresponding to or at position 385 is other than leucine;

the amino acid corresponding to or at position 386 is other than glycine;

the amino acid corresponding to or at position 390 is other than threonine;

the amino acid corresponding to or at position 392 is other than phenylalanine;

the amino acid corresponding to or at position 393 is other than an isoleucine;

the amino acid corresponding to or at position 419 is other than phenylalanine;

the amino acid corresponding to or at position 421 is other than lysine;

the amino acid corresponding to or at position 422 is other than glycine;

the amino acid corresponding to or at position 424 is other than phenylalanine;

the amino acid corresponding to or at position 427 is other than leucine;

the amino acid corresponding to or at position 431 is other than isoleucine;

the amino acid corresponding to or at position 425 is other than serine;

the amino acid corresponding to or at position 269 is other than valine.

In some embodiments, the mut-HPPD enzyme comprises one or more substitutions at positions corresponding to the following positions of SEQ ID NO: 53:

the amino acid corresponding to or at position 228 is Thr, or Ala;

the amino acid corresponding to or at position 230 is Ala, or His;

the amino acid corresponding to or at position 251 is Ser, or Arg;

the amino acid corresponding to or at position 253 is Val, or Ala;

the amino acid corresponding to or at position 265 is Val, or Met;

the amino acid corresponding to or at position 267 is threonine;

the amino acid corresponding to or at position 280 is Ala;

the amino acid corresponding to or at position 282 is Tyr, or Gln;

the amino acid corresponding to or at position 291 is Arg, or Ala;

the amino acid corresponding to or at position 293 is alanine, leucine, isoleucine, valine, histidine, asparagine or serine, preferably histidine, asparagine or serine;

the amino acid corresponding to or at position 294 is threonine;

the amino acid corresponding to or at position 324 is Lys, or Ala;

the amino acid corresponding to or at position 335 is alanine, tryptophane, phenylalanine, leucine, isoleucine, valine, asparagine, glutamine, histidine, tyrosine, serine, threonine or cysteine, preferably Gln, Asn, His, or Tyr;

the amino acid corresponding to or at position 336 is alanine, arginine, Gly, or Asn, preferably alanine or glycine;

the amino acid corresponding to or at position 337 is alanine, threonine or proline, preferably threonine or proline;

the amino acid corresponding to or at position 339 is deleted;

the amino acid corresponding to or at position 340 is glycine;

the amino acid corresponding to or at position 363 is glutamine;

the amino acid corresponding to or at position 368 is methionine or tyrosine, preferably methionine;

the amino acid corresponding to or at position 381 is Ile, Leu, or Tyr, preferably Isoleucine or leucine;

the amino acid corresponding to or at position 385 is valine, alanine, Gln, or Asp, preferably valine or aspartic acid;

the amino acid corresponding to or at position 386 is Ile, or Phe;

the amino acid corresponding to or at position 390 is Pro;

the amino acid corresponding to or at position 392 is alanine, leucine or serine, preferably alanine;

the amino acid corresponding to or at position 393 is Ala, Leu, Phe, Val, preferably leucine;

the amino acid corresponding to or at position 419 is Leu or Pro;

the amino acid corresponding to or at position 421 is threonine;

the amino acid corresponding to or at position 422 is histidine, methionine, phenylalanine, or cysteine, preferably histidine or cysteine;

the amino acid corresponding to or at position 424 is Ile or His;

the amino acid corresponding to or at position 427 is phenylalanine, tryptophan, Ala, Ser, or Met, preferably phenylalanine;

the amino acid corresponding to or at position 431 is Val or Phe;

the amino acid corresponding to or at position 425 is glycine;

the amino acid corresponding to or at position 269 is alanine.

Furthermore, the inventors of the present invention have found that by substituting at least two of the key amino acid residues of SEQ ID NO: 53 with specific residues, the herbicide tolerance or resistance could be remarkably increased as compared to the activity of the wild type HPPD enzymes or HPPD enzymes in which only one amino acid residue had been substituted. Therefore, in another preferred embodiment the present invention the variant or derivative of the mut-HPPD refers to a polypeptide of SEQ ID NO: 53, a homologue, orthologue, or paralogue thereof, wherein two, three, four or five key amino acids are substituted by another amino acid residue. Particularly preferred double, triple, quadruple, or quintuple mutations are described in Table 4d.

TABLE 4d (reference to Sequence ID No: 53): combined amino acid substitutions

| Combination No | Key amino acid position | Substituents | Preferred substituents |
|---|---|---|---|
| 1 | Pro336 | Ala, Arg | Ala |
| | Glu363 | Gln | Gln |

TABLE 4d-continued (reference to Sequence ID No: 53): combined amino acid substitutions

| Combination No | Key amino acid position | Substituents | Preferred substituents |
|---|---|---|---|
| 2 | Pro336 | Ala, Arg | Ala |
| | Glu363 | Gln | Gln |
| | Leu385 | Ala, Val | Val |
| 3 | Pro336 | Ala, Arg | Ala |
| | Glu363 | Gln | Gln |
| | Leu385 | Ala, Val | Val |
| | Ile393 | Ala, Leu | Leu |
| 4 | Leu385 | Ala, Val | Val |
| | Ile393 | Ala, Leu | Leu |
| 5 | Met335 | Ala, Trp, Phe, Leu, Ile, Val, Asn, Gln, His, Tyr, Ser, Thr, Cys | Gln, Asn, His, Tyr |
| | Pro336 | Ala, Arg, Gly | Ala, Gly |
| 6 | Met335 | Ala, Trp, Phe, Leu, Ile, Val, Asn, Gln, His, Tyr, Ser, Thr, Cys | Gln, Asn, His, Tyr |
| | Pro336 | Ala, Arg, Gly | Ala, Gly |
| | Glu363 | Gln | Gln |
| 7 | Met335 | Ala, Trp, Phe, Leu, Ile, Val, Asn, Gln, His, Tyr, Ser, Thr, Cys | Gln, Asn, His, Tyr, Leu |
| | Pro336 | Ala, Arg, Gly | Ala, Arg, Gly |
| | Ser337 | Ala, Pro, Thr | Pro, Thr |
| | Pro339 | Deletion | Deletion |
| | Pro340 | Gly | Gly |

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Ala, or Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Ala, Arg, and the amino acid corresponding to or at position 363 of SEQ ID NO:53 is Gln, and the amino acid corresponding to or at position 385 of SEQ ID NO:53 is Ala, Val.

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, Arg, and the amino acid corresponding to or at position 363 of SEQ ID NO:53 is Gln, and the amino acid corresponding to or at position 385 of SEQ ID NO:53 is Ala, Val, and the amino acid corresponding to or at position 393 of SEQ ID NO:53 is Ala, Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Ala, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 336 of SEQ ID NO:53 is Arg, and the amino acid corresponding to or at position 363 of SEQ ID NO:53 is Gln, and the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, Val, and the amino acid corresponding to or at position 393 of SEQ ID NO:53 is Ala, Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Ala, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Val, and the amino acid corresponding to or at position 393 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 385 of SEQ ID NO:53 is Val, and the amino acid corresponding to or at position 393 of SEQ ID NO:53 is Leu.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ala, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Val, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Asn, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Gln, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Ala.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Arg.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Phe, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Phe, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Phe, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Leu, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Leu, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Leu, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Ala, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Arg, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Gly, and the amino acid corresponding to or at position 363 of SEQ ID NO:53 is Gln.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, Trp, Phe, Leu, Ile, Val, Asn, Gln, His, Tyr, Ser, Thr, Cys, and the amino acid corresponding to or at position 336 of SEQ ID NO:53 is Ala, Arg, Gly, and the amino acid corresponding to or at position 337 of SEQ ID NO:53 is Ala, Pro, Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ala, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Trp, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Phe, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Leu, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ile, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Val, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Asn, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Gln, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is His, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Tyr, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Ser, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:
the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Thr, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Ala, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Arg, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Ala, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Pro, and the amino acid corresponding to or at position 339 of SEQ ID NO:53 is deleted, and the amino acid corresponding to or at position 340 of SEQ ID NO:53 is Gly.

In another preferred embodiment, the mut-HPPD comprises a sequence of SEQ ID NO: 53 a variant, derivative, orthologue, paralogue or homologue thereof, in which:

the amino acid corresponding to or at position 335 of SEQ ID NO:53 is Cys, and the amino acid corresponding to or at position 336 of SEQ ID NO:53 is Gly, and the amino acid corresponding to or at position 337 of SEQ ID NO:53 is Thr, and the amino acid corresponding to or at position 339 of SEQ ID NO:53 is deleted, and the amino acid corresponding to or at position 340 of SEQ ID NO:53 is Gly.

In another embodiment, the variant or derivative of the HPPD enzyme of SEQ ID NO: 67 comprises one or more of the following substitutions:

the alanine corresponding to or at position 8 is substituted by threonine;

the glycine corresponding to or at position 68 is substituted by alanine;

the valine at position 261 is substituted by alanine;

the methionine corresponding to or at position 301 is substituted by isoleucine;

the methionine corresponding to or at position 327 is substituted by leucine;

the alanine corresponding to or at position 328 is substituted by proline;

the threonine corresponding to or at position 331 is substituted by proline;

the arginine corresponding to or at position 341 is substituted by glutamic acid;

the lysine corresponding to or at position 352 is substituted by asparagine;

the leucine corresponding to or at position 360 is substituted by methionine;

The leucine corresponding to or at position 383 is substituted by phenylalanine;

The glycine corresponding to or at position 414 is substituted by aspartic acid.

In another embodiment, the variant or derivative of the HPPD enzyme of SEQ ID NO: 67 comprises one or more of the following substitutions:

the alanine corresponding to or at position 8 is substituted by threonine;
the histidine corresponding to or at position 44 is substituted by glutamine;
the glycine at position 68 is substituted by alanine;
the alanine corresponding to or at position 71 is substituted by valine;
the phenylalanine at position 98 is substituted by leucine;
the phenylalanine corresponding to or at position 233 is substituted by methionine;
the alanine corresponding to or at position 253 is substituted by threonine;
the valine corresponding to or at position 261 is substituted by alanine;
the methionine corresponding to or at position 301 is substituted by isoleucine;
the glutamine corresponding to or at position 316 is substituted by arginine;
the methionine corresponding to or at position 327 is substituted by leucine;
the alanine corresponding to or at position 328 is substituted by proline;
the threonine corresponding to or at position 331 is substituted by proline;
the arginine corresponding to or at position 341 is substituted by cysteine;
the lysine corresponding to or at position 352 is substituted by asparagine;
the leucine corresponding to or at position 360 is substituted by methionine;
the leucine corresponding to or at position 383 is substituted by phenylalanine;
the serine corresponding to or at position 417 is substituted by glycine.

In a further preferred embodiment, the amino acid sequence differs from an amino acid sequence of an HPPD of SEQ ID NO: 57 corresponding to or at position 418. Preferably, the amino acid corresponding to or at position 418 is other than alanine. More preferably, the amino acid corresponding to or at position 418 is threonine.

In a further preferred embodiment, the amino acid sequence differs from an amino acid sequence of an HPPD of SEQ ID NO: 57 corresponding to or at position 237. Preferably, the amino acid corresponding to or at position 237 is other than serine. More preferably, the amino acid corresponding to or at position 237 is leucine.

The corresponding positions, i.e. preferred sites to be substituted are listed in the following-Table 4 e)

TABLE 4e

| SEQ-ID | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 | Pos 14 | Pos 15 | Pos 16 | Pos 17 | Pos 18 | Pos 19 |
|---|---|---|---|---|---|---|---|---|---|---|---|---|---|---|---|---|---|---|---|
| 53 | A227 | V228 | N230 | A251 | F253 | L265 | S267 | V269 | P280 | N282 | K291 | Q293 | I294 | R324 | M335 | P336 | S337 | P339 | P340 |
| 2  | V212 | V213 | N215 | A236 | F238 | L250 | S252 | V254 | P265 | N267 | R276 | Q278 | I279 | R309 | L320 | P321 | P322 | L324 | P325 |
| 5  | A270 | V271 | N273 | A294 | F296 | L308 | S310 | V312 | P323 | N325 | K333 | Q335 | I336 | R366 | M378 | K379 | R380 | S382 | E383 |
| 8  | A227 | V228 | N230 | A251 | F253 | L265 | S267 | V269 | P280 | N282 | K291 | Q293 | I294 | R324 | M335 | P336 | R337 | S339 | P340 |
| 11 | T192 | V193 | N195 | A216 | F218 | L230 | S232 | V234 | P245 | N247 | K255 | Q257 | I258 | R288 | M300 | K301 | R302 | S304 | D305 |
| 14 | V152 | V153 | N155 | Q178 | F180 | L189 | S191 | A193 | N204 | N206 | N212 | Q214 | I215 | R245 | L252 | S253 | V254 | N256 | S257 |
| 17 | G160 | V161 | N163 | R186 | F188 | L197 | S199 | V201 | P212 | N214 | N220 | Q222 | I223 | K253 | L260 | D261 | I262 | P264 | S265 |
| 20 | V145 | V146 | N148 | Q171 | F173 | L182 | S184 | A186 | N197 | N199 | S205 | Q207 | I208 | R238 | L245 | K246 | I247 | T249 | G250 |
| 22 | V218 | V219 | N221 | A242 | F244 | L256 | S258 | V260 | P271 | N273 | R282 | Q284 | I285 | R315 | M326 | A327 | P328 | Q330 | A331 |
| 24 | V218 | V219 | N221 | A242 | F244 | L256 | S258 | V260 | P271 | N273 | R282 | Q284 | I285 | R315 | M326 | A327 | P328 | Q330 | A331 |
| 26 | I218 | V219 | N221 | A242 | F244 | L256 | S258 | V260 | P271 | N273 | R282 | Q284 | I285 | Q315 | M326 | A327 | P328 | A330 | P331 |
| 28 | I218 | V219 | N221 | A242 | F244 | L256 | S258 | V260 | P271 | N273 | R282 | Q284 | I285 | Q315 | M326 | A327 | P328 | A330 | P331 |
| 30 | V212 | V213 | N215 | A236 | F238 | L250 | S252 | V254 | P265 | N267 | R276 | Q278 | I279 | Q309 | M320 | A321 | P322 | Q324 | P325 |
| 32 | V212 | V213 | N215 | A236 | F238 | L250 | S252 | V254 | P265 | N267 | R276 | Q278 | I279 | Q309 | M320 | A321 | P322 | Q324 | P325 |
| 34 | V218 | V219 | N221 | A242 | F244 | L256 | S258 | V260 | P271 | N273 | R282 | Q284 | I285 | R315 | M326 | A327 | P328 | Q330 | A331 |
| 36 | V144 | V145 | N147 | Y170 | Y172 | L181 | S183 | V185 | A196 | N198 | A204 | Q206 | I207 | R237 | L244 | Q245 | V246 | P248 | Q249 |
| 38 | V184 | V185 | N187 | W210 | A212 | L224 | S226 | V228 | P239 | N241 | K249 | Q251 | I252 | R282 | L289 | E290 | V291 | P293 | K294 |
| 40 | I176 | V177 | N179 | I202 | F204 | L216 | S218 | V220 | P230 | N232 | K240 | Q242 | I243 | E273 | L280 | K281 | T282 | G284 | S285 |
| 42 | M194 | V195 | N197 | I220 | F222 | L234 | S236 | V258 | P249 | N251 | K259 | Q261 | I262 | R292 | L299 | Y300 | V301 | D303 | T304 |
| 44 | A207 | V208 | N210 | A233 | F235 | L247 | S249 | V251 | P262 | N264 | K272 | Q274 | I275 | R305 | L312 | N313 | T314 | D316 | A317 |
| 46 | A207 | V208 | N210 | A233 | F235 | L247 | S249 | V251 | P262 | N264 | K272 | Q274 | I275 | R305 | L312 | N313 | T314 | D316 | A317 |
| 55 | A213 | V214 | N216 | S237 | F239 | L251 | S253 | V255 | P266 | N268 | K277 | Q279 | I280 | R310 | M321 | P322 | R323 | N325 | A326 |
| 57 | A213 | V214 | N216 | S237 | F239 | L251 | S253 | V255 | P266 | N268 | K277 | Q279 | I280 | R310 | M321 | P322 | R323 | N325 | A326 |
| 58 | A214 | V215 | N217 | A238 | F240 | L252 | S254 | V256 | P267 | N269 | K278 | Q280 | I281 | R311 | M322 | P323 | K324 | P326 | P327 |
| 59 | V224 | V225 | N227 | A248 | F250 | L262 | S264 | V266 | P277 | N279 | R288 | Q290 | I291 | R321 | L332 | A333 | P334 | P336 | P337 |
| 60 | V214 | V215 | N217 | A238 | F240 | L252 | S254 | V256 | P267 | N269 | R278 | Q280 | I281 | R311 | L322 | P323 | P324 | C326 | R327 |
| 61 | I219 | V220 | N222 | A243 | F245 | L257 | S259 | V261 | P272 | N274 | R283 | Q285 | I286 | Q316 | M327 | A328 | P329 | T331 | S332 |
| 62 | A226 | V227 | N229 | A250 | F252 | L264 | S266 | V268 | P279 | N281 | K290 | Q292 | I293 | R323 | M334 | P335 | S336 | P338 | P339 |
| 63 | T223 | V224 | N226 | A247 | F249 | L261 | S263 | V265 | P276 | N278 | K287 | Q289 | I290 | R320 | M331 | P332 | S333 | P335 | P336 |
| 64 | L163 | T164 | N166 | R189 | F191 | L200 | S202 | A204 | P215 | N217 | A224 | Q226 | I227 | K257 | M264 | T265 | A266 | P268 | D269 |
| 65 | L163 | T164 | N166 | R189 | F191 | L200 | S202 | A204 | P215 | N217 | A224 | Q226 | I227 | K257 | M264 | T265 | A266 | P268 | D269 |
| 66 | V218 | V219 | N221 | A242 | F244 | L256 | S258 | V260 | P271 | N273 | R282 | Q284 | I285 | R315 | M326 | A327 | P328 | Q330 | A331 |
| 67 | I219 | V220 | N222 | A243 | F245 | L257 | S259 | V261 | P272 | N274 | R283 | Q285 | I286 | Q316 | M327 | A328 | P329 | T331 | S332 |

| SEQ-ID | Pos 20 | Pos 21 | Pos 22 | Pos 23 | Pos 24 | Pos 25 | Pos 26 | Pos 27 | Pos 28 | Pos 29 | Pos 30 | Pos 31 | Pos 32 | Pos 33 | Pos 34 | Pos 35 | Pos 36 | Pos 37 |
|---|---|---|---|---|---|---|---|---|---|---|---|---|---|---|---|---|---|---|
| 53 | R349 | E363 | L368 | F381 | L385 | G386 | T390 | F392 | I393 | G418 | F419 | K421 | G422 | F424 | S425 | E426 | L427 | I431 |
| 2  | L334 | Q348 | L353 | F366 | V370 | G371 | T375 | F377 | L378 | G403 | F404 | K406 | G407 | F409 | S410 | E411 | L412 | I416 |
| 5  | R392 | E406 | L411 | F424 | V428 | G429 | T433 | F435 | F436 | G467 | F468 | K470 | G471 | F473 | R474 | E475 | L476 | I480 |
| 8  | R349 | E363 | L368 | F381 | L385 | G386 | T390 | F392 | F393 | G423 | F424 | K426 | G427 | F429 | S430 | E431 | L432 | I436 |
| 11 | R314 | E328 | L333 | F346 | L350 | G351 | T355 | F357 | L358 | G396 | F397 | Q399 | G400 | F402 | R403 | E404 | L405 | I409 |
| 14 | R267 | E283 | L288 | F304 | I308 | F309 | T313 | F315 | F316 | G327 | F328 | Q330 | G331 | F333 | Q334 | A335 | L336 | I340 |
| 17 | E275 | E287 | L292 | F308 | I312 | F313 | T317 | F319 | F320 | G331 | F332 | Q334 | R335 | F337 | L338 | A339 | L340 | M344 |
| 20 | Y260 | Q272 | L277 | F293 | C297 | Y298 | T302 | F304 | W305 | G316 | F317 | Q319 | G320 | F322 | Q323 | A324 | L325 | V329 |
| 22 | L340 | Q354 | L359 | F372 | V376 | G377 | T381 | F383 | L384 | G409 | F410 | K412 | G413 | F415 | S416 | E417 | L418 | I422 |

TABLE 4e-continued

| | | | | | | | | | | | | | | | | | | |
|---|---|---|---|---|---|---|---|---|---|---|---|---|---|---|---|---|---|---|
| 24 | L340 | Q354 | L359 | F372 | V376 | G377 | T381 | F383 | L384 | G409 | F410 | K412 | G413 | F415 | S416 | E417 | L418 | I422 |
| 26 | R340 | Q354 | L359 | F372 | V376 | G377 | T381 | F383 | L384 | G409 | F410 | K412 | G413 | F415 | S416 | Q417 | L418 | I422 |
| 28 | R340 | Q354 | L359 | F372 | V376 | G377 | T381 | F383 | L384 | G409 | F410 | K412 | G413 | F415 | S416 | Q417 | L418 | I422 |
| 30 | I334 | Q348 | L353 | F366 | V370 | G371 | T375 | F377 | L378 | G403 | F404 | K406 | G407 | F409 | S410 | E411 | L412 | I416 |
| 32 | I334 | Q348 | L353 | F366 | V370 | G371 | T375 | F377 | L378 | G403 | F404 | K406 | G407 | F409 | S410 | E411 | L412 | I416 |
| 34 | I340 | Q354 | L359 | F372 | V376 | G377 | T381 | F383 | L384 | G409 | F410 | K412 | G413 | F415 | S416 | E417 | L418 | I422 |
| 36 | G259 | V276 | L281 | F301 | L305 | F306 | T310 | F312 | F313 | G324 | F325 | E327 | A328 | F330 | Q331 | A332 | L333 | L337 |
| 38 | R302 | E318 | L323 | F336 | V340 | E341 | T345 | F347 | Y348 | G358 | F359 | I361 | G362 | F364 | K365 | A366 | L367 | L371 |
| 40 | R293 | E305 | L310 | F323 | V327 | T328 | T332 | F334 | F335 | S345 | F346 | N348 | G349 | F351 | K352 | A353 | L354 | I358 |
| 42 | R312 | K324 | L329 | F342 | I346 | V347 | T351 | F353 | F354 | S364 | F365 | V367 | G368 | F370 | K371 | A372 | L373 | I377 |
| 44 | R327 | Q339 | L344 | F357 | L361 | G362 | T366 | F368 | F369 | G379 | F380 | A382 | G383 | F385 | Q386 | A387 | L388 | I392 |
| 46 | R327 | Q339 | L344 | F357 | L361 | G362 | T366 | F368 | F369 | G379 | F380 | A382 | G383 | F385 | Q386 | A387 | L388 | I392 |
| 55 | R335 | E349 | L354 | F367 | L371 | G372 | T376 | F378 | I379 | G410 | F411 | K413 | G414 | F416 | G417 | A418 | L419 | I423 |
| 57 | R335 | E349 | L354 | F367 | L371 | G372 | T376 | F378 | I379 | G410 | F411 | K413 | G414 | F416 | G417 | A418 | L419 | I423 |
| 58 | R336 | D350 | L355 | F368 | V372 | G373 | S377 | F379 | V380 | G406 | F407 | K409 | G410 | F412 | S413 | E414 | L415 | I419 |
| 59 | R346 | Q360 | L365 | F378 | V382 | G383 | T387 | F389 | L390 | G415 | F416 | K418 | G419 | F421 | S422 | E423 | L424 | I428 |
| 60 | I336 | Q350 | L355 | F368 | V372 | G373 | T377 | F379 | L380 | G405 | F406 | K408 | G409 | F411 | S412 | E413 | L414 | I418 |
| 61 | R341 | Q355 | L360 | F373 | V377 | G378 | T382 | F384 | L385 | G410 | F411 | K413 | G414 | F416 | S417 | Q418 | L419 | I423 |
| 62 | R348 | E362 | L367 | F380 | V384 | G385 | T389 | F391 | I392 | G417 | F418 | K420 | G421 | F423 | S424 | E425 | L426 | I430 |
| 63 | R345 | E359 | L364 | F377 | L381 | G382 | T386 | F388 | I389 | G414 | F415 | K417 | G418 | F420 | S421 | E422 | L423 | I427 |
| 64 | R278 | Q290 | L295 | F312 | L316 | M317 | — | F321 | F322 | G332 | F333 | E335 | G336 | F338 | K339 | A340 | L341 | I345 |
| 65 | R278 | Q290 | L295 | F312 | L316 | M317 | — | F321 | F322 | G332 | F333 | E335 | G336 | F338 | K339 | A340 | L341 | I345 |
| 66 | I340 | Q354 | L359 | F372 | V376 | G377 | T381 | F383 | L384 | G409 | F410 | K412 | G413 | F415 | S416 | E417 | L418 | I422 |
| 67 | R341 | Q355 | L360 | F373 | V377 | G378 | T382 | F384 | L385 | G410 | F411 | K413 | G414 | F416 | S417 | Q418 | L419 | I423 |

It will be within the knowledge of the skilled artisan to identify conserved regions and motifs shared between the homologues, orthologues and paralogues of of SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, and respectively SEQ ID NO: 48 or 50, such as those depicted in Table 1. Having identified such conserved regions that may represent suitable binding motifs, amino acids corresponding to the amino acids listed in Table 4a and 4b, 4c, and 4d can be chosen to be substituted by any other amino acid, preferably by conserved amino acids as shown in table 3, and more preferably by the amino acids of tables 4a and 4b, 4c, and 4d.

In addition, the present invention refers to a method for identifying a HPPD-inhibiting herbicide by using a mut-HPPD encoded by a nucleic acid which comprises the nucleotide sequence of SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof, and/or by using a mut-HST encoded by a nucleic acid which comprises the nucleotide sequence of SEQ ID NO: 47 or 49, or a variant or derivative thereof.

Said method comprises the steps of:
a) generating a transgenic cell or plant comprising a nucleic acid encoding a mut-HPPD, wherein the mut-HPPD is expressed;
b) applying a HPPD-inhibiting herbicide to the transgenic cell or plant of a) and to a control cell or plant of the same variety;
c) determining the growth or the viability of the transgenic cell or plant and the control cell or plant after application of said HPPD-inhibiting herbicide, and
d) selecting "HPPD-inhibiting herbicides" which confer reduced growth to the control cell or plant as compared to the growth of the transgenic cell or plant.

By "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

Another object refers to a method of identifying a nucleotide sequence encoding a mut-HPPD which is resistant or tolerant to a HPPD-inhibiting herbicide, the method comprising:
a) generating a library of mut-HPPD-encoding nucleic acids,
b) screening a population of the resulting mut-HPPD-encoding nucleic acids by expressing each of said nucleic acids in a cell or plant and treating said cell or plant with a HPPD-inhibiting herbicide,
c) comparing the HPPD-inhibiting herbicide-tolerance levels provided by said population of mut-HPPD encoding nucleic acids with the HPPD-inhibiting herbicide-tolerance level provided by a control HPPD-encoding nucleic acid,
d) selecting at least one mut-HPPD-encoding nucleic acid that provides a significantly increased level of tolerance to a HPPD-inhibiting herbicide as compared to that provided by the control HPPD-encoding nucleic acid.

In a preferred embodiment, the mut-HPPD-encoding nucleic acid selected in step d) provides at least 2-fold as much resistance or tolerance of a cell or plant to a HPPD-inhibiting herbicide as compared to that provided by the control HPPD-encoding nucleic acid.

In a further preferred embodiment, the mut-HPPD-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a HPPD-inhibiting herbicide as compared to that provided by the control HPPD-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a mut-HPPD or mut-HST which is resistant or tolerant to a HPPD-inhibiting herbicide, the method comprising:

a) identifying an effective amount of a HPPD-inhibiting herbicide in a culture of plant cells or green algae that leads to death of said cells.
b) treating said plant cells or green algae with a mutagenizing agent,
c) contacting said mutagenized cells population with an effective amount of HPPD-inhibiting herbicide, identified in a),
d) selecting at least one cell surviving these test conditions,
e) PCR-amplification and sequencing of HPPD and/or HST genes from cells selected in d) and comparing such sequences to wild-type HPPD or HST gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mut-HPPD from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mut-HPPD-encoding sequences. Nucleic acids comprising candidate and control HPPD encoding sequences can be expressed in yeast, in a bacterial host strain, in an alga or in a higher plant such as tobacco or *Arabidopsis* and the relative levels of inherent tolerance of the HPPD encoding sequences screened according to a visible indicator phenotype of the transformed strain or plant in the presence of different concentrations of the selected HPPD-inhibiting herbicide. Dose responses and relative shifts in dose responses associated with these indicator phenotypes (formation of brown color, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD. For example, in a relatively rapid assay system based upon transformation of a bacterium such as *E. coli*, each mut-HPPD encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different HPPD sequences. Such strains expressing nucleic acids comprising alternative candidate HPPD sequences may be plated out on different concentrations of the selected HPPD-inhibiting herbicide in, optionally, a tyrosine supplemented medium and the relative levels of inherent tolerance of the expressed HPPD enzymes estimated on the basis of the extent and MIC for inhibition of the formation of the brown, ochronotic pigment.

In another embodiment, candidate nucleic acids are transformed into plant material to generate a transgenic plant, regenerated into morphologically normal fertile plants which are then measured for differential tolerance to selected HPPD-inhibiting—herbicides. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nuclaic acid expressing the control HPPD. Alternatively, an untransformed dicot plant such as *Arabidopsis* or Tobacco can be used as a control since this, in any case, expresses its own endogenous HPPD. The average, and distribution, of herbicide tolerance levels of a range of primary plant transformation events or their progeny to HPPD-inhibiting herbicides, for example the benzamides selected from Table 2 are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post-emergence.

Another object refers to an isolated nucleic acid encoding a mut-HPPD, wherein the nucleic acid is identifiable by a method as defined above.

In another embodiment, the invention refers to a plant cell transformed by a wild-type or a mut-HPPD nucleic acid according to the present invention or or a plant cell which has been mutated to obtain a plant expressing a wild-type or a mut-HPPD nucleic acid, wherein expression of the nucleic acid in the plant cell results in increased resistance or tolerance to a HPPD-inhibiting herbicide as compared to a wild type variety of the plant cell.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the HPPD-inhibiting herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via Agrobacterium-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for Agrobacterium-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming Agrobacterium tumefaciens, for example pBin19 (Bevan et al., Nucl. Acids Res. 12 (1984) 8711). Agrobacteria transformed by such a vector can then be used in known manner for the transformation of plants, such as plants used as a model, like Arabidopsis (Arabidopsis thaliana is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of Agrobacterium tumefaciens is described, for example, by Hbfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of Arabidopsis are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in Arabidopsis Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of Arabidopsis, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds is harvested in both cases, and these seeds can be distinguished from non-transgenic seeds by growing under the above-described selective conditions. In addition the stable transformation of plastids is of advantages because plastids are inherited maternally in most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mut-HPPD nucleic acid (a) or wild-type or mut-HST nucleic acid (b) comprises a polynucleotide sequence selected from the group consisting of: a) a polynucleotide as shown in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof; b) a polynucleotide as shown in SEQ ID NO: 47 or 49, or a variant or derivative thereof; c) a polynucleotide encoding a polypeptide as shown in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative thereof; d) a polynucleotide comprising at least 60 consecutive nucleotides of any of a) through c); and e) a polynucleotide complementary to the polynucleotide of any of a) through d).

Preferably, the expression of the nucleic acid in the plant results in the plants increased resistance to HPPD-inhibiting herbicide as compared to a wild type variety of the plant.

In another embodiment, the invention refers to a plant, preferably a transgenic plant, comprising a plant cell according to the present invention, wherein expression of the nucleic acid in the plant results in the plants increased resistance to HPPD-inhibiting herbicide as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention,
or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously.

However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mut-HPPD nucleic acids, the nucleic acids can be derived from different genomes or from the same genome. Alternatively, in embodiments wherein the plant is non-transgenic and comprises multiple mut-HPPD nucleic acids, the nucleic acids are located on different genomes or on the same genome.

In certain embodiments, the present invention involves herbidicide-resistant plants that are produced by mutation breeding. Such plants comprise a polynucleotide encoding a mut-HPPD and/or a mut-HST and are tolerant to one or more "HPPD-inhibiting herbicides". Such methods can involve, for example, exposing the plants or seeds to a mutagen, particularly a chemical mutagen such as, for example, ethyl methanesulfonate (EMS) and selecting for plants that have enhanced tolerance to at least one or more HPPD-inhibiting herbicide.

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 250 to 290 nm), and chemical mutagens such as base analogues (e.g., 5-bromouracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mut-HPPD nucleic acid or over-expressed wild-type HPPD nucleic acid, and has increased tolerance to a HPPD-inhibiting herbicide as compared to a wild-type variety of the plant. It is possible for the plants of the present invention to have multiple wild-type or mut-HPPD nucleic acids from different genomes since these plants can contain more than one genome. For example, a plant contains two genomes, usually referred to as the A and B genomes. Because HPPD is a required metabolic enzyme, it is assumed that each genome has at least one gene coding for the HPPD enzyme (i.e. at least one HPPD gene). As used herein, the term "HPPD gene locus" refers to the position of an HPPD gene on a genome, and the terms "HPPD gene" and "HPPD nucleic acid" refer to a nucleic acid encoding the HPPD enzyme. The HPPD nucleic acid on each genome differs in its nucleotide sequence from an HPPD nucleic acid on another genome. One of skill in the art can determine the genome of origin of each HPPD nucleic acid through genetic crossing and/or either sequencing methods or exonuclease digestion methods known to those of skill in the art.

The present invention includes plants comprising one, two, three, or more mut-HPPD alleles, wherein the plant has increased tolerance to a HPPD-inhibiting herbicide as compared to a wild-type variety of the plant. The mut-HPPD alleles can comprise a nucleotide sequence selected from the group consisting of a polynucleotide as defined in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof, a polynucleotide encoding a polypeptide as defined in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a HPPD gene of the plant or seed.

In some embodiments, traditional plant breeding is employed whereby the HPPD-inhibiting herbicides-tolerant trait is introduced in the progeny plant resulting therefrom. In one embodiment, the present invention provides a method for producing a HPPD-inhibiting herbicides-tolerant progeny plant, the method comprising: crossing a parent plant with a HPPD-inhibiting herbicides-tolerant plant to introduce the HPPD-inhibiting herbicides-tolerance characteristics of the HPPD-inhibiting herbicides-tolerant plant into the germplasm of the progeny plant, wherein the progeny plant has increased tolerance to the HPPD-inhibiting herbicides relative to the parent plant. In other embodiments, the method further comprises the step of introgressing the HPPD-inhibiting herbicides-tolerance characteristics through traditional plant breeding techniques to obtain a descendent plant having the HPPD-inhibiting herbicides-tolerance characteristics.

The herbicide-resistant plants of the invention that comprise polynucleotides encoding mut-HPPD and/or mut-HST polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mut-HPPD and/or mut-HST polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being HPPD-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, HPPD-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, HPPD-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other HPPD inhibitors; and to GS inhibitors, such as glufosinate.

In addition to these classes of inhibitors, HPPD-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity. HPPD-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, HPPD-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA (b), CryIIIA, CryIIIB(bl) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the HPPD-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (Anthrenus spp., Attagenus spp.); the cowpea weevil Callosobruchus maculates; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna vaivestis*; the old house borer *Hylotropes bajulus*; the luceme weevil *Hypera postica*; the shiny spider beetle *Gibbium psylloides*; the cigarette beetle *Lasioderma serricome*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeuc* s; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle Psylliodes *chrysocephala*; Ptinus spp. (spider beetles); the lesser grain borer *Rhizopertha dominica*; the pea and been weevil *Sitona lineatus*; the rice and granary beetles *Sitophilus oryzae* and *Sitophilus* granaries; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *psylla Cacopsylla pyricola*; the currant aphid *Cryptomyzus ribis*; the grape *phylloxera* Daktulosphaira vitifoliae; the citrus *psylla* Diaphorina *citri*; the potato leafhopper *Empoasca fabae*; the bean leafhopper *Empoasca* Solana; the vine leafhopper *Empoasca vitis*; the woolly aphid *Eriosoma lanigerum*; the European fruit scale *Eulecanium comi*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); Carpocapsa *pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), Homeosoma electellum (sunflower moth); Homona magnanima (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae*

(cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco thrips *Frankliniella fusca*, the flower thrips *Frankliniella intonsa*, the western flower thrips *Frankliniella* occidentalism the cotton bud thrips *Frankliniella schultzei*, the banded greenhouse thrips Hercinothrips *femoralis*, the soybean thrips Neohydatothrips *variabilis*, Kelly's citrus thrips Pezothrips kellyanus, the avocado thrips *Scirtothrips perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the HPPD-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the HPPD-inhibiting herbicides-tolerant plants is effective for controlling cabbage seedpod weevil, the Bertha armyworm, *Lygus* bugs, or the diamondback moth.

It is to be understood that the plant of the present invention can comprise a wild type HPPD nucleic acid in addition to a mut-HPPD nucleic acid. It is contemplated that the HPPD-inhibiting herbicide tolerant lines may contain a mutation in only one of multiple HPPD iso-enzymes. Therefore, the present invention includes a plant comprising one or more mut-HPPD nucleic acids in addition to one or more wild type HPPD nucleic acids.

In another embodiment, the invention refers to a seed produced by a transgenic plant comprising a plant cell of the present invention, wherein the seed is true breeding for an increased resistance to a HPPD-inhibiting herbicide as compared to a wild type variety of the seed.

In another embodiment, the invention refers to a method of producing a transgenic plant cell with an increased resistance to a HPPD-inhibiting herbicide as compared to a wild type variety of the plant cell comprising, transforming the plant cell with an expression cassette comprising a nucleic acid encoding a wildtype or a mut-HPPD as defined SUPRA.

In another embodiment, the invention refers to a method of producing a transgenic plant comprising, (a) transforming a plant cell with an expression cassette comprising a nucleic acid encoding a wildtype or a mut-HPPD, and (b) generating a plant with an increased resistance to HPPD-inhibiting herbicide from the plant cell.

Consequently, HPPD nucleic acids encoding a wildtype or a mut-HPPD useful for the invention are provided in expression cassettes for expression in the plant of interest. The cassette will include regulatory sequences operably linked to a HPPD nucleic acid sequence encoding a wildtype or a mut-HPPD of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the HPPD nucleic acid sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a mut-HPPD nucleic acid sequence of the invention, and a transcriptional and translational termination region (i.e., termination region) functional in plants. The promoter may be native or analogous, or foreign or heterologous, to the plant host and/or to the HPPD nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the HPPD nucleic acid sequence of the invention, it is intended that the promoter is not the native or naturally occurring promoter for the operably linked HPPD nucleic acid sequence of the invention. As used herein, a chimeric gene comprises a coding sequence operably linked to a transcription initiation region that is heterologous to the coding sequence.

While it may be preferable to express the HPPD nucleic acids of the invention using heterologous promoters, the native promoter sequences may be used. Such constructs would change expression levels of the HPPD protein in the plant or plant cell. Thus, the phenotype of the plant or plant cell is altered.

The termination region may be native with the transcriptional initiation region, may be native with the operably linked HPPD sequence of interest, may be native with the plant host, or may be derived from another source (i.e., foreign or heterologous to the promoter, the HPPD nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize AdhI, intronI gene (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize mut-HPPD gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) Proc. Natl. Acad. ScL USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and trans versions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced HPPD expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254 (3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression. In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the HPPD nucleic acid of the invention such that the two sequences are contiguous and in the same reading frame. See, for example, Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. Any chloroplast transit peptide known in the art can be fused to the amino acid sequence of a mature HPPD protein of the invention by operably linking a chloroplast-targeting sequence to the 5'-end of a nucleotide sequence encoding a mature mut-HPPD protein of the invention. Chloroplast targeting sequences are known in the art and include the chloroplast small subunit of ribulose-1, 5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem.

270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305. The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

In a preferred embodiment, the HPPD nucleic acid encoding a wildtype or a mut-HPPD (a) or the HST nucleic acid (b) comprises a polynucleotide sequence selected from the group consisting of: a) a polynucleotide as shown in SEQ ID NO: 1, 51, 3, 4, 6, 7, 9, 10, 12, 13, 15, 16, 18, 19, 21, 23, 25, 27, 29, 31, 33, 35, 37, 39, 41, 43, 45, 52, 54, 56, 68, 69, or a variant or derivative thereof; b) a polynucleotide as shown in SEQ ID NO: 47 or 49, or a variant or derivative thereof; c) a polynucleotide encoding a polypeptide as shown in SEQ ID NO: 2, 5, 8, 11, 14, 17, 20, 22, 24, 26, 28, 30, 32, 34, 36, 38, 40, 42, 44, 46, 53, 55, 57, 58, 59, 60, 61, 62, 63, 64, 65, 66, 67, or a variant or derivative thereof; d) a polynucleotide comprising at least 60 consecutive nucleotides of any of a) through c); and e) a polynucleotide complementary to the polynucleotide of any of a) through d) Preferably, the expression cassette further comprises a transcription initiation regulatory region and a translation initiation regulatory region that are functional in the plant.

While the polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairnm et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

The invention further provides an isolated recombinant expression vector comprising the expression cassette containing a HPPD nucleic acid as described above, wherein expression of the vector in a host cell results in increased tolerance to a HPPD-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mut-HPPD polypeptides, fusion polypeptides, etc.).

In a preferred embodiment of the present invention, the HPPD polypeptides are expressed in plants and plants cells such as unicellular plant cells (such as algae) (See Falciatore et al., 1999, Marine Biotechnology 1(3):239-251 and references therein) and plant cells from higher plants (e.g., the spermatophytes, such as crop plants). A HPPD polynucleotide may be "introduced" into a plant cell by any means, including transfection, transformation or transduction, electroporation, particle bombardment, agroinfection, biolistics, and the like.

Suitable methods for transforming or transfecting host cells including plant cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As increased tolerance to HPPD-inhibiting herbicides is a general trait wished to be inherited into a wide variety of plants like maize, wheat, rye, oat, triticale, rice, barley, soybean, pea-nut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. In a preferred embodiment, the plant is a crop plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a mut-HPPD polynucleotide into a plant is achieved by Agrobacterium mediated gene transfer. One transformation method known to those of skill in the art is the dipping of a flowering plant into an Agrobacteria solution, wherein the Agrobacteria contains the mut-HPPD nucleic acid, followed by breeding of the transformed gametes. Agrobacterium mediated plant transformation can be performed using for example the GV3101(pMP90) (Koncz and Schell, 1986, Mol. Gen. Genet. 204:383-396) or LBA4404 (Clontech) Agrobacterium tumefaciens strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced HPPD polynucleotide may be maintained in the plant cell stably if it is incorporated into a non-chromosomal autonomous replicon or integrated into the plant chromosomes. Alternatively, the introduced mut-HPPD polynucleotide may be present on an extra-chromosomal non-replicating vector and be transiently expressed or transiently active. In one embodiment, a homologous recombinant microorganism can be created wherein the mut-HPPD polynucleotide is integrated into a chromosome, a vector is prepared which contains at least a portion of an HPPD gene into which a deletion, addition, or substitution has been introduced to thereby alter, e.g., functionally disrupt, the endogenous HPPD gene and to create a mut-HPPD gene. To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene therapy American Scientist 87(3):240-247). Other homologous recombination procedures in Triticum species are also well known in the art and are contemplated for use herein.

In the homologous recombination vector, the wildtype or mut-HPPD gene can be flanked at its 5' and 3' ends by an additional nucleic acid molecule of the HPPD gene to allow for homologous recombination to occur between the exogenous wildtype or mut-HPPD gene carried by the vector and an endogenous HPPD gene, in a microorganism or plant. The additional flanking HPPD nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987, Cell 51:503 for a description of homologous recombination vectors or Strepp et al., 1998, PNAS, 95(8):4368-4373 for cDNA based recombination in Physcomitrella patens). However, since the mut-HPPD gene normally differs from the HPPD gene at very few amino acids, a flanking sequence is not always necessary. The homologous recombination vector is introduced into a microorganism or plant cell (e.g., via polyethylene glycol mediated DNA), and cells in which the introduced mut-HPPD gene has homologously recombined with the endogenous HPPD gene are selected using art-known techniques.

In another embodiment, recombinant microorganisms can be produced that contain selected systems that allow for regulated expression of the introduced gene. For example, inclusion of a mut-HPPD gene on a vector placing it under control of the lac operon permits expression of the mut-HPPD gene only in the presence of IPTG. Such regulatory systems are well known in the art.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell.

Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a mut-HPPD polynucleotide can be expressed in bacterial cells such as *C. glutamicum*, insect cells, fungal cells, or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) a mut-HPPD polynucleotide. Accordingly, the invention further provides methods for producing mut-HPPD polypeptides using the host cells of the invention. In one embodiment, the method comprises culturing the host cell of invention (into which a recombinant expression vector encoding a mut-HPPD polypeptide has been introduced, or into which genome has been introduced a gene encoding a wild-type or mut-HPPD polypeptide) in a suitable medium until mut-HPPD polypeptide is produced. In another embodiment, the method further comprises isolating mut-HPPD polypeptides from the medium or the host cell. Another aspect of the invention pertains to isolated mut-HPPD polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of mut-HPPD polypeptide in which the polypeptide is separated from some of the cellular components of the cells in which it is naturally or recombinantly produced. In one embodiment, the language "substantially free of cellular material" includes preparations of a mut-HPPD polypeptide having less than about 30% (by dry weight) of non-mut-HPPD material (also referred to herein as a "contaminating polypeptide"), more preferably less than about 20% of non-mut-HPPD material, still more preferably less than about 10% of non-mut-HPPD material, and most preferably less than about 5% non-mut-HPPD material.

When the mut-HPPD polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of mut-HPPD polypeptide in which the polypeptide is separated from chemical precursors or other chemicals that are involved in the synthesis of the polypeptide. In one embodiment, the language "substantially free of chemical precursors or other chemicals" includes preparations of a mut-HPPD polypeptide having less than about 30% (by dry weight) of chemical precursors or non-mut-HPPD chemicals, more preferably less than about 20% chemical precursors or non-mut-HPPD chemicals, still more preferably less than about 10% chemical precursors or non-mut-HPPD chemicals, and most preferably less than about 5% chemical precursors or non-mut-HPPD chemicals. In preferred embodiments, isolated polypeptides, or biologically active portions thereof, lack contaminating polypeptides from the same organism from which the mut-HPPD polypeptide is derived. Typically, such polypeptides are produced by recombinant expression of, for example, a mut-HPPD polypeptide in plants other than, or in microorganisms such as *C. glutamicum*, ciliates, algae, or fungi.

As described above, the present invention teaches compositions and methods for increasing the HPPD-inhibiting herbicide, particularly benzamide tolerance of a crop plant or seed as compared to a wild-type variety of the plant or seed. In a preferred embodiment, the HPPD-inhibiting herbicide, particularly benzamide tolerance of a crop plant or seed is increased such that the plant or seed can withstand a HPPD-inhibiting herbicide, particularly benzamide application of preferably approximately 1-1000 g ai ha$^{-1}$, more preferably 10-500 g ai ha$^{-1}$, still more preferably 20-200 g ai ha$^{-1}$ and most preferably 40-100 g ai ha$^{-1}$. As used herein, to "withstand" a HPPD-inhibiting herbicide, particularly benzamide application means that the plant is either not killed or not injured by such application.

Furthermore, the present invention provides methods that involve the use of at least one HPPD-inhibiting herbicide, particularly benzamide as depicted in Table 2.

In these methods, the HPPD-inhibiting herbicide, particularly benzamide can be applied by any method known in the art including, but not limited to, seed treatment, soil treatment, and foliar treatment. Prior to application, the HPPD-inhibiting herbicide, particularly benzamide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to HPPD-inhibiting herbicide, particularly benzamide, a wide variety of formulations can be employed for protecting plants from weeds, so as to enhance plant growth and reduce competition for nutrients. A HPPD-inhibiting herbicide, particularly benzamide, can be used by itself for pre-emergence, post-emergence, pre-planting, and at-planting control of weeds in areas surrounding the crop plants described herein, or a HPPD-inhibiting herbicide formulation can be used that contains other additives. The HPPD-inhibiting herbicide, particularly benzamide, can also be used as a seed treatment. Additives found in a HPPD-inhibiting herbicide formulation include other herbicides, detergents, adjuvants, spreading agents, sticking agents, stabilizing agents, or the like. The HPPD-inhibiting herbicide formulation can be a wet or dry preparation and can include, but is not limited to, flowable powders, emulsifiable concentrates, and liquid concentrates. The HPPD-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Cloning of HPPD Encoding Genes (A) Cloning of *Arabidopsis thaliana* HPPD The partial *Arabidopsis thaliana* AtHPPD coding sequence (SEQ ID No: 52) is amplified by standard PCR techniques from *Arabidopsis thaliana* cDNA using primers HuJ101 and HuJ102 (Table 5).

TABLE 5

PCR primers for AtHPPD amplification (SEQ ID NO: 70, 71)

| Primer name | Primer sequence (5' → 3') |
|---|---|
| HuJ101 | GGCCACCAAAACGCCG |
| HuJ102 | TCATCCCACTAACTGTTTGGCTTC |

The PCR-product is cloned in vector pEXP5-NT/TOPO® (Invitrogen, Carlsbad, USA) according to the manufacturer's instructions. The resulting plasmid pEXP5-NT/TOPO®-AtHPPD is isolated from *E. coli* TOP10 by performing a plasmid minipreparation. The expression cassette encoding N-terminally His6-tagged AtHPPD is confirmed by DNA sequencing.

(B) Cloning of *Chlamydomonas reinhardtii* HPPD1

The *C. reinhardtii* HPPD1 (CrHPPD1) coding sequence (SEQ ID No: 54) is codon-optimized for expression in *E. coli* and provided as a synthetic gene (Entelechon, Regensburg, Germany). The partial synthetic gene is amplified by standard PCR techniques using primers Ta1-1 and Ta1-2 (Table 6).

TABLE 6

PCR primers for CrHPPD1 amplification (SEQ ID NO: 72, 73)

| Primer name | Primer sequence (5' → 3') |
|---|---|
| Ta1-1 | GGCGCTGGCGGTGCGTCCACTAC |
| Ta1-2 | TCAAACGTTCAGGGTACGCTCGTAGTCTTCGATG |

The PCR-product is cloned in vector pEXP5-NT/TOPO® (Invitrogen, Carlsbad, USA) according to the manufacturer's instructions. The resulting plasmid pEXP5-NT/TOPO®-CrHPPD1 is isolated from *E. coli* TOP10 by performing a plasmid minipreparation. The expression cassette encoding N-terminally His6-tagged CrHPPD1 is confirmed by DNA sequencing.

(C) Cloning of *C. reinhardtii* HPPD2

The *C. reinhardtii* HPPD2 (CrHPPD2) coding sequence (SEQ ID No: 56) is codon-optimized for expression in *E. coli* and provided as a synthetic gene (Entelechon, Regensburg, Germany). The partial synthetic gene is amplified by standard PCR techniques using primers Ta1-3 and Ta1-4 (Table 7).

TABLE 7

PCR primers for CrHPPD2 amplification (SEQ ID NO: 74, 75)

| Primer name | Primer sequence (5' → 3') |
|---|---|
| Ta1-3 | GGTGCGGGTGGCGCTGGCACC |
| Ta1-4 | TCAAACGTTCAGGGTACGTTCGTAGTCCTCGATGG |

The PCR-product is cloned in vector pEXP5-NT/TOPO® (Invitrogen, Carlsbad, USA) according to the manufacturer's instructions. The resulting plasmid pEXP5-NT/TOPO®-CrHPPD2 is isolated from *E. coli* TOP10 by performing a plasmid minipreparation. The expression cassette encoding N-terminally His6-tagged CrHPPD2 is confirmed by DNA sequencing.

(D) Cloning of *Glycine max* HPPD

The *Glycine max* HPPD (GmHPPD; Glyma14g03410) coding sequence is codon-optimized for expression in *E. coli* and provided as a synthetic gene (Entelechon, Regensburg, Germany). The partial synthetic gene is amplified by standard PCR techniques using primers Ta2-65 and Ta2-66 (Table 8).

TABLE 8

PCR primers for GmHPPD amplification (SEQ ID NO: 76, 77)

| Primer name | Primer sequence (5' → 3') |
|---|---|
| Ta2-65 | CCAATCCCAATGTGCAACG |
| Ta2-66 | TTATGCGGTACGTTTAGCCTCC |

The PCR-product is cloned in vector pEXP5-NT/TOPO® (Invitrogen, Carlsbad, USA) according to the manufacturer's instructions. The resulting plasmid pEXP5-NT/TOPO®-GmHPPD is isolated from *E. coli* TOP10 by performing a plasmid minipreparation. The expression cassette encoding N-terminally His6-tagged GmHPPD is confirmed by DNA sequencing.

(E) Cloning of *Zea mays* HPPD

The *Zea mays* HPPD (ZmHPPD; GRMZM2G088396) coding sequence is codon-optimized for expression in *E. coli* and provided as a synthetic gene (Entelechon, Regensburg, Germany). The partial synthetic gene is amplified by standard PCR techniques using primers Ta2-45 and Ta2-46 (Table 9).

TABLE 9

PCR primer for ZmHPPD amplification (SEQ ID NO: 78, 79)

| Primer name | Primer sequence (5' → 3') |
|---|---|
| Ta2-45 | CCACCGACTCCGACCGCCGCAGC |
| Ta2-46 | TCAGGAACCCTGTGCAGCTGCCGCAG |

The PCR-product is cloned in vector pEXP5-NT/TOPO® (Invitrogen, Carlsbad, USA) according to the manufacturer's instructions. The resulting plasmid pEXP5-NT/TOPO®-ZmHPPD is isolated from *E. coli* TOP10 by performing a plasmid minipreparation. The expression cassette encoding N-terminally His6-tagged ZmHPPD is confirmed by DNA sequencing.

(F) Cloning of Oryza sativa HPPD

The Oryza sativa HPPD (OsHPPD; Os02g07160) coding sequence is codon-optimized for expression in E. coli and provided as a synthetic gene (Entelechon, Regensburg, Germany). The partial synthetic gene is amplified by standard PCR techniques using primers Ta2-63 and Ta2-64 (Table 10).

TABLE 10

PCR primer for OsHPPD amplification (SEQ ID NO: 80, 81)

| Primer name | Primer sequence (5' → 3') |
|---|---|
| Ta2-63 | CCGCCGACTCCAACCCC |
| Ta2-64 | TTAAGAACCCTGAACGGTCGG |

The PCR-product is cloned in vector pEXP5-NT/TOPO® (Invitrogen, Carlsbad, USA) according to the manufacturer's instructions. The resulting plasmid pEXP5-NT/TOPO®-OsHPPD is isolated from E. coli TOP10 by performing a plasmid minipreparation. The expression cassette encoding N-terminally His6-tagged OsHPPD is confirmed by DNA sequencing.

(G) Gene Synthesis and Subcloning

Other wildtype HPPD encoding genes, such as Hordeum vulgare (SEQ ID NO:1/2) or Picrophilus torridus HPPD gene (Seq ID NO: 39/40) were synthesized by Geneart (Regensburg, Germany) or Entelechon (Regensburg, Germany) and subcloned into a modified pET24D (Novagen) expression vector resulting in N-terminally His-tagged expression constructs.

Example 2: Heterologous Expression and Purification of Recombinant HPPD Enzymes

Recombinant HPPD enzymes are produced and overexpressed in E. coli. Chemically competent BL21 (DE3) cells (Invitrogen, Carlsbad, USA) are transformed with pEXP5-NT/TOPO® (see EXAMPLE 1) or with other expression vectors according to the manufacturer's instructions.

Transformed cells are grown in autoinduction medium (ZYM 5052 supplemented with 100 µg/ml ampicillin) for 6 h at 37° C. followed by 24 h at 25° C.

At an OD600 (optical density at 600 nm) of 8 to 12, cells are harvested by centrifugation (8000×g). The cell pellet is resuspended in a lysis buffer (50 mM sodium phosphate buffer, 0.5 M NaCl, 10 mM Imidazole, pH 7.0) supplemented with complete EDTA free protease inhibitor mix (Roche-Diagnostics) and homogenized using an Avestin Press. The homogenate is cleared by centrifugation (40,000× g). His$_6$-tagged HPPD or mutant variants are purified by affinity chromatography on a Protino Ni-IDA 1000 Packed Column (Macherey-Nagel) according to the manufacturer's instructions. Purified HPPD or mutant variants are dialyzed against 100 mM sodium phosphate buffer pH 7.0, supplemented with 10% glycerin and stored at −86° C. Protein content is determined according to Bradford using the Bio-Rad protein assay (Bio-Rad Laboratories, Hercules, USA). The purity of the enzyme preparation is estimated by SDS-PAGE.

Example 3: Assay for HPPD Activity

HPPD produces homogentisic acid and $CO_2$ from 4-hydroxyphenylpyruvate (4-HPP) and $O_2$. The activity assay for HPPD is based on the analysis of homogentisic acid by reversed phase HPLC.

The assay mixture can contain 150 mM potassium phosphate buffer pH 7.0, 50 mM L-ascorbic acid, 100 µM Catalase (Sigma-Aldrich), 1 µM $FeSO_4$ and 0.2 units of purified HPPD enzyme in a total volume of 505 µl. 1 unit is defined as the amount of enzyme that is required to produce 1 nmol of HGA per minute at 20° C.

After a preincubation of 30 min the reaction is started by adding 4-HPP to a final concentration of 0.05 mM. The reaction is allowed to proceed for 45 min at room temperature. The reaction is stopped by the addition of 50 µl of 4.5 M phosphoric acid. The sample is filtered using a 0.2 µM pore size PVDF filtration device.

5 µl of the cleared sample is analyzed on an UPLC HSS T3 column (particle size 1.8 µm, dimensions 2,1×50 mm; Waters) by isocratic elution using 90% 20 mM $NaH_2PO_4$ pH 2.2, 10% methanol (v/v).

HGA is detected electrochemically at 750 mV (mode: DC; polarity: positive) and quantified by integrating peak areas (Empower software; Waters).

Inhibitors are dissolved in DMSO (dimethylsulfoxide) to a concentration of 0.5 mM. From this stock solution serial five-fold dilutions are prepared in DMSO, which are used in the assay. The respective inhibitor solution accounts for 1% of the assay volume. Thus, final inhibitor concentrations range from 5 µM to 320 µM, respectively. Activities are normalized by setting the uninhibited enzyme activity to 100%. $IC_{50}$ values are calculated using non-linear regression.

Example 4: In Vitro Characterization of Wildtype HPPD Enzymes

Using methods which are described in the above examples or well known in the art, purified, recombinant wildtype HPPD enzymes are characterized with respect to their kinetic properties and sensitivity towards HPPD inhibiting herbicides. Apparent michaelis constants ($K_m$) and maximal reaction velocities ($V_{max}$) are calculated by non-linear regression with the software GraphPad Prism 5 (GraphPad Software, La Jolla, USA) using a substrate inhibition model. Apparent $k_{cat}$ values are calculated from $V_{max}$ assuming 100% purity of the enzyme preparation. Weighted means (by standard error) of $K_m$ and $IC_{50}$ values are calculated from at least three independent experiments. The Cheng-Prusoff equation for competitive inhibition (Cheng, Y. C.; Prusoff, W. H. Biochem Pharmacol 1973, 22, 3099-3108) is used to calculate dissociation constants ($K_i$).

Field performance of the HPPD enzyme, which is used as a herbicide tolerance trait, may depend not only on its lack of sensitivity towards HPPD inhibiting herbicides but also on its activity. To assess the potential performance of a herbicide tolerance trait a tolerance index (TI) is calculated using the following formula:

$$TI = \frac{k_{cat} \times K_i}{K_m}$$

Easy comparison and ranking of each trait is enabled by normalizing tolerance indexes on Arabidopsis wild-type HPPD.

Examples of the data obtained in an in vitro assay are depicted in Table 11 and in Table 12.

TABLE 11

Determination of michaelis constants ($K_m$) for 4-HPP, turnover numbers ($k_{cat}$), catalytic efficiencies ($k_{cat}/K_m$) and dissociation constants ($K_i$) for various HPPD enzymes.

| Enzyme | $K_m$ [µM] (4-HPP) | $k_{cat}$ [s$^{-1}$] | $k_{cat}/K_m$ [µM$^{-1}$ s$^{-1}$] | $K_i$ [nM] (Inhibitor 1)* | $K_i$ [nM] (Inhibitor 2)* | TI (Inhibitor 1)* | TI (Inhibitor 2)* |
|---|---|---|---|---|---|---|---|
| Arabidopsis | 13 | 12.9 | 1 | 15 | 20 | 15E−3 | 19.5E−3 |
| Hordeum | 26 | 11.5 | 0.44 | 3.7 | 11 | 1.6E−3 | 5E−3 |

*HPPD inhibiting herbicides used in this example are 2,4-dichloro-6-fluoro-3-methylsulfonyl-N-(1-methyltetrazol-5-yl)benzamide (Inhibitor 1) and 2,4-dichloro-6-fluoro-3-methylsulfanyl-N-(1-methyltetrazol-5-yl)benzamide (Inhibitor 2)

TABLE 12

Normalized tolerance indexes of various HPPD enzymes

| HPPD Enzyme | TI Inhibitor 1* | TI Inhibitor 2* | TI Inhibitor 3* |
|---|---|---|---|
| Hordeum | 1 | 1 | 1 |
| Rhodococcus HPPD2 | 2.8 | 0.4 | 12.5 |
| Rhodococcus HPPD1 | 2.8 | 0.4 | 0.4 |
| Kordia | 1.2 | 0.4 | 3.1 |
| Picrophilus | 2.1 | 0.4 | 0.7 |
| Avena | 2.8 | 3.8 | 2.8 |
| Lolium | 4.2 | 3.0 | 1.7 |
| Seq ID 67 | 5 | 12.3 | 3.8 |
| Seq ID 69 | 1.4 | 3 | 0.7 |

*HPPD inhibiting herbicides used in this example are 2,4-dichloro-6-fluoro-3-methylsulfonyl-N-(1-methyltetrazol-5-yl)benzamide (Inhibitor 1) and 2,4-dichloro-6-fluoro-3-methylsulfanyl-N-(1-methyltetrazol-5-yl)benzamide (Inhibitor 2) 2,4-dichloro-6-fluoro-3-methylsulfanyl-N-(2-methyl-1,2,4-triazol-3-yl)benzamide (Inhibitor 3), The reference SEQ ID NO:2 was included as a comparative control in a representative number of experiments and the values given in Table 12 are the average values from a number of experiments. The TI values given for various HPPD enzymes from different organisms are normalized to the value of the reference SEQ ID NO:2.

It can be seen from the above example that polynucleotides comprising a region which encode Rhodococcus HPPD1 or HPPD2 can be selected as transgenes which encode an inhibitor-resistant HPPD because it was found that those enzymes were more tolerant to benzamide-derivative HPPD-inhibiting herbicides than the reference Hordeum HPPD enzyme. In detail, the tolerance indexes of the Rhodococcus enzymes were 2.8-fold increased for Inhibitor 1 whereas a 12.5-fold increased tolerance was observed for Rhodococcus HPPD2 for Inhibitor 3 compared to the benchmark enzyme (SEQ-ID:2). It can be further seen that the enzyme encoded by a polynucleotide comprising the Avena HPPD was 2.8-fold more tolerant to Inhibitor 1, 3.8-fold more tolerant to Inhibitor 2, and a 2.8-fold more tolerant to Inhibitor 3 compared to the control wild-type Hordeum enzyme. The two transgenes comprising the Zea mays HPPD mutants (SEQ-ID:67, SEQ-ID:69) are of outstanding interest because those enzymes showed a good tolerance against all HPPD inhibitors tested in the present invention. It is evident that any HPPD enzyme that is resistant towards herbicides, even if this protein is not exemplified in this text, is part of the subject-matter of this invention.

Example 5: Rational Mutagenesis

By means of structural biology and sequence alignment it is possible to choose a certain number of amino acids which can either directly or indirectly be involved in the binding of "HPPD-inhibiting herbicides" and then to mutagenize them and obtain tolerant HPPD enzymes.

(A) Site-Directed Mutagenesis

PCR-based site directed mutagenesis of pEXP5-NT/TOPO®-AtHPPD is done with the QuikChange II Site-Directed Mutagenesis Kit (Stratagene, Santa Clara, USA) according to the manufacturers instructions. This technique requires two chemically synthesized DNA primers (forward and reverse primer) for each mutation. Exemplified primers that can be used for site directed mutagenesis of AtHPPD (SEQ ID NO:52/53) are listed in Table 13.

TABLE 13

PCR primers for site directed mutagenesis of AtHPPD (SEQ ID NOs: 82 to 147)

| Primer name | Primer sequence (5' → 3') | Mutation AtHPPD |
|---|---|---|
| HuJ141 | GAGGATTCGACTTCGCGCCTTCTCCTCC | Met335 → Ala |
| HuJ142 | GGAGGAGAAGGCGCGAAGTCGAATCCTC | Met335 → Ala |
| HuJ143 | GAGGATTCGACTTCTGGCCTTCTCCTCCG | Met335 → Trp |
| HuJ144 | CGGAGGAGAAGGCCAGAAGTCGAATCCTC | Met335 → Trp |
| HuJ145 | GGAGGATTCGACTTCTTTCCTTCTCCTCCGC | Met335 → Phe |
| HuJ146 | GCGGAGGAGAAGGAAAGAAGTCGAATCCTCC | Met335 → Phe |
| HuJ147 | GTGACAGGCCGACGATAGCTATAGAGATAATCCAG | Phe392 → Ala |
| HuJ148 | CTGGATTATCTCTATAGCTATCGTCGGCCTGTCAC | Phe392 → Ala |
| HuJ153 | GACTTCATGCCTCCTCCTCCGCCTACTTAC | Ser337 → Pro |

TABLE 13-continued

PCR primers for site directed
mutagenesis of AtHPPD (SEQ ID NOs: 82 to 147)

| Primer name | Primer sequence (5' → 3') | Mutation AtHPPD |
|---|---|---|
| HuJ154 | GTAAGTAGGCGGAGGAGGAGGCATGAAGTC | Ser337 → Pro |
| HuJ155 | GATTCGACTTCATGGCTTCTCCTCCGCCTAC | Pro336 → Ala |
| HuJ156 | GTAGGCGGAGGAGAAGCCATGAAGTCGAATC | Pro336 → Ala |
| HuJ157 | CAGATCAAGGAGTGTCAGGAATTAGGGATTCTTG | Glu363 → Gln |
| HuJ158 | CAAGAATCCCTAATTCCTGACACTCCTTGATCTG | Glu363 → Gln |
| HuJ159 | CGGAACAAAGAGGAAGAGTGAGATTCAGACGTATTTGG | Gln293 → Val |
| HuJ160 | CCAAATACGTCTGAATCTCACTCTTCCTCTTTGTTCCG | Gln293 → Val |
| HuJ169 | CGTTGCTTCAAATCTTCCCGAAACCACTAGGTGACAGGCC | Thr382 → Pro |
| HuJ170 | GGCCTGTCACCTAGTGGTTTCGGGAAGATTTGAAGCAACG | Thr382 → Pro |
| HuJ171 | CAAATCTTCACAAAACCAGTGGGTGACAGGCCGACGAT | Leu385 → Val |
| HuJ172 | ATCGTCGGCCTGTCACCCACTGGTTTTGTGAAGATTTG | Leu385 → Val |
| HuJ173 | TGACAGGCCGACGATATTTCTGGAGATAATCCAGAGAGTA | Ile393 → Leu |
| HuJ174 | TACTCTCTGGATTATCTCCAGAAATATCGTCGGCCTGTCA | Ile393 → Leu |
| HuJ175 | GACTTCATGCCTGCGCCTCCGCCTACTTAC | Ser337 → Ala |
| HuJ176 | GTAAGTAGGCGGAGGCGCAGGCATGAAGTC | Ser337 → Ala |
| HuJ177 | GGCAATTTCTCTGAGTTCTTCAAGTCCATTGAAG | Leu427 → Phe |
| HuJ178 | CTTCAATGGACTTGAAGAACTCAGAGAAATTGCC | Leu427 → Phe |
| HuJ185 | GGAACAAAGAGGAAGAGTGTGATTCAGACGTATTTGG | Gln293 → Val |
| HuJ186 | CCAAATACGTCTGAATCACACTCTTCCTCTTTGTTCC | Gln293 → Val |
| Ta2-55 | GAGGATTCGACTTCAACCCTTCTCCTCC | Met335 → Asn |
| Ta2-56 | GGAGGAGAAGGGTTGAAGTCGAATCCTC | Met335 → Asn |
| Ta2-57 | GAGGATTCGACTTCCAGCCTTCTCCTCC | Met335 → Gln |
| Ta2-58 | GGAGGAGAAGGCTGGAAGTCGAATCCTC | Met335 → Gln |
| Ta2-59 | GGAACAAAGAGGAAGAGTAACATTCAGACGTATTTGG | Gln293 → Asn |
| Ta2-60 | CCAAATACGTCTGAATGTTACTCTTCCTCTTTGTTCC | Gln293 → Asn |
| Ta2-61 | GGAACAAAGAGGAAGAGTCACATTCAGACGTATTTGG | Gln293 → His |
| Ta2-62 | CCAAATACGTCTGAATGTGACTCTTCCTCTTTGTTCC | Gln293 → His |
| Ta2-126 | GGAACAAAGAGGAAGAGTGCGATTCAGACGTATTTGG | Gln293 → Ala |
| Ta2-127 | CCAAATACGTCTGAATCGCACTCTTCCTCTTTGTTCC | Gln293 → Ala |
| Ta2-140 | GGAACAAAGAGGAAGAGTCTGATTCAGACGTATTTGG | Gln293 → Leu |
| Ta2-141 | CCAAATACGTCTGAATCAGACTCTTCCTCTTTGTTCC | Gln293 → Leu |
| Ta2-138 | GGAACAAAGAGGAAGAGTATAATTCAGACGTATTTGG | Gln293 → Ile |
| Ta2-139 | CCAAATACGTCTGAATTATACTCTTCCTCTTTGTTCC | Gln293 → Ile |
| Ta2-150 | GGAACAAAGAGGAAGAGTTCGATTCAGACGTATTTGG | Gln293 → Ser |
| Ta2-151 | CCAAATACGTCTGAATCGAACTCTTCCTCTTTGTTCC | Gln293 → Ser |
| Ta2-194 | GAGGATTCGACTTCCACCCTTCTCCTCC | Met335 → His |
| Ta2-195 | GGAGGAGAAGGGTGGAAGTCGAATCCTC | Met335 → His |

TABLE 13-continued

PCR primers for site directed mutagenesis of AtHPPD (SEQ ID NOs: 82 to 147)

| Primer name | Primer sequence (5' → 3') | Mutation AtHPPD |
|---|---|---|
| Ta2-196 | GAGGATTCGACTTCTACCCTTCTCCTCC | Met335 → Tyr |
| Ta2-197 | GGAGGAGAAGGGTAGAAGTCGAATCCTC | Met335 → Tyr |
| Ta2-190 | GAGGATTCGACTTCAGCCCTTCTCCTCC | Met335 → Ser |
| Ta2-191 | GGAGGAGAAGGGCTGAAGTCGAATCCTC | Met335 → Ser |
| Ta2-192 | GAGGATTCGACTTCACACCTTCTCCTCC | Met335 → Thr |
| Ta2-193 | GGAGGAGAAGGTGTGAAGTCGAATCCTC | Met335 → Thr |
| Ta2-188 | GAGGATTCGACTTCTGTCCTTCTCCTCC | Met335 → Cys |
| Ta2-189 | GGAGGAGAAGGACAGAAGTCGAATCCTC | Met335 → Cys |
| Ta2-215 | GGATTCGACTTCATGCGTTCTCCTCCGCC | Pro336 → Arg |
| Ta2-216 | GGCGGAGGAGAACGCATGAAGTCGAATCC | Pro336 → Arg |
| Ta2-200 | GAGGAATTAGGGATTTGGGTAGACAGAGATG | Leu368 → Trp |
| Ta2-201 | CATCTCTGTCTACCCAAATCCCTAATTCCTC | Leu368 → Trp |
| Ta2-198 | GAGGAATTAGGGATTATGGTAGACAGAGATG | Leu368 → Met |
| Ta2-199 | CATCTCTGTCTACCATAATCCCTAATTCCTC | Leu368 → Met |
| Ta2-204 | GGTGGTTTTGGCAAACACAATTTCTCTGAG | Gly422 → His |
| Ta2-205 | CTCAGAGAAATTGTGTTTGCCAAAACCACC | Gly422 → His |
| Ta2-202 | GGTGGTTTTGGCAAATGCAATTTCTCTGAG | Gly422 → Cys |
| Ta2-203 | CTCAGAGAAATTGCATTTGCCAAAACCACC | Gly422 → Cys |
| Ta2-217 | GGTGGTTTTGGCACAGGCAATTTCTCTGAG | Lys421 → Thr |
| Ta2-218 | CTCAGAGAAATTGCCTGTGCCAAAACCACC | Lys421 → Thr |

Exemplified primers that can be used for site directed mutagenesis of HvHPPD (SEQ ID NO:1/2) are listed in Table 14.

TABLE 14

PCR primers for site directed mutagenesis of HvHPPD (SEQ ID NOs: 148 to 155)

| Primer name | Sequence (5' → 3') | Mutation HvHPPD |
|---|---|---|
| Ta2-279 | GGGAGGGTTTGACTTTCATCCACCTCCGCTG | Leu320 → His |
| Ta2-280 | CAGCGGAGGTGGATGAAGTCAAACCCTCCC | |
| Ta2-246 | GGCTTCGACTTCTATCCACCCCCGCTG | Leu320 → Tyr |
| Ta2-247 | CAGCGGGGGTGGATAGAAGTCGAAGCC | |
| Ta2-248 | GGGTTCGGCAAATGCAACTTCTCCGAGCTG | Gly407 → Cys |
| Ta2-249 | CAGCTCGGAGAAGTTGCATTTGCCGAACCC | |

TABLE 14-continued

PCR primers for site directed mutagenesis of HvHPPD (SEQ ID NOs: 148 to 155)

| Primer name | Sequence (5' → 3') | Mutation HvHPPD |
|---|---|---|
| Ta2-281 | GGAGGGTTTGACTTTCATGCACCTCCGCTG | Pro321 → Ala |
| Ta2-282 | CAGCGGAGGTGCATGAAAGTCAAACCCTCC | |

Mutant plasmids are isolated from *E. coli* TOP10 by performing a plasmid minipreparation and confirmed by DNA sequencing.

The combination of single amino acid substitutions is achieved by a stepwise mutagenesis approach.

(B) In Vitro Characterization of HPPD Mutants

Purified, mutant HPPD enzymes are obtained by the methods described above. Dose response and kinetic measurements are carried out using the described HPPD activity assay. Apparent michaelis constants ($K_m$) and maximal reaction velocities ($V_{max}$) are calculated by non-linear regression with the software GraphPad Prism 5 (GraphPad Software, La Jolla, USA) using a substrate inhibition model. Apparent $k_{cat}$ values are calculated from $V_{max}$ assuming 100% purity of the enzyme preparation. Weighted means (by standard error) of $K_m$ and $IC_{50}$ values are calculated from at least three independent experiments. The Cheng-Prusoff equation for competitive inhibition (Cheng, Y. C.; Prusoff, W. H. Biochem Pharmacol 1973, 22, 3099-3108) is used to calculate dissociation constants ($K_i$).

Field performance of the optimized HPPD enzyme, which is used as a herbicide tolerance trait may depend not only on its lack of sensitivity towards HPPD inhibiting herbicides but also on its activity. To assess the potential performance of a herbicide tolerance trait a tolerance index (TI) is calculated using the following formula:

$$TI = \frac{k_{cat} \times K_i}{K_m}$$

Easy comparison and ranking of each trait is enabled by normalizing tolerance indexes on *Arabidopsis* wild-type HPPD.

Examples of the data obtained are depicted in Table 15 and in Table 16.

TABLE 15

Normalized tolerance indexes of various HPPD mutants generated in the *Arabidopsis* HPPD (SEQ ID: 53).

| *Arabidopsis* HPPD variant | TI Inhibitor 1* | TI Inhibitor 2* | TI Inhibitor 3* |
|---|---|---|---|
| Wildtype | 1 | 1 | 1 |
| M335H, P336A | 0.6 | 0.8 | 0.2 |
| M335H, P336G, E363Q | 0.2 | 1.1 | 0.3 |
| F381I | 4.6 | 0.6 | 0.1 |
| F381L | 1.2 | 0.8 | 0.2 |
| M335H, P336G | 0.5 | 0.9 | 0.1 |

*HPPD inhibiting herbicides used in this example are 2,4-dichloro-6-fluoro-3-methylsulfonyl-N-(1-methyltetrazol-5-yl)benzamide (Inhibitor 1) and 2,4-dichloro-6-fluoro-3-methylsulfanyl-N-(1-methyltetrazol-5-yl)benzamide (Inhibitor 2) 2,4-dichloro-6-fluoro-3-methylsulfanyl-N-(2-methyl-1,2,4-triazol-3-yl)benzamide (Inhibitor 3), n.d. not determined.

TABLE 16

Normalized tolerance indexes of various HPPD mutants generated in the *Hordeum* HPPD (SEQ ID NO: 2).

| *Hordeum* HPPD variant | TI Inhibitor 1* | TI Inhibitor 2* | TI Inhibitor 3* |
|---|---|---|---|
| Wild-type | 1 | 1 | 1 |
| L320H | 4.6 | 4.5 | 1.9 |
| L320H, P321A | 3.7 | 3.6 | 14.3 |
| L320N | 5.2 | 0.6 | n.d. |
| L353M, P321R, L320N | 1.9 | 1.2 | 0.9 |
| L353M, P321R, L320Q | 2.5 | 3 | n.d. |
| F404L | 1.6 | 0.9 | 1.8 |
| L250M | 3.1 | 0.8 | 1 |
| F377L | 11.8 | 2.1 | 2 |
| S252T | 1.8 | 7.3 | 11.1 |
| R309K | 2.6 | 2.1 | 3 |

*HPPD inhibiting herbicides used in this example are 2,4-dichloro-6-fluoro-3-methylsulfonyl-N-(1-methyltetrazol-5-yl)benzamide (Inhibitor 1) and 2,4-dichloro-6-fluoro-3-methylsulfanyl-N-(1-methyltetrazol-5-yl)benzamide (Inhibitor 2) 2,4-dichloro-6-fluoro-3-methylsulfanyl-N-(2-methyl-1,2,4-triazol-3-yl)benzamide (Inhibitor 3), n.d. not determined.

A number of conclusions can be derived from the data in Tables 15 and 16. The properties of HPPD mutants indicated that certain amino acid substitutions within the coding sequence provided significant improvements relative to HPPD SEQ ID NOS: 2 and 53 in respect to the tolerance indexes for HPPD-inhibiting herbicides.

It can be seen from the results depicted in Table 15 that the substitution of phenylalanine at position 381 in SEQ ID NO:53 by isoleucine provided an improvement to the HPPD enzyme. This particular mutant had an increased tolerance index for Inhibitor 1 relative to the reference enzyme (SEQ ID NO:53)

The results depicted in Table 16 showed that mutations introduced in the *Hordeum* HPPD sequence (SEQ ID:2) resulted in significant improvements in comparison to the benchmark enzyme and a tolerance for benzamide-derivative herbicides could be observed. In more detail, it can be seen that the substitution of leucine to histidine at position 320 in SEQ ID NO:2 provided significant improvements to the HPPD enzyme compared to the control. This particular mutant had a 4-fold increased tolerance for Inhibitor 1 and Inhibitor 2, whereas the tolerance for Inhibitor 3 was 1.9-fold increased in direct comparison to the control. It can be further seen, that the additional exchange of proline 321 to alanine resulted in 14.3-fold increased tolerance for Inhibitor 3, whereas the tolerance for the other tested inhibitors was ~3.6-fold increased compared to the benchmark enzyme.

Thus, some mutants, preferably the mutant encoding a polynucleotide comprising barley HPPD where leucine 320 is exchanged to histidine and proline 321 is substituted by alanine, can be selected as mutants which encode an inhibitor-resistant HPPD and are useful for generating herbicide tolerant plants.

In addition, a polynucleotide comprising a region which encodes barley HPPD (SEQ ID NO:2) where argine 309 is exchanged to lysine, can be selected as one that encodes an inhibitor-resistant HPPD because it is found that the tolerance index of the mutant is improved against all inhibitors tested in the present invention.

It can be further seen that a polynucleotide comprising a region which encodes *Hordeum* HPPD (SEQ ID NO:2) in which serine 252 is exchanged to threonine can be selected as one that encodes an inhibitor-resistant HPPD enzyme because it is found that the tolerance index of the mutant is significantly improved against all inhibitors tested in the present invention.

It is evident that any mutation or combination of mutations which would make it possible to obtain a HPPD enzyme that is resistant to benzamide herbicides, even if this protein is not exemplified in this text, is part of the subject-matter of this invention.

Example 6 Preparation of Plants which Express Heterologous HPPD and/or HST Enzymes and which are Tolerant to "HPPD-Inhibiting Herbicides"

Various methods for the production of stably transformed plants are well known in the art. HPPD-inhibiting herbicide tolerant soybean (*Glycine max*) or corn (*Zea mays*) plants can be produced by a method described by Olhoft et al. (US patent 2009/0049567). Briefly, HPPD or HST encoding polynucleotides are cloned into a binary vector using standard cloning techniques as described by Sambrook et al. (Molecular cloning (2001) Cold Spring Harbor Laboratory Press). The final vector construct contains an HPPD or HST encoding sequence flanked by a promoter sequence (e.g. the ubiquitin promoter (PcUbi) sequence) and a terminator sequence (e.g. the nopaline synthase terminator (NOS) sequence) and a resistance marker gene cassette (e.g. AHAS) (FIG. 2). Optionally, the HPPD or HST gene can provide the means of selection.

*Agrobacterium*-mediated transformation is used to introduce the DNA into soybean's axillary meristem cells at the primary node of seedling explants. After inoculation and co-cultivation with Agrobacteria, the explants are transferred to shoot induction medium without selection for one week. The explants are subsequently transferred to shoot induction medium with 1-3 µM imazapyr (Arsenal) for 3 weeks to select for transformed cells. Explants with healthy callus/shoot pads at the primary node are then transferred to shoot elongation medium containing 1-3 µM imazapyr until a shoot elongates or the explant dies. After regeneration, transformants are transplanted to soil in small pots, placed in growth chambers (16 hr day/8 hr night; 25° C. day/23° C. night; 65% relative humidity; 130-150 mE m-2 s-1) and subsequently tested for the presence of the T-DNA via Taqman analysis. After a few weeks, healthy, transgenic positive, single copy events are transplanted to larger pots and allowed to grow in the growth chamber.

Transformation of corn plants is done by a method described by McElver and Singh (WO 2008/124495). Plant transformation vector constructs containing HPPD or HST sequences are introduced into maize immature embryos via *Agrobacterium*-mediated transformation. Transformed cells are selected in selection media supplemented with 0.5-1.5 µM imazethapyr for 3-4 weeks. Transgenic plantlets are regenerated on plant regeneration media and rooted afterwards. Transgenic plantlets are subjected to TaqMan analysis for the presence of the transgene before being transplanted to potting mixture and grown to maturity in greenhouse.

*Arabidopsis thaliana* is transformed with HPPD or HST sequences by floral dip method as described by McElver and Singh (WO 2008/124495). Transgenic *Arabidopsis* plants are subjected to TaqMan analysis for analysis of the number of integration loci.

Transformation of *Oryza sativa* (rice) are done by protoplast transformation as described by Peng et al. (U.S. Pat. No. 6,653,529)

T0 or T1 transgenic plant of soybean, corn, rice and *Arabidopsis thaliana* containing HPPD or HST sequences are tested for improved tolerance to HPPD-inhibiting herbicides in greenhouse studies.

Example 7: Greenhouse Experiments

Transgenic plants expressing heterologous HPPD or HST enzymes are tested for tolerance against HPPD-inhibiting herbicides in greenhouse experiments.

For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides.

For post emergence treatment, the test plants are first grown to a height of 3 to 15 cm, depending on the plant habit, and only then treated with the herbicides. For this purpose, the test plants are either sown directly and grown in the same containers, or they are first grown separately and transplanted into the test containers a few days prior to treatment. For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated.

Depending on the species, the plants are kept at 10-25° C. or 20-35° C. The test period ex-tends over 3 weeks. During this time, the plants are tended and their response to the individual treatments is evaluated. Herbicide injury evaluations are taken at 2 and 3 weeks after treatment. Plant injury is rated on a scale of 0 to 9, 0 being no injury and 9 being complete death.

Tolerance to HPPD-inhibiting herbicides can also be assessed in *Arabidopsis*. In this case transgenic *Arabidopsis thaliana* plants are assayed for improved tolerance to HPPD-inhibiting herbicides in 48-well plates. Seeds are surface sterilized by stirring for 5 min in ethanol+water (70+30 by volume), rinsing one time with ethanol+water (70+30 by volume) and two times with a sterile, deionized water. The seeds are resuspended in 0.1% agar dissolved in water (w/v). Four to five seeds per well are plated on solid nutrient medium consisting of half-strength Murashige Skoog nutrient solution, pH 5.8 (Murashige and Skoog (1962) Physiologia *Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*m-2*s-1 with 14: 10 h light: dark photoperiod. Seven to ten days after seedling growth inhibition is evaluated by comparison to wild type plants. Tolerance factor is calculated by dividing the plant growth IC50 value of transgenic plants containing a HPPD and/or HST sequence by that of wildtype plants.

Additionally, T1 and T2 transgenic *Arabidopsis* plants can be tested for improved tolerance to HPPD-inhibiting herbicides in a greenhouse studies. Herbicide injury scoring is done 2-3 weeks after treatment and is rated on a scale of 0 to 100%, 0% being no injury and 100% being complete death.

TABLE 18

Greenhouse testing of transgenic *Arabidopsis* plants (T2). Injury evaluations, on a scale of 0-100%, were taken two weeks after herbicide treatment. Each data point represents a mean value of at least two independent transgenic lines. Selected transgenic lines are shown in FIG. 3.

| Herbicide | Transgene Dose [g/ha] | None | HvL320H, P321A | HvL320H | AtM335H, P336A, E363Q | AtF381I | RjHPPD |
|---|---|---|---|---|---|---|---|
| Inhibitor 2* | 12.5 | 94 | 8 | 33 | 47 | 40 | 46 |
| | 6.25 | 98 | 7 | 18 | 7 | 25 | 13 |
| | 3.125 | 87 | 5 | 12 | 7 | 20 | 12 |
| | 1.56 | 86 | 0 | 0 | 0 | n.d. | 2 |

*HPPD inhibiting herbicide used in this example is 2,4-dichloro-6-fluoro-3-methylsulfanyl-N-(1-methyl-tetrazol-5-yl)benzamide (Inhibitor 2), n.d. not determined.

Transgenic *Arabidopsis* plants were sprayed with a range of doses from 1.56-12.5 g/ha with the HPPD-inhibiting benzamide herbicide and injury evaluations were taken two weeks after treatment. It can be seen from the above example that plants comprising a polynucleotide encoding for HPPD can be selected as plants tolerant to benzamide-derivative herbicides because it was found that transgenic plants had a broader tolerance to the HPPD-inhibiting herbicide than it was the case for the untransformed wild-type plants. As depicted in Table 18, control plants were severely injured by all doses of herbicide applied, with at least 86% of leaf material being damaged at the lowest application rate. For example, the HPPD mutant version with three amino acid substitutions such as methionine 335 to histidine, proline 336 to alanine, and glutamate 363 to glutamine (numbering corresponding to SEQ ID: 53), exhibited a significant tolerance against the HPPD inhibitor tested in the above example. Application of 12.5 g/ha active ingredient resulted in 47% total leaf damage in transgenic plants expressing the mutated version of *Arabidopsis* HPPD whereas the injury in the wild-type plants reached 94%, indicating a 2-fold increased tolerance at this application rate. The tolerance factor of the triple mutant for the benzamide-derivative herbicide was significantly increased with lower application rates as the mutant showed only 7% leaf damage in contrast to 87-98% damage in wild-type control plants (Table 18). Thus, the polynucleotide comprising *Arabidopsis* HPPD with M335H,P336A,E363Q can be selected as a transgene that mediates tolerance for benzamide herbicides because plants encoding this particular transgene had an improved behavior in the spray test of the present invention.

In addition, transgenic *Arabidopsis* plants comprising a polynucleotide encoding SEQ ID NO:2 with leucine 320 exchanged to histidine are more resistant to Inhibitor 2 than the untransformed wild-type plants. The combined mutation of leucine 320 to histidine and proline 321 to alanine resulted in a HPPD inhibitor resistant plant line which had an outstanding tolerance factor for Inhibitor 2 at the highest rate active ingredient applied. Compared to the control, plants expressing *Rhodococcus* HPPD (SEQ ID NO:46) are more resistant to HPPD inhibitors tested in the present invention because transgenic lines expressing this HPPD enzyme did show only 2% leaf damage with the lowest application rate. In addition, when the active ingredient was applied with the highest concentration, the transgene conferred 2-fold tolerance for Inhibitor 2 compared to the untransformed wild-type control.

It is evident that any mutation or combination of mutations which would make it possible to obtain a HPPD enzyme that is resistant to benzamide-derivative herbicides, even if this protein is not exemplified in this text, is part of the subject-matter of this invention.

TABLE 19

Greenhouse testing of transgenic Corn plants (homozygous T2). Injury evaluations, on a scale of 0-100%, were taken two weeks after herbicide treatment. Corresponding pictures are shown in FIG. 4.

| Herbicide | Dose [g/ha] | WT | AtL385V, I393L Event 1 | AtL385V, I393L Event 2 | AtM335H |
|---|---|---|---|---|---|
| Inhibitor 3 * | 62.5 | 40 | 3 | 6 | 3 |
| | 125 | 63 | 7 | 10 | 4 |
| | 250 | 86 | 10 | 47 | 6 |

* HPPD inhibiting herbicide used in this example is 2,4-dichloro-6-fluoro-3-methylsulfanyl-N-(2-methyl-1,2,4-triazol-3-yl)benzamide (Inhibitor 3).

Transgenic corn plants were sprayed with doses from 62.5-250 g/ha with the benzamide-derivative HPPD-inhibiting herbicide and injury evaluations were taken two weeks after treatment. It can be seen from the above example that transgenic corn plants expressing a polynucleotide comprising a mutant HPPD enzyme can be selected as ones which are resistant to benzamide-derivative herbicides because it was found that transgenic plants had a broader tolerance to the HPPD-inhibiting herbicide than it was the case for the untransformed wild-type control. As depicted in Table 19, control plants were severely injured by all doses of herbicide applied, with 86% of leaf material being damaged at the highest rate applied. For example, corn plants carrying a transgene encoding for the HPPD mutant version with amino acids leucine 385 substituted by valine and isoleucine 393 exchanged to leucine (SEQ ID: 53) exhibited a significant tolerance against the HPPD inhibitor depicted in the above example. Application of 250 g/ha active ingredient resulted only in 10% leaf damage (event 1) in transgenic plants which gave in direct comparison with wild-type plants (injury value is 86%) an 8-fold increased tolerance at this application rate. In addition, transgenic corn plants comprising a transgene encoding the mutated version of *Arabidopsis* HPPD with methionine 335 exchanged to histidine, are tolerant for the benzamide-derivative inhibitor tested in the present invention. Those plants had a 14-fold increased tolerance compared to non-transgenic control plants.

It is evident that any mutation or combination of mutations which would make it possible to obtain a HPPD enzyme that is resistant to benzamide-derivative herbicides and can be used to generate crop plants tolerant for benzamide-derivative herbicides, even if this protein is not exemplified in this text, is part of the subject-matter of this invention.

Table 20: Greenhouse testing of transgenic Soy plants (T2). Injury evaluations, on a scale of 0-100%, were taken two weeks after herbicide treatment. Corresponding pictures are shown in FIG. 5.

TABLE 20

| Herbicide | Dose [g/ha] | none | AtHPPD Event 1 | AtHPPD Event 2 | AtL385V, I393L Event 1 | AtL385V, I393L Event 2 | AtP336A, E363Q, L385V, I393L | AtM335H Event 1 | AtM335H Event 2 | AtM335Y | GmHPPD1 |
|---|---|---|---|---|---|---|---|---|---|---|---|
| Inhibitor 3* | 31.25 | 49 | 10 | 13 | NA | 20 | 30 | 10 | 14 | 9 | 15 |
|  | 62.5 | 68 | 16 | 23 | NA | 35 | 30 | 21 | 29 | 45 | 29 |
|  | 125 | 79 | 44 | 40 | NA | 38 | 50 | 33 | 31 | 46 | 46 |

*HPPD inhibiting herbicide used in this example is 2,4-dichloro-6-fluoro-3-methylsulfanyl-N-(2-methyl-1,2,4-triazol-3-yl)benzamide (Inhibitor 3).

Transgenic soy plants were sprayed with doses from 31.25-125 g/ha with the benzamide-derivative HPPD-inhibiting herbicide (Inhibitor 3) tested in the present example and injury evaluations were taken two weeks after treatment. It can be seen from the above example that transgenic soy plants expressing a polynucleotide comprising a mutant HPPD enzyme can be selected as one which mediates resistance to benzamide-derivative herbicides because it was found that transgenic plants had a broader tolerance to the HPPD-inhibiting herbicide than it was the case for the untransformed wild-type control. As depicted in Table 20, control plants were severely injured by all doses of herbicide applied, with 79% of leaf material being damaged at the highest application rate. For example, soy plants carrying a transgene encoding for *Arabidopsis* HPPD (SEQ ID: 53) had an improved tolerance for the HPPD-inhibiting herbicide tested in the above example. Application of 31,25 g/ha active ingredient resulted only in 10-13% of leaf damage in two independent transgenic plant lines. Thus, in direct comparison with wild-type plants (injury value is 49%), a 4-fold increased tolerance could be observed after spraying with 31,25 g/ha. In addition, transgenic soy plants comprising a transgene encoding the *Glycine max* HPPD were more tolerant than nontrangenic control plants for the benzamide-derivative herbicide tested in the present invention. Those plants had a comparable tolerance as it was found for transgenic soy plants expressing *Arabidopsis* HPPD.

Therefore, the example shown above clearly demonstrates that one can select a polynucleotide comprising *Arabidopsis* HPPD or *Glycine max* HPPD to generate transgenic plants that are more tolerant to treatments with benzamide-derivate herbicides. It is evident that any other polynucleotide encoding a wild-type or mutated version of the HPPD enzyme can be used to generate crop plants tolerant for benzamide-derivative herbicides, even if this protein is not exemplified in this text and is part of the subject matter of this invention.

The invention claimed is:

1. A plant, or seed thereof, that expresses a mutagenized or recombinant mutated hydroxyphenyl pyruvate dioxygenase (mut-HPPD) comprising a variant of the wild-type Hordeum HPPD amino acid sequence of SEQ ID NO:2, or of the amino acid sequence of a wild-type homologue HPPD, wild-type orthologue HPPD, or wild-type paralogue HPPD thereof (i) having an amino acid sequence with at least 90% identity to SEQ ID NO: 2 over the entirety length, and (ii) having HPPD activity, wherein the amino acid sequence of the variant differs from that of the wild-type HPPD amino acid sequence in that it comprises at least one substitution in which:

the amino acid corresponding to or at position 320 of SEQ ID NO:2 is Gln, His, or Tyr substituting for leucine; the amino acid corresponding to or at position 321 of SEQ ID NO:2 is Ala, or Gly substituting for proline;

or the amino acid corresponding to or at position 278 of SEQ ID NO:2 is His, Asn, or Ser substituting for glutamine; and wherein said plant, expressing said mutagenized or recombinant mut-HPPD, possesses a phenotype of increased herbicide tolerance to a compound selected from 2,4-dichloro-6-fluoro-3-methylsulfonyl-N-(1-methyltetrazol-5-yl)benzamide (Inhibitor 1), 2,4-dichloro-6-fluoro-3-methylsulfanyl-N-(1-methyltetrazol-5-yl)benzamide (Inhibitor 2), or 2,4-dichloro-6-fluoro-3-methylsulfanyl-N-(2-methyl-1,2,4-triazol-3-yl) benzamide (Inhibitor 3), as compared to the corresponding wild-type variety of the plant.

2. The seed according to claim 1, wherein said seed further comprises a seed treatment comprising an HPPD-inhibiting herbicide.

3. The seed according to claim 2, wherein said HPPD-inhibiting herbicide comprises a benzamide herbicide.

\* \* \* \* \*

SEQUENCE LISTING

<160> NUMBER OF SEQ ID NOS: 155

<210> SEQ ID NO 1
<211> LENGTH: 1305
<212> TYPE: DNA
<213> ORGANISM: Hordeum vulgare

<400> SEQUENCE: 1

```
atgccgccca cccccaccac cccgcggct accggcgccg ccgccgcggt gacgccggag      60
cacgcgcgac cgcaccgaat ggtccgcttc aacccgcgca gcgaccgctt ccacacgctc     120
tccttccacc acgtcgagtt ctggtgcgcg gacgccgcct ccgccgccgg ccgcttcgcg     180
ttcgcgctcg gcgcgccgct cgccgccagg tccgacctct ccacggggaa ctccgcgcac     240
gcctcccagc tgctccgctc gggctccctc gccttcctct tcaccgcgcc ctacgccaac     300
ggctgcgacg ccgccaccgc ctccctgccc tccttctccg ccgacgccgc gcgccggttc     360
tccgccgacc acgggatcgc ggtgcgctcc gtagcgctgc gcgtcgcaga cgccgccgag     420
gccttccgcg ccagcgtcga cggggcgcg cgcccggcct tcgcccccgt ggacctcggc     480
cgcggcttcg gcttcgcgga ggtcgagctc tacggcgacg tcgtgctccg cttcgtcagc     540
cacccggacg gcacggacgt gccccttcttg ccggggttcg agggcgtgac caaccgggac     600
gccgtggact acggcctgac gcggttcgac cacgtcgtcg gcaacgtccc ggagcttgcc     660
cccgccgcag cctacatcgc cgggttcacg gggttccacg agttcgccga gttcacggcg     720
gaggacgtgg gcacgaccga gagcgggctc aactcggtgg tgctcgccaa caactcggag     780
ggcgtgctgc tgccgctcaa cgagccggtg cacggcacca agcgccggag ccagatacag     840
acgttcctgg aacaccacgg cggcccgggc gtgcagcaca tcgcggtggc cagcagtgac     900
```

-continued

```
gtgctcagga cgctcaggaa gatgcgtgcg cgctccgcca tgggcggctt cgacttcctg      960 ccaccccgc tgccgaagta ctacgaaggc gtgcgacgcc ttgccgggga tgtcctctcg      1020
gaggcgcaga tcaaggaatg ccaggagctg gtgtgctcg tcgataggga cgaccaaggg      1080
gtgttgctcc aaatcttcac caagccagta ggggacaggc cgaccttgtt cctggagatg    1140
atccagagga tcgggtgcat ggagaaggac gagagagggg aagagtacca gaagggtggc    1200
tgcggcgggt tcggcaaagg caacttctcc gagctgttca gtccattga agattacgag     1260 aagtcccttg aagccaagca atctgctgca gttcaggat catag                     1305
```

<210> SEQ ID NO 2
<211> LENGTH: 434
<212> TYPE: PRT
<213> ORGANISM: Hordeum vulgare

<400> SEQUENCE: 2

```
Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Val Asp Gly Gly Ala Arg Pro Ala Phe Ala Pro Val Asp Leu Gly
145                 150                 155                 160

Arg Gly Phe Gly Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
            260                 265                 270

Thr Lys Arg Arg Ser Gln Ile Gln Thr Phe Leu Glu His His Gly Gly
        275                 280                 285

Pro Gly Val Gln His Ile Ala Val Ala Ser Ser Asp Val Leu Arg Thr
    290                 295                 300
```

```
Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
        355                 360                 365

Pro Val Gly Asp Arg Pro Thr Leu Phe Leu Glu Met Ile Gln Arg Ile
    370                 375                 380

Gly Cys Met Glu Lys Asp Glu Arg Gly Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Ala Val Gln
            420                 425                 430

Gly Ser

<210> SEQ ID NO 3
<211> LENGTH: 1470
<212> TYPE: DNA
<213> ORGANISM: Fragilariopsis cylindrus

<400> SEQUENCE: 3
atgggtttct cttcagtatc gttatttccg ctatcgtggt cggcgtcggc agtaacatca      60
acctatctcg agacgtccac tagtacacaa tcgaatgaag ctgctactac cacttcgaca     120
acggcgtggg aaccaaaatt atcatcatta gaagaaagaa tagaaacgga aacgattgag     180
tcgatcggtt tccatcatat agaattttat tgtggagatg ctcgtagtat ggcaaatcaa     240
ttcgctgtct cattgggtat gtccgtcacg ggtatcaccg ccaatccac ggggaatgat      300
caatgcattt cctatggatt acaaagtgga gagcagtttc gactattatt aactgctccc     360
tattcacgag cgagagccac tactcgcgat gacgacgacg acgacgacga caacagtcct     420
gatttggatg ccgacgctcc gatgccactc cctaattata atgtagaaga tgctcatact     480
ttcttccaaa atcatggctt agcagctcga gcggttggca tagaagtcat ggatgccaaa     540
aaagctttcg aggtatccgt ggccaatggc gcaattccag tactggaacc aacctttctt     600
cccaacggat gctacatctc agaagttgaa ttgtacggtg acgttgtgtt gagatacgtg     660
agtttcatca tcgaatgaa aaatcatact tataatgatg atgcatcaca accatttcta     720
cctcatttag caccaataat tgatcaaagt aggaagagg atgatgataa taatgatgat     780
ggttttgggt tatataaaat cgaccatgcc gttgggaatg ttcccaattt acaagaggta     840
tactcacata tccaaaaatt tacaggattt catgaatttg ctgaatttac atcagaagat     900
gttggaactg tagactctgg attaaattct gttgttttag ccagtgacag tgaagcgatt     960
ctgttaccta taaatgaacc aactaatgga cgacgaaaat cacaaattca aacgtatcta    1020
gaacagaacg agggccctgg tctacaacat ttagcagtca aaacgaaaga tatattttca    1080
accgtccgaa agatgcgaag aagtcaacaa ggtatgtcgg gatttgaatt gatgaaacga    1140
ccgagtgagg aatattacaa agaacttcct gatcgacttg gtgatcaatt gacacccacg    1200
cagtatcaag aattagagga acttggtatc cttgcggatt ccgatgagga aggaatttg     1260
atgcaaattt ttaccaagcc cgtcggtgat cgacctacat tcttttttga actaattcaa    1320
cgaatcggtt gcgtcattga gcatgacgat gacgacaggc aggagttatc agttgatctt    1380
```

```
gaacgaccag gatgtggtgg ttttggtaag ggtaatttcc gagaactttt cagatcaatt    1440
gaagagcacg agaaaacttt aaaggtatag                                     1470

<210> SEQ ID NO 4
<211> LENGTH: 1467
<212> TYPE: DNA
<213> ORGANISM: Fragilariopsis cylindrus

<400> SEQUENCE: 4
atgggtttta gcagcgttag cctgtttccg ctgagctggt cagcaagcgc agttaccagc      60
acctatctgg aaaccagcac cagcacccag agcaatgaag cagcaaccac caccagtacc     120
accgcatggg aaccgaaact gagcagcctg aagaacgta ttgaaaccga aaccattgaa      180
agcattggct ttcatcacat tgaattttat tgcggtgatg cacgtagcat ggcaaatcag     240
tttgcagtta gcctgggtat gagcgttacc ggtattaccg gtcagagcac cggtaatgat     300
cagtgtatta gctatggtct gcagagcggt aacagtttc gtctgctgct gaccgcaccg      360
tatagccgtg cacgtgcaac cacccgtgat gatgatgatg acgatgacga taatagtccg     420
gatctggatg cagatgcacc gatgccgctg ccgaattata atgttgaaga tgcccatacc     480
ttttttcaga atcatggtct ggcagcacgt gcagttggta ttgaagttat ggatgccaaa     540
aaagcctttg aagttagcgt tgcaaatggt gcaattccgg ttctggaacc gacctttctg     600
ccgaatggtt gttatatttc tgaagtggaa ctgtatggtg atgttgttct gcgttatgtg     660
agctttatta ccagcaatga aaccacacc tacaatgatg atgccagcca gccgtttctg       720
ccgcatctgg caccgattat tgatcagagc cgtaaagaag atgatgataa taatgatgat     780
ggctttggcc tgtataaaat tgatcatgcc gttggtaatg tgccgaatct gcaagaagtt     840
tatagccata ttcagaaatt taccggcttt catgaatttg ccgaatttac cagcgaagat     900
gttggcaccg ttgatagcgg tctgaatagc gttgttctgg caagcgatag cgaagcaatt     960
ctgctgccga ttaatgaacc gaccaatggt cgtcgtaaaa gccagattca gacatatctg    1020
gaacagaatg aaggtccggg tctgcagcat ctggccgtta aaaccaaaga tatttttagc    1080
accgtgcgta aaatgcgtcg tagccagcag ggtatgagcg ttttgaact gatgaaacgt      1140 ccgagcgaag aatattataa agaactgccg gatcgtctgg gtgatcagct gaccccgacc    1200
cagtatcaag aattagaaga actgggtatt ctggcagata tgatgaaga aggtattctg      1260 atgcagattt ttaccaaacc ggttggtgat cgtccgacct ttttttttga actgattcag    1320
cgtattggct gcgtgattga acatgatgat gatgatcgtc aagaactgag cgttgatctg    1380
gaacgtccgg ttgtggtgg ttttggtaaa ggtaatttc gtgaactgtt tcgcagcatt       1440
gaagaacatg aaaaaaccct gaaagtg                                        1467

<210> SEQ ID NO 5
<211> LENGTH: 489
<212> TYPE: PRT
<213> ORGANISM: Fragilariopsis cylindrus

<400> SEQUENCE: 5

Met Gly Phe Ser Ser Val Ser Leu Phe Pro Leu Ser Trp Ser Ala Ser
1               5                  10                  15

Ala Val Thr Ser Thr Tyr Leu Glu Thr Ser Thr Ser Thr Gln Ser Asn
            20                  25                  30

Glu Ala Ala Thr Thr Thr Ser Thr Ala Trp Glu Pro Lys Leu Ser
        35                  40                  45
```

```
Ser Leu Glu Glu Arg Ile Glu Thr Glu Thr Ile Glu Ser Ile Gly Phe
     50                  55                  60

His His Ile Glu Phe Tyr Cys Gly Asp Ala Arg Ser Met Ala Asn Gln
 65                  70                  75                  80

Phe Ala Val Ser Leu Gly Met Ser Val Thr Gly Ile Thr Gly Gln Ser
                 85                  90                  95

Thr Gly Asn Asp Gln Cys Ile Ser Tyr Gly Leu Gln Ser Gly Glu Gln
                100                 105                 110

Phe Arg Leu Leu Leu Thr Ala Pro Tyr Ser Arg Ala Arg Ala Thr Thr
                115                 120                 125

Arg Asp Asp Asp Asp Asp Asp Asp Asn Ser Pro Asp Leu Asp Ala
            130                 135                 140

Asp Ala Pro Met Pro Leu Pro Asn Tyr Asn Val Glu Asp Ala His Thr
145                 150                 155                 160

Phe Phe Gln Asn His Gly Leu Ala Ala Arg Ala Val Gly Ile Glu Val
                165                 170                 175

Met Asp Ala Lys Lys Ala Phe Glu Val Ser Val Ala Asn Gly Ala Ile
            180                 185                 190

Pro Val Leu Glu Pro Thr Phe Leu Pro Asn Gly Cys Tyr Ile Ser Glu
            195                 200                 205

Val Glu Leu Tyr Gly Asp Val Val Leu Arg Tyr Val Ser Phe Ile Thr
        210                 215                 220

Ser Asn Glu Asn His Thr Tyr Asn Asp Asp Ala Ser Gln Pro Phe Leu
225                 230                 235                 240

Pro His Leu Ala Pro Ile Ile Asp Gln Ser Arg Lys Glu Asp Asp Asp
                245                 250                 255

Asn Asn Asp Asp Gly Phe Gly Leu Tyr Lys Ile Asp His Ala Val Gly
            260                 265                 270

Asn Val Pro Asn Leu Gln Glu Val Tyr Ser His Ile Gln Lys Phe Thr
        275                 280                 285

Gly Phe His Glu Phe Ala Glu Phe Thr Ser Glu Asp Val Gly Thr Val
    290                 295                 300

Asp Ser Gly Leu Asn Ser Val Val Leu Ala Ser Asp Ser Glu Ala Ile
305                 310                 315                 320

Leu Leu Pro Ile Asn Glu Pro Thr Asn Gly Arg Arg Lys Ser Gln Ile
                325                 330                 335

Gln Thr Tyr Leu Glu Gln Asn Glu Gly Pro Gly Leu Gln His Leu Ala
                340                 345                 350

Val Lys Thr Lys Asp Ile Phe Ser Thr Val Arg Lys Met Arg Arg Ser
            355                 360                 365

Gln Gln Gly Met Ser Gly Phe Glu Leu Met Lys Arg Pro Ser Glu Glu
    370                 375                 380

Tyr Tyr Lys Glu Leu Pro Asp Arg Leu Gly Asp Gln Leu Thr Pro Thr
385                 390                 395                 400

Gln Tyr Gln Glu Leu Glu Glu Leu Gly Ile Leu Ala Asp Ser Asp Glu
                405                 410                 415

Glu Gly Ile Leu Met Gln Ile Phe Thr Lys Pro Val Gly Asp Arg Pro
            420                 425                 430

Thr Phe Phe Phe Glu Leu Ile Gln Arg Ile Gly Cys Val Ile Glu His
                435                 440                 445

Asp Asp Asp Asp Arg Gln Glu Leu Ser Val Asp Leu Glu Arg Pro Gly
450                 455                 460
```

Cys Gly Gly Phe Gly Lys Gly Asn Phe Arg Glu Leu Phe Arg Ser Ile
465                 470                 475                 480

Glu Glu His Glu Lys Thr Leu Lys Val
            485

<210> SEQ ID NO 6
<211> LENGTH: 1341
<212> TYPE: DNA
<213> ORGANISM: Chlorella sp.

<400> SEQUENCE: 6

| | | | | | |
|---|---|---|---|---|---|
| atggtggtcg | aggctgcggc | cgcctccaac | ggcaatggcg | caggggagga | ggtgttcagc | 60 |
| aagaagctcg | tgggatatga | cggttttcag | cgccacaacc | cacgctccga | ccgcttcccc | 120 |
| atgcacaagt | tccaccacgt | cgagttctgg | tgcggcgatg | ccaccaccac | cagctgcagg | 180 |
| caagcgcgcc | cccagaagc | acccatgttt | gggtatgggc | tgggcctgac | tctggtggcc | 240 |
| aagagcgacc | agtccacggg | caaccaccac | tacgcgtcgt | acgtcatgca | gtcgggcgat | 300 |
| cttgtgatgg | cctttaccgc | gccctacagc | acccagacag | caagagcgg | cagcagcccg | 360 |
| cccgcagcgt | acgaccagga | cgccgcctac | gccttcctca | gaagcacgg | catggcggtg | 420 |
| cgcgcctttg | gaatcctggt | ggacgatgcc | gcggaggcgt | accgcatagc | cactgcccac | 480 |
| ggcggggtgg | gtgtggcgcc | acccaccacc | cgcacggacg | cagccagcgg | caccagcctg | 540 |
| acgtggagcg | aggtgcagct | gtacggcgac | tgcgtgctgc | gctttgtcag | cggcgactac | 600 |
| gagggcgcct | tcatccccgg | ctaccagccc | gtggaagacg | cgcccaagt | ctcctacggc | 660 |
| ctgcagcgcc | tggaccatgc | ggtgggcaac | gtgccagagc | tgatccctca | agtggagtac | 720 |
| atggctcgca | gcctgggctg | gcacgagttt | gctgagttca | ctgccgagga | tgtgggcact | 780 |
| gtggactcgg | gcctcaactc | catggtcatg | gccaacaaca | acgagatgat | tctgctgccg | 840 |
| gtcaacgagc | ccacccacgg | caccaagcgc | aagagccaga | tccagacctt | cctggagcag | 900 |
| aatgaggggc | ccgggctgca | gcacatggcc | ctgaaaacag | acgacatcgt | agccaccatg | 960 |
| cgacagctcc | gggccaggtc | tgcgtttggc | ggcttcgact | tcatgcccag | gccttcgcct | 1020 |
| gactactacc | gcaagctgcc | tgcccgcatc | ggcagcctgc | tgacggcgca | gcagtacaag | 1080 |
| gacgttgagg | agctggggct | gcttgtggac | aaggatgacc | agggcgtgct | gctccagatc | 1140 |
| ttcaccaagc | cgctgggcga | ccgacccacc | gtgttttcg | aaatcatcca | gcgcctgtgc | 1200 |
| gccctggagc | cgcaggcgcc | caagagccag | cgcggcgcgg | tgccttccga | ggtcggcggc | 1260 |
| tgcggcggct | ttggcaaggg | caacttcagt | gagctgttca | agagcatcga | ggtgtacgag | 1320 |
| acggatctgg | gcatcaacta | a | | | | 1341 |

<210> SEQ ID NO 7
<211> LENGTH: 1341
<212> TYPE: DNA
<213> ORGANISM: Chlorella sp

<400> SEQUENCE: 7

| | | | | | |
|---|---|---|---|---|---|
| atggttgttg | aagcagcagc | agcaagcaat | ggtaatggtg | ccggtgaaga | agtgtttagc | 60 |
| aaaaaactgg | tgggctatga | tggttttcag | cgtcataatc | cgcgtagcga | tcgttttccg | 120 |
| atgcataaat | tcatcatgt | ggaattttgg | tgtggtgatg | caaccaccac | cagttgtcgt | 180 |
| caggcacgtc | ctccggaagc | accgatgttt | ggttatggtc | tgggtctgac | cctggttgca | 240 |
| aaaagcgatc | agagcaccgg | taatcatcat | tatgcaagct | atgttatgca | gagcggtgat | 300 |
| ctggttatgg | catttaccgc | accgtatagc | acccagaccg | ataaaagcgg | tagcagtccg | 360 |

```
cctgcagcat acgatcagga tgcagcatac gcctttctga aaaaacatgg tatggcagtt    420
cgtgcatttg gtattctggt tgatgatgca gcagaagcat atcgtattgc aaccgcacat    480
ggtggtgttg gtgttgcacc tccgaccacc cgtaccgatg cagcaagcgg caccagcctg    540
acctggtctg aagttcagct gtatggtgat tgtgttctgc gttttgttag cggtgattat    600
gaaggtgcat ttattccggg ttatcagccg gttgaagatg caccgcaggt tagctatggt    660
ctgcagcgtc tggatcatgc agttggtaat gttccggaac tgattccgca ggttgaatat    720
atggcacgta gcctgggttg catgaatttt gcagaattta ccgcagaaga tgttggcacc    780
gttgatagcg gtctgaatag catggttatg gccaataaca atgaaatgat tctgctgccg    840
gtgaatgaac cgacccacgg caccaaacgt aaaagccaga ttcagacctt tctggaacag    900
aatgaaggtc cgggtctgca gcacatggca ctgaaaaccg atgatattgt tgcaaccatg    960
cgtcagctgc gtgcacgtag cgcatttggt ggttttgatt ttatgcctcg tccgagtccg   1020
gattattatc gtaaactgcc tgcacgtatt ggtagcctgc tgaccgcaca gcagtataaa   1080
gatgttgaag aactgggtct gctggttgat aaagatgatc agggtgttct gctgcagatt   1140
tttaccaaac cgctgggtga tcgtccgacc gttttttttg aaattattca gcgtctgtgt   1200
gcactggaac cgcaggcacc gaaaagccag cgtggtgcag ttccgagcga agttggtggt   1260
tgtggtggtt ttggtaaagg taattttagc gaactgttta aaagcattga agtgtatgaa   1320
accgatctgg gcatcaatta a                                             1341
```

<210> SEQ ID NO 8
<211> LENGTH: 446
<212> TYPE: PRT
<213> ORGANISM: Chlorella sp

<400> SEQUENCE: 8

```
Met Val Val Glu Ala Ala Ala Ser Asn Gly Asn Gly Ala Gly Glu
1               5                   10                  15

Glu Val Phe Ser Lys Lys Leu Val Gly Tyr Asp Gly Phe Gln Arg His
            20                  25                  30

Asn Pro Arg Ser Asp Arg Phe Pro Met His Lys Phe His His Val Glu
        35                  40                  45

Phe Trp Cys Gly Asp Ala Thr Thr Thr Ser Cys Arg Gln Ala Arg Pro
    50                  55                  60

Pro Glu Ala Pro Met Phe Gly Tyr Gly Leu Gly Leu Thr Leu Val Ala
65                  70                  75                  80

Lys Ser Asp Gln Ser Thr Gly Asn His His Tyr Ala Ser Tyr Val Met
                85                  90                  95

Gln Ser Gly Asp Leu Val Met Ala Phe Thr Ala Pro Tyr Ser Thr Gln
            100                 105                 110

Thr Asp Lys Ser Gly Ser Ser Pro Ala Ala Tyr Asp Gln Asp Ala
        115                 120                 125

Ala Tyr Ala Phe Leu Lys Lys His Gly Met Ala Val Arg Ala Phe Gly
    130                 135                 140

Ile Leu Val Asp Asp Ala Ala Glu Ala Tyr Arg Ile Ala Thr His
145                 150                 155                 160

Gly Gly Val Gly Val Ala Pro Pro Thr Thr Arg Thr Asp Ala Ala Ser
                165                 170                 175

Gly Thr Ser Leu Thr Trp Ser Glu Val Gln Leu Tyr Gly Asp Cys Val
            180                 185                 190
```

Leu Arg Phe Val Ser Gly Asp Tyr Glu Gly Ala Phe Ile Pro Gly Tyr
        195                 200                 205

Gln Pro Val Glu Asp Ala Pro Gln Val Ser Tyr Gly Leu Gln Arg Leu
    210                 215                 220

Asp His Ala Val Gly Asn Val Pro Glu Leu Ile Pro Gln Val Glu Tyr
225                 230                 235                 240

Met Ala Arg Ser Leu Gly Trp His Glu Phe Ala Glu Phe Thr Ala Glu
            245                 250                 255

Asp Val Gly Thr Val Asp Ser Gly Leu Asn Ser Met Val Met Ala Asn
                260                 265                 270

Asn Asn Glu Met Ile Leu Leu Pro Val Asn Glu Pro Thr His Gly Thr
            275                 280                 285

Lys Arg Lys Ser Gln Ile Gln Thr Phe Leu Glu Gln Asn Glu Gly Pro
        290                 295                 300

Gly Leu Gln His Met Ala Leu Lys Thr Asp Asp Ile Val Ala Thr Met
305                 310                 315                 320

Arg Gln Leu Arg Ala Arg Ser Ala Phe Gly Gly Phe Asp Phe Met Pro
                325                 330                 335

Arg Pro Ser Pro Asp Tyr Tyr Arg Lys Leu Pro Ala Arg Ile Gly Ser
            340                 345                 350

Leu Leu Thr Ala Gln Gln Tyr Lys Asp Val Glu Glu Leu Gly Leu Leu
        355                 360                 365

Val Asp Lys Asp Asp Gln Gly Val Leu Leu Gln Ile Phe Thr Lys Pro
    370                 375                 380

Leu Gly Asp Arg Pro Thr Val Phe Phe Glu Ile Ile Gln Arg Leu Cys
385                 390                 395                 400

Ala Leu Glu Pro Gln Ala Pro Lys Ser Gln Arg Gly Ala Val Pro Ser
                405                 410                 415

Glu Val Gly Gly Cys Gly Gly Phe Gly Lys Gly Asn Phe Ser Glu Leu
            420                 425                 430

Phe Lys Ser Ile Glu Val Tyr Glu Thr Asp Leu Gly Ile Asn
        435                 440                 445

<210> SEQ ID NO 9
<211> LENGTH: 1257
<212> TYPE: DNA
<213> ORGANISM: Thalassiosira

<400> SEQUENCE: 9
tttcatcata ttgaattctt cgccagtgat gcgcttacga cagccaagcg gtttgagcta      60
gcgttgggat tgccaattac gtgttggagt tcattggcta cggggaacga tgtttgtgtt     120
acctacggat tggaggggat gcaaactcga aagattgaaa ccgacaacgc aaacaagaac     180 ggagggcag atccaatgt acaaatgact gcacctcttc ctcttccggg gtatgatatt       240
gacaaagctc atgagtttta ctcgaagcac ggtttggcag tacgagctgt gggagtggaa     300
gtgaaggatg caactgtagc ttatgcaaat gctgttgaga atggtgctac aggagtattg     360
gagcctacga ttgttgaaaa ctttaacagc gatggagatt cgcagaagtg tcatatggct     420
gaggtggaat tgtatggtga tgtggtgttg agattagtca gttttcatgg agattgtagt     480
gccgaacaat ctacattcct tcctcacttg tcgccgtatc catccaacag caacaagaac     540
aaaccaactt acggacttgc tcgtctagat cacacggtgg gcaatgttcc caacctcctc     600
gcgacgcaac gatacattca acattcacc aactaccatc ccttcgcaga gttcactccg      660
gaagatgtgg gaacagtcga ctctggtctt aatagtgtag tacttgcatc agacaacgag     720

```
aatgttttgc tgcctctcaa tgaacctacc gaaggtaaac gaaagagtca gattcaaaca    780
tatctagagc agaacgaggg accgggactg cagcatattg ccatcaagac gaatgatatc    840
tttgatacca ttgcaaagat gagacacgca aagagaact  ttggaggttt cgagttgatg    900
aaacgtccat cggatgagta ttacaaagag ttgccttcga gattgggtga taagttgact    960
gtcgagcaat acaaacagct ggaagagttg gaatactgg  cagatgcaga tgacgaaggt   1020
atattgcttc aaatattcac aaagccattg ggagacaggc ccaccttgtt ccttgagatt   1080
attcagcgaa ttgggtgtgt gttaccggat gacgatgaag caactgatga aggggaagct   1140
aagaatgcac acaatagaat agtcagagaa cgtcccggat gtggtggatt tggtcagggc   1200
aacttccgtg aactcttcaa agcaattgaa gaacatgaga agacactcaa ggtctaa     1257

<210> SEQ ID NO 10
<211> LENGTH: 1257
<212> TYPE: DNA
<213> ORGANISM: Thalassiosira

<400> SEQUENCE: 10
tttcatcata tcgaattttt tgcctcagat gcactgacca ccgcaaaacg ctttgaactg     60
gcactgggtc tgccgattac ctgttggagc agcctggcaa ccggtaatga tgtttgtgtt    120
acctatggtc tggaaggtat gcagacccgt aaaattgaaa ccgataacgc caataaaaac    180
ggtggtgcag gtagcaatgt tcagatgacc gcaccgctgc cgctgcctgg ttatgatatt    240
gataaagccc atgaattcta tagcaaacat ggtctggcag ttcgtgcagt tggtgttgaa    300
gttaaagatg caaccgttgc ctatgcaaat gcagttgaaa atggtgcaac cggtgttctg    360
gaaccgacca ttgttgaaaa cttttaatagt gatggcgata gccagaaatg tcacatggcc    420
gaagttgaac tgtatggtga tgttgttctg cgtctggtta gctttcatgg tgattgtagc    480
gcagaacaga gcaccttcct gccgcatctg agcccgtatc cgagcaatag caataaaaac    540
aaaccgacct atggcctggc acgtctggat cataccgttg gtaatgttcc gaatctgctg    600
gcaacccagc gttatattca gaccttacc  aactatcatc cgtttgcaga atttacaccg    660
gaagatgttg gcaccgttga tagcggtctg aatagcgttg ttctggcaag cgataatgaa    720
aatgttctgc tgccgctgaa tgaaccgacc gaaggtaaac gtaaaagcca gattcagacc    780
tatctggaac agaatgaagg tccgggtctg cagcatattg caattaaaac caatgatatt    840
tttgatacca ttgccaaaat gcgccatgcc gaagaaaatt ttggtggttt tgaactgatg    900
aaacgtccgt ccgatgaata ctataaagaa ctgccgagcc gtctgggtga taaactgacc    960
gttgaacagt ataaacagct ggaagaactg gtattctgg  cagatgcaga tgatgaaggt   1020
attctgctgc agatttttac caaaccgctg ggtgatcgtc cgaccctgtt tctggaaatt   1080
attcagcgta ttggttgtgt tctgccggat gatgatgaag caaccgatga aggtgaagca   1140
aaaaatgccc ataatcgtat tgttcgtgaa cgtccgggtt gtggtggttt tggtcagggt   1200
aattttcgcg aactgtttaa agccattgaa gaacatgaaa aaaccctgaa agtttaa     1257

<210> SEQ ID NO 11
<211> LENGTH: 418
<212> TYPE: PRT
<213> ORGANISM: Thalassiosira pseudonana

<400> SEQUENCE: 11

Phe His His Ile Glu Phe Phe Ala Ser Asp Ala Leu Thr Thr Ala Lys
1               5                   10                  15
```

```
Arg Phe Glu Leu Ala Leu Gly Leu Pro Ile Thr Cys Trp Ser Ser Leu
         20                  25                  30

Ala Thr Gly Asn Asp Val Cys Val Thr Tyr Gly Leu Glu Gly Met Gln
         35                  40                  45

Thr Arg Lys Ile Glu Thr Asp Asn Ala Asn Lys Asn Gly Gly Ala Gly
 50                  55                  60

Ser Asn Val Gln Met Thr Ala Pro Leu Pro Leu Pro Gly Tyr Asp Ile
 65                  70                  75                  80

Asp Lys Ala His Glu Phe Tyr Ser Lys His Gly Leu Ala Val Arg Ala
             85                  90                  95

Val Gly Val Glu Val Lys Asp Ala Thr Val Ala Tyr Ala Asn Ala Val
             100                 105                 110

Glu Asn Gly Ala Thr Gly Val Leu Glu Pro Thr Ile Val Glu Asn Phe
         115                 120                 125

Asn Ser Asp Gly Asp Ser Gln Lys Cys His Met Ala Glu Val Glu Leu
130                 135                 140

Tyr Gly Asp Val Val Leu Arg Leu Val Ser Phe His Gly Asp Cys Ser
145                 150                 155                 160

Ala Glu Gln Ser Thr Phe Leu Pro His Leu Ser Pro Tyr Pro Ser Asn
                 165                 170                 175

Ser Asn Lys Asn Lys Pro Thr Tyr Gly Leu Ala Arg Leu Asp His Thr
             180                 185                 190

Val Gly Asn Val Pro Asn Leu Leu Ala Thr Gln Arg Tyr Ile Gln Thr
             195                 200                 205

Phe Thr Asn Tyr His Pro Phe Ala Glu Phe Thr Pro Glu Asp Val Gly
         210                 215                 220

Thr Val Asp Ser Gly Leu Asn Ser Val Val Leu Ala Ser Asp Asn Glu
225                 230                 235                 240

Asn Val Leu Leu Pro Leu Asn Glu Pro Thr Glu Gly Lys Arg Lys Ser
                 245                 250                 255

Gln Ile Gln Thr Tyr Leu Glu Gln Asn Glu Gly Pro Gly Leu Gln His
             260                 265                 270

Ile Ala Ile Lys Thr Asn Asp Ile Phe Asp Thr Ile Ala Lys Met Arg
         275                 280                 285

His Ala Glu Glu Asn Phe Gly Gly Phe Glu Leu Met Lys Arg Pro Ser
         290                 295                 300

Asp Glu Tyr Tyr Lys Glu Leu Pro Ser Arg Leu Gly Asp Lys Leu Thr
305                 310                 315                 320

Val Glu Gln Tyr Lys Gln Leu Glu Glu Leu Gly Ile Leu Ala Asp Ala
                 325                 330                 335

Asp Asp Glu Gly Ile Leu Leu Gln Ile Phe Thr Lys Pro Leu Gly Asp
             340                 345                 350

Arg Pro Thr Leu Phe Leu Glu Ile Ile Gln Arg Ile Gly Cys Val Leu
         355                 360                 365

Pro Asp Asp Asp Glu Ala Thr Asp Glu Gly Glu Ala Lys Asn Ala His
         370                 375                 380

Asn Arg Ile Val Arg Glu Arg Pro Gly Cys Gly Gly Phe Gly Gln Gly
385                 390                 395                 400

Asn Phe Arg Glu Leu Phe Lys Ala Ile Glu Glu His Glu Lys Thr Leu
                 405                 410                 415

Lys Val
```

<210> SEQ ID NO 12
<211> LENGTH: 1092
<212> TYPE: DNA
<213> ORGANISM: Cyanothece

<400> SEQUENCE: 12

```
atggaaatcg atcatattca tttctacgtt gaagatgcag cacatcaacg agattggttt      60
attgataaaa tggggtttca atccatcagc aacagtatcc atgatgacac ttatagcgaa     120
gtagtaggga atcagtctgt ttactttatc ttatcttctc ccctcaacga tgctagtcca     180
gtttcttatt acttgaaatc tcatcctccg ggggttgctg atgttgcttt tcgtgttgac     240
aatcttaatt ttttattaga caaagtatcc cgttttaagg tcgaaattat taatcaatct     300
agtctaacag cttttcctct aaataaacca gtgaaattcg cgaaacttaa aggatggggt     360
tctgtcaatc ataccttaat tgatcaggca gtcctagga cttttattag ctcaaaaatg     420
attgctaaaa gcgatattat tgggattgat catgttgttt taaatgttcc tcaaggtgaa     480
ctccccttag ccataaattg gtacaaaaat gtatttgatt ttataagtca tcaacagttc     540
aacatccaaa cagaacattc ggggttatct agtgaagcct agttgatag ttcaggaaaa      600
gtacaattta atattaatca accaagttct actaattctc agattcagga attttagac     660
cataataacg gttcaggcat tcaacatatt ggtttaaaat caagtaatat tttacaaagt     720
gttgcacaaa tgcgtcaaag gggattaccc tttttatccg ttcctaattc ctattaccaa     780
aacctaaaag aattgattag aaaatcgaca atttcttgtt taagccaaca ggaactagaa     840
caaattgaaa ctgaacaaat tctagtttgt tggccagaag ataacccgac ttcaatcctg     900
atgcaaattt tcactcaacc catttttaag cagccgactt tctttttga attaattcaa     960
agacgcaacc aagcacaggg atttggccaa ggtaattttc aagcgttatt tgaagccata    1020
gaatcagaac aaatcaagag aaatagggta tcctcacgag tcactttaca ggctgtaaca    1080
ccccaatctt ga                                                         1092
```

<210> SEQ ID NO 13
<211> LENGTH: 1089
<212> TYPE: DNA
<213> ORGANISM: Cyanothece

<400> SEQUENCE: 13

```
atggaaattg atcatattca tttttatgtg gaagatgcag cccatcagcg tgattggttt      60
attgataaaa tgggctttca gagcattagc aatagcattc atgatgatac ctatagcgaa     120
gttgtgggta atcagagcgt gtatttcatt ctgagcagtc cgctgaatga tgcaagtccg     180
gttagctatt atctgaaaag ccatcctccg ggtgttgcag atgttgcatt tcgtgttgat     240
aatctgaatt ttctgctgga taaagtgagc cgctttaaag tggaaatcat taatcagagc     300
agcctgaccg catttccgct gaataaaccg gttaaatttg ccaaactgaa aggttgggt     360
agcgttaatc ataccctgat tgatcaggca gtccgcgta cctttattag cagcaaaatg     420
attgccaaaa gcgatattat tggcattgat catgtggttc tgaatgttcc gcagggtgaa     480
ctgccgctgg caattaattg gtacaaaaat gtgtttgatt ttattagcca tcagcagttt     540
aatattcaga ccgaacatag cggtctgagc agcgaagcac tggttgatag cagcggtaaa     600
gttcagttta atattaatca gccgagcagc accaatagcc agattcaaga atttctggat     660
cataataatg gcagcggcat tcagcatatt ggtctgaaaa gcagcaatat tctgcagagc     720
gttgcacaga tgcgtcagcg tggtctgccg tttctgagcg ttccgaatag ctattatcag     780
```

-continued

```
aatctgaaag aactgattcg caaaagcacc attagctgtc tgagccagca agaactggaa    840
caaattgaaa ccgaacaaat tctggtttgt tggcctgaag ataatccgac cagcattctg    900
atgcagattt ttacccagcc gattttaaa cagccgacct ttttttttga actgattcag     960
cgtcgtaatc aggcacaggg ttttggtcag ggtaattttc aggcactgtt tgaagcaatt   1020
gaaagtgaac aaattaaacg taatcgtgtt agcagccgtg ttaccctgca ggcagttaca   1080
ccgcagagc                                                           1089
```

<210> SEQ ID NO 14
<211> LENGTH: 363
<212> TYPE: PRT
<213> ORGANISM: Cyanothece

<400> SEQUENCE: 14

```
Met Glu Ile Asp His Ile His Phe Tyr Val Glu Asp Ala Ala His Gln
1               5                  10                  15

Arg Asp Trp Phe Ile Asp Lys Met Gly Phe Gln Ser Ile Ser Asn Ser
            20                  25                  30

Ile His Asp Asp Thr Tyr Ser Glu Val Val Gly Asn Gln Ser Val Tyr
        35                  40                  45

Phe Ile Leu Ser Ser Pro Leu Asn Asp Ala Ser Pro Val Ser Tyr Tyr
    50                  55                  60

Leu Lys Ser His Pro Pro Gly Val Ala Asp Val Ala Phe Arg Val Asp
65                  70                  75                  80

Asn Leu Asn Phe Leu Leu Asp Lys Val Ser Arg Phe Lys Val Glu Ile
                85                  90                  95

Ile Asn Gln Ser Ser Leu Thr Ala Phe Pro Leu Asn Lys Pro Val Lys
            100                 105                 110

Phe Ala Lys Leu Lys Gly Trp Gly Ser Val Asn His Thr Leu Ile Asp
        115                 120                 125

Gln Ala Ser Pro Arg Thr Phe Ile Ser Ser Lys Met Ile Ala Lys Ser
    130                 135                 140

Asp Ile Ile Gly Ile Asp His Val Val Leu Asn Val Pro Gln Gly Glu
145                 150                 155                 160

Leu Pro Leu Ala Ile Asn Trp Tyr Lys Asn Val Phe Asp Phe Ile Ser
                165                 170                 175

His Gln Gln Phe Asn Ile Gln Thr Glu His Ser Gly Leu Ser Ser Glu
            180                 185                 190

Ala Leu Val Asp Ser Ser Gly Lys Val Gln Phe Asn Ile Asn Gln Pro
        195                 200                 205

Ser Ser Thr Asn Ser Gln Ile Gln Glu Phe Leu Asp His Asn Asn Gly
    210                 215                 220

Ser Gly Ile Gln His Ile Gly Leu Lys Ser Ser Asn Ile Leu Gln Ser
225                 230                 235                 240

Val Ala Gln Met Arg Gln Arg Gly Leu Pro Phe Leu Ser Val Pro Asn
                245                 250                 255

Ser Tyr Tyr Gln Asn Leu Lys Glu Leu Ile Arg Lys Ser Thr Ile Ser
            260                 265                 270

Cys Leu Ser Gln Gln Glu Leu Glu Gln Ile Glu Thr Glu Gln Ile Leu
        275                 280                 285

Val Cys Trp Pro Glu Asp Asn Pro Thr Ser Ile Leu Met Gln Ile Phe
    290                 295                 300

Thr Gln Pro Ile Phe Lys Gln Pro Thr Phe Phe Phe Glu Leu Ile Gln
305                 310                 315                 320
```

Arg Arg Asn Gln Ala Gln Gly Phe Gly Gln Gly Asn Phe Gln Ala Leu
            325                 330                 335

Phe Glu Ala Ile Glu Ser Glu Gln Ile Lys Arg Asn Arg Val Ser Ser
            340                 345                 350

Arg Val Thr Leu Gln Ala Val Thr Pro Gln Ser
            355                 360

<210> SEQ ID NO 15
<211> LENGTH: 1068
<212> TYPE: DNA
<213> ORGANISM: Acaryochloris marina

<400> SEQUENCE: 15

| | |
|---|---|
| atggattttg atcatattca tttttatgtt catgattcca agcaatgcca gcgttggttt | 60 |
| actaacgttt taggatttca atatcttggg agcaatacta cggctgatcg gcagattgaa | 120 |
| gttgtctctt ctggggcgat tgtctgtata ttttccagcc ctctaaaccg aaccagccca | 180 |
| gttgcccagt atctacaaca caccctcct ggtgtcgttg atttggcttt cttggtcccg | 240 |
| gacgttcagg ctacgcttac ctgcgctgtc cagtcaggag caacccttt acaacctttg | 300 |
| accgaagaaa aaacgacca aggaacgtta acttggggaa aagtacgagg gtggggagcg | 360 |
| ttagaacata ccttggtaga gcgaagaggg caaacctcca ctctgccatc cagcattttt | 420 |
| cccatctcaa ttcatgggca tgatgcccat cagagtctat ttacccagat tgatcatggg | 480 |
| gttttgaatg tgggtaagca tcagctgcaa gctgctgtga ttggtatca gcgcatattt | 540 |
| ggatttaaaa ctcaccgata ttttgatatt caaacgcgtc gttcaggtct gcgcagtgaa | 600 |
| gtgttgaccc atccccaagg ccaaatcaag tttccgatca atgaaccca ctcagcgaat | 660 |
| tcccaaatcc aagaatttct agaggtcaat cggggggcag gtattcaaca tatcgcattg | 720 |
| ggaacttcta atattgttga acggttact cagcttaagc atcgagggct atccatccta | 780 |
| gatattccac ccagctacta tcaacgctta cgacaccagt ttgagcaagt ctattcccac | 840 |
| ctcgattggc atgccctgga acacaacat attctggctg attttgagga agatgctgga | 900 |
| gccggaattc tattgcaaac cttcacaaag cctatctttc acaacccac ttttttcttt | 960 |
| gaaattattg agcgccaacg gcaggcccaa gggttcggac aacgaaactt tttggccctt | 1020 |
| tttcaagcca tggagcggga acaacagaaa cggggagtat tgctatag | 1068 |

<210> SEQ ID NO 16
<211> LENGTH: 1065
<212> TYPE: DNA
<213> ORGANISM: Acaryochloris marina

<400> SEQUENCE: 16

| | |
|---|---|
| atggattttg atcacatcca cttttatgtg catgacagca aacagtgtca gcgttggttt | 60 |
| accaatgttc tgggttttca gtatctgggt agcaatacca ccgcagatcg tcagattgaa | 120 |
| gttgttagca gcggtgcaat tgtttgcatt tttagcagtc cgctgaatcg taccagtccg | 180 |
| gttgcacagt atctgcagca gcatccgcct ggtgttgttg atctggcatt tctggttccg | 240 |
| gatgttcagg caaccctgac ctgtgcagtt cagagcggtg ccaccctgct gcagccgctg | 300 |
| accgaagaaa aaatgatca gggtacactg acctggggta aagttcgtgg ttggggtgca | 360 |
| ctggaacaca ccctggttga acgtcgtggt cagaccagca ccctgccgag cagcattttt | 420 |
| ccgattagca ttcatggtca tgatgcacat cagagcctgt ttacccagat tgatcatggt | 480 |
| gttctgaatg ttggtaaaca tcagctgcag gcagcagtta gctggtatca gcgtattttt | 540 |

```
ggctttaaaa cccaccgcta ttttgatatt cagacccgtc gtagcggtct gcgtagcgaa    600
gttctgaccc atccgcaggg tcagatcaaa tttccgatca atgaaccgac cagcgcaaat    660
agccagattc aagaatttct ggaagttaat cgtggtgccg gtattcagca tattgcactg    720
ggcaccagca atattgttga aaccgttacc cagctgaaac atcgtggtct gagcattctg    780
gatattccgc ctagctatta tcagcgtctg cgtcatcagt ttgaacaggt ttatagccat    840
ctggattggc atgccctgga aacccagcat attctggcag attttgaaga agatgcaggc    900
gcaggtattc tgctgcaaac ctttaccaaa ccgatttttc cgcagccgac ctttttttc     960 gaaattattg aacgtcagcg tcaggcacag ggttttggtc agcgcaattt tctggcactg    1020
tttcaggcaa tggaacgtga acagcagaaa cgtggtgtgc tgctg                    1065
```

<210> SEQ ID NO 17
<211> LENGTH: 355
<212> TYPE: PRT
<213> ORGANISM: Acaryochloris marina

<400> SEQUENCE: 17

```
Met Asp Phe Asp His Ile His Phe Tyr Val His Asp Ser Lys Gln Cys
 1               5                  10                  15

Gln Arg Trp Phe Thr Asn Val Leu Gly Phe Gln Tyr Leu Gly Ser Asn
            20                  25                  30

Thr Thr Ala Asp Arg Gln Ile Glu Val Val Ser Ser Gly Ala Ile Val
        35                  40                  45

Cys Ile Phe Ser Ser Pro Leu Asn Arg Thr Ser Pro Val Ala Gln Tyr
    50                  55                  60

Leu Gln Gln His Pro Pro Gly Val Val Asp Leu Ala Phe Leu Val Pro
65                  70                  75                  80

Asp Val Gln Ala Thr Leu Thr Cys Ala Val Gln Ser Gly Ala Thr Leu
                85                  90                  95

Leu Gln Pro Leu Thr Glu Glu Lys Asn Asp Gln Gly Thr Leu Thr Trp
            100                 105                 110

Gly Lys Val Arg Gly Trp Gly Ala Leu Glu His Thr Leu Val Glu Arg
        115                 120                 125

Arg Gly Gln Thr Ser Thr Leu Pro Ser Ser Ile Phe Pro Ile Ser Ile
    130                 135                 140

His Gly His Asp Ala His Gln Ser Leu Phe Thr Gln Ile Asp His Gly
145                 150                 155                 160

Val Leu Asn Val Gly Lys His Gln Leu Gln Ala Ala Val Ser Trp Tyr
                165                 170                 175

Gln Arg Ile Phe Gly Phe Lys Thr His Arg Tyr Phe Asp Ile Gln Thr
            180                 185                 190

Arg Arg Ser Gly Leu Arg Ser Glu Val Leu Thr His Pro Gln Gly Gln
        195                 200                 205

Ile Lys Phe Pro Ile Asn Glu Pro Thr Ser Ala Asn Ser Gln Ile Gln
    210                 215                 220

Glu Phe Leu Glu Val Asn Arg Gly Ala Gly Ile Gln His Ile Ala Leu
225                 230                 235                 240

Gly Thr Ser Asn Ile Val Glu Thr Val Thr Gln Leu Lys His Arg Gly
                245                 250                 255

Leu Ser Ile Leu Asp Ile Pro Pro Ser Tyr Tyr Gln Arg Leu Arg His
            260                 265                 270

Gln Phe Glu Gln Val Tyr Ser His Leu Asp Trp His Ala Leu Glu Thr
```

```
                275                 280                 285
Gln His Ile Leu Ala Asp Phe Glu Glu Asp Ala Gly Ala Gly Ile Leu
                    290                 295                 300
Leu Gln Thr Phe Thr Lys Pro Ile Phe Pro Gln Pro Thr Phe Phe Phe
305                 310                 315                 320
Glu Ile Ile Glu Arg Gln Arg Gln Ala Gln Gly Phe Gly Gln Arg Asn
                325                 330                 335
Phe Leu Ala Leu Phe Gln Ala Met Glu Arg Glu Gln Gln Lys Arg Gly
                340                 345                 350
Val Leu Leu
        355

<210> SEQ ID NO 18
<211> LENGTH: 1020
<212> TYPE: DNA
<213> ORGANISM: Synechocystis sp. PCC 6803

<400> SEQUENCE: 18
atggaattcg actatcttca tttatacgtt gacgattatc agtcagctca tcgttgttat        60
caacgtcaat ggggtttcac ttgcgtaaat aaaattatta ctgaccaagg aattactggc       120
atctaccaac aggggcaaat acttctgcta atttcggcat cggaatctag tttgagtaga       180
tatgccgact atctccagaa acatcccccc ggcgtaggtg aagtcgcttg caggtggcc        240 aattggcaaa aaattcagca tcaattatca gaattacaga tagaaaccac accagttatt       300
catcctctga ctaaagcaga aggattaact ttttgctct ggggagatgt gcaccatagc        360
atttatcctg ttcgttctga gctaaatcag aataaaacat tgcatggtgt tggtttaacg       420
accatcgacc atgtggtgct aaacattgcc gccgatcaat ttacccaggc ttcccaatgg       480
tatcaacagg tgtttggctg gtcggtgcag cagagttta ctgtcaatac gccccattct       540
ggtctgtata gcgaagccct ggccagtgcc aatgggaaag tccaatttaa cctcaattgt       600
cccaccaata acagttccca aattcaaact ttttttagcca ataaccatgg ggctggtatt      660
caacatgtcg cttttccac tacgagtatt acgcgaactg tggctcatct gcgggaaagg       720
ggcgtaaatt ttttaaaat cccactggc tattatcaac agcaaagaaa cagtagctat        780
tttaattatg caagtttgga ttgggatacc ttacagtgcc tagaaatttt gctggatgat       840
caagataata cggggagcg attactgcta caattttta gtcagcctg ctatggagta         900 ggcactctat tttgggaaat tattgaacgc cgccaccggg caaaaggatt tggtcaagga      960
aactttcaag ctctctatga agcggtggag actttagaaa aacagttaga agtgccataa     1020

<210> SEQ ID NO 19
<211> LENGTH: 1020
<212> TYPE: DNA
<213> ORGANISM: Synechocystis sp. PCC 6803

<400> SEQUENCE: 19
atggaattcg attacctgca tctgtatgtt gatgactatc agagcgctca ccgttgttac        60
cagcgtcagt ggggctttac ttgtgtgaac aaaatcatca ccgaccaggg tatcactggt       120
atttaccagc agggtcagat cctgctgctg atcagcgctt ctgaatcttc cctctctcgc       180
tatgccgatt acctccagaa acatccgcca ggtgtaggtg aagtcgcctg caggtcgca        240 aactggcaga aaattcagca ccagctgtcc gaactgcaga ttgaaactac cccggtgatt       300
cacccactga ccaaagcaga aggcctgact ttcctgctgt ggggtgacgt tcaccactcc       360
```

```
atctacccag tacgtagcga gctgaaccag aacaaaaccc tgcatggcgt tggtctgacc      420
actatcgatc acgtggttct gaacatcgca gcggaccagt tcacccaggc gagccagtgg      480
tatcagcagg tattcggttg gtccgttcag cagtctttca cggttaacac cccgcattcc      540
ggtctgtact ctgaagctct ggcgtctgcg aacggcaaag ttcagttcaa cctgaactgc      600
ccgaccaaca acagctccca gattcagacc ttcctggcga acaaccacgg tgctggtatc      660
cagcacgttg cattctctac tacctctatc acccgtacgg tcgctcacct gcgtgaacgt      720
ggcgtgaact tcctgaaaat cccgaccggt tactatcagc agcagcgcaa cagctcctac      780
ttcaactacg cgtctctgga ttgggatacc ctgcagtgcc tggagattct gctggacgac      840
caggacaaca ctggcgaacg cctgctgctg cagatctttt ctcagccgtg ctatggcgtg      900
ggtacgctgt tttgggaaat tatcgagcgc cgtcaccgtg ctaaaggctt tggccagggc      960
aactttcagg cactgtacga ggcagtagaa accctggaaa acagctcga  agtgccataa      1020
```

<210> SEQ ID NO 20
<211> LENGTH: 339
<212> TYPE: PRT
<213> ORGANISM: Synechocystis sp. PCC 6803

<400> SEQUENCE: 20

Met Glu Phe Asp Tyr Leu His Leu Tyr Val Asp Asp Tyr Gln Ser Ala
1               5                   10                  15

His Arg Cys Tyr Gln Arg Gln Trp Gly Phe Thr Cys Val Asn Lys Ile
            20                  25                  30

Ile Thr Asp Gln Gly Ile Thr Gly Ile Tyr Gln Gln Gly Gln Ile Leu
        35                  40                  45

Leu Leu Ile Ser Ala Ser Glu Ser Ser Leu Ser Arg Tyr Ala Asp Tyr
    50                  55                  60

Leu Gln Lys His Pro Pro Gly Val Gly Glu Val Ala Trp Gln Val Ala
65                  70                  75                  80

Asn Trp Gln Lys Ile Gln His Gln Leu Ser Glu Leu Gln Ile Glu Thr
                85                  90                  95

Thr Pro Val Ile His Pro Leu Thr Lys Ala Glu Gly Leu Thr Phe Leu
            100                 105                 110

Leu Trp Gly Asp Val His His Ser Ile Tyr Pro Val Arg Ser Glu Leu
        115                 120                 125

Asn Gln Asn Lys Thr Leu His Gly Val Gly Leu Thr Thr Ile Asp His
    130                 135                 140

Val Val Leu Asn Ile Ala Ala Asp Gln Phe Thr Gln Ala Ser Gln Trp
145                 150                 155                 160

Tyr Gln Gln Val Phe Gly Trp Ser Val Gln Gln Ser Phe Thr Val Asn
                165                 170                 175

Thr Pro His Ser Gly Leu Tyr Ser Glu Ala Leu Ala Ser Ala Asn Gly
            180                 185                 190

Lys Val Gln Phe Asn Leu Asn Cys Pro Thr Asn Ser Ser Gln Ile
        195                 200                 205

Gln Thr Phe Leu Ala Asn Asn His Gly Ala Gly Ile Gln His Val Ala
    210                 215                 220

Phe Ser Thr Thr Ser Ile Thr Arg Thr Val Ala His Leu Arg Glu Arg
225                 230                 235                 240

Gly Val Asn Phe Leu Lys Ile Pro Thr Gly Tyr Tyr Gln Gln Gln Arg
                245                 250                 255

Asn Ser Ser Tyr Phe Asn Tyr Ala Ser Leu Asp Trp Asp Thr Leu Gln

Cys Leu Glu Ile Leu Leu Asp Asp Gln Asp Asn Thr Gly Glu Arg Leu
            275                 280                 285

Leu Leu Gln Ile Phe Ser Gln Pro Cys Tyr Gly Val Gly Thr Leu Phe
        290                 295                 300

Trp Glu Ile Ile Glu Arg Arg His Arg Ala Lys Gly Phe Gly Gln Gly
305                 310                 315                 320

Asn Phe Gln Ala Leu Tyr Glu Ala Val Glu Thr Leu Glu Lys Gln Leu
                325                 330                 335

Glu Val Pro

<210> SEQ ID NO 21
<211> LENGTH: 1326
<212> TYPE: DNA
<213> ORGANISM: Alopecurus myosuroides

<400> SEQUENCE: 21

```
atgcctccga ccaccgcaac cgcaaccggt gctgcagcag cagccgttac accggaacat     60
gcagcacgtc gttttccgcg tgttgttcgt gttaatccgc gtagcgatcg ttttccggtt    120
ctggcatttc atcatgttga attttggtgt gccgatgcag caagcgcagc aggtcgtttt    180
agctttgcac tgggtgcacc gctggcagca cgtagcgatc tgagcaccgg taatagcagc    240
catgcaagcc atctgctgcg tagtggtgca ctggcatttc tgtttaccgc accgtatgca    300
ccgcctccgc aggatgcagc agatgcagcc gctaccgcca gcattccgag ctttagcacc    360
gaagcagcac gtacctttag cagcgcacat ggtctggcag ttcgtagcgt tgcaattcgt    420
gttgcagatg ccgcagaagc atttcatacc agcgttgcgg tggtgcacg tccggcattt    480
gcaccggcag atctgggtag cggttttggt ctggccgaag ttgaactgta tggtgatgtt    540
gttctgcgtt ttgttagtca tccggatggt gatgatgttc cgttctgcc gggttttgaa    600
ggtgttagcc gtccgggtgc aatggattat ggtctgaccc gttttgatca tgttgttggt    660
aatgttccgg aaatggcacc ggttgcagca tatatgaaag gttttaccgg ctttcatgaa    720
tttgccgaat ttaccgcaga agatgttggc accgcagaaa gcggtctgaa tagcgttgtt    780
ctggcaaata tagcgaagc agttctgctg ccgctgaatg aaccggtgca tggcaccaaa    840
cgtcgtagcc agattcagac ctatctggat tatcatggtg gtccgggtgt tcagcatatt    900
gcactggcaa gcagtgatgt tctgcgtacc ctgcgtgaaa tgcgtgcacg tagcgcaatg    960
ggtggttttg aatttatggc accgccgcag gcaaaatatt atgaaggtgt tcgtcgtctg   1020
gctggtgatg ttctgagcga agcacagatt aaagaatgtc aggaactggg cgttctggtt   1080
gatcgtgatg atcagggtgt tctgctgcag attttttacca aaccggttgg tgatcgtcgt   1140
ccgacctttt ttctggaaat gattcagcgt attggctgca tggaaaaaga tgaaattggc   1200
caggaatatc agaaaggcgg ctgtggtggt tttggtaaag gtaattttag cgaactgttt   1260
aaaagcattg aagattatga aaaagcctg gaagccaaac agagcgcagt tgcacagcag   1320
agctaa                                                              1326
```

<210> SEQ ID NO 22
<211> LENGTH: 441
<212> TYPE: PRT
<213> ORGANISM: Alopecurus myosuroides

<400> SEQUENCE: 22

Met Pro Pro Thr Thr Ala Thr Ala Thr Gly Ala Ala Ala Ala Ala Val

-continued

```
1               5                   10                  15
Thr Pro Glu His Ala Ala Arg Arg Phe Pro Arg Val Val Arg Val Asn
                20                  25                  30

Pro Arg Ser Asp Arg Phe Pro Val Leu Ala Phe His His Val Glu Phe
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ser
65                  70                  75                  80

His Ala Ser His Leu Leu Arg Ser Gly Ala Leu Ala Phe Leu Phe Thr
                85                  90                  95

Ala Pro Tyr Ala Pro Pro Gln Asp Ala Ala Asp Ala Ala Ala Thr
                100                 105                 110

Ala Ser Ile Pro Ser Phe Ser Thr Glu Ala Ala Arg Thr Phe Ser Ser
            115                 120                 125

Ala His Gly Leu Ala Val Arg Ser Val Ala Ile Arg Val Ala Asp Ala
        130                 135                 140

Ala Glu Ala Phe His Thr Ser Val Ala Gly Ala Arg Pro Ala Phe
145                 150                 155                 160

Ala Pro Ala Asp Leu Gly Ser Gly Phe Gly Leu Ala Glu Val Glu Leu
                165                 170                 175

Tyr Gly Asp Val Val Leu Arg Phe Val Ser His Pro Asp Gly Asp Asp
                180                 185                 190

Val Pro Phe Leu Pro Gly Phe Glu Gly Val Ser Arg Pro Gly Ala Met
            195                 200                 205

Asp Tyr Gly Leu Thr Arg Phe Asp His Val Val Gly Asn Val Pro Glu
        210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
                245                 250                 255

Asn Ser Val Val Leu Ala Asn Asn Ser Glu Ala Val Leu Leu Pro Leu
                260                 265                 270

Asn Glu Pro Val His Gly Thr Lys Arg Arg Ser Gln Ile Gln Thr Tyr
            275                 280                 285

Leu Asp Tyr His Gly Gly Pro Gly Val Gln His Ile Ala Leu Ala Ser
        290                 295                 300

Ser Asp Val Leu Arg Thr Leu Arg Glu Met Arg Ala Arg Ser Ala Met
305                 310                 315                 320

Gly Gly Phe Glu Phe Met Ala Pro Pro Gln Ala Lys Tyr Tyr Glu Gly
                325                 330                 335

Val Arg Arg Leu Ala Gly Asp Val Leu Ser Glu Ala Gln Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Arg Pro Thr Phe Phe
        370                 375                 380

Leu Glu Met Ile Gln Arg Ile Gly Cys Met Glu Lys Asp Glu Ile Gly
385                 390                 395                 400

Gln Glu Tyr Gln Lys Gly Gly Cys Gly Gly Phe Gly Lys Gly Asn Phe
                405                 410                 415

Ser Glu Leu Phe Lys Ser Ile Glu Asp Tyr Glu Lys Ser Leu Glu Ala
            420                 425                 430
```

Lys Gln Ser Ala Val Ala Gln Gln Ser
        435                 440

<210> SEQ ID NO 23
<211> LENGTH: 1323
<212> TYPE: DNA
<213> ORGANISM: Alopecurus myosuroides

<400> SEQUENCE: 23

```
atgccaccaa ctactgctac tgctacaggt gctgctgctg cagctgttac tccagaacat      60
gctgctagaa ggttcccaag agttgttaga gttaacccaa ggtctgatag gttcccagtt     120
cttgctttcc atcatgttga gttttggtgt gctgatgctg cttctgctgc tggaagattt     180
tcttttgctc ttggtgctcc acttgctgct agatctgatt tgtctactgg aaactcttct     240
cacgcttctc acctttgag atctggtgct cttgcttcc ttttcactgc tccttatgct       300
ccaccaccac aagatgctgc agatgcagca gctactgctt ctattccatc tttttcaact     360
gaggctgcta ggactttctc ttctgctcat ggattggctg ttagatctgt ggctattaga     420
gttgcagatg ctgcagaggc tttccatact tctgttgctg gtggtgctag accagctttt     480
gctccagctg atcttggatc tggatttgga cttgctgagg ttgagcttta cggtgatgtt     540
gttcttagat cgtgtctca cccagatggt gatgatgttc catttcttcc aggattcgag      600
ggtgttagta gaccaggtgc tatggattat ggactcacta ggttcgatca cgttgtggga     660
aatgttccag aaatggctcc agttgctgct tacatgaagg gattcactgg atttcatgag     720
ttcgctgagt tcactgctga ggatgttgga actgctgagt ctggacttaa ctctgttgtg     780
cttgctaaca actctgaggc tgttctttg ccacttaatg agccagttca cggcactaag      840
agaagatctc agattcagac ttacctcgat taccatggtg gaccaggtgt tcaacatatt     900
gctcttgctt catctgatgt gcttaggact cttagagaga tgagagctag atctgctatg     960
ggaggatttg agtttatggc tccaccacaa gctaagtatt acgaaggtgt tagaaggctt    1020
gctggtgatg ttcttctga ggctcaaatc aaagagtgcc aagagcttgg agttcttgtg     1080
gatagagatg atcagggtgt gcttctccag atttttcacta agccagttgg agataggcca    1140
acattcttct tggagatgat tcagaggatc ggctgcatgg aaaaggatga gattggacaa    1200
gagtaccaaa agggcggatg tggtggattt ggaaagggaa attttctccga gcttttcaag    1260
tccatcgagg attacgagaa gtctcttgag gctaagcaat ctgctgttgc tcaacagtct    1320
tga                                                                  1323
```

<210> SEQ ID NO 24
<211> LENGTH: 440
<212> TYPE: PRT
<213> ORGANISM: Alopecurus myosuroides

<400> SEQUENCE: 24

Met Pro Pro Thr Thr Ala Thr Ala Thr Gly Ala Ala Ala Ala Val
1               5                   10                  15

Thr Pro Glu His Ala Ala Arg Arg Phe Pro Arg Val Val Arg Val Asn
                20                  25                  30

Pro Arg Ser Asp Arg Phe Pro Val Leu Ala Phe His His Val Glu Phe
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ser

His Ala Ser His Leu Leu Arg Ser Gly Ala Leu Ala Phe Leu Phe Thr
 65                  70                  75                  80

Ala Pro Tyr Ala Pro Pro Gln Asp Ala Ala Asp Ala Ala Ala Thr
             85                  90                  95

Ala Ser Ile Pro Ser Phe Ser Thr Glu Ala Ala Arg Thr Phe Ser Ser
                100                 105                 110

Ala His Gly Leu Ala Val Arg Ser Val Ala Ile Arg Val Ala Asp Ala
            115                 120                 125

Ala Glu Ala Phe His Thr Ser Val Ala Gly Ala Arg Pro Ala Phe
130                 135                 140

Ala Pro Ala Asp Leu Gly Ser Gly Phe Gly Leu Ala Glu Val Glu Leu
145                 150                 155                 160

Tyr Gly Asp Val Val Leu Arg Phe Val Ser His Pro Asp Gly Asp
        165                 170                 175

Val Pro Phe Leu Pro Gly Phe Glu Gly Val Ser Arg Pro Gly Ala Met
            180                 185                 190

Asp Tyr Gly Leu Thr Arg Phe Asp His Val Val Gly Asn Val Pro Glu
            195                 200                 205

Met Ala Pro Val Ala Ala Tyr Met Lys Gly Phe Thr Gly Phe His Glu
            210                 215                 220

Phe Ala Glu Phe Thr Ala Glu Asp Val Gly Thr Ala Glu Ser Gly Leu
225                 230                 235                 240

Asn Ser Val Val Leu Ala Asn Asn Ser Glu Ala Val Leu Leu Pro Leu
            245                 250                 255

Asn Glu Pro Val His Gly Thr Lys Arg Arg Ser Gln Ile Gln Thr Tyr
            260                 265                 270

Leu Asp Tyr His Gly Gly Pro Gly Val Gln His Ile Ala Leu Ala Ser
            275                 280                 285

Ser Asp Val Leu Arg Thr Leu Arg Glu Met Arg Ala Arg Ser Ala Met
            290                 295                 300

Gly Gly Phe Glu Phe Met Ala Pro Pro Gln Ala Lys Tyr Tyr Glu Gly
305                 310                 315                 320

Val Arg Arg Leu Ala Gly Asp Val Leu Ser Glu Ala Gln Ile Lys Glu
                325                 330                 335

Cys Gln Glu Leu Gly Val Leu Val Asp Arg Asp Gln Gly Val Leu
            340                 345                 350

Leu Gln Ile Phe Thr Lys Pro Val Gly Asp Arg Pro Thr Phe Phe Leu
            355                 360                 365

Glu Met Ile Gln Arg Ile Gly Cys Met Glu Lys Asp Glu Ile Gly Gln
385                 370 (continuing)

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Ala Lys
            420                 425                 430

Gln Ser Ala Val Ala Gln Gln Ser
            435                 440

<210> SEQ ID NO 25
<211> LENGTH: 1323
<212> TYPE: DNA
<213> ORGANISM: Sorghum halapense

<400> SEQUENCE: 25

```
atgcctccga ccccgaccac cgcagcagca acaggtgccg cagttgcagc agcaagcgca    60
gaacaggcag catttcgtct ggttggtcat cgtaattttg ttcgtgttaa tccgcgtagc   120
gatcgttttc ataccctggc atttcatcat gttgaactgt ggtgtgccga tgcagccagc   180
gcagcaggtc gttttagctt tggtctgggt gcaccgctgg cagcacgtag cgatctgagc   240
accggtaata ccgcacatgc aagcctgctg ctgcgttcag gtgcactggc atttctgttt   300
accgcaccgt atgcccatgg tgctgatgca gcaaccgcaa gcctgccgag ctttagcgca   360
gcagaagcac gtcgttttgc agcagatcat ggtctggcag ttcgtgccgt tgcactgcgt   420
gttgcagatg ccgaagatgc atttcgtgca agcgttgcag ccggtgcacg tccggcattt   480
gaaccggttg aactgggtct gggttttcgt ctggccgaag ttgaactgta tggtgatgtt   540
gttctgcgtt atgttagcta tccggatgat gcagatgcaa gctttctgcc gggttttgtt   600
ggtgttagca gtccgggtgc ggcagattat ggcctgcgtc gttttgatca tattgtgggt   660
aatgttccgg aactggcacc ggcagcggca tattttgcag gttttaccgg ctttcatgaa   720
tttgcagaat ttaccgcaga agatgttggc accaccgaaa gcggtctgaa tagcatggtt   780
ctggcaaata tgccgaaaaa tgttctgctg ccgctgaatg aaccggtgca tggcaccaaa   840
cgtcgtagcc agattcagac cttictggat catcatggtg gtccgggtgt tcagcacatg   900
gcactggcaa gtgatgatgt gctgcgtacc ctgcgtgaaa tgcaggcatg tagtgcaatg   960
ggtggttttg aatttatggc accgccggca ccggaatatt atgatggtgt tcgtcgtcgt  1020
gccggtgatg ttctgaccga agcacagatt aaagaatgtc aggaactggg cgttctggtt  1080
gatcgtgatg atcagggtgt tctgctgcag attittacca aaccggttgg tgatcgcccg  1140
acctttttic tggaaattat tcagcgtatt ggttgcatgg aaaaagatga aaaaggccag  1200
gaatatcaga aaggcggttg tggtggtttt ggtaaaggta ttittagcca gctgtttaaa  1260
agcattgaag attatgaaaa aagcctggaa gcaaaacagg cagctgcagc acagggtccg  1320
taa                                                                 1323
```

<210> SEQ ID NO 26
<211> LENGTH: 440
<212> TYPE: PRT
<213> ORGANISM: Sorghum halapense

<400> SEQUENCE: 26

```
Met Pro Pro Thr Pro Thr Thr Ala Ala Ala Thr Gly Ala Ala Val Ala
1               5                   10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
```

```
            130                 135                 140
Glu Asp Ala Phe Arg Ala Ser Val Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Asp Asp Ala Asp
                180                 185                 190

Ala Ser Phe Leu Pro Gly Phe Val Gly Val Ser Ser Pro Gly Ala Ala
                195                 200                 205

Asp Tyr Gly Leu Arg Arg Phe Asp His Ile Val Gly Asn Val Pro Glu
210                 215                 220

Leu Ala Pro Ala Ala Ala Tyr Phe Ala Gly Phe Thr Gly Phe His Glu
225                 230                 235                 240

Phe Ala Glu Phe Thr Ala Glu Asp Val Gly Thr Thr Glu Ser Gly Leu
                245                 250                 255

Asn Ser Met Val Leu Ala Asn Asn Ala Glu Asn Val Leu Leu Pro Leu
                260                 265                 270

Asn Glu Pro Val His Gly Thr Lys Arg Arg Ser Gln Ile Gln Thr Phe
                275                 280                 285

Leu Asp His His Gly Gly Pro Gly Val Gln His Met Ala Leu Ala Ser
                290                 295                 300

Asp Asp Val Leu Arg Thr Leu Arg Glu Met Gln Ala Cys Ser Ala Met
305                 310                 315                 320

Gly Gly Phe Glu Phe Met Ala Pro Pro Ala Pro Glu Tyr Tyr Asp Gly
                325                 330                 335

Val Arg Arg Arg Ala Gly Asp Val Leu Thr Glu Ala Gln Ile Lys Glu
                340                 345                 350

Cys Gln Glu Leu Gly Val Leu Val Asp Arg Asp Gln Gly Val Leu
                355                 360                 365

Leu Gln Ile Phe Thr Lys Pro Val Gly Asp Arg Pro Thr Phe Phe Leu
                370                 375                 380

Glu Ile Ile Gln Arg Ile Gly Cys Met Glu Lys Asp Glu Lys Gly Gln
385                 390                 395                 400

Glu Tyr Gln Lys Gly Gly Cys Gly Gly Phe Gly Lys Gly Asn Phe Ser
                405                 410                 415

Gln Leu Phe Lys Ser Ile Glu Asp Tyr Glu Lys Ser Leu Glu Ala Lys
                420                 425                 430

Gln Ala Ala Ala Gln Gly Pro
435                 440

<210> SEQ ID NO 27
<211> LENGTH: 1323
<212> TYPE: DNA
<213> ORGANISM: Sorghum halapense

<400> SEQUENCE: 27
atgcctccga ccccgaccac cgcagcagca acaggtgccg cagttgcagc agcaagcgca      60
gaacaggcag catttcgtct ggttggtcat cgtaattttg ttcgtgttaa tccgcgtagc     120
gatcgttttc ataccctggc atttcatcat gttgaactgt ggtgtgccga tgcagccagc     180
gcagcaggtc gttttagctt tggtctgggt gcaccgctgg cagcacgtag cgatctgagc     240
accggtaata ccgcacatgc aagcctgctg ctgcgttcag gtgcactggc atttctgttt     300
accgcaccgt atgcccatgg tgctgatgca gcaaccgcaa gcctgccgag ctttagcgca     360
```

```
gcagaagcac gtcgttttgc agcagatcat ggtctggcag ttcgtgccgt tgcactgcgt    420
gttgcagatg ccgaagatgc atttcgtgca agcgttgcag ccggtgcacg tccggcattt    480
gaaccggttg aactgggtct gggttttcgt ctggccgaag ttgaactgta tggtgatgtt    540
gttctgcgtt atgttagcta tccggatgat gcagatgcaa gctttctgcc gggttttgtt    600
ggtgttacca gtccgggtgc ggcagattat ggcctgaaac gttttgatca tattgtgggt    660
aatgttccgg aactgcaccg gcagcggca tattttgcag gttttaccgg ctttcatgaa    720
tttgcagaat ttaccgcaga agatgttggc accaccgaaa gcggtctgaa tagcatggtt    780
ctggcaaata tgccgaaaaa tgttctgctg ccgctgaatg aaccggtgca tggcaccaaa    840
cgtcgtagcc agattcagac ctttctggat catcatggtg gtccgggtgt tcagcacatg    900
gcactggcaa gtgatgatgt gctgcgtacc ctgcgtgaaa tgcaggcacg tagtgcaatg    960
ggtggttttg aatttatggc accgccggca ccggaatatt atgatggtgt tcgtcgtcgt   1020
gccggtgatg ttctgaccga agcacagatt aaagaatgtc aggaactggg cgttctggtt   1080
gatcgtgatg atcagggtgt tctgctgcag atttttacca aaccggttgg tgatcgcccg   1140
acctttttc tggaaattat tcagcgtatt ggttgcatgg aaaaagatga aaaaggccag   1200
gaatatcaga aggcggttg tggtggtttt ggtaaaggta ttttagccag ctgtgtttaaa   1260
agcattgaag attatgaaaa aagcctggaa gcaaacagg cagctgcagc acagggtccg   1320
taa                                                                  1323
```

<210> SEQ ID NO 28
<211> LENGTH: 453
<212> TYPE: PRT
<213> ORGANISM: Sorghum halapense

<400> SEQUENCE: 28

```
Met Pro Pro Thr Pro Thr Thr Ala Ala Thr Gly Ala Ala Val Ala
 1               5                  10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Arg Ser Gly Ala Leu
                85                  90                  95

Ala Phe Leu Phe Thr Ala Pro Tyr Ala His Gly Ala Asp Ala Thr
               100                 105                 110

Ala Ser Leu Pro Ser Phe Ser Ala Ala Glu Ala Arg Arg Phe Ala Ala
           115                 120                 125

Asp His Gly Leu Ala Val Arg Val Ala Leu Arg Val Ala Asp Ala
       130                 135                 140

Glu Asp Ala Phe Arg Ala Ser Val Ala Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Thr Thr Arg Thr
            180                 185                 190

Arg Pro Ser Cys Arg Gly Ser Trp Ala Asp Asp Ala Asp Ala Ser Phe
```

```
            195                 200                 205
Leu Pro Gly Phe Val Gly Val Thr Ser Pro Gly Ala Ala Asp Tyr Gly
    210                 215                 220

Leu Lys Arg Phe Asp His Ile Val Gly Asn Val Pro Glu Leu Ala Pro
225                 230                 235                 240

Ala Ala Ala Tyr Phe Ala Gly Phe Thr Gly Phe His Glu Phe Ala Glu
                245                 250                 255

Phe Thr Ala Glu Asp Val Gly Thr Thr Glu Ser Gly Leu Asn Ser Met
            260                 265                 270

Val Leu Ala Asn Asn Ala Glu Asn Val Leu Leu Pro Leu Asn Glu Pro
        275                 280                 285

Val His Gly Thr Lys Arg Arg Ser Gln Ile Gln Thr Phe Leu Asp His
    290                 295                 300

His Gly Gly Pro Gly Val Gln His Met Ala Leu Ala Ser Asp Asp Val
305                 310                 315                 320

Leu Arg Thr Leu Arg Glu Met Gln Ala Arg Ser Ala Met Gly Gly Phe
                325                 330                 335

Glu Phe Met Ala Pro Pro Ala Pro Glu Tyr Tyr Asp Gly Val Arg Arg
            340                 345                 350

Arg Ala Gly Asp Val Leu Thr Glu Ala Gln Ile Lys Glu Cys Gln Glu
        355                 360                 365

Leu Gly Val Leu Val Asp Arg Asp Asp Gln Gly Val Leu Leu Gln Ile
    370                 375                 380

Phe Thr Lys Pro Val Gly Asp Arg Pro Thr Phe Phe Leu Glu Ile Ile
385                 390                 395                 400

Gln Arg Ile Gly Cys Met Glu Lys Asp Glu Lys Gly Gln Glu Tyr Gln
                405                 410                 415

Lys Gly Gly Cys Gly Gly Phe Gly Lys Gly Asn Phe Ser Gln Leu Phe
            420                 425                 430

Lys Ser Ile Glu Asp Tyr Glu Lys Ser Leu Glu Ala Lys Gln Ala Ala
        435                 440                 445

Ala Ala Gln Gly Pro
    450

<210> SEQ ID NO 29
<211> LENGTH: 1311
<212> TYPE: DNA
<213> ORGANISM: Poa annua

<400> SEQUENCE: 29
atgcctccga ccaccgcaac cgccaccgca gcagcaaccg ttacaccgga acatgcagca      60
cgtcgttttc cgcgtgttgt tcgtgttaat ccgcgtagcg atcgttttcc ggttctgagc     120
tttcatcatg ttgaattttg gtgtgccgat gcagcaagcg cagcaggtcg ttttagcttt     180
gcactgggtg caccgctggc agcacgtagc gatctgagca ccgtaatag cgcacatgca      240 agcctgctgc tgcgttcagg tgcactggca tttctgttta ccgcaccgta tgcaccgcag     300
ccgcaggatg cagataccgc aagcattccg agctttagcg cagatgcagc acgtgcattt     360
agcgcagcac atggtctggc agttcgtagc gttgcagttc gtgttgcaga tgccgcagat     420
gcatttcgtg caagcattgc agccggtgca cgtccggcat ttcaccggc agatctgggt      480 cgtggttttg gtctggccga agttgaactg tatggtgatg ttgttctgcg ttttgttagc     540
catccggatg cagatgatgc accgccgttt ctgccgggtt ttgaagcagt tagccgtcgt     600
ccgggtgccg ttgattatgg tctgacccgt tttgatcatg ttgttggtaa tgttccggaa     660
```

```
atgggtccgg tgattgatta tattaaaggc tttatgggct tcatgaatt tgccgaattt      720 accgcagaag atgttggcac caccgaaagc ggtctgaata gcgttgttct ggcaaataat     780
agcgaagcag ttctgctgcc gctgaatgaa ccggtgcatg caccaaacg tcgtagccag      840 attcagacct atctggaata tcatggtggt ccgggtgttc agcatattgc actggcaagc    900
agtgatgttc tgcgtaccct gcgtgaaatg caggcacgtt cagcaatggg tggttttgaa   960
tttatggcac cgccgcagcc gaaatattat gaaggtgttc gtcgtattgc cggtgatgtt  1020
ctgagcgaag cacagattaa agaatgtcag gaactgggcg ttctggttga tcgtgatgat  1080
cagggtgttc tgctgcagat ttttaccaaa ccggttggtg atcgtccgac ctttttctg   1140 gaaatgattc agcgtattgg ctgcatggaa aaagatgaac gtggtcagga atatcagaaa  1200
ggcggttgtg gcggttttgg taaaggtaat tttagcgaac tgtttaaaag cattgaagat  1260
tatgaaaaaa gcctggaagc caaacagagc gcagttgcac agcagagcta a           1311
```

<210> SEQ ID NO 30
<211> LENGTH: 436
<212> TYPE: PRT
<213> ORGANISM: Poa annua

<400> SEQUENCE: 30

```
Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
        50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
            100                 105                 110

Ser Ala Asp Ala Ala Arg Ala Phe Ser Ala Ala His Gly Leu Ala Val
        115                 120                 125

Arg Ser Val Ala Val Arg Val Ala Asp Ala Ala Asp Ala Phe Arg Ala
    130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Ala Pro Pro Phe Leu Pro
            180                 185                 190

Gly Phe Glu Ala Val Ser Arg Arg Pro Gly Ala Val Asp Tyr Gly Leu
        195                 200                 205

Thr Arg Phe Asp His Val Val Gly Asn Val Pro Glu Met Gly Pro Val
    210                 215                 220

Ile Asp Tyr Ile Lys Gly Phe Met Gly Phe His Glu Phe Ala Glu Phe
225                 230                 235                 240

Thr Ala Glu Asp Val Gly Thr Thr Glu Ser Gly Leu Asn Ser Val Val
                245                 250                 255
```

```
Leu Ala Asn Asn Ser Glu Ala Val Leu Pro Leu Asn Glu Pro Val
            260                 265                 270

His Gly Thr Lys Arg Arg Ser Gln Ile Gln Thr Tyr Leu Glu Tyr His
        275                 280                 285

Gly Gly Pro Gly Val Gln His Ile Ala Leu Ala Ser Ser Asp Val Leu
            290                 295                 300

Arg Thr Leu Arg Glu Met Gln Ala Arg Ser Ala Met Gly Gly Phe Glu
305                 310                 315                 320

Phe Met Ala Pro Pro Gln Pro Lys Tyr Tyr Glu Gly Val Arg Arg Ile
                325                 330                 335

Ala Gly Asp Val Leu Ser Glu Ala Gln Ile Lys Glu Cys Gln Glu Leu
            340                 345                 350

Gly Val Leu Val Asp Arg Asp Asp Gln Gly Val Leu Leu Gln Ile Phe
        355                 360                 365

Thr Lys Pro Val Gly Asp Arg Pro Thr Phe Phe Leu Glu Met Ile Gln
    370                 375                 380

Arg Ile Gly Cys Met Glu Lys Asp Glu Arg Gly Gln Glu Tyr Gln Lys
385                 390                 395                 400

Gly Gly Cys Gly Gly Phe Gly Lys Gly Asn Phe Ser Glu Leu Phe Lys
                405                 410                 415

Ser Ile Glu Asp Tyr Glu Lys Ser Leu Glu Ala Lys Gln Ser Ala Val
            420                 425                 430

Ala Gln Gln Ser
        435
```

<210> SEQ ID NO 31
<211> LENGTH: 1305
<212> TYPE: DNA
<213> ORGANISM: Poa annua

<400> SEQUENCE: 31

```
atgccaccaa ctactgctac tgctacagct gctgctactg ttactccaga acatgctgct      60
agaaggttcc caagagttgt tagagttaac ccaaggtctg ataggttccc agttctttct     120
ttccaccacg ttgaattttg tgtgctgat gctgcttctg ctgctggaag attttctttt      180
gctcttggtg ctccacttgc tgctagatct gatttgtcta ctggaaattc tgctcacgct     240
tctttgcttt tgaggtctgg tgctcttgct ttccttttta ctgctcctta tgctccacaa     300
ccacaggatg ctgatactgc atcaattcca tctttctcag ctgatgctgc aagggctttt     360
tctgctgctc atggattggc tgttagatct gttgctgtta gagttgctga tgcagctgat     420
gctttcagag cttctattgc tgcaggtgct agaccagctt ttgctccagc tgatcttgga     480
agaggatttg gacttgctga ggttgagctt tacggtgatg ttgttcttag attcgtgtct     540
cacccagatg ctgatgatgc tccatttctt ccaggatttg aggctgtttc tagaccaggt     600
gctgttgatt atggactcac taggttcgat cacgttgtgg aaatgttcc agaaatggga      660
ccagtgatcg attacatcaa gggattcatg ggattccatg agttcgctga gtttactgct     720
gaggatgttg aactactga gtctggactt aactctgttg tgcttgctaa caactctgag      780
gctgttcttt tgccacttaa tgagccagtt cacggcacta agagaagatc tcagattcag     840
acttaccttg agtaccatgg tggaccaggt gttcaacata ttgctcttgc ttcatctgat     900
gtgcttagga ctcttagaga gatgcaagct agatctgcta tgggaggatt tgagtttatg     960
gctccaccac aacctaagta ttacgagggt gttagaagga ttgctggtga tgttctttcc    1020
gaggctcaaa tcaaagagtg tcaagagctt ggagtgcttg tggatagaga tgatcagggt    1080
```

```
gtgcttctcc agattttcac taagccagtt ggagataggc caacattctt cttggagatg    1140
attcagagga tcggctgcat ggaaaaggat gagagaggtc aagagtatca aaagggcgga    1200
tgtggtggat ttggaaaggg aaatttctcc gagcttttca agtccatcga ggattacgag    1260
aagtctcttg aggctaagca atctgctgtt gctcaacagt cttga                   1305
```

<210> SEQ ID NO 32
<211> LENGTH: 434
<212> TYPE: PRT
<213> ORGANISM: Poa annua

<400> SEQUENCE: 32

```
Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
        50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
                100                 105                 110

Ser Ala Asp Ala Ala Arg Ala Phe Ser Ala Ala His Gly Leu Ala Val
            115                 120                 125

Arg Ser Val Ala Val Arg Val Ala Asp Ala Ala Asp Ala Phe Arg Ala
        130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Asp Ala Pro Phe Leu Pro Gly
                180                 185                 190

Phe Glu Ala Val Ser Arg Pro Gly Ala Val Asp Tyr Gly Leu Thr Arg
            195                 200                 205

Phe Asp His Val Val Gly Asn Val Pro Glu Met Gly Pro Val Ile Asp
        210                 215                 220

Tyr Ile Lys Gly Phe Met Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Ala Val Leu Leu Pro Leu Asn Glu Pro Val His Gly
                260                 265                 270

Thr Lys Arg Arg Ser Gln Ile Gln Thr Tyr Leu Glu Tyr His Gly Gly
            275                 280                 285

Pro Gly Val Gln His Ile Ala Leu Ala Ser Ser Asp Val Leu Arg Thr
        290                 295                 300

Leu Arg Glu Met Gln Ala Arg Ser Ala Met Gly Gly Phe Glu Phe Met
305                 310                 315                 320

Ala Pro Pro Gln Pro Lys Tyr Tyr Glu Gly Val Arg Arg Ile Ala Gly
                325                 330                 335
```

```
Asp Val Leu Ser Glu Ala Gln Ile Lys Glu Cys Gln Glu Leu Gly Val
            340                 345                 350

Leu Val Asp Arg Asp Gln Gly Val Leu Leu Gln Ile Phe Thr Lys
        355                 360                 365

Pro Val Gly Asp Arg Pro Thr Phe Phe Leu Glu Met Ile Gln Arg Ile
    370                 375                 380

Gly Cys Met Glu Lys Asp Glu Arg Gly Gln Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Val Ala Gln
            420                 425                 430

Gln Ser
```

<210> SEQ ID NO 33
<211> LENGTH: 1323
<212> TYPE: DNA
<213> ORGANISM: Lolium multiflorum

<400> SEQUENCE: 33

| | | |
|---|---|---|
| atgcctccga caccggcaac cgcaaccggt gctgcagcag cagcagttac accggaacat | 60 |
| gcagcacgta gctttccgcg tgttgttcgt gttaatccgc gtagcgatcg ttttccggtt | 120 |
| ctgagctttc atcatgttga actgtggtgt gccgatgcag caagcgcagc aggtcgtttt | 180 |
| agctttgcac tgggtgctcc gctggcagcc cgtagcgatc tgagcaccgg taatagcgca | 240 |
| catgcaagcc tgctgctgcg tagcggtgca ctggcatttc tgtttaccgc accgtatgca | 300 |
| ccgcctccgc aggaagcagc aaccgcagct gcaaccgcaa gcattccgag ctttagcgca | 360 |
| gatgcagccc gtacctttgc agcagcacat ggtctggcag ttcgtagcgt tggtgttcgt | 420 |
| gttgccgatg cagcggaagc atttcgtgtt agcgttgccg gtggtgcacg tccggcattt | 480 |
| gcaccggcag atctgggtca tggttttggt ctggccgaag ttgaactgta tggtgatgtt | 540 |
| gttctgcgtt ttgttagcta tccggatgaa accgatctgc cgtttctgcc gggttttgaa | 600 |
| cgtgttagca gtccgggtgc cgttgattat ggtctgaccc gttttgatca tgttgttggt | 660 |
| aatgttccgg aaatggcacc ggttattgat tatatgaaag ctttctgggg ctttcatgaa | 720 |
| tttgcagaat ttaccgcaga agatgttggc accaccgaaa gcggtctgaa tagcgttgtt | 780 |
| ctggcaaata tagcgaaaa tgttctgctg ccgctgaatg aaccggtgca tggcaccaaa | 840 |
| cgtcgtagcc agattcagac ctatctggat tatcatggtg gtccgggtgt tcagcatatt | 900 |
| gcactggcaa gcaccgatgt tctgcgtacc ctgcgtgaaa tgcgtgcacg taccccgatg | 960 |
| ggtggttttg aatttatggc accgccgcag gcaaaatatt atgaaggtgt tcgtcgtatt | 1020 |
| gccggtgatg ttctgagcga agaacaaatt aaagaatgtc aggaactggg cgttctggtt | 1080 |
| gatcgtgatg atcagggtgt tctgctgcag atttttacca aaccggttgg tgatcgtccg | 1140 |
| acctttttc tggaaatgat tcagcgtatt ggctgcatgg aaaaagatga agttggtcag | 1200 |
| gaatatcaga aaggcggttg tggtggtttt ggtaaaggta attttagcga actgtttaaa | 1260 |
| agcattgaag attatgaaaa aaccctggaa gccaaacaga gcgttgttgc acagaaaagc | 1320 |
| taa | 1323 |

<210> SEQ ID NO 34
<211> LENGTH: 440
<212> TYPE: PRT

-continued

<213> ORGANISM: Lolium multiflorum

<400> SEQUENCE: 34

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
            115                 120                 125

Ala His Gly Leu Ala Val Arg Ser Val Gly Val Arg Val Ala Asp Ala
    130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
            165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Asn Val Leu Leu Pro Leu
            260                 265                 270

Asn Glu Pro Val His Gly Thr Lys Arg Arg Ser Gln Ile Gln Thr Tyr
        275                 280                 285

Leu Asp Tyr His Gly Gly Pro Gly Val Gln His Ile Ala Leu Ala Ser
    290                 295                 300

Thr Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Gln Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400
```

Glu Tyr Gln Lys Gly Gly Cys Gly Gly Phe Gly Lys Gly Asn Phe Ser
            405                 410                 415

Glu Leu Phe Lys Ser Ile Glu Asp Tyr Glu Lys Thr Leu Glu Ala Lys
        420                 425                 430

Gln Ser Val Val Ala Gln Lys Ser
        435                 440

<210> SEQ ID NO 35
<211> LENGTH: 1053
<212> TYPE: DNA
<213> ORGANISM: Synechococcus sp

<400> SEQUENCE: 35

| | | |
|---|---|---|
| atgaaccegt ccattcgaat tgtccaaggg atccaccacc tgcacttcta cctttgggat | 60 |
| ctgccccgtt ggcgggaaca cttttgtcgg gtttggggct tccgggtggc aagcgacgcc | 120 |
| ggcaacaccc tggagctgga gcagggatcc ctgcgcttgc gcctgtctca gccggcacgg | 180 |
| gcggggacg aggtggaccg ccatttgcag cggcatgggc cggggtggt ggatgtggcc | 240 |
| ttggcggtgg gagagcagga gctaccggcc ttggcggagc tgttgcgggg ccgaggcgcc | 300 |
| caactggcgt ggatcccggc agcagcggcg ctctgcctcc acacccccta cgggatccgg | 360 |
| cattctctga tccctggccc cttggatgcc gccctgccg aagcgggcct gttttcccac | 420 |
| tgggatcacg tggtgttgaa cgtggagcag ggatccctgc aggcggcagc cgactggtat | 480 |
| gggcgggtgc tgggctggcg gcggctgtac cgctacagca tcggcaccgc cacctccggc | 540 |
| ctggaaagcg tggtggtggg ggatccggaa gcggggatcc aatgggccat caacgagccc | 600 |
| acctgtgccg cttcccagat tcaggagttt ttgcatgccc atgccggccc gggcattcag | 660 |
| cacgcggcgc tgcacagctc agacattgtt gccagcctgc gccggttgcg gcagggggga | 720 |
| gtggactttt tgcaagtggc gccgcagtac tacaccagcc tggaaaggga gctggggttg | 780 |
| gcgctccgtt ctgcccttgg gcaggccatc tcctggcaag acctggtgga gcagcagatc | 840 |
| cttctggatg ctaccctgcc cgcttctgat ggccaggatc gccccttct gctgcagacc | 900 |
| tttacccagc ccctctttgg tcggcccacc tttttctttg aagtcattca acggctaggc | 960 |
| ggggccacgg gctttggcga ggccaattt caggctttgt tcgaggccct ggaacggcaa | 1020 |
| cagcgacagc gacaccaggc gctgaccct tag | 1053 |

<210> SEQ ID NO 36
<211> LENGTH: 350
<212> TYPE: PRT
<213> ORGANISM: Synechococcus sp

<400> SEQUENCE: 36

Met Asn Pro Ser Ile Arg Ile Val Gln Gly Ile His His Leu His Phe
1               5                   10                  15

Tyr Leu Trp Asp Leu Pro Arg Trp Arg Glu His Phe Cys Arg Val Trp
            20                  25                  30

Gly Phe Arg Val Ala Ser Asp Ala Gly Asn Thr Leu Glu Leu Glu Gln
        35                  40                  45

Gly Ser Leu Arg Leu Arg Leu Ser Gln Pro Ala Arg Ala Gly Asp Glu
    50                  55                  60

Val Asp Arg His Leu Gln Arg His Gly Pro Gly Val Val Asp Val Ala
65                  70                  75                  80

Leu Ala Val Gly Glu Gln Glu Leu Pro Ala Leu Ala Glu Leu Leu Arg
                85                  90                  95

```
Gly Arg Gly Ala Gln Leu Ala Trp Ile Pro Ala Ala Ala Leu Cys
                100                 105                 110

Leu His Thr Pro Tyr Gly Ile Arg His Ser Leu Ile Pro Gly Pro Leu
            115                 120                 125

Asp Ala Ala Pro Ala Glu Ala Gly Leu Phe Ser His Trp Asp His Val
        130                 135                 140

Val Leu Asn Val Glu Gln Gly Ser Leu Gln Ala Ala Asp Trp Tyr
145                 150                 155                 160

Gly Arg Val Leu Gly Trp Arg Arg Leu Tyr Arg Tyr Ser Ile Gly Thr
                165                 170                 175

Ala Thr Ser Gly Leu Glu Ser Val Val Val Gly Asp Pro Glu Ala Gly
            180                 185                 190

Ile Gln Trp Ala Ile Asn Glu Pro Thr Cys Ala Ala Ser Gln Ile Gln
        195                 200                 205

Glu Phe Leu His Ala His Gly Gly Pro Gly Ile Gln His Ala Ala Leu
    210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
                245                 250                 255

Glu Leu Gly Leu Ala Leu Arg Ser Ala Leu Gly Gln Ala Ile Ser Trp
            260                 265                 270

Gln Asp Leu Val Glu Gln Ile Leu Leu Asp Ala Thr Leu Pro Ala
        275                 280                 285

Ser Asp Gly Gln Asp Arg Pro Leu Leu Leu Gln Thr Phe Thr Gln Pro
    290                 295                 300

Leu Phe Gly Arg Pro Thr Phe Phe Glu Val Ile Gln Arg Leu Gly
305                 310                 315                 320

Gly Ala Thr Gly Phe Gly Ala Asn Phe Gln Ala Leu Phe Glu Ala
                325                 330                 335

Leu Glu Arg Gln Gln Arg Gln Arg His Gln Ala Leu Thr Pro
            340                 345                 350

<210> SEQ ID NO 37
<211> LENGTH: 1149
<212> TYPE: DNA
<213> ORGANISM: Blepharisma japonicum

<400> SEQUENCE: 37
atgacttatt acgacaagca agaaacgcgt ccagatcttg gcgaattcta tggtttccat      60
cacgttcgtt tttacgtctc caactcagag caagccgctt cgttctacac atctcgcttt    120
gggttttctc cggttgccta tgaaggattg gaaacaggaa accaaaaatt ctgtaccaat    180
gtcgtccgaa gcaaccatgt agtcatcgct tttacctcag ctctcactcc tgaagacaat    240
gaagtgaacc gtcacgttgg caagcatagt gatggagttc aagacattgc ctttagtgta    300
agtgacgcaa gagggatgta tgagaaagcg atagctaaag gctgtaaaag cttccgtgag    360
ccacaggttt tacaagatca atttggatct gttataatag cgtctctcca gacttatgga    420
gacactgttc acacattagt ccaaaatgtc gactatacag dacccttttt gcctggcttc    480
agagcaatca caaaagatga tccattaaac tctgcctttc ctcaggtaaa ttatgacatt    540
attgatcatg ttgtaggaaa tcagcctggt ggcgatatga ctcctacagt agaatggtat    600
gagaaatatc tagaatttca tcgatattgg tctgctgatg agtctgtaat ccataccgat    660
tattcagcat taaggtctgt tgtggttgct gattgggatg aagtgatcaa aatgcctatt    720
```

```
aatgagcctg ctgatggact tagaaaaagt caaatccaag aatatgtcga atattatggt   780
ggagcaggcg tacaacatat tgccttaaaa gtcaatgata ttatttcagt aataagcacc   840
ttaagggcta gaggtgtgga attcttagaa gttcctccta aatattatga tagcttaaga   900
aaaagacttg cgcattctgc ggtacaaatt gaagaagact taaaaagaat tgaagacctt   960
catattttgg ttgactttga cgaccgtggg tatttacttc agattttcac aaaaccagta  1020
gaagacagac ctactctgtt ttatgaaatt attcaaagac ataataacaa tggattcgga  1080
attggaaatt ttaaagcccc atttgaatca ttggaacaag agcaagaaag aagaggtaat  1140
ttgatctaa                                                         1149
```

<210> SEQ ID NO 38
<211> LENGTH: 350
<212> TYPE: PRT
<213> ORGANISM: Blephrisman japonicum

<400> SEQUENCE: 38

```
Met Asn Pro Ser Ile Arg Ile Val Gln Gly Ile His His Leu His Phe
1               5                   10                  15

Tyr Leu Trp Asp Leu Pro Arg Trp Arg Glu His Phe Cys Arg Val Trp
            20                  25                  30

Gly Phe Arg Val Ala Ser Asp Ala Gly Asn Thr Leu Glu Leu Glu Gln
        35                  40                  45

Gly Ser Leu Arg Leu Arg Leu Ser Gln Pro Ala Arg Ala Gly Asp Glu
    50                  55                  60

Val Asp Arg His Leu Gln Arg His Gly Pro Val Val Asp Val Ala
65                  70                  75                  80

Leu Ala Val Gly Glu Gln Glu Leu Pro Ala Leu Ala Glu Leu Leu Arg
                85                  90                  95

Gly Arg Gly Ala Gln Leu Ala Trp Ile Pro Ala Ala Ala Leu Cys
            100                 105                 110

Leu His Thr Pro Tyr Gly Ile Arg His Ser Leu Ile Pro Gly Pro Leu
        115                 120                 125

Asp Ala Ala Pro Ala Glu Ala Gly Leu Phe Ser His Trp Asp His Val
    130                 135                 140

Val Leu Asn Val Glu Gln Gly Ser Leu Gln Ala Ala Ala Asp Trp Tyr
145                 150                 155                 160

Gly Arg Val Leu Gly Trp Arg Arg Leu Tyr Arg Tyr Ser Ile Gly Thr
                165                 170                 175

Ala Thr Ser Gly Leu Glu Ser Val Val Val Gly Asp Pro Glu Ala Gly
            180                 185                 190

Ile Gln Trp Ala Ile Asn Glu Pro Thr Cys Ala Ala Ser Gln Ile Gln
        195                 200                 205

Glu Phe Leu His Ala His Gly Gly Pro Gly Ile Gln His Ala Ala Leu
    210                 215                 220

His Ser Ser Asp Ile Val Ala Ser Leu Arg Arg Leu Arg Gln Gly Gly
225                 230                 235                 240

Val Asp Phe Leu Gln Val Ala Pro Gln Tyr Tyr Thr Ser Leu Glu Arg
                245                 250                 255

Glu Leu Gly Leu Ala Leu Arg Ser Ala Leu Gly Gln Ala Ile Ser Trp
            260                 265                 270

Gln Asp Leu Val Glu Gln Gln Ile Leu Leu Asp Ala Thr Leu Pro Ala
        275                 280                 285
```

```
Ser Asp Gly Gln Asp Arg Pro Leu Leu Leu Gln Thr Phe Thr Gln Pro
    290                 295                 300

Leu Phe Gly Arg Pro Thr Phe Phe Glu Val Ile Gln Arg Leu Gly
305                 310                 315                 320

Gly Ala Thr Gly Phe Gly Glu Ala Asn Phe Gln Ala Leu Phe Glu Ala
                325                 330                 335

Leu Glu Arg Gln Gln Arg Gln Arg His Gln Ala Leu Thr Pro
            340                 345                 350
```

<210> SEQ ID NO 39
<211> LENGTH: 1107
<212> TYPE: DNA
<213> ORGANISM: Picrophilus torridus

<400> SEQUENCE: 39

```
atgtatggca aaaatttaat ctcagaacta agggaaaagg agatctttaa acgattacat      60
cacgtggaat tttacgttag cagtgccaaa acatggtcat atttcatgaa cagggggtctt    120
ggatttaaaa cagtggcata tgccggtcca gaaaccggga taaggacaa gatatcctat     180
gttatgtccc agggcactgc aaggatatct tttacatcat caatgaatga tgatagctat    240
atatcgaatc atgttaaaaa acacggggat ggcgtaaagg atatagcact tgaggtcgat    300
gatctggacg aggcaaaaag cctgatagaa agtatggaa caaggttttc aaaaataaat    360
gaaataaagg atggaaatgg aagataaga actgcagaga taaaaacgta cggtgaaacc    420
gttcatacat taatagaaac cggggattac aatggcgtat tcatgcccgg ttatgaggaa    480
tctgaaataa attcaaaaaa cactgggata aaaaagatcg atcatatagt tggaaatgtc    540
tatgagggcg atatggatag ctgggttaat ttttacatag aaaaacttgg ctttgagcat    600
ttaataacct tgatgataa agatataaga actgattaca gcgcattaag atcaaaggtt    660
gtaaaataca atgacgatat cgtatttcca ataaatgagc ctgcaaaggg cttaagaaaa    720
tcacagatag aggaatatct tgactattac aggtctgagg gcgttcagca catagcactg    780
ttaactgatg atataataaa aactgtatcc atgatggagg aaaacggcat agaatttta    840
aaaacaccag atcatacta tgaatcccta tcatcaagga taggctcaat agacgaggat    900
ttaaatgaaa tagagaaaca taacatactt gtggatcgtg atgagaacgg atacctatta    960
cagatcttca caaagcctgt tactgacagg ccaacgttct tctttgaggt catacagaga   1020
aagggtgcaa ggtcattcgg caacggtaac tttaaggcac ttttttgaggc gatagaaagg   1080
gagcaggcaa agagaggaaa cctatga                                       1107
```

<210> SEQ ID NO 40
<211> LENGTH: 368
<212> TYPE: PRT
<213> ORGANISM: Picrophilus torridus

<400> SEQUENCE: 40

```
Met Tyr Gly Lys Asn Leu Ile Ser Glu Leu Arg Glu Lys Glu Ile Phe
1               5                  10                  15

Lys Arg Leu His His Val Glu Phe Tyr Val Ser Ser Ala Lys Thr Trp
            20                  25                  30

Ser Tyr Phe Met Asn Arg Gly Leu Gly Phe Lys Thr Val Ala Tyr Ala
        35                  40                  45

Gly Pro Glu Thr Gly Ile Arg Asp Lys Ile Ser Tyr Val Met Ser Gln
    50                  55                  60

Gly Thr Ala Arg Ile Ser Phe Thr Ser Ser Met Asn Asp Asp Ser Tyr
```

```
                65                  70                  75                  80
Ile Ser Asn His Val Lys Lys His Gly Asp Gly Val Lys Asp Ile Ala
                    85                  90                  95

Leu Glu Val Asp Asp Leu Asp Glu Ala Lys Ser Leu Ile Glu Lys Tyr
                    100                 105                 110

Gly Thr Lys Val Ser Lys Ile Asn Glu Ile Lys Asp Gly Asn Gly Lys
                    115                 120                 125

Ile Arg Thr Ala Glu Ile Lys Thr Tyr Gly Glu Thr Val His Thr Leu
            130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                    165                 170                 175

Val Gly Asn Val Tyr Glu Gly Glu Met Asp Ser Trp Val Asn Phe Tyr
                    180                 185                 190

Ile Glu Lys Leu Gly Phe Glu His Leu Ile Thr Phe Asp Asp Lys Asp
                    195                 200                 205

Ile Arg Thr Asp Tyr Ser Ala Leu Arg Ser Lys Val Val Lys Tyr Asn
            210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Tyr Arg Ser Glu Gly Val Gln
                    245                 250                 255

His Ile Ala Leu Leu Thr Asp Asp Ile Ile Lys Thr Val Ser Met Met
                    260                 265                 270

Glu Glu Asn Gly Ile Glu Phe Leu Lys Thr Pro Gly Ser Tyr Tyr Glu
                    275                 280                 285

Ser Leu Ser Ser Arg Ile Gly Ser Ile Asp Glu Asp Leu Asn Glu Ile
            290                 295                 300

Glu Lys His Asn Ile Leu Val Asp Arg Asp Glu Asn Gly Tyr Leu Leu
305                 310                 315                 320

Gln Ile Phe Thr Lys Pro Val Thr Asp Arg Pro Thr Phe Phe Phe Glu
                    325                 330                 335

Val Ile Gln Arg Lys Gly Ala Arg Ser Phe Gly Asn Gly Asn Phe Lys
                    340                 345                 350

Ala Leu Phe Glu Ala Ile Glu Arg Glu Gln Ala Lys Arg Gly Asn Leu
                    355                 360                 365

<210> SEQ ID NO 41
<211> LENGTH: 1164
<212> TYPE: DNA
<213> ORGANISM: Kordia algicida

<400> SEQUENCE: 41
atggcagcag aaataaaaaa cttaaaagat ttacaaaata cagaatacgg actcaaaaaa      60
ttatttgacg aagcagaaga ctttcttcca cttttaggaa cagactacgt agaattatac    120
gtcgggaacg ccaaacaatc ggcacatttc tacaaaacgg cttttggttt tcaatcagaa    180
gcttacgcag gattggaaac aggattaacc gacagagttt catacgtatt aaaacaagat    240
aaaattcgct tggtcttaac aacaccatta ggaaaaggtg gcgaaatcaa tgagcatatc    300
gatttacacg gcgatggcgt aaaagtagta gcactttggg tagaagatgc tacaaaagcc    360
tttgaagaaa cgaccaaaag aggcgcaaaa ccgtacatgg aaccaacaaa agaagaagat    420 gaaacggat atgtaattcg ctcaggaatc tatacgtacg gagaaacggt tcatgttttt    480
```

```
gtagaacgta aaaactataa cggagtcttt ttaccaggat atcaaagatg ggaatctcac       540
tacaatccgg agccagttgg cttaaaattc atcgatcaca tggtaggaaa tgtaggttgg       600
ggagaaatga agaatggtg tgaattctac gcgaaagtaa tgggatttgc gcaaattatc        660
tcctttacag atgatgatat ttctaccgat tttactgcgt tgatgagtaa agtaatgagt       720
aatggaaatg gtagaatcaa atttccaatc aatgaacccg cagaaggaaa aaagaaatcg       780
caaattgaag aatatctaga cttttacaat ggttcaggag tacaacatat tgcggttgct       840
acagacaata ttattgatac ggtttcgcaa atgcgcgaac gtggagtaga attcttatac       900
gttccagata catattatga tgacttgtta aacgtgttg gcgacatcga tgaagatgta        960
gaagaactca aaaaacacgg aatcttaatt gatcgtgatg aagaaggata cttattgcag      1020
ttatttacca aaaccattgt agacagacca acaatgttct ttgaagtcat tcagcgtaaa      1080
ggcgcacaat catttggagt aggaaacttt aaagctttat ttgaagcgat agaaagagaa      1140
caagctgctc gcggaacatt gtaa                                             1164
```

<210> SEQ ID NO 42
<211> LENGTH: 368
<212> TYPE: PRT
<213> ORGANISM: Kordia algicida

<400> SEQUENCE: 42

```
Met Tyr Gly Lys Asn Leu Ile Ser Glu Leu Arg Glu Lys Glu Ile Phe
1               5                   10                  15

Lys Arg Leu His His Val Glu Phe Tyr Val Ser Ser Ala Lys Thr Trp
            20                  25                  30

Ser Tyr Phe Met Asn Arg Gly Leu Gly Phe Lys Thr Val Ala Tyr Ala
        35                  40                  45

Gly Pro Glu Thr Gly Ile Arg Asp Lys Ile Ser Tyr Val Met Ser Gln
    50                  55                  60

Gly Thr Ala Arg Ile Ser Phe Thr Ser Ser Met Asn Asp Asp Ser Tyr
65                  70                  75                  80

Ile Ser Asn His Val Lys Lys His Gly Asp Gly Val Lys Asp Ile Ala
                85                  90                  95

Leu Glu Val Asp Asp Leu Asp Glu Ala Lys Ser Leu Ile Glu Lys Tyr
            100                 105                 110

Gly Thr Lys Val Ser Lys Ile Asn Glu Ile Lys Asp Gly Asn Gly Lys
        115                 120                 125

Ile Arg Thr Ala Glu Ile Lys Thr Tyr Gly Thr Val His Thr Leu
    130                 135                 140

Ile Glu Thr Gly Asp Tyr Asn Gly Val Phe Met Pro Gly Tyr Glu Glu
145                 150                 155                 160

Ser Glu Ile Asn Ser Lys Asn Thr Gly Ile Lys Lys Ile Asp His Ile
                165                 170                 175

Val Gly Asn Val Tyr Glu Gly Glu Met Asp Ser Trp Val Asn Phe Tyr
            180                 185                 190

Ile Glu Lys Leu Gly Phe Glu His Leu Ile Thr Phe Asp Asp Lys Asp
        195                 200                 205

Ile Arg Thr Asp Tyr Ser Ala Leu Arg Ser Lys Val Val Lys Tyr Asn
    210                 215                 220

Asp Asp Ile Val Phe Pro Ile Asn Glu Pro Ala Lys Gly Leu Arg Lys
225                 230                 235                 240

Ser Gln Ile Glu Glu Tyr Leu Asp Tyr Tyr Arg Ser Glu Gly Val Gln
```

```
                245             250                 255
His Ile Ala Leu Leu Thr Asp Asp Ile Ile Lys Thr Val Ser Met Met
            260                 265                 270

Glu Glu Asn Gly Ile Glu Phe Leu Lys Thr Pro Gly Ser Tyr Tyr Glu
            275                 280             285

Ser Leu Ser Ser Arg Ile Gly Ser Ile Asp Glu Asp Leu Asn Glu Ile
        290                 295                 300

Glu Lys His Asn Ile Leu Val Asp Arg Asp Asn Gly Tyr Leu Leu
305                 310                 315                 320

Gln Ile Phe Thr Lys Pro Val Thr Asp Arg Pro Thr Phe Phe Glu
                325                 330                 335

Val Ile Gln Arg Lys Gly Ala Arg Ser Phe Gly Asn Gly Asn Phe Lys
            340                 345                 350

Ala Leu Phe Glu Ala Ile Glu Arg Glu Gln Ala Lys Arg Gly Asn Leu
            355                 360                 365

<210> SEQ ID NO 43
<211> LENGTH: 1206
<212> TYPE: DNA
<213> ORGANISM: Rhodococcus sp.

<400> SEQUENCE: 43
atgacgatcg agcagactct caccgacaag gaacgcctgg caggtctcga cctcggccag      60
ctcgagcagt tggtcgggct cgtcgagtac gacggcaccc gcgacccgtt cccggtcagc     120
ggctgggatg ccgtcgtctg ggtggtcggc aacgccaccc agaccgccca ctacttccag     180
tccgcgttcg ggatgaccct cgtcgcctac tccggaccca ccaccggcaa ccgcgaccac     240
cacagcttcg tcctcgaatc cggggccgtc cgcttcgtca tcaaaggcgc cgtgaacccg     300
gacagccccc tgatcgacca ccaccgcacc cacggcgacg gcgtcgtcga catcgccctc     360
gccgtccccg acgtcgacaa gtgcatcgcc cacgcccgcg cccagggcgc caccgtcctc     420
gacgaacccc acgacgtgac cgacgaccac ggcaccgtcc gcctcgccgc gatcgccacc     480
tacggcgaca cccgccacac cctcgtcgac cgcagccact acaccggccc ctacctgccc     540
ggctacaccc cccgcacctc cggccacacc aaacgggacg gggcacccaa cgcctgttc      600
caggccctcg accacgtcgt cggcaacgtc gaactcggca agatggacca ctgggtcgac     660
ttctacaacc gggtcatggg ctttacgaac atggccgagt cgtcggcga ggacatcgcc      720
accgactact ccgcgctgat gagcaaggtc gtctccaacg gcaaccaccg ggtcaagttc     780
cccctcaacg aacccgccct cgccaagaaa cgctcgcaga tcgacgaata cctcgacttc     840
taccgcggcc ccggcgccca gcacctggcc ctggccacca atgacatcct caccgccgtc     900
gaccagctga ccgccgaggg cgtcgagttc ctggccaccc ccgactccta ctacgaggac     960
cccgaactgc gggcccggat cggcaacgtc cgcgccccca tcgccgaact gcagaaacgc    1020
ggcatcctcg tcgaccgcga cgaagacggc tacctgctgc agatcttcac caaacccctc    1080
gtcgaccggc ccaccgtgtt cttcgaactc atcgaacgcc acggctccct cggcttcggc    1140
atcggcaact tcaaagccct cttcgaggcc atcgaacgcg aacaagccgc ccgcggaaac    1200
ttctga                                                              1206

<210> SEQ ID NO 44
<211> LENGTH: 401
<212> TYPE: PRT
<213> ORGANISM: Rhodococcus sp.
```

<400> SEQUENCE: 44

```
Met Thr Ile Glu Gln Thr Leu Thr Asp Lys Glu Arg Leu Ala Gly Leu
1               5                   10                  15

Asp Leu Gly Gln Leu Glu Gln Leu Val Gly Leu Val Glu Tyr Asp Gly
            20                  25                  30

Thr Arg Asp Pro Phe Pro Val Ser Gly Trp Asp Ala Val Val Trp Val
        35                  40                  45

Val Gly Asn Ala Thr Gln Thr Ala His Tyr Phe Gln Ser Ala Phe Gly
    50                  55                  60

Met Thr Leu Val Ala Tyr Ser Gly Pro Thr Thr Gly Asn Arg Asp His
65                  70                  75                  80

His Ser Phe Val Leu Glu Ser Gly Ala Val Arg Phe Val Ile Lys Gly
                85                  90                  95

Ala Val Asn Pro Asp Ser Pro Leu Ile Asp His His Arg Thr His Gly
            100                 105                 110

Asp Gly Val Val Asp Ile Ala Leu Ala Val Pro Asp Val Asp Lys Cys
        115                 120                 125

Ile Ala His Ala Arg Ala Gln Gly Ala Thr Val Leu Asp Glu Pro His
    130                 135                 140

Asp Val Thr Asp Asp His Gly Thr Val Arg Leu Ala Ala Ile Ala Thr
145                 150                 155                 160

Tyr Gly Asp Thr Arg His Thr Leu Val Asp Arg Ser His Tyr Thr Gly
                165                 170                 175

Pro Tyr Leu Pro Gly Tyr Thr Ala Arg Thr Ser Gly His Thr Lys Arg
            180                 185                 190

Asp Gly Ala Pro Lys Arg Leu Phe Gln Ala Leu Asp His Val Val Gly
        195                 200                 205

Asn Val Glu Leu Gly Lys Met Asp His Trp Val Asp Phe Tyr Asn Arg
    210                 215                 220

Val Met Gly Phe Thr Asn Met Ala Glu Phe Val Gly Glu Asp Ile Ala
225                 230                 235                 240

Thr Asp Tyr Ser Ala Leu Met Ser Lys Val Val Ser Asn Gly Asn His
                245                 250                 255

Arg Val Lys Phe Pro Leu Asn Glu Pro Ala Leu Ala Lys Lys Arg Ser
            260                 265                 270

Gln Ile Asp Glu Tyr Leu Asp Phe Tyr Arg Gly Pro Gly Ala Gln His
        275                 280                 285

Leu Ala Leu Ala Thr Asn Asp Ile Leu Thr Ala Val Asp Gln Leu Thr
    290                 295                 300

Ala Glu Gly Val Glu Phe Leu Ala Thr Pro Asp Ser Tyr Tyr Glu Asp
305                 310                 315                 320

Pro Glu Leu Arg Ala Arg Ile Gly Asn Val Arg Ala Pro Ile Ala Glu
                325                 330                 335

Leu Gln Lys Arg Gly Ile Leu Val Asp Arg Asp Glu Asp Gly Tyr Leu
            340                 345                 350

Leu Gln Ile Phe Thr Lys Pro Leu Val Asp Arg Pro Thr Val Phe Phe
        355                 360                 365

Glu Leu Ile Glu Arg His Gly Ser Leu Gly Phe Gly Ile Gly Asn Phe
    370                 375                 380

Lys Ala Leu Phe Glu Ala Ile Glu Arg Glu Gln Ala Ala Arg Gly Asn
385                 390                 395                 400

Phe
```

<210> SEQ ID NO 45
<211> LENGTH: 1209
<212> TYPE: DNA
<213> ORGANISM: Rhodococcus sp

<400> SEQUENCE: 45

| | | | | | |
|---|---|---|---|---|---|
| atgactaccg | ccgacattcg | cctgacgccc | cgcgaggtgg | ccgcacatct | ggagaccgac | 60 |
| gagctccggc | agttggtcgg | gctcgtcgaa | cacgacgacg | cgtcggatcc | gtttcccgtg | 120 |
| gtcgcgatgg | atgccgtggt | gttcgtgtgc | ggcaacgcga | cgcagagcac | gcagtacttc | 180 |
| gtctccacgt | ggggcatgac | cctcgtcgcc | tacgccgggc | cggagaccgg | tcagcgctcg | 240 |
| cacaagtcct | tcgtcctcga | gtcggggtcg | gcacggttcg | tgctgcacgg | cgccgtcgat | 300 |
| ccgaagagcc | cgctcgcgga | ccatcaccgg | gcgcacggcg | acggcgtggt | ggacctggcg | 360 |
| atggaagttc | tcgacgtcga | ccgctgcatc | gcgcatgcac | gctcgcaggg | ggccaccatt | 420 |
| ctcgaggagc | cgcgcgacgt | cacggatcag | ttcggcaccg | tgcggctcgc | ggcgatcgcc | 480 |
| acgtacggca | gcacccggca | caccatcgtc | gaccgaagcc | gatacgacgg | cccctacctc | 540 |
| cccggattcg | tcgcgcgctc | cagcggtttc | gcggcgcgac | cgggtaaacc | cccgcgattg | 600 |
| ttccaggcgc | tcgaccacgc | cgtcggcaac | gtcgagatgg | gccggatgga | tcactgggtc | 660 |
| cggttctaca | accgcgtcat | gggcttcacg | aacatggccg | aattcgtcgg | cgacgacatc | 720 |
| gccacggagt | actcggcgct | gatgtcgaag | gtcgtggcga | acggcaatca | ccgggtgaag | 780 |
| ttcccgctca | cgaacccgc | ggtgggaaag | aagaagtcgc | agatcgacga | atatctcgag | 840 |
| ttctacggtg | agccgggctg | ccagcatctg | gccctcgcga | ccggagacat | cctcgcgacg | 900 |
| gtggacgcgt | gcgggccga | gggtgtcgaa | ttcctgaaca | cccccgacgc | gtactacgag | 960 |
| gacccacagc | tgcgcgcccg | gatcggcagg | gtgcgggtgc | cggtggagga | actgcagaag | 1020 |
| cgccggaatcc | tcgtcgaccg | cgacgaggac | ggatacctcc | tgcagatctt | caccaaaccg | 1080 |
| ctcggcgacc | ggccgaccgt | gttcttcgag | gtgatcgaac | ggcacggttc | gctcgggttc | 1140 |
| ggggcgggta | acttccaggc | cctgttcgaa | tccatcgagc | gtgagcaggc | ggcgcgcggc | 1200 |
| aatctgtga | | | | | | 1209 |

<210> SEQ ID NO 46
<211> LENGTH: 402
<212> TYPE: PRT
<213> ORGANISM: Rhodococcus sp

<400> SEQUENCE: 46

Met Thr Thr Ala Asp Ile Arg Leu Thr Pro Arg Glu Val Ala Ala His
1               5                   10                  15

Leu Glu Thr Asp Glu Leu Arg Gln Leu Val Gly Leu Val Glu His Asp
            20                  25                  30

Asp Ala Ser Asp Pro Phe Pro Val Ala Met Asp Ala Val Val Phe
        35                  40                  45

Val Cys Gly Asn Ala Thr Gln Ser Thr Gln Tyr Phe Val Ser Thr Trp
    50                  55                  60

Gly Met Thr Leu Val Ala Tyr Ala Gly Pro Glu Thr Gly Gln Arg Ser
65                  70                  75                  80

His Lys Ser Phe Val Leu Glu Ser Gly Ser Ala Arg Phe Val Leu His
                85                  90                  95

Gly Ala Val Asp Pro Lys Ser Pro Leu Ala Asp His His Arg Ala His
            100                 105                 110

Gly Asp Gly Val Val Asp Leu Ala Met Glu Val Leu Asp Val Asp Arg
            115                 120                 125

Cys Ile Ala His Ala Arg Ser Gln Gly Ala Thr Ile Leu Glu Glu Pro
        130                 135                 140

Arg Asp Val Thr Asp Gln Phe Gly Thr Val Arg Leu Ala Ala Ile Ala
145                 150                 155                 160

Thr Tyr Gly Ser Thr Arg His Thr Ile Val Asp Arg Ser Arg Tyr Asp
                165                 170                 175

Gly Pro Tyr Leu Pro Gly Phe Val Ala Arg Ser Ser Gly Phe Ala Ala
            180                 185                 190

Arg Pro Gly Lys Pro Arg Leu Phe Gln Ala Leu Asp His Ala Val
        195                 200                 205

Gly Asn Val Glu Met Gly Arg Met Asp His Trp Val Arg Phe Tyr Asn
    210                 215                 220

Arg Val Met Gly Phe Thr Asn Met Ala Glu Phe Val Gly Asp Asp Ile
225                 230                 235                 240

Ala Thr Glu Tyr Ser Ala Leu Met Ser Lys Val Val Ala Asn Gly Asn
                245                 250                 255

His Arg Val Lys Phe Pro Leu Asn Glu Pro Ala Val Gly Lys Lys Lys
            260                 265                 270

Ser Gln Ile Asp Glu Tyr Leu Glu Phe Tyr Gly Glu Pro Gly Cys Gln
        275                 280                 285

His Leu Ala Leu Ala Thr Gly Asp Ile Leu Ala Thr Val Asp Ala Leu
    290                 295                 300

Arg Ala Glu Gly Val Glu Phe Leu Asn Thr Pro Asp Ala Tyr Tyr Glu
305                 310                 315                 320

Asp Pro Gln Leu Arg Ala Arg Ile Gly Arg Val Arg Val Pro Val Glu
                325                 330                 335

Glu Leu Gln Lys Arg Gly Ile Leu Val Asp Arg Asp Glu Asp Gly Tyr
            340                 345                 350

Leu Leu Gln Ile Phe Thr Lys Pro Leu Gly Asp Arg Pro Thr Val Phe
        355                 360                 365

Phe Glu Val Ile Glu Arg His Gly Ser Leu Gly Phe Gly Ala Gly Asn
    370                 375                 380

Phe Gln Ala Leu Phe Glu Ser Ile Glu Arg Glu Gln Ala Ala Arg Gly
385                 390                 395                 400

Asn Leu

<210> SEQ ID NO 47
<211> LENGTH: 1161
<212> TYPE: DNA
<213> ORGANISM: Arabidopsis thaliana

<400> SEQUENCE: 47
atggagctct cgatctcaca atcaccgcgt gttcggttct cgtctctggc gcctcgtttc        60
ttagcagctt ctcatcatca tcgtccttct gtgcatttag ctgggaagtt tataagcctc       120
cctcgagatg ttcgcttcac gagcttatca acttcaagaa tgcggtccaa atttgtttca       180
accaattata gaaaaatctc aatccgggca tgttctcagg ttggtgctgc tgagtctgat       240
gatccagtgc tggatagaat tgcccggttc caaaatgctt gctggagatt cttagaccc        300 catacaatcc gcggaacagc tttaggatcc actgccttgg tgacaagagc tttgatagag       360
aacactcatt tgatcaaatg gagtcttgta ctaaaggcac tttcaggtct tcttgctctt       420
atttgtggga atggttatat agtcggcatc aatcagatct acgacattgg aatcgacaaa       480

```
gtgaacaaac catacttgcc aatagcagca ggagatctat cagtgcagtc tgcttggttg     540
ttagtgatat tttttgcgat agcagggctt ttagttgtcg gatttaactt tggtccattc     600
attacaagcc tatactctct tggccttttt ctgggaacca tctattctgt tccacccctc     660
agaatgaaaa gattcccagt tgcagcattt cttattattg ccacggtacg aggtttcctt     720
cttaactttg gtgtgtacca tgctacaaga gctgctcttg gacttccatt tcagtggagt     780
gcacctgtgg cgttcatcac atcttttgtg acactgtttg cactggtcat tgctattaca     840
aaggaccttc tgatgttga aggagatcga aagttccaaa tatcaaccct ggcaacaaaa     900
cttggagtga gaaacattgc attcctcggt tctggacttc tgctagtaaa ttatgtttca     960
gccatatcac tagctttcta catgcctcag gtttttagag gtagcttgat gattcctgca    1020
catgtgatct tggcttcagg cttaattttc cagacatggg tactagaaaa agcaaaactac   1080 accaaggaag ctatctcagg atattatcgg tttatatgga atctcttcta cgcagagtat   1140
ctgttattcc ccttcctcta g                                               1161
```

<210> SEQ ID NO 48
<211> LENGTH: 386
<212> TYPE: PRT
<213> ORGANISM: Arabidopsis thaliana

<400> SEQUENCE: 48

```
Met Glu Leu Ser Ile Ser Gln Ser Pro Arg Val Arg Phe Ser Leu
1               5                   10                  15

Ala Pro Arg Phe Leu Ala Ala Ser His His Arg Pro Ser Val His
            20                  25                  30

Leu Ala Gly Lys Phe Ile Ser Leu Pro Arg Asp Val Arg Phe Thr Ser
        35                  40                  45

Leu Ser Thr Ser Arg Met Arg Ser Lys Phe Val Ser Thr Asn Tyr Arg
50                  55                  60

Lys Ile Ser Ile Arg Ala Cys Ser Gln Val Gly Ala Ala Glu Ser Asp
65                  70                  75                  80

Asp Pro Val Leu Asp Arg Ile Ala Arg Phe Gln Asn Ala Cys Trp Arg
                85                  90                  95

Phe Leu Arg Pro His Thr Ile Arg Gly Thr Ala Leu Gly Ser Thr Ala
            100                 105                 110

Leu Val Thr Arg Ala Leu Ile Glu Asn Thr His Leu Ile Lys Trp Ser
        115                 120                 125

Leu Val Leu Lys Ala Leu Ser Gly Leu Leu Ala Leu Ile Cys Gly Asn
    130                 135                 140

Gly Tyr Ile Val Gly Ile Asn Gln Ile Tyr Asp Ile Gly Ile Asp Lys
145                 150                 155                 160

Val Asn Lys Pro Tyr Leu Pro Ile Ala Ala Gly Asp Leu Ser Val Gln
                165                 170                 175

Ser Ala Trp Leu Leu Val Ile Phe Phe Ala Ile Ala Gly Leu Leu Val
            180                 185                 190

Val Gly Phe Asn Phe Gly Pro Phe Ile Thr Ser Leu Tyr Ser Leu Gly
        195                 200                 205

Leu Phe Leu Gly Thr Ile Tyr Ser Val Pro Pro Leu Arg Met Lys Arg
    210                 215                 220

Phe Pro Val Ala Ala Phe Leu Ile Ile Ala Thr Val Arg Gly Phe Leu
225                 230                 235                 240

Leu Asn Phe Gly Val Tyr His Ala Thr Arg Ala Ala Leu Gly Leu Pro
```

```
                245                 250                 255
Phe Gln Trp Ser Ala Pro Val Ala Phe Ile Thr Ser Phe Val Thr Leu
            260                 265                 270

Phe Ala Leu Val Ile Ala Ile Thr Lys Asp Leu Pro Asp Val Glu Gly
        275                 280                 285

Asp Arg Lys Phe Gln Ile Ser Thr Leu Ala Thr Lys Leu Gly Val Arg
    290                 295                 300

Asn Ile Ala Phe Leu Gly Ser Gly Leu Leu Val Asn Tyr Val Ser
305                 310                 315                 320

Ala Ile Ser Leu Ala Phe Tyr Met Pro Gln Val Phe Arg Gly Ser Leu
                325                 330                 335

Met Ile Pro Ala His Val Ile Leu Ala Ser Gly Leu Ile Phe Gln Thr
            340                 345                 350

Trp Val Leu Glu Lys Ala Asn Tyr Thr Lys Glu Ala Ile Ser Gly Tyr
        355                 360                 365

Tyr Arg Phe Ile Trp Asn Leu Phe Tyr Ala Glu Tyr Leu Leu Phe Pro
    370                 375                 380

Phe Leu
385

<210> SEQ ID NO 49
<211> LENGTH: 1113
<212> TYPE: DNA
<213> ORGANISM: Chlamydomonas

<400> SEQUENCE: 49
atggaccttt gcagctcaac tggaagagga gcatgccttt cgccggcatc cacgtcgcgg      60
ccgtgcccag caccagtgca tttgcgcggc cgacgcctgg ctttctctcc ggctcagcct     120
gctggacggc gccacttgcc ggtgctctca tctgcagcgg tccccgctcc cctcccaaat     180
ggtggaaacg acgagagctt cgcacaaaaa ctggctaact tccaaacgc cttctggaag      240 ttcctgcggc cacacaccat ccgggggact atcctgggca ccacagctgt gaccgccaag     300
gtccttatgg agaaccccgg ctgcatagac tgggcactgc tgccgaaggc gctgctcggc     360
ctggtggcgc tgctgtgcgg caacggctac attgtgggca tcaaccaaat ctacgacgtc     420
gacattgacg tggtcaacaa gccattcctc cccgtggcgt cgggcgagct gtcgccggcg     480
ctggcgtggg gcctgtgtct gtcgctggcg gctgcgggcg cgggcatcgt agccgccaac     540
ttcggcaacc tcatcaccag cctctacacc tttggcctct tcctgggcac cgtgtacagt     600
gtgcctcccc tgcgcctgaa gcagtacgcg gtgccggcct tcatgatcat cgccacggtg     660
cgcggcttcc tgctcaactt cggcgtgtac agcgccacgc gggcggcact gggactgccc     720
ttcgagtgga gccggccgt cagcttcatc acggtgtttg tgacgctgtt tgccactgtg     780
atcgccatca ccaaggacct gccggacgtg gagggcgacc aggccaacaa catctccacc     840
ttcgccacgc gcatgggcgt gcgcaacgtg gcactgctgg ccatcggcct tctcatggcc     900
aactacctgg tgccatcgc gctggcactc acctactcca ccgccttcaa cgtgccgctc     960
atggcgggcg cgcacgccat cctggccgcc acgctggcgc tgcgcacgct caagctgcac    1020
gccgccagct acagccggga ggcggtgcg tccttctacc gctggatctg gaacctgttc     1080
tacgccgagt acgcgctgct gccgttcctg tag                                  1113

<210> SEQ ID NO 50
<211> LENGTH: 370
<212> TYPE: PRT
```

<213> ORGANISM: Chlamydomonas

<400> SEQUENCE: 50

```
Met Asp Leu Cys Ser Ser Thr Gly Arg Gly Ala Cys Leu Ser Pro Ala
 1               5                  10                  15
Ser Thr Ser Arg Pro Cys Pro Ala Pro Val His Leu Arg Gly Arg Arg
             20                  25                  30
Leu Ala Phe Ser Pro Ala Gln Pro Ala Gly Arg Arg His Leu Pro Val
         35                  40                  45
Leu Ser Ser Ala Ala Val Pro Ala Pro Leu Pro Asn Gly Gly Asn Asp
     50                  55                  60
Glu Ser Phe Ala Gln Lys Leu Ala Asn Phe Asn Ala Phe Trp Lys
 65                  70                  75                  80
Phe Leu Arg Pro His Thr Ile Arg Gly Thr Ile Leu Gly Thr Ala
                 85                  90                  95
Val Thr Ala Lys Val Leu Met Glu Asn Pro Gly Cys Ile Asp Trp Ala
                100                 105                 110
Leu Leu Pro Lys Ala Leu Leu Gly Leu Val Ala Leu Cys Gly Asn
            115                 120                 125
Gly Tyr Ile Val Gly Ile Asn Gln Ile Tyr Asp Val Asp Ile Asp Val
        130                 135                 140
Val Asn Lys Pro Phe Leu Pro Val Ala Ser Gly Glu Leu Ser Pro Ala
145                 150                 155                 160
Leu Ala Trp Gly Leu Cys Leu Ser Leu Ala Ala Ala Gly Ala Gly Ile
                165                 170                 175
Val Ala Ala Asn Phe Gly Asn Leu Ile Thr Ser Leu Tyr Thr Phe Gly
                180                 185                 190
Leu Phe Leu Gly Thr Val Tyr Ser Val Pro Pro Leu Arg Leu Lys Gln
            195                 200                 205
Tyr Ala Val Pro Ala Phe Met Ile Ile Ala Thr Val Arg Gly Phe Leu
        210                 215                 220
Leu Asn Phe Gly Val Tyr Ser Ala Thr Arg Ala Ala Leu Gly Leu Pro
225                 230                 235                 240
Phe Glu Trp Ser Pro Ala Val Ser Phe Ile Thr Val Phe Val Thr Leu
                245                 250                 255
Phe Ala Thr Val Ile Ala Ile Thr Lys Asp Leu Pro Asp Val Glu Gly
                260                 265                 270
Asp Gln Ala Asn Asn Ile Ser Thr Phe Ala Thr Arg Met Gly Val Arg
            275                 280                 285
Asn Val Ala Leu Leu Ala Ile Gly Leu Leu Met Ala Asn Tyr Leu Gly
        290                 295                 300
Ala Ile Ala Leu Ala Leu Thr Tyr Ser Thr Ala Phe Asn Val Pro Leu
305                 310                 315                 320
Met Ala Gly Ala His Ala Ile Leu Ala Ala Thr Leu Ala Leu Arg Thr
                325                 330                 335
Leu Lys Leu His Ala Ala Ser Tyr Ser Arg Glu Ala Val Ala Ser Phe
            340                 345                 350
Tyr Arg Trp Ile Trp Asn Leu Phe Tyr Ala Glu Tyr Ala Leu Leu Pro
        355                 360                 365
Phe Leu
    370
```

<210> SEQ ID NO 51
<211> LENGTH: 1305

```
<212> TYPE: DNA
<213> ORGANISM: Hordeum vulgare

<400> SEQUENCE: 51
atggcacctc caactccaac aacacctgcc gctactggtg cagccgcagc tgtaactcct      60
gaacatgcga ggccacatcg gatggttcga ttcaatccga gatctgatag attccatact     120
ctgagcttcc atcatgtgga attctggtgt gctgatgcag cttctgcagc tggacgtttc     180
gcttttgccc ttggagctcc tttagcagcg agatcagact tgagcacagg aaacagtgca     240
cacgcatctc aacttctgcg ttcaggaagc cttgcgttcc tgtttactgc accgtatgct     300
aacggatgcg acgcagcaac tgcctcactt ccttctttca gtgcagatgc agctagacga     360
ttctcagccg atcatggaat tgcagtcaga tctgtggctt tgcgagttgc tgatgctgcc     420
gaagcttcca gggcatcagt tgatggaggt gctaggcctg cttttgctcc tgtggacttg     480
ggtagaggat ttggctttgc cgaggtcgaa ctctatggtg atgtggttct ccggtttgtc     540
tctcacccag atgaacagaa tgttcctttc ttgccagggt ttgagggagt gacaaaccca     600
gatgcggtag attacggtct cacgagattc gaccatgtag tgggcaatgt accggaattg     660
gctcctgcgg ctgcttacat agctggcttt acgggatttc acgaattcgc ggaattcacc     720
gctgaggatg tcggaaccac agaatcaggg ctgaattccg tcgtccttgc caacaattcc     780
gaagggtat tgctgcctct taacgagcct gtgcatggca cgaaaagacg tagccagata     840
cagaccttcc tagaacatca cggtggacca ggtgttcaac acattgctgt tgccagcagt     900
gatgtactca ggacgcttcg taagatgaga gctaggagtg cgatgggagg gtttgacttt     960
ctaccacctc cgctgccaaa atactatgag ggtgtgagga actggctgg tgatgttttg    1020
tctgaagcgc agatcaagga gtgtcaggaa ttaggggtgc tcgttgacag agatgatcaa    1080
ggggtgcttc tccagatctt tactaagccg gttggtgata ggcctaccct ctttctagag    1140
atgattcaac gtatcgggtg tatggaaaag gacgagagag tgaggagta tcaaaagggt    1200
ggatgcggcg gttttgggaa aggtaatttc tccgagctgt tcaagtcgat cgaagattac    1260
gagaaatccc ttgaggcgaa acaatctgca gctgttcaag gatcg                    1305

<210> SEQ ID NO 52
<211> LENGTH: 1338
<212> TYPE: DNA
<213> ORGANISM: Arabidopsis

<400> SEQUENCE: 52
atgggccacc aaaacgccgc cgtttcagag aatcaaaacc atgatgacgg cgctgcgtcg      60
tcgccgggat tcaagctcgt cggatttttcc aagttcgtaa gaaagaatcc aaagtctgat    120
aaattcaagg ttaagcgctt ccatcacatc gagttctggt gcggcgacgc aaccaacgtc    180
gctcgtcgct tctcctgggg tctggggatg agattctccg ccaaatccga tcttttccacc    240
ggaaacatgg ttcacgcctc ttacctactc acctccggtg acctccgatt ccttttcact    300
gctccttact ctccgtctct ctccgccgga gagattaaac cgacaaccac agcttctatc    360
ccaagtttcg atcacggctc ttgtcgttcc ttcttctctt cacatggtct cggtgttaga    420
gccgttgcga ttgaagtaga agacgcagag tcagctttct ccatcagtgt agctaatggc    480
gctattcctt cgtcgcctcc tatcgtcctc aatgaagcag ttacgatcgc tgaggttaaa    540
ctatacggcg atgttgttct ccgatatgtt agttacaaag cagaagatac cgaaaaatcc    600
gaattcttgc cagggttcga gcgtgtagag gatgcgtcgt cgttcccatt ggattatggt    660
```

-continued

```
atccggcggc ttgaccacgc cgtgggaaac gttcctgagc ttggtccggc tttaacttat   720
gtagcggggt tcactggttt tcaccaattc gcagagttca cagcagacga cgttggaacc   780
gccgagagcg gtttaaattc agcggtcctg gctagcaatg atgaaatggt tcttctaccg   840
attaacgagc cagtgcacgg aacaaagagg aagagtcaga ttcagacgta tttggaacat   900
aacgaaggcg cagggctaca catctggct  ctgatgagtg aagacatatt caggaccctg   960
agagagatga ggaagaggag cagtattgga ggattcgact tcatgccttc tcctccgcct  1020
acttactacc agaatctcaa gaaacgggtc ggcgacgtgc tcagcgatga tcagatcaag  1080
gagtgtgagg aattagggat tcttgtagac agagatgatc aagggacgtt gcttcaaatc  1140
ttcacaaaac cactaggtga caggccgacg atatttatag agataatcca gagagtagga  1200
tgcatgatga agatgagga  agggaaggct taccagagtg gaggatgtgg tggttttggc  1260
aaaggcaatt tctctgagct cttcaagtcc attgaagaat acgaaaagac tcttgaagcc  1320
aaacagttag tgggatga                                                1338
```

<210> SEQ ID NO 53
<211> LENGTH: 445
<212> TYPE: PRT
<213> ORGANISM: Arabidopsis

<400> SEQUENCE: 53

```
Met Gly His Gln Asn Ala Ala Val Ser Glu Asn Gln Asn His Asp Asp
  1               5                  10                  15

Gly Ala Ala Ser Ser Pro Gly Phe Lys Leu Val Gly Phe Ser Lys Phe
             20                  25                  30

Val Arg Lys Asn Pro Lys Ser Asp Lys Phe Lys Val Lys Arg Phe His
         35                  40                  45

His Ile Glu Phe Trp Cys Gly Asp Ala Thr Asn Val Ala Arg Arg Phe
     50                  55                  60

Ser Trp Gly Leu Gly Met Arg Phe Ser Ala Lys Ser Asp Leu Ser Thr
 65                  70                  75                  80

Gly Asn Met Val His Ala Ser Tyr Leu Leu Thr Ser Gly Asp Leu Arg
                 85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
    210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255
```

```
Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
            340                 345                 350

Val Leu Ser Asp Asp Gln Ile Lys Glu Cys Glu Glu Leu Gly Ile Leu
        355                 360                 365

Val Asp Arg Asp Asp Gln Gly Thr Leu Leu Gln Ile Phe Thr Lys Pro
    370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445

<210> SEQ ID NO 54
<211> LENGTH: 1299
<212> TYPE: DNA
<213> ORGANISM: Chlamydomonas

<400> SEQUENCE: 54
atgggcgctg gtggcgcttc taccacggta gcgaatggcg ggatcaagtt ggtagggcac      60
aagaattttg tgcgctataa tccacaatcc gaccggtttg ctattaagag gttccatagc     120
ttcgagttct ggtgcgcgga tgcgaccaac acatacaagc ggttctctta tggcctgggc     180
atgccgctgg tcgccaagtc cgaccagtcc accaacaacc agctctttgc ctcctacgtg     240
ctgcgctcca cgacctggt cttcaccttc accgcgccct acagccgcaa gtgcgcctcg     300
gtcagcgagg gcgttccgct gcgtcactac aacatcgacc atgcgtatga gttcatcaac     360
tcgcacgggc tggcggtgcg ggcagtaggc ctgctggtgg atgacgccaa gacggcgtac     420
gaggtgtctg tggcgcacgg ggccaagggc gtgctgccgc cggtggagtt gcgggatgag     480
gcgagcggca ccagccaggt catctcggag gtcattgttt acgggacgt cgttttccgc     540 tacgtgtcgg gctccttcga gggccctttc atggccggct acacgccagt cacagactcg     600
ccggtcgcgt cgattgggtt acagcgcgtg gaccacgcgg tgggcaacac acacgacctg     660
atcaaggccg tggagtacat caccgggttc tgtggcttcc acgagttctc agagtttgtt     720
gcggaggacg tgggcactgt ggacagcggc ctgaacagca tggtgcttgc caacaacgag     780
gagaccatat tgatgcctgt gaacgagccc accttcggca cgccgcgcaa gagccaaatc     840
cagacctacc tggagcagaa cgaggggccg gggctgcagc acctggcgct gctcagcaac     900
gacatcttca ccaccctgcg ggagatgcgc gcgcgcagcg agctgggtgg cttcgagttc     960
atgccgcggg caaatgcgaa gtactacaaa gacatgtacg cccgcatcgg cgactcgctc    1020
```

-continued

```
acgccgcagc agtacaggga ggtggaggag ctgggcatcc tggtggacaa ggacgaccag    1080
ggcgtgctgc tgcagatctt caccaagccg ctgggcgacc ggcccacggt gtttattgag    1140
atcatccagc gtgtgggctg catgcgggag gtgaaggagc tgctacgggg cgctgtggtg    1200
gggacggagc aggcggctgg ctgcggcggc ttcgggaaag gcaacttcgg cgccctcttc    1260
aagtccattg aggactatga gcgcacccta aatgtgtag                            1299
```

<210> SEQ ID NO 55
<211> LENGTH: 432
<212> TYPE: PRT
<213> ORGANISM: Chamydomonas

<400> SEQUENCE: 55

```
Met Gly Ala Gly Gly Ala Ser Thr Thr Val Ala Asn Gly Gly Ile Lys
1               5                   10                  15

Leu Val Gly His Lys Asn Phe Val Arg Tyr Asn Pro Gln Ser Asp Arg
            20                  25                  30

Phe Ala Ile Lys Arg Phe His Ser Phe Glu Phe Trp Cys Ala Asp Ala
        35                  40                  45

Thr Asn Thr Tyr Lys Arg Phe Ser Tyr Gly Leu Gly Met Pro Leu Val
    50                  55                  60

Ala Lys Ser Asp Gln Ser Thr Asn Asn Gln Leu Phe Ala Ser Tyr Val
65                  70                  75                  80

Leu Arg Ser Asn Asp Leu Val Phe Thr Phe Thr Ala Pro Tyr Ser Arg
                85                  90                  95

Lys Cys Ala Ser Val Ser Glu Gly Val Pro Leu Arg His Tyr Asn Ile
            100                 105                 110

Asp His Ala Tyr Glu Phe Ile Asn Ser His Gly Leu Ala Val Arg Ala
        115                 120                 125

Val Gly Leu Leu Val Asp Asp Ala Lys Thr Ala Tyr Glu Val Ser Val
    130                 135                 140

Ala His Gly Ala Lys Gly Val Leu Pro Pro Val Glu Leu Arg Asp Glu
145                 150                 155                 160

Ala Ser Gly Thr Ser Gln Val Ile Ser Glu Val Ile Val Tyr Gly Asp
                165                 170                 175

Val Val Phe Arg Tyr Val Ser Gly Ser Phe Glu Gly Pro Phe Met Ala
            180                 185                 190

Gly Tyr Thr Pro Val Thr Asp Ser Pro Val Ala Ser Ile Gly Leu Gln
        195                 200                 205

Arg Val Asp His Ala Val Gly Asn Thr His Asp Leu Ile Lys Ala Val
    210                 215                 220

Glu Tyr Ile Thr Gly Phe Cys Gly Phe His Glu Phe Ser Glu Phe Val
225                 230                 235                 240

Ala Glu Asp Val Gly Thr Val Asp Ser Gly Leu Asn Ser Met Val Leu
                245                 250                 255

Ala Asn Asn Glu Glu Thr Ile Leu Met Pro Val Asn Glu Pro Thr Phe
            260                 265                 270

Gly Thr Pro Arg Lys Ser Gln Ile Gln Thr Tyr Leu Glu Gln Asn Glu
        275                 280                 285

Gly Pro Gly Leu Gln His Leu Ala Leu Leu Ser Asn Asp Ile Phe Thr
    290                 295                 300

Thr Leu Arg Glu Met Arg Ala Arg Ser Glu Leu Gly Gly Phe Glu Phe
305                 310                 315                 320

Met Pro Arg Ala Asn Ala Lys Tyr Tyr Lys Asp Met Tyr Ala Arg Ile
```

```
                      325                 330                 335
Gly Asp Ser Leu Thr Pro Gln Gln Tyr Arg Glu Val Glu Glu Leu Gly
                340                 345                 350

Ile Leu Val Asp Lys Asp Gln Gly Val Leu Leu Gln Ile Phe Thr
            355                 360                 365

Lys Pro Leu Gly Asp Arg Pro Thr Val Phe Ile Glu Ile Ile Gln Arg
        370                 375                 380

Val Gly Cys Met Arg Glu Val Lys Glu Pro Ala Thr Gly Ala Val Val
385                 390                 395                 400

Gly Thr Glu Gln Ala Ala Gly Cys Gly Gly Phe Gly Lys Gly Asn Phe
                405                 410                 415

Gly Ala Leu Phe Lys Ser Ile Glu Asp Tyr Glu Arg Thr Leu Asn Val
                420                 425                 430

<210> SEQ ID NO 56
<211> LENGTH: 1299
<212> TYPE: DNA
<213> ORGANISM: Chlamydomonas

<400> SEQUENCE: 56
```

| | | | | | |
|---|---|---|---|---|---|
| atgggagcgg | gtggtgcagg | caccggagat | cgggaggggg | gcattaagct | cgtgggctac | 60 |
| aagaatttcg | tgcgccagaa | cccgctttca | gacaaattca | ccgtccacaa | gtttcatcac | 120 |
| atcgatttct | ggtgcggaga | tgcaacaaac | acatcgaagc | ggttctccta | cggcctgggc | 180 |
| atgccgctgg | tcgccaagtc | cgaccagtcc | accaacaacc | agctctttgc | ctcctacgtg | 240 |
| ctgcgctcca | cgacctggt | cttcaccttc | accgcgccct | acagccgcaa | gtgcgcctcg | 300 |
| gtcagcgagg | gcgttccgct | gcgtcactac | aacatcgacc | atgcgtatga | gttcatcaac | 360 |
| tcgcacgggc | tggcggtgcg | ggcagtaggc | ctgctggtgg | atgacgccaa | gacggcgtac | 420 |
| gaggtgtctg | tggcgcacgg | ggccaagggc | gtgctgccgc | cggtggagct | gcgggatgag | 480 |
| gcgagcggca | ccagccaggt | catctcggag | gtgctgctgt | acggcgaggt | cgtgctgcgc | 540 |
| tacgtgtcgg | gctccttcca | gggcccttc | ctggccggct | acacgcccgt | cacagactcg | 600 |
| gccgtgacct | ccttcggcct | gcaacgtctg | gaccacgcgg | tgggcaacac | ccatgacctg | 660 |
| atcaaggccg | tggagtacat | caccggcttc | acaggtttcc | acgagttctc | agagtttgtt | 720 |
| gcggaggacg | tgggcactgt | ggacagcggc | ctgaacagca | tggtgctggc | ctccaacaac | 780 |
| gaggcagtgc | tgctgcctgt | gaacgagccc | acctttggca | cgccgcgcaa | gagccaaatc | 840 |
| cagacctacc | tggagcagaa | cgaggggccg | ggctgcagc | acctggcgct | gctcagcaac | 900 |
| gacatcttca | ccaccctgcg | ggagatgcgc | gcgcgcagcg | agctgggtgg | cttcgagttc | 960 |
| atgccacggg | caaatgccaa | gtactacaaa | gacatgtacg | cccgcatcgg | cgactcgctc | 1020 |
| acgccgcagc | agtacaggga | ggtggaggag | ctgggcatcc | tggtggacaa | ggacgaccag | 1080 |
| ggcgtgctgc | tgcagatctt | caccaagccg | ctgggcgacc | ggcccacggt | gtttattgag | 1140 |
| atcatccagc | gtgtgggctg | catgcgggag | gtgaaagagc | ctgctacggg | cgctgtggtg | 1200 |
| gggacggagc | aggcggctgg | ctgcggcggc | ttcgggaaag | gcaacttcgg | tgccctcttc | 1260 |
| aagtccattg | aggactatga | gcgcacctta | aatgtttaa | | | 1299 |

```
<210> SEQ ID NO 57
<211> LENGTH: 432
<212> TYPE: PRT
<213> ORGANISM: Chlamydomonas

<400> SEQUENCE: 57
```

-continued

```
Met Gly Ala Gly Gly Ala Gly Thr Gly Asp Arg Glu Gly Gly Ile Lys
1               5                   10                  15

Leu Val Gly Tyr Lys Asn Phe Val Arg Gln Asn Pro Leu Ser Asp Lys
            20                  25                  30

Phe Thr Val His Lys Phe His Ile Asp Phe Trp Cys Gly Asp Ala
        35                  40                  45

Thr Asn Thr Ser Lys Arg Phe Ser Tyr Gly Leu Gly Met Pro Leu Val
    50                  55                  60

Ala Lys Ser Asp Gln Ser Thr Asn Asn Gln Leu Phe Ala Ser Tyr Val
65                  70                  75                  80

Leu Arg Ser Asn Asp Leu Val Phe Thr Phe Thr Ala Pro Tyr Ser Arg
                85                  90                  95

Lys Cys Ala Ser Val Ser Glu Gly Val Pro Leu Arg His Tyr Asn Ile
                100                 105                 110

Asp His Ala Tyr Glu Phe Ile Asn Ser His Gly Leu Ala Val Arg Ala
        115                 120                 125

Val Gly Leu Leu Val Asp Asp Ala Lys Thr Ala Tyr Glu Val Ser Val
    130                 135                 140

Ala His Gly Ala Lys Gly Val Leu Pro Pro Val Glu Leu Arg Asp Glu
145                 150                 155                 160

Ala Ser Gly Thr Ser Gln Val Ile Ser Glu Val Leu Leu Tyr Gly Glu
                165                 170                 175

Val Val Leu Arg Tyr Val Ser Gly Ser Phe Gln Gly Pro Phe Leu Ala
                180                 185                 190

Gly Tyr Thr Pro Val Thr Asp Ser Ala Val Thr Ser Phe Gly Leu Gln
            195                 200                 205

Arg Leu Asp His Ala Val Gly Asn Thr His Asp Leu Ile Lys Ala Val
    210                 215                 220

Glu Tyr Ile Thr Gly Phe Thr Gly Phe His Glu Phe Ser Glu Phe Val
225                 230                 235                 240

Ala Glu Asp Val Gly Thr Val Asp Ser Gly Leu Asn Ser Met Val Leu
                245                 250                 255

Ala Ser Asn Asn Glu Ala Val Leu Leu Pro Val Asn Glu Pro Thr Phe
            260                 265                 270

Gly Thr Pro Arg Lys Ser Gln Ile Gln Thr Tyr Leu Glu Gln Asn Glu
    275                 280                 285

Gly Pro Gly Leu Gln His Leu Ala Leu Leu Ser Asn Asp Ile Phe Thr
    290                 295                 300

Thr Leu Arg Glu Met Arg Ala Arg Ser Glu Leu Gly Gly Phe Glu Phe
305                 310                 315                 320

Met Pro Arg Ala Asn Ala Lys Tyr Tyr Lys Asp Met Tyr Ala Arg Ile
            325                 330                 335

Gly Asp Ser Leu Thr Pro Gln Gln Tyr Arg Glu Val Glu Glu Leu Gly
            340                 345                 350

Ile Leu Val Asp Lys Asp Gln Gly Val Leu Leu Gln Ile Phe Thr
        355                 360                 365

Lys Pro Leu Gly Asp Arg Pro Thr Val Phe Ile Glu Ile Ile Gln Arg
    370                 375                 380

Val Gly Cys Met Arg Glu Val Lys Glu Pro Ala Thr Gly Ala Val Val
385                 390                 395                 400

Gly Thr Glu Gln Ala Ala Gly Cys Gly Gly Phe Gly Lys Gly Asn Phe
                405                 410                 415
```

```
Gly Ala Leu Phe Lys Ser Ile Glu Asp Tyr Glu Arg Thr Leu Asn Val
            420                 425                 430

<210> SEQ ID NO 58
<211> LENGTH: 433
<212> TYPE: PRT
<213> ORGANISM: Physcomitrella

<400> SEQUENCE: 58

Met Gly Leu Asp Lys Ser Glu Ser Glu Gly Ser Val Val Gly Pro Leu
1               5                   10                  15

His Leu Val Gly Cys Glu Arg Phe Val Arg Asn Asn Pro Lys Thr Asp
            20                  25                  30

Arg Phe Gly Val Glu Arg Phe His Val Glu Phe Trp Cys Gly Asp
        35                  40                  45

Ala Ser Asn Thr Trp Arg Arg Phe Ser Trp Gly Leu Gly Met His Leu
    50                  55                  60

Val Ala Lys Ser Asp Gln Thr Thr Gly Asn Gln Thr Tyr Cys Ser Tyr
65                  70                  75                  80

Ala Ile Gln Ser Asn Glu Leu Val Phe Ala Phe Thr Ala Pro Tyr Ser
                85                  90                  95

Ser Thr Ile Asp Gln Thr Asn Thr Lys Met Pro His Pro Gly Tyr Lys
            100                 105                 110

Ser Asp Glu Ala Arg Ser Phe Thr Asp Ser His Gly Leu Ala Val Arg
        115                 120                 125

Ala Val Gly Ile Leu Val Asp Asp Ala Asp Glu Ala Phe Arg Ile Ser
    130                 135                 140

Val Glu His Gly Ala Val Ser Val Leu Glu Pro His Val Leu Ser Asp
145                 150                 155                 160

Asp Ala Lys Gly Gly Lys Met Val Met Ala Glu Val Lys Leu Tyr Gly
                165                 170                 175

Asp Val Val Leu Arg Tyr Val Ser Glu Gln Gly Tyr Lys Gly Ser Met
            180                 185                 190

Leu Pro Asn Tyr Glu Glu Val Glu Ser Leu Pro Leu Ser Tyr Gly Leu
        195                 200                 205

Val Arg Leu Asp His Ala Val Gly Asn Val His Asn Leu Ala Glu Ala
    210                 215                 220

Val Asn Tyr Ile Ala Lys Phe Thr Gly Phe His Glu Phe Ala Glu Phe
225                 230                 235                 240

Thr Ala Gly Asp Val Gly Thr Thr Glu Ser Gly Leu Asn Ser Met Val
                245                 250                 255

Val Ala Ser Asn Asn Glu Met Val Leu Leu Pro Ile Asn Glu Pro Thr
            260                 265                 270

Phe Gly Thr Lys Arg Lys Ser Gln Ile Gln Thr Tyr Leu Glu His Asn
        275                 280                 285

Glu Gly Pro Gly Leu Gln His Leu Ala Leu Ile Cys Asp Asn Ile Phe
    290                 295                 300

Ser Thr Leu Arg Glu Met Arg Thr Arg Thr His Ile Gly Gly Phe Asp
305                 310                 315                 320

Phe Met Pro Lys Pro Pro Pro Tyr Tyr Lys Asn Leu Ala Asn Arg
                325                 330                 335

Val Gly Asp Ile Leu Thr Ala Glu Gln Ile Lys Glu Cys Asp Glu Leu
            340                 345                 350

Gly Ile Leu Val Asp Lys Asp Asp Gln Gly Val Leu Leu Gln Ile Phe
        355                 360                 365
```

```
Thr Lys Pro Val Gly Asp Arg Pro Ser Ile Phe Val Glu Ile Ile Gln
    370                 375                 380

Arg Ile Gly Cys Met Asp Lys Asp Glu Ser Thr Gly Ala Thr Val Gln
385                 390                 395                 400

Lys Gly Gly Cys Gly Gly Phe Gly Lys Gly Asn Phe Ser Glu Leu Phe
                405                 410                 415

Lys Ser Ile Glu Glu Tyr Glu Lys Thr Leu Asp Gly Thr Leu Lys Val
            420                 425                 430

His
```

```
<210> SEQ ID NO 59
<211> LENGTH: 446
<212> TYPE: PRT
<213> ORGANISM: Oryza

<400> SEQUENCE: 59

Met Pro Pro Thr Pro Thr Pro Thr Ala Thr Thr Gly Ala Val Ser Ala
1               5                   10                  15

Ala Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
        35                  40                  45

Phe His His Val Glu Leu Trp Cys Ala Asp Ala Ala Ser Ala Ala Gly
    50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Leu Arg Ser Ala Ser
                85                  90                  95

Val Ala Phe Leu Phe Thr Ala Pro Tyr Gly Gly Asp His Gly Val Gly
            100                 105                 110

Ala Asp Ala Ala Thr Thr Ala Ser Ile Pro Ser Phe Ser Pro Gly Ala
        115                 120                 125

Ala Arg Arg Phe Ala Ala Asp His Gly Leu Ala Val His Ala Val Ala
    130                 135                 140

Leu Arg Val Ala Asp Ala Ala Asp Ala Phe Arg Ala Ser Val Ala Ala
145                 150                 155                 160

Gly Ala Arg Pro Ala Phe Gln Pro Ala Asp Leu Gly Gly Gly Phe Gly
                165                 170                 175

Leu Ala Glu Val Glu Leu Tyr Gly Asp Val Val Leu Arg Phe Val Ser
            180                 185                 190

His Pro Asp Gly Ala Asp Ala Pro Phe Leu Pro Gly Phe Glu Gly Val
        195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
            260                 265                 270

Thr Val Leu Leu Pro Leu Asn Glu Pro Val His Gly Thr Lys Arg Arg
        275                 280                 285

Ser Gln Ile Gln Thr Tyr Leu Asp His His Gly Gly Pro Gly Val Gln
    290                 295                 300
```

```
His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro Pro
            325                 330                 335

Pro Asn Tyr Tyr Asp Gly Val Arg Arg Arg Ala Gly Asp Val Leu Ser
        340                 345                 350

Glu Glu Gln Ile Asn Glu Cys Gln Glu Leu Gly Val Leu Val Asp Arg
    355                 360                 365

Asp Asp Gln Gly Val Leu Leu Gln Ile Phe Thr Lys Pro Val Gly Asp
370                 375                 380

Arg Pro Thr Phe Phe Leu Glu Met Ile Gln Arg Ile Gly Cys Met Glu
385                 390                 395                 400

Lys Asp Glu Ser Gly Gln Glu Tyr Gln Lys Gly Gly Cys Gly Gly Phe
                405                 410                 415

Gly Lys Gly Asn Phe Ser Glu Leu Phe Lys Ser Ile Glu Glu Tyr Glu
            420                 425                 430

Lys Ser Leu Glu Ala Lys Gln Ala Pro Thr Val Gln Gly Ser
            435                 440                 445

<210> SEQ ID NO 60
<211> LENGTH: 436
<212> TYPE: PRT
<213> ORGANISM: Triticum

<400> SEQUENCE: 60

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Arg Met Val Arg Phe
            20                  25                  30

Asn Pro Arg Ser Asp Arg Phe His Thr Leu Ser Phe His His Val Glu
        35                  40                  45

Phe Trp Cys Ala Asp Ala Ala Ser Ala Ala Gly Arg Phe Ala Phe Ala
    50                  55                  60

Leu Gly Ala Pro Leu Ala Ala Arg Ser Asp Leu Ser Thr Gly Asn Ser
65                  70                  75                  80

Val His Ala Ser Gln Leu Leu Arg Ser Gly Asn Leu Ala Phe Leu Phe
                85                  90                  95

Thr Ala Pro Tyr Ala Asn Gly Cys Asp Ala Ala Thr Ala Ser Leu Pro
            100                 105                 110

Ser Phe Ser Ala Asp Ala Ala Arg Arg Phe Ser Ala Asp His Gly Leu
        115                 120                 125

Ala Val Arg Ser Ile Ala Leu Arg Val Ala Asp Ala Ala Glu Ala Phe
    130                 135                 140

Arg Ala Ser Val Asp Gly Gly Ala Arg Pro Ala Phe Ser Pro Val Asp
145                 150                 155                 160

Leu Gly Arg Gly Phe Gly Phe Ala Glu Val Glu Leu Tyr Gly Asp Val
                165                 170                 175

Val Leu Arg Phe Val Ser His Pro Asp Asp Thr Asp Val Pro Phe Leu
            180                 185                 190

Pro Gly Phe Glu Gly Val Ser Asn Pro Asp Ala Val Asp Tyr Gly Leu
        195                 200                 205

Thr Arg Phe Asp His Val Val Gly Asn Val Pro Glu Leu Ala Pro Ala
    210                 215                 220

Ala Ala Tyr Val Ala Gly Phe Ala Gly Phe His Glu Phe Ala Glu Phe
```

```
            225                 230                 235                 240
    Thr Thr Glu Asp Val Gly Thr Ala Glu Ser Gly Leu Asn Ser Met Val
                    245                 250                 255

Leu Ala Asn Asn Ser Glu Gly Val Leu Leu Pro Leu Asn Glu Pro Val
                    260                 265                 270

His Gly Thr Lys Arg Arg Ser Gln Ile Gln Thr Phe Leu Glu His His
                    275                 280                 285

Gly Gly Ser Gly Val Gln His Ile Ala Val Ala Ser Ser Asp Val Leu
                    290                 295                 300

Arg Thr Leu Arg Glu Met Arg Ala Arg Ser Ala Met Gly Gly Phe Asp
    305                 310                 315                 320

Phe Leu Pro Pro Arg Cys Arg Lys Tyr Tyr Glu Gly Val Arg Arg Ile
                    325                 330                 335

Ala Gly Asp Val Leu Ser Glu Ala Gln Ile Lys Glu Cys Gln Glu Leu
                    340                 345                 350

Gly Val Leu Val Asp Arg Asp Gln Gly Val Leu Leu Gln Ile Phe
                    355                 360                 365

Thr Lys Pro Val Gly Asp Arg Pro Thr Leu Phe Leu Glu Met Ile Gln
    370                 375                 380

Arg Ile Gly Cys Met Glu Lys Asp Glu Arg Gly Glu Tyr Gln Lys
    385                 390                 395                 400

Gly Gly Cys Gly Gly Phe Gly Lys Gly Asn Phe Ser Glu Leu Phe Lys
                    405                 410                 415

Ser Ile Glu Asp Tyr Glu Lys Ser Leu Glu Ala Lys Gln Ser Ala Ala
                    420                 425                 430

Val Gln Gly Ser
            435

<210> SEQ ID NO 61
<211> LENGTH: 444
<212> TYPE: PRT
<213> ORGANISM: Zea

<400> SEQUENCE: 61

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe His Thr Leu Ala Phe
                35                  40                  45

His His Val Glu Leu Trp Cys Ala Asp Ala Ala Ser Ala Ala Gly Arg
            50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Phe Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Glu Ala Phe Arg Thr Ser Val Ala Ala Gly Ala Arg Pro Ala Phe
145                 150                 155                 160
```

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Ala Ala
        180                 185                 190

Gly Glu Pro Phe Leu Pro Gly Phe Glu Gly Val Ala Ser Pro Gly Ala
    195                 200                 205

Ala Asp Tyr Gly Leu Ser Arg Phe Asp His Ile Val Gly Asn Val Pro
210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Pro Lys Pro Val Gly Asp Arg Pro Thr Leu Phe
370                 375                 380

Leu Glu Ile Ile Gln Arg Ile Gly Cys Met Glu Arg Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Met Gln Ala Ala Ala Ala Ala Thr Ala Gln Gly Ser
        435                 440

<210> SEQ ID NO 62
<211> LENGTH: 443
<212> TYPE: PRT
<213> ORGANISM: Glycine
<220> FEATURE:
<221> NAME/KEY: misc_feature
<222> LOCATION: (393)..(393)
<223> OTHER INFORMATION: Xaa can be any naturally occurring amino acid

<400> SEQUENCE: 62

Met Cys Asn Glu Ile Gln Ala Gln Ala Gln Ala Gln Pro Gly
1               5                   10                  15

Phe Lys Leu Val Gly Phe Lys Asn Phe Val Arg Thr Asn Pro Lys Ser
            20                  25                  30

Asp Arg Phe Gln Val Asn Arg Phe His His Ile Glu Phe Trp Cys Thr
        35                  40                  45

Asp Ala Thr Asn Ala Ser Arg Arg Phe Ser Trp Gly Leu Gly Met Pro
    50                  55                  60

Ile Val Ala Lys Ser Asp Leu Ser Thr Gly Asn Gln Ile His Ala Ser

```
            65                  70                  75                  80
Tyr Leu Leu Arg Ser Gly Asp Leu Ser Phe Leu Phe Ser Ala Pro Tyr
                    85                  90                  95

Ser Pro Ser Leu Ser Ala Gly Ser Ala Ala Ser Ser Ala Ser Ile
                100                 105                 110

Pro Ser Phe Asp Ala Ala Thr Cys Leu Ala Phe Ala Ala Lys His Gly
            115                 120                 125

Phe Gly Val Arg Ala Ile Ala Leu Glu Val Ala Asp Ala Glu Ala Ala
130                 135                 140

Phe Ser Ala Ser Val Ala Lys Gly Ala Glu Pro Ala Ser Pro Pro Val
145                 150                 155                 160

Leu Val Asp Asp Arg Thr Gly Phe Ala Glu Val Arg Leu Tyr Gly Asp
                165                 170                 175

Val Val Leu Arg Tyr Val Ser Tyr Lys Asp Ala Ala Pro Gln Ala Pro
            180                 185                 190

His Ala Asp Pro Ser Arg Trp Phe Leu Pro Gly Phe Glu Ala Ala Ala
            195                 200                 205

Ser Ser Ser Ser Phe Pro Glu Leu Asp Tyr Gly Ile Arg Arg Leu Asp
    210                 215                 220

His Ala Val Gly Asn Val Pro Glu Leu Ala Pro Ala Val Arg Tyr Leu
225                 230                 235                 240

Lys Gly Phe Ser Gly Phe His Glu Phe Ala Glu Phe Thr Ala Glu Asp
                245                 250                 255

Val Gly Thr Ser Glu Ser Gly Leu Asn Ser Val Val Leu Ala Asn Asn
            260                 265                 270

Ser Glu Thr Val Leu Leu Pro Leu Asn Glu Pro Val Tyr Gly Thr Lys
            275                 280                 285

Arg Lys Ser Gln Ile Glu Thr Tyr Leu Glu His Asn Glu Gly Ala Gly
            290                 295                 300

Val Gln His Leu Ala Leu Val Thr His Asp Ile Phe Thr Thr Leu Arg
305                 310                 315                 320

Glu Met Arg Lys Arg Ser Phe Leu Gly Gly Phe Glu Phe Met Pro Ser
                325                 330                 335

Pro Pro Pro Thr Tyr Tyr Ala Asn Leu His Asn Arg Ala Ala Asp Val
            340                 345                 350

Leu Thr Val Asp Gln Ile Lys Gln Cys Glu Glu Leu Gly Ile Leu Val
            355                 360                 365

Asp Arg Asp Asp Gln Gly Thr Leu Leu Gln Ile Phe Thr Lys Pro Val
370                 375                 380

Gly Asp Arg Pro Thr Ile Phe Ile Xaa Ile Ile Gln Arg Ile Gly Cys
385                 390                 395                 400

Met Val Glu Asp Glu Gly Lys Val Tyr Gln Lys Gly Ala Cys Gly
                405                 410                 415

Gly Phe Gly Lys Gly Asn Phe Ser Glu Leu Phe Lys Ser Ile Glu Glu
                420                 425                 430

Tyr Glu Lys Thr Leu Glu Ala Lys Arg Thr Ala
            435                 440

<210> SEQ ID NO 63
<211> LENGTH: 445
<212> TYPE: PRT
<213> ORGANISM: Vitis

<400> SEQUENCE: 63
```

```
Met Gly Lys Gln Asn Thr Thr Thr Asn Asn Pro Ala Pro Gly Phe Lys
1               5                   10                  15

Leu Val Gly Phe Ser Asn Phe Leu Arg Thr Asn Pro Met Ser Asp Arg
            20                  25                  30

Phe Gly Val Lys Arg Phe His His Ile Glu Phe Trp Ser Thr Asp Ala
            35                  40                  45

Thr Asn Leu Ala Arg Arg Phe Ser Trp Gly Leu Gly Met Pro Ile Val
50                      55                  60

Ala Lys Ser Asp Leu Ser Thr Gly Asn Val Ile His Ala Ser Tyr Leu
65                  70                  75                  80

Thr Arg Ser Gly Asp Leu Asn Phe Leu Phe Thr Ala Pro Tyr Ser Pro
                85                  90                  95

Ser Ile Ala Gly Asp Leu Glu Asn Ala Ala Thr Ala Ser Ile Pro
                100                 105                 110

Ser Phe Asp His Ser Ala Cys His Ala Phe Ala Ala Ser His Gly Leu
            115                 120                 125

Gly Val Arg Ala Ile Ala Ile Glu Val Asp Ala Glu Gly Ala Phe
            130                 135                 140

His Thr Ser Val Ala His Gly Ala Arg Pro Met Ser Pro Pro Val Thr
145                 150                 155                 160

Met Gly Gly Ser Val Val Ile Ser Glu Val His Leu Tyr Gly Asp Ala
                165                 170                 175

Val Leu Arg Tyr Val Ser Tyr Lys Asn Pro Asn Pro Asn Ala Thr Ser
                180                 185                 190

Asp Pro Ser Ser Trp Phe Leu Pro Gly Phe Glu Ala Val Asp Glu Gly
            195                 200                 205

Ser Ser Phe Pro Val Asp Phe Gly Leu Arg Arg Val Asp His Thr Val
    210                 215                 220

Gly Asn Val Pro Lys Leu Ala Pro Val Val Thr Tyr Leu Lys Gln Phe
225                 230                 235                 240

Thr Gly Phe His Glu Phe Ala Glu Phe Thr Ala Glu Asp Val Gly Thr
                245                 250                 255

Ser Glu Ser Gly Leu Asn Ser Val Val Leu Ala Ser Asn Asn Glu Met
            260                 265                 270

Val Leu Leu Pro Leu Asn Glu Pro Val Phe Gly Thr Lys Arg Lys Ser
        275                 280                 285

Gln Ile Gln Thr Tyr Leu Glu His Asn Glu Gly Pro Gly Val Gln His
    290                 295                 300

Leu Ala Leu Met Ser Asp Asp Ile Phe Arg Thr Leu Arg Glu Met Arg
305                 310                 315                 320

Arg Arg Ser Gly Val Gly Gly Phe Asp Phe Met Pro Ser Pro Pro Pro
                325                 330                 335

Thr Tyr Tyr Arg Asn Val Lys Lys Arg Ala Gly Asp Val Leu Thr Asp
                340                 345                 350

Asp Gln Ile Lys Glu Cys Glu Glu Leu Gly Ile Leu Val Asp Lys Asp
            355                 360                 365

Asp Gln Gly Thr Leu Leu Gln Ile Phe Thr Lys Pro Leu Gly Asp Arg
        370                 375                 380

Pro Thr Ile Phe Ile Glu Ile Ile Gln Arg Leu Gly Cys Met Val Lys
385                 390                 395                 400

Asp Asp Glu Gly Lys Val Ser Gln Lys Gly Gly Cys Gly Gly Phe Gly
                405                 410                 415

Lys Gly Asn Phe Ser Glu Leu Phe Lys Ser Ile Glu Glu Tyr Glu Lys
```

```
            420                 425                 430
Thr Leu Gly Ala Lys Arg Ile Val Asp Pro Ala Pro Val
            435                 440                 445

<210> SEQ ID NO 64
<211> LENGTH: 358
<212> TYPE: PRT
<213> ORGANISM: Pseudomonas fluorescens

<400> SEQUENCE: 64

Met Ala Asp Gln Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Gln Pro Asp
        50                  55                  60

Ser Leu Ala Ser Tyr Phe Ala Ala Glu His Gly Pro Ser Val Cys Gly
65                  70                  75                  80

Met Ala Phe Arg Val Lys Asp Ser Gln Gln Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Asp Arg Asn Pro Val Gly Ala Gly Leu Lys Val Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Glu Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ala Arg Gly Ile Leu Leu Asp Gly Ser Ser Ile Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350
```

Gly Val Leu Thr Thr Asp
        355

<210> SEQ ID NO 65
<211> LENGTH: 358
<212> TYPE: PRT
<213> ORGANISM: Pseudomonas fluorescens

<400> SEQUENCE: 65

Met Ala Asp Leu Tyr Glu Asn Pro Met Gly Leu Met Gly Phe Glu Phe
1               5                   10                  15

Ile Glu Leu Ala Ser Pro Thr Pro Asn Thr Leu Glu Pro Ile Phe Glu
            20                  25                  30

Ile Met Gly Phe Thr Lys Val Ala Thr His Arg Ser Lys Asp Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Lys Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Phe
    130                 135                 140

Leu Glu Gly Val Asp Arg His Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Ser Asp Asp Leu Ile Lys Thr Trp Asp His Leu
                245                 250                 255

Lys Ser Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Gly Glu
        275                 280                 285

Leu Gln Ala Arg Gly Ile Leu Leu Asp Gly Ser Ser Glu Ser Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Ser Thr Asp
        355

<210> SEQ ID NO 66
<211> LENGTH: 440
<212> TYPE: PRT
<213> ORGANISM: Avena sativa

<400> SEQUENCE: 66

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Glu Tyr His Gly Gly Pro Gly Val Gln His Ile Ala Leu Ala Ser
    290                 295                 300

Asn Asp Val Leu Arg Thr Leu Arg Glu Met Arg Ala Arg Thr Pro Met
305                 310                 315                 320

Gly Gly Phe Glu Phe Met Ala Pro Gln Ala Lys Tyr Tyr Glu Gly
                325                 330                 335

Val Arg Arg Ile Ala Gly Asp Val Leu Ser Glu Gln Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Pro Thr Phe Phe Leu

```
                370               375               380
Glu Met Ile Gln Arg Ile Gly Cys Met Glu Lys Asp Glu Val Gly Gln
385               390               395               400
Glu Tyr Gln Lys Gly Gly Cys Gly Gly Phe Gly Lys Gly Asn Phe Ser
            405               410               415
Glu Leu Phe Lys Ser Ile Glu Asp Tyr Glu Lys Ser Leu Glu Val Lys
            420               425               430
Gln Ser Val Val Ala Gln Lys Ser
            435               440

<210> SEQ ID NO 67
<211> LENGTH: 444
<212> TYPE: PRT
<213> ORGANISM: Zea mays

<400> SEQUENCE: 67

Met Gly Pro Thr Pro Thr Ala Ala Ala Gly Ala Ala Val Ala Ala
1               5                 10                15
Ala Ser Ala Ala Glu Gln Ala Ala Phe Arg Leu Val Gly His Arg Asn
            20                25                30
Phe Val Arg Phe Asn Pro Arg Ser Asp Arg Phe His Thr Leu Ala Phe
            35                40                45
His His Val Glu Leu Trp Cys Ala Asp Ala Ala Ser Ala Ala Gly Arg
    50                55                60
Phe Ser Phe Gly Leu Gly Ala Pro Leu Ala Ala Arg Ser Asp Leu Ser
65              70                75                80
Thr Gly Asn Ser Ala His Ala Ser Leu Leu Arg Ser Gly Ser Leu
            85                90                95
Ser Phe Leu Phe Thr Ala Pro Tyr Ala His Gly Ala Asp Ala Ala Thr
            100               105               110
Ala Ala Leu Pro Ser Phe Ser Ala Ala Ala Arg Arg Phe Ala Ala
            115               120               125
Asp His Gly Leu Ala Val Arg Ala Val Ala Leu Arg Val Ala Asp Ala
    130               135               140
Glu Asp Ala Phe Arg Ala Ser Val Ala Ala Gly Ala Arg Pro Ala Phe
145               150               155               160
Gly Pro Val Asp Leu Gly Arg Gly Phe Arg Leu Ala Glu Val Glu Leu
            165               170               175
Tyr Gly Asp Val Val Leu Arg Tyr Val Ser Tyr Pro Asp Gly Ala Ala
            180               185               190
Gly Glu Pro Phe Leu Pro Gly Phe Glu Gly Val Ala Ser Pro Gly Ala
            195               200               205
Ala Asp Tyr Gly Leu Ser Arg Phe Asp His Ile Val Gly Asn Val Pro
    210               215               220
Glu Leu Ala Pro Ala Ala Tyr Phe Ala Gly Phe Thr Gly Phe His
225               230               235               240
Glu Phe Ala Glu Phe Thr Thr Glu Asp Val Gly Thr Ala Glu Ser Gly
            245               250               255
Leu Asn Ser Met Val Leu Ala Asn Ser Glu Asn Val Leu Leu Pro
            260               265               270
Leu Asn Glu Pro Val His Gly Thr Lys Arg Arg Ser Gln Ile Gln Thr
            275               280               285
Phe Leu Asp His His Gly Gly Pro Gly Val Gln His Met Ala Leu Ala
    290               295               300
```

```
Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Ala Gln Gly Ser
        435                 440
```

<210> SEQ ID NO 68
<211> LENGTH: 1332
<212> TYPE: DNA
<213> ORGANISM: Zea mays

<400> SEQUENCE: 68

```
atgggtccga cccccgaccgc aacagcagcc ggtgcagcag ttgcagcagc aagcgcagca      60
gaacaggcag catttcgtct ggttggtcat cgtaattttg ttcgttttaa tccgcgttcc     120
gatcgttttc ataccctggc atttcatcat gttgaactgt ggtgtgcaga tgcagcatca     180
gcagcaggtc gttttagctt tgcactgggt gcaccgctgg cagcacgtag cgatctgagc     240
accggtaata gcgcacatgc aagtctgctg ctgcgtagcg gtagcctgag ctttctgttt     300
accgcaccgt atgcacatgg tgccgatgca gccaccgcag cactgccgag ctttagcgca     360
gccgcagccc gtcgttttgc agcagatcat ggtctggcag ttcgtgcagt tgcactgcgt     420
gttgcagatg ccgaagatgc atttcgtgca agcgttgcag cgggtgcacg tccggcattt     480
ggtccggttg atctgggtcg tggttttcgc ctggccgaag tggaactgta tggtgatgtt     540
gttctgcgtt atgttagcta tccgatggt gccgcaggcg aaccgttct gcctggtttt     600
gaaggtgttg caagtccggg tgcagccgat tatggcctga ccgttttga tcatattgtt     660
ggtaatgtgc cggaactggc accggcagca gcatattttg caggtttac cggttttcat     720
gaatttgccg aatttaccac cgaagatgtt ggcaccgcag aaagcggtct gaatagcatg     780
gcactggcaa ataatagcga aaatgtactg ctgccgctga tgaaccggt gcatggcacc     840
aaacgtcgta gccagattca gaccttctg gatcatcatg gtggtccggg tgttcagcat     900
attgcactgg catcagatga tgtgctgcgt accctgcgtg aaatgcaggc acgtagtgca     960
atgggtggct ttgaatttct gcctccgcct ccgagcgatt attatgatgg tgttcgtcgt    1020
gaagccggtg atgttctgac cgaagcacag attaatgaat gtcaagaact gggtgttatg    1080
gtggatcgta tgatcagggg tgtcctgctg cagattttta ccaaaccggt tggtgatcgt    1140
ccgacctttt ttctggaaat tattcagcgt attggctgca tggaaaaaga tgaaaaaggc    1200
caagaatatc agaaaggtgg ttgtggtggt tttggcaaag ataacttag ccagctgttt    1260
aaaagcatcg aggattatga aaaaagcctg gaagcaaaac aagccgcagc agccgcaacc    1320
```

```
gcacagggta gc                                                             1332

<210> SEQ ID NO 69
<211> LENGTH: 1332
<212> TYPE: DNA
<213> ORGANISM: Zea mays

<400> SEQUENCE: 69
atgggtccga ccccgaccgc aacagcagcc ggtgcagcag ttgcagcagc aagcgcagca         60
gaacaggcag catttcgtct ggttggtcat cgtaattttg ttcgttttaa tccgcgtagc        120
gatcgttttc agaccctggc atttcatcat gttgaactgt ggtgtgcaga tgcagcatca        180
gcagcaggtc gttttagctt tgcactgggt gttccgctgg cagcacgtag tgatctgagc        240
accggtaata gcgcacatgc aagtctgctg ctgcgtagcg gtagcctgag cctgctgttt        300
accgcaccgt atgcacatgg tgccgatgca gccaccgcag cactgccgag ctttagcgca        360
gccgcagccc gtcgttttgc agcagatcat ggtctggcag ttcgtgcagt tgccctgcgt        420
gttgcagatg ccgaagatgc atttcgtgca agcgttgcag cgggtgcacg tccggcattt        480
ggtccggttg atctgggtcg tggttttcgc ctggccgaag tggaactgta tggtgatgtt        540
gttctgcgtt atgttagcta tccggatggt gccgcaggcg aaccgtttct gcctggtttt        600
gaaggtgttg caagtccggg tgcagccgat tatggcctga ccgttttga tcatattgtt         660 ggtaatgtgc cggaactggc accggcagca gcatatatgg caggttttac cggttttcat        720
gaatttgcag aatttaccac cgaagatgtt ggcaccaccg aaagcggtct gaatagcatg        780
gcactggcaa ataatagcga aaatgtactg ctgccgctga tgaaccggt gcatggcacc         840 aaacgtcgta gccagattca gccttttctg gatcatcatg gtggtccggg tgttcagcat        900
attgcactgg catcagatga tgtgctgcgt accctgcgtg aaatgcgtgc acgtagcgca        960
atgggtggct ttgaatttct gcctccgcct ctgagcgatt attatgatgg tgttcgtcgt       1020
tgtgccggtg atgttctgac cgaagcacag attaatgaat gtcaagaact gggtgtgatg       1080
gtggatcgtg atgatcaggg tgtcctgctg cagatttta ccaaaccggt tggtgatcgt        1140 ccgaccttt ttctggaaat tattcagcgt attggctgca tggaaaaaga tgaaaaaggc        1200
caagaatatc agaaaggtgg ttgtggtggt tttggcaaag gtaattttgg tcagctgttt       1260
aaaagcatcg aggactatga aaaaagcctg gaagcaaaac aagccgcagc agccgcaacc       1320
gcacagggta gc                                                           1332

<210> SEQ ID NO 70
<211> LENGTH: 16
<212> TYPE: DNA
<213> ORGANISM: Artificial
<220> FEATURE:
<223> OTHER INFORMATION: Primer

<400> SEQUENCE: 70
ggccaccaaa acgccg                                                         16

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71
tcatcccact aactgtttgg cttc                                                24
```

<210> SEQ ID NO 72
<211> LENGTH: 23
<212> TYPE: DNA
<213> ORGANISM: Artificial
<220> FEATURE:
<223> OTHER INFORMATION: Primer

<400> SEQUENCE: 72
ggcgctggcg gtgcgtccac tac                                    23

<210> SEQ ID NO 73
<211> LENGTH: 34
<212> TYPE: DNA
<213> ORGANISM: Artificial
<220> FEATURE:
<223> OTHER INFORMATION: Primer

<400> SEQUENCE: 73
tcaaacgttc agggtacgct cgtagtcttc gatg                        34

<210> SEQ ID NO 74
<211> LENGTH: 21
<212> TYPE: DNA
<213> ORGANISM: Artificial
<220> FEATURE:
<223> OTHER INFORMATION: Primer

<400> SEQUENCE: 74
ggtgcgggtg gcgctggcac c                                      21

<210> SEQ ID NO 75
<211> LENGTH: 35
<212> TYPE: DNA
<213> ORGANISM: Artificial
<220> FEATURE:
<223> OTHER INFORMATION: Primer

<400> SEQUENCE: 75
tcaaacgttc agggtacgtt cgtagtcctc gatgg                       35

<210> SEQ ID NO 76
<211> LENGTH: 19
<212> TYPE: DNA
<213> ORGANISM: Artificial
<220> FEATURE:
<223> OTHER INFORMATION: Primer

<400> SEQUENCE: 76
ccaatcccaa tgtgcaacg                                         19

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
ttatgcggta cgtttagcct cc                                     22

<210> SEQ ID NO 78
<211> LENGTH: 23
<212> TYPE: DNA
<213> ORGANISM: Artificial
<220> FEATURE:

<223> OTHER INFORMATION: Primer

<400> SEQUENCE: 78
ccaccgactc cgaccgccgc agc                                         23

<210> SEQ ID NO 79
<211> LENGTH: 26
<212> TYPE: DNA
<213> ORGANISM: Artificial
<220> FEATURE:
<223> OTHER INFORMATION: Primer

<400> SEQUENCE: 79
tcaggaaccc tgtgcagctg ccgcag                                      26

<210> SEQ ID NO 80
<211> LENGTH: 17
<212> TYPE: DNA
<213> ORGANISM: Artificial
<220> FEATURE:
<223> OTHER INFORMATION: Primer

<400> SEQUENCE: 80
ccgccgactc caacccc                                                17

<210> SEQ ID NO 81
<211> LENGTH: 21
<212> TYPE: DNA
<213> ORGANISM: Artificial
<220> FEATURE:
<223> OTHER INFORMATION: Primer

<400> SEQUENCE: 81
ttaagaaccc tgaacggtcg g                                           21

<210> SEQ ID NO 82
<211> LENGTH: 28
<212> TYPE: DNA
<213> ORGANISM: Artificial
<220> FEATURE:
<223> OTHER INFORMATION: Primer

<400> SEQUENCE: 82
gaggattcga cttcgcgcct tctcctcc                                    28

<210> SEQ ID NO 83
<211> LENGTH: 28
<212> TYPE: DNA
<213> ORGANISM: Artificial
<220> FEATURE:
<223> OTHER INFORMATION: Primer

<400> SEQUENCE: 83
ggaggagaag gcgcgaagtc gaatcctc                                    28

<210> SEQ ID NO 84
<211> LENGTH: 29
<212> TYPE: DNA
<213> ORGANISM: Artificial
<220> FEATURE:
<223> OTHER INFORMATION: Primer

<400> SEQUENCE: 84
gaggattcga cttctggcct tctcctccg                                   29

```
<210> SEQ ID NO 85
<211> LENGTH: 29
<212> TYPE: DNA
<213> ORGANISM: Artificial
<220> FEATURE:
<223> OTHER INFORMATION: Primer

<400> SEQUENCE: 85
cggaggagaa ggccagaagt cgaatcctc                                              29

<210> SEQ ID NO 86
<211> LENGTH: 31
<212> TYPE: DNA
<213> ORGANISM: Artificial
<220> FEATURE:
<223> OTHER INFORMATION: Primer

<400> SEQUENCE: 86
ggaggattcg acttctttcc ttctcctccg c                                           31

<210> SEQ ID NO 87
<211> LENGTH: 31
<212> TYPE: DNA
<213> ORGANISM: Artificial
<220> FEATURE:
<223> OTHER INFORMATION: Primer

<400> SEQUENCE: 87
gcggaggaga aggaaagaag tcgaatcctc c                                           31

<210> SEQ ID NO 88
<211> LENGTH: 35
<212> TYPE: DNA
<213> ORGANISM: Artificial
<220> FEATURE:
<223> OTHER INFORMATION: Primer

<400> SEQUENCE: 88
gtgacaggcc gacgatagct atagagataa tccag                                       35

<210> SEQ ID NO 89
<211> LENGTH: 35
<212> TYPE: DNA
<213> ORGANISM: Artificial
<220> FEATURE:
<223> OTHER INFORMATION: Primer

<400> SEQUENCE: 89
ctggattatc tctatagcta tcgtcggcct gtcac                                       35

<210> SEQ ID NO 90
<211> LENGTH: 30
<212> TYPE: DNA
<213> ORGANISM: Artificial
<220> FEATURE:
<223> OTHER INFORMATION: Primer

<400> SEQUENCE: 90
gacttcatgc ctcctcctcc gcctacttac                                             30

<210> SEQ ID NO 91
<211> LENGTH: 30
<212> TYPE: DNA
<213> ORGANISM: Artificial
<220> FEATURE:
<223> OTHER INFORMATION: Primer
```

-continued

```
<400> SEQUENCE: 91
gtaagtaggc ggaggaggag gcatgaagtc                                    30

<210> SEQ ID NO 92
<211> LENGTH: 31
<212> TYPE: DNA
<213> ORGANISM: Artificial
<220> FEATURE:
<223> OTHER INFORMATION: Primer

<400> SEQUENCE: 92
gattcgactt catggcttct cctccgccta c                                  31

<210> SEQ ID NO 93
<211> LENGTH: 31
<212> TYPE: DNA
<213> ORGANISM: Artificial
<220> FEATURE:
<223> OTHER INFORMATION: Primer

<400> SEQUENCE: 93
gtaggcggag gagaagccat gaagtcgaat c                                  31

<210> SEQ ID NO 94
<211> LENGTH: 34
<212> TYPE: DNA
<213> ORGANISM: Artificial
<220> FEATURE:
<223> OTHER INFORMATION: Primer

<400> SEQUENCE: 94
cagatcaagg agtgtcagga attagggatt cttg                               34

<210> SEQ ID NO 95
<211> LENGTH: 34
<212> TYPE: DNA
<213> ORGANISM: Artificial
<220> FEATURE:
<223> OTHER INFORMATION: Primer

<400> SEQUENCE: 95
caagaatccc taattcctga cactccttga tctg                               34

<210> SEQ ID NO 96
<211> LENGTH: 38
<212> TYPE: DNA
<213> ORGANISM: Artificial
<220> FEATURE:
<223> OTHER INFORMATION: Primer

<400> SEQUENCE: 96
cggaacaaag aggaagagtg agattcagac gtatttgg                           38

<210> SEQ ID NO 97
<211> LENGTH: 38
<212> TYPE: DNA
<213> ORGANISM: Artificial
<220> FEATURE:
<223> OTHER INFORMATION: Primer

<400> SEQUENCE: 97
ccaaatacgt ctgaatctca ctcttcctct tgttccg                            38

<210> SEQ ID NO 98
<211> LENGTH: 40
```

```
<212> TYPE: DNA
<213> ORGANISM: Artificial
<220> FEATURE:
<223> OTHER INFORMATION: Primer

<400> SEQUENCE: 98
cgttgcttca atcttcccg aaaccactag gtgacaggcc                    40

<210> SEQ ID NO 99
<211> LENGTH: 40
<212> TYPE: DNA
<213> ORGANISM: Artificial
<220> FEATURE:
<223> OTHER INFORMATION: Primer

<400> SEQUENCE: 99
ggcctgtcac ctagtggttt cgggaagatt tgaagcaacg                    40

<210> SEQ ID NO 100
<211> LENGTH: 38
<212> TYPE: DNA
<213> ORGANISM: Artificial
<220> FEATURE:
<223> OTHER INFORMATION: Primer

<400> SEQUENCE: 100
caaatcttca caaaaccagt gggtgacagg ccgacgat                      38

<210> SEQ ID NO 101
<211> LENGTH: 38
<212> TYPE: DNA
<213> ORGANISM: Artificial
<220> FEATURE:
<223> OTHER INFORMATION: Primer

<400> SEQUENCE: 101
atcgtcggcc tgtcacccac tggttttgtg aagatttg                      38

<210> SEQ ID NO 102
<211> LENGTH: 40
<212> TYPE: DNA
<213> ORGANISM: Artificial
<220> FEATURE:
<223> OTHER INFORMATION: Primer

<400> SEQUENCE: 102
tgacaggccg acgatatttc tggagataat ccagagagta                    40

<210> SEQ ID NO 103
<211> LENGTH: 40
<212> TYPE: DNA
<213> ORGANISM: Artificial
<220> FEATURE:
<223> OTHER INFORMATION: Primer

<400> SEQUENCE: 103
tactctctgg attatctcca gaaatatcgt cggcctgtca                    40

<210> SEQ ID NO 104
<211> LENGTH: 30
<212> TYPE: DNA
<213> ORGANISM: Artificial
<220> FEATURE:
<223> OTHER INFORMATION: Primer

<400> SEQUENCE: 104
```
gacttcatgc ctgcgcctcc gcctacttac                                           30

<210> SEQ ID NO 105
<211> LENGTH: 30
<212> TYPE: DNA
<213> ORGANISM: Artificial
<220> FEATURE:
<223> OTHER INFORMATION: Primer

<400> SEQUENCE: 105
gtaagtaggc ggaggcgcag gcatgaagtc                                           30

<210> SEQ ID NO 106
<211> LENGTH: 34
<212> TYPE: DNA
<213> ORGANISM: Artificial
<220> FEATURE:
<223> OTHER INFORMATION: Primer

<400> SEQUENCE: 106
ggcaatttct ctgagttctt caagtccatt gaag                                      34

<210> SEQ ID NO 107
<211> LENGTH: 34
<212> TYPE: DNA
<213> ORGANISM: Artificial
<220> FEATURE:
<223> OTHER INFORMATION: Primer

<400> SEQUENCE: 107
cttcaatgga cttgaagaac tcagagaaat tgcc                                      34

<210> SEQ ID NO 108
<211> LENGTH: 37
<212> TYPE: DNA
<213> ORGANISM: Artificial
<220> FEATURE:
<223> OTHER INFORMATION: Primer

<400> SEQUENCE: 108
ggaacaaaga ggaagagtgt gattcagacg tatttgg                                   37

<210> SEQ ID NO 109
<211> LENGTH: 37
<212> TYPE: DNA
<213> ORGANISM: Artificial
<220> FEATURE:
<223> OTHER INFORMATION: Primer

<400> SEQUENCE: 109
ccaaatacgt ctgaatcaca ctcttcctct ttgttcc                                   37

<210> SEQ ID NO 110
<211> LENGTH: 28
<212> TYPE: DNA
<213> ORGANISM: Artificial
<220> FEATURE:
<223> OTHER INFORMATION: Primer

<400> SEQUENCE: 110
gaggattcga cttcaaccct tctcctcc                                             28

<210> SEQ ID NO 111
<211> LENGTH: 28
<212> TYPE: DNA
<213> ORGANISM: Artificial

```
<220> FEATURE:
<223> OTHER INFORMATION: Primer

<400> SEQUENCE: 111
ggaggagaag ggttgaagtc gaatcctc                                             28

<210> SEQ ID NO 112
<211> LENGTH: 28
<212> TYPE: DNA
<213> ORGANISM: Artificial
<220> FEATURE:
<223> OTHER INFORMATION: Primer

<400> SEQUENCE: 112
gaggattcga cttccagcct tctcctcc                                             28

<210> SEQ ID NO 113
<211> LENGTH: 28
<212> TYPE: DNA
<213> ORGANISM: Artificial
<220> FEATURE:
<223> OTHER INFORMATION: Primer

<400> SEQUENCE: 113
ggaggagaag gctggaagtc gaatcctc                                             28

<210> SEQ ID NO 114
<211> LENGTH: 37
<212> TYPE: DNA
<213> ORGANISM: Artificial
<220> FEATURE:
<223> OTHER INFORMATION: Primer

<400> SEQUENCE: 114
ggaacaaaga ggaagagtaa cattcagacg tatttgg                                   37

<210> SEQ ID NO 115
<211> LENGTH: 37
<212> TYPE: DNA
<213> ORGANISM: Artificial
<220> FEATURE:
<223> OTHER INFORMATION: Primer

<400> SEQUENCE: 115
ccaaatacgt ctgaatgtta ctcttcctct tgttcc                                    37

<210> SEQ ID NO 116
<211> LENGTH: 37
<212> TYPE: DNA
<213> ORGANISM: Artificial
<220> FEATURE:
<223> OTHER INFORMATION: Primer

<400> SEQUENCE: 116
ggaacaaaga ggaagagtca cattcagacg tatttgg                                   37

<210> SEQ ID NO 117
<211> LENGTH: 37
<212> TYPE: DNA
<213> ORGANISM: Artificial
<220> FEATURE:
<223> OTHER INFORMATION: Primer

<400> SEQUENCE: 117
ccaaatacgt ctgaatgtga ctcttcctct tgttcc                                    37
```

<210> SEQ ID NO 118
<211> LENGTH: 37
<212> TYPE: DNA
<213> ORGANISM: Artificial
<220> FEATURE:
<223> OTHER INFORMATION: Primer Ta2-126

<400> SEQUENCE: 118
ggaacaaaga ggaagagtgc gattcagacg tatttgg      37

<210> SEQ ID NO 119
<211> LENGTH: 37
<212> TYPE: DNA
<213> ORGANISM: Artificial
<220> FEATURE:
<223> OTHER INFORMATION: Primer Ta2-127

<400> SEQUENCE: 119
ccaaatacgt ctgaatcgca ctcttcctct ttgttcc      37

<210> SEQ ID NO 120
<211> LENGTH: 37
<212> TYPE: DNA
<213> ORGANISM: Artificial
<220> FEATURE:
<223> OTHER INFORMATION: Primer

<400> SEQUENCE: 120
ggaacaaaga ggaagagtct gattcagacg tatttgg      37

<210> SEQ ID NO 121
<211> LENGTH: 37
<212> TYPE: DNA
<213> ORGANISM: Artificial
<220> FEATURE:
<223> OTHER INFORMATION: Primer

<400> SEQUENCE: 121
ccaaatacgt ctgaatcaga ctcttcctct ttgttcc      37

<210> SEQ ID NO 122
<211> LENGTH: 37
<212> TYPE: DNA
<213> ORGANISM: Artificial
<220> FEATURE:
<223> OTHER INFORMATION: Primer

<400> SEQUENCE: 122
ggaacaaaga ggaagagtat aattcagacg tatttgg      37

<210> SEQ ID NO 123
<211> LENGTH: 37
<212> TYPE: DNA
<213> ORGANISM: Artificial
<220> FEATURE:
<223> OTHER INFORMATION: Primer

<400> SEQUENCE: 123
ccaaatacgt ctgaattata ctcttcctct ttgttcc      37

<210> SEQ ID NO 124
<211> LENGTH: 37
<212> TYPE: DNA
<213> ORGANISM: Artificial
<220> FEATURE:
<223> OTHER INFORMATION: Primer

```
<400> SEQUENCE: 124
ggaacaaaga ggaagagttc gattcagacg tatttgg                              37

<210> SEQ ID NO 125
<211> LENGTH: 37
<212> TYPE: DNA
<213> ORGANISM: Artificial
<220> FEATURE:
<223> OTHER INFORMATION: Primer

<400> SEQUENCE: 125
ccaaatacgt ctgaatcgaa ctcttcctct ttgttcc                              37

<210> SEQ ID NO 126
<211> LENGTH: 28
<212> TYPE: DNA
<213> ORGANISM: Artificial
<220> FEATURE:
<223> OTHER INFORMATION: Primer

<400> SEQUENCE: 126
gaggattcga cttccaccct tctcctcc                                        28

<210> SEQ ID NO 127
<211> LENGTH: 28
<212> TYPE: DNA
<213> ORGANISM: Artificial
<220> FEATURE:
<223> OTHER INFORMATION: Primer

<400> SEQUENCE: 127
ggaggagaag ggtggaagtc gaatcctc                                        28

<210> SEQ ID NO 128
<211> LENGTH: 28
<212> TYPE: DNA
<213> ORGANISM: Artificial
<220> FEATURE:
<223> OTHER INFORMATION: Primer

<400> SEQUENCE: 128
gaggattcga cttctaccct tctcctcc                                        28

<210> SEQ ID NO 129
<211> LENGTH: 28
<212> TYPE: DNA
<213> ORGANISM: Artificial
<220> FEATURE:
<223> OTHER INFORMATION: Primer

<400> SEQUENCE: 129
ggaggagaag ggtagaagtc gaatcctc                                        28

<210> SEQ ID NO 130
<211> LENGTH: 28
<212> TYPE: DNA
<213> ORGANISM: Artificial
<220> FEATURE:
<223> OTHER INFORMATION: Primer

<400> SEQUENCE: 130
gaggattcga cttcagccct tctcctcc                                        28

<210> SEQ ID NO 131
```

```
<211> LENGTH: 28
<212> TYPE: DNA
<213> ORGANISM: Artificial
<220> FEATURE:
<223> OTHER INFORMATION: Primer

<400> SEQUENCE: 131
ggaggagaag ggctgaagtc gaatcctc                                      28

<210> SEQ ID NO 132
<211> LENGTH: 28
<212> TYPE: DNA
<213> ORGANISM: Artificial
<220> FEATURE:
<223> OTHER INFORMATION: Primer

<400> SEQUENCE: 132
gaggattcga cttcacacct tctcctcc                                      28

<210> SEQ ID NO 133
<211> LENGTH: 28
<212> TYPE: DNA
<213> ORGANISM: Artificial
<220> FEATURE:
<223> OTHER INFORMATION: Primer

<400> SEQUENCE: 133
ggaggagaag gtgtgaagtc gaatcctc                                      28

<210> SEQ ID NO 134
<211> LENGTH: 28
<212> TYPE: DNA
<213> ORGANISM: Artificial
<220> FEATURE:
<223> OTHER INFORMATION: Primer

<400> SEQUENCE: 134
gaggattcga cttctgtcct tctcctcc                                      28

<210> SEQ ID NO 135
<211> LENGTH: 28
<212> TYPE: DNA
<213> ORGANISM: Artificial
<220> FEATURE:
<223> OTHER INFORMATION: Primer

<400> SEQUENCE: 135
ggaggagaag gacagaagtc gaatcctc                                      28

<210> SEQ ID NO 136
<211> LENGTH: 29
<212> TYPE: DNA
<213> ORGANISM: Artificial
<220> FEATURE:
<223> OTHER INFORMATION: Primer

<400> SEQUENCE: 136
ggattcgact tcatgcgttc tcctccgcc                                     29

<210> SEQ ID NO 137
<211> LENGTH: 29
<212> TYPE: DNA
<213> ORGANISM: Artificial
<220> FEATURE:
<223> OTHER INFORMATION: Primer

<400> SEQUENCE: 137
```

```
<210> SEQ ID NO 138
<211> LENGTH: 31
<212> TYPE: DNA
<213> ORGANISM: Artificial
<220> FEATURE:
<223> OTHER INFORMATION: Primer

<400> SEQUENCE: 138
gaggaattag ggatttgggt agacagagat g                                  31

<210> SEQ ID NO 139
<211> LENGTH: 31
<212> TYPE: DNA
<213> ORGANISM: Artificial
<220> FEATURE:
<223> OTHER INFORMATION: Primer

<400> SEQUENCE: 139
catctctgtc tacccaaatc cctaattcct c                                  31

<210> SEQ ID NO 140
<211> LENGTH: 31
<212> TYPE: DNA
<213> ORGANISM: Artificial
<220> FEATURE:
<223> OTHER INFORMATION: Primer

<400> SEQUENCE: 140
gaggaattag ggattatggt agacagagat g                                  31

<210> SEQ ID NO 141
<211> LENGTH: 31
<212> TYPE: DNA
<213> ORGANISM: Artificial
<220> FEATURE:
<223> OTHER INFORMATION: Primer

<400> SEQUENCE: 141
catctctgtc taccataatc cctaattcct c                                  31

<210> SEQ ID NO 142
<211> LENGTH: 30
<212> TYPE: DNA
<213> ORGANISM: Artificial
<220> FEATURE:
<223> OTHER INFORMATION: Primer

<400> SEQUENCE: 142
ggtggttttg gcaaacacaa tttctctgag                                    30

<210> SEQ ID NO 143
<211> LENGTH: 30
<212> TYPE: DNA
<213> ORGANISM: Artificial
<220> FEATURE:
<223> OTHER INFORMATION: Primer

<400> SEQUENCE: 143
ctcagagaaa ttgtgtttgc caaaaccacc                                    30

<210> SEQ ID NO 144
<211> LENGTH: 30
<212> TYPE: DNA
```
ggcggaggag aacgcatgaa gtcgaatcc                                     29

```
<213> ORGANISM: Artificial
<220> FEATURE:
<223> OTHER INFORMATION: Primer

<400> SEQUENCE: 144
ggtggttttg gcaaatgcaa tttctctgag                                30

<210> SEQ ID NO 145
<211> LENGTH: 30
<212> TYPE: DNA
<213> ORGANISM: Artificial
<220> FEATURE:
<223> OTHER INFORMATION: Primer

<400> SEQUENCE: 145
ctcagagaaa ttgcatttgc caaaaccacc                                30

<210> SEQ ID NO 146
<211> LENGTH: 30
<212> TYPE: DNA
<213> ORGANISM: Artificial
<220> FEATURE:
<223> OTHER INFORMATION: Primer

<400> SEQUENCE: 146
ggtggttttg gcacaggcaa tttctctgag                                30

<210> SEQ ID NO 147
<211> LENGTH: 30
<212> TYPE: DNA
<213> ORGANISM: Artificial
<220> FEATURE:
<223> OTHER INFORMATION: Primer

<400> SEQUENCE: 147
ctcagagaaa ttgcctgtgc caaaaccacc                                30

<210> SEQ ID NO 148
<211> LENGTH: 31
<212> TYPE: DNA
<213> ORGANISM: Artificial
<220> FEATURE:
<223> OTHER INFORMATION: Primer

<400> SEQUENCE: 148
gggagggttt gactttcatc cacctccgct g                              31

<210> SEQ ID NO 149
<211> LENGTH: 31
<212> TYPE: DNA
<213> ORGANISM: Artificial
<220> FEATURE:
<223> OTHER INFORMATION: Primer

<400> SEQUENCE: 149
cagcggaggt ggatgaaagt caaaccctcc c                              31

<210> SEQ ID NO 150
<211> LENGTH: 27
<212> TYPE: DNA
<213> ORGANISM: Artificial
<220> FEATURE:
<223> OTHER INFORMATION: Primer

<400> SEQUENCE: 150
ggcttcgact tctatccacc cccgctg                                   27
```

```
<210> SEQ ID NO 151
<211> LENGTH: 27
<212> TYPE: DNA
<213> ORGANISM: Artificial
<220> FEATURE:
<223> OTHER INFORMATION: Primer

<400> SEQUENCE: 151 cagcggggt ggatagaagt cgaagcc                                              27

<210> SEQ ID NO 152
<211> LENGTH: 30
<212> TYPE: DNA
<213> ORGANISM: Artificial
<220> FEATURE:
<223> OTHER INFORMATION: Primer

<400> SEQUENCE: 152
gggttcggca aatgcaactt ctccgagctg                                          30

<210> SEQ ID NO 153
<211> LENGTH: 30
<212> TYPE: DNA
<213> ORGANISM: Artificial
<220> FEATURE:
<223> OTHER INFORMATION: Primer

<400> SEQUENCE: 153
cagctcggag aagttgcatt tgccgaaccc                                          30

<210> SEQ ID NO 154
<211> LENGTH: 30
<212> TYPE: DNA
<213> ORGANISM: Artificial
<220> FEATURE:
<223> OTHER INFORMATION: Primer

<400> SEQUENCE: 154
ggagggtttg actttcatgc acctccgctg                                          30

<210> SEQ ID NO 155
<211> LENGTH: 30
<212> TYPE: DNA
<213> ORGANISM: Artificial
<220> FEATURE:
<223> OTHER INFORMATION: Primer

<400> SEQUENCE: 155
cagcggaggt gcatgaaagt caaaccctcc                                          30
```